(12) United States Patent
Iwanowicz et al.

(10) Patent No.: US 7,312,209 B2
(45) Date of Patent: Dec. 25, 2007

(54) ACRIDONE INHIBITORS OF IMPDH ENZYME

(75) Inventors: Edwin J. Iwanowicz, West Windsor, NJ (US); Scott H. Watterson, Pennington, NJ (US); Ping Chen, Belle Mead, NJ (US); T. G. Murali Dhar, Newtown, PA (US); Henry H. Gu, Bordentown, NJ (US); Yufen Zhao, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 691 days.

(21) Appl. No.: 10/324,306

(22) Filed: Dec. 20, 2002

(65) Prior Publication Data

US 2004/0053955 A1 Mar. 18, 2004

Related U.S. Application Data

(60) Provisional application No. 60/343,234, filed on Dec. 21, 2001.

(51) Int. Cl.
| C07D 417/00 | (2006.01) |
| C07D 265/36 | (2006.01) |
| C07D 413/00 | (2006.01) |
| C07D 401/00 | (2006.01) |
| C07D 239/02 | (2006.01) |

(52) U.S. Cl. .............. 514/218; 514/228.2; 514/230.5; 514/232.8; 514/253.03; 514/266.21; 514/269; 514/274; 514/297; 540/553; 544/61; 544/105; 544/126; 544/284; 544/315; 544/319; 544/361; 546/103

(58) Field of Classification Search ............. 514/63, 514/218, 228.2, 230.5, 232.8, 253.03, 266.21, 514/269, 274, 297; 546/79, 103; 540/553; 544/61, 105, 126, 284, 315, 319, 361
See application file for complete search history.

(56) References Cited

U.S. PATENT DOCUMENTS

| 3,835,139 A | 9/1974 | Pfister et al. |
| 3,950,342 A | 4/1976 | Gorvin |
| 3,987,088 A | 10/1976 | Hodson et al. |
| 4,061,768 A | 12/1977 | Gorvin |
| 4,250,182 A * | 2/1981 | Gorvin .................. 514/297 |
| 4,374,984 A * | 2/1983 | Eichler et al. ............... 544/80 |
| 4,686,234 A | 8/1987 | Nelson et al. |
| 4,725,622 A | 2/1988 | Nelson et al. |
| 4,727,069 A | 2/1988 | Nelson et al. |
| 4,753,935 A | 6/1988 | Nelson et al. |
| 4,786,637 A | 11/1988 | Allison et al. |
| 4,808,592 A | 2/1989 | Nelson et al. |
| 4,861,776 A | 8/1989 | Nelson et al. |
| 4,868,153 A | 9/1989 | Allison et al. |
| 4,948,793 A | 8/1990 | Allison et al. |
| 4,952,579 A | 8/1990 | Nelson et al. |
| 4,959,387 A | 9/1990 | Nelson et al. |
| 4,992,467 A | 2/1991 | Allison et al. |
| 5,247,083 A | 9/1993 | Knox et al. |
| 5,380,879 A | 1/1995 | Sjogren |
| 5,444,072 A | 8/1995 | Patterson et al. |
| 5,665,583 A | 9/1997 | Collart et al. |
| 5,807,876 A | 9/1998 | Armistead et al. |
| 2003/0181497 A1 | 9/2003 | Chen et al. |

FOREIGN PATENT DOCUMENTS

| CA | 1009576 | 5/1977 |
| CA | 1009660 | 5/1977 |
| GB | 1382259 | * 12/1971 |
| GB | 1382259 | 1/1975 |
| JP | 63-305173 | 12/1988 |
| WO | WO 94/01105 | 1/1994 |
| WO | WO 97/40028 | 10/1997 |
| WO | WO 98/15546 | 4/1998 |
| WO | WO 98/40381 | 9/1998 |
| WO | WO 00/23415 | 4/2000 |
| WO | WO 00/23416 | 4/2000 |
| WO | WO 02/099424 | 12/2002 |
| WO | WO 03/055447 | 7/2003 |

OTHER PUBLICATIONS

Burger's Medicinal Chemistry and Drug Discovery, 5th edition, vol. 1, Manfred E. Wolff, Feb. 8, 1995, pp. 975-977.*

(Continued)

*Primary Examiner*—Bruck Kifle
(74) *Attorney, Agent, or Firm*—Terence J. Bogie

(57) ABSTRACT

Compounds having the formula (I),

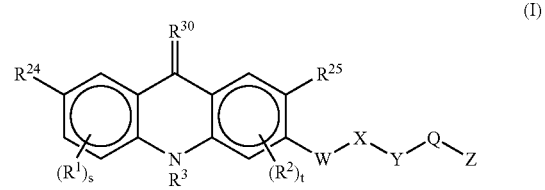

wherein $R^3$ is selected from H, OH and $NH_2$; $R^{30}$ is selected from $=O$ and $=S$; W is $-C(=O)-$, $-S(=O)-$, or $-S(O)_2-$; or W may be $-CH_2-$ if X is $-C(=O)-$; X is selected from $-CH_2-$, $-N(R^4)-$, and $-O-$, except that when W is $-CH_2-$, X is $-C(=O)-$; Y is a bond or $-C(R^{40})(R^{45})-$; Q is a linker; Z is optionally substituted alkyl, alkenyl, alkynyl, cycloalkyl, aryl, heteroaryl, or heterocyclyl; and $R^1$, $R^2$, $R^{24}$, and $R^{25}$ are as defined in the specification.

29 Claims, No Drawings

OTHER PUBLICATIONS

Modern Pharmacuetics, 3rd edition, Banker et al., Feb. 1995, p. 596.*
Kavadias (Chimica Chronika (1994), 23(4), 79-95. (Abstract).*
Stewart, G. et al., Aust. J. Chem., vol. 37, pp. 1939-1950 (1984).
Chemical Abstracts, vol. 123, No. 3 (1995), abstract No. 32927 g.
Canelos, P.A. et al., Abstract 486: "Rolipram, a Type 4 Phosphodiesterase (PDE) Inhibitor, Promotes Induction of Neoantigen Tolerance in Murine T Cells" (593), J. Allergy Clin. Immunol. vol. 107, No. 2, p. S147, 2001.
Carr, S.F. et al., "Characterization of Human Type I and Type II IMP Dehydrogenases", The Journal of Biological Chemistry, vol. 268, No. 36, pp. 27286-27290 (1993).
Collart, F.R. et al., "Cloning and Sequence Analysis of the Human and Chinese Hamster Inosine-5'-monophosphate Dehydrogenase cDNAs", The Journal of Biological Chemistry, vol. 263, No. 30, pp. 15769-15772 (1988).
Jackson, R.C. et al., "IMP dehydrogenase, an enzyme linked with proliferation and malignancy", Nature, vol. 256, pp. 331-333 (1975).
Konno, Y. et al., "Expression of Human IMP Dehydrogenase Types I and II in *Escherichia coli* and Distribution in Human Normal Lymphocytes and Leukemic Cell Lines", The Journal of Biological Chemistry, vol. 266, No. 1, pp. 506-509 (1991).
Natsumeda, Y. et al., "Two Distinct cDNAs for Human IMP Dehydrogenase", The Journal of Biological Chemistry, vol. 265, No. 9, pp. 5292-5295 (1990).

* cited by examiner

ACRIDONE INHIBITORS OF IMPDH ENZYME

RELATED APPLICATIONS

This application claims the benefit of U.S. Provisional Application No. 60/343,234, filed Dec. 21, 2001, incorporated herein by reference.

FIELD OF THE INVENTION

The present invention relates to compounds which inhibit IMPDH, to methods of making such compounds, and to pharmaceutical compositions containing these compounds. The compounds and pharmaceutical compositions of the invention can be used as therapeutic agents for IMPDH-associated disorders.

BACKGROUND OF THE INVENTION

Inosine monophosphate dehydrogenase (IMPDH) has been shown to be a key enzyme in the regulation of cell proliferation and differentiation. Nucleotides are required for cells to divide and replicate. In mammals, nucleotides may be synthesized through one of two pathways: the de novo synthesis pathway or the salvage pathway. The extent of utilization of each pathway is dependent on the cell type. This selectivity has ramifications with regard to therapeutic utility as described below.

IMPDH is involved in the de novo synthesis of guanosine nucleotides. IMPDH catalyzes the irreversible NAD-dependent oxidation of inosine-5'-monophosphate ("IMP") to xanthosine-5'-monophosphate ("XMP"), Jackson et al., *Nature*, 256:331-333 (1975).

IMPDH is ubiquitous in eukaryotes, bacteria and protozoa. The prokaryotic forms share 30-40% sequence identity with the human enzyme.

Two distinct cDNA's encoding IMPDH have been identified and isolated. These transcripts are labeled type I and type II and are of identical size (514 amino acids). Collart et al., *J. Biol. Chem.*, 263:15769-15772 (1988); Natsumeda et al., *J. Biol. Chem.*, 265:5292-5295 (1990); and U.S. Pat. No. 5,665,583 to Collart et al. These isoforms share 84% sequence identity. IMPDH type I and type II form tetramers in solution, the enzymatically active unit.

B and T-lymphocytes depend on the de novo, rather than salvage pathway, to generate sufficient levels of nucleotides necessary to initiate a proliferative response to mitogen or antigen. Due to the B and T cell's unique reliance on the de novo pathway, IMPDH is an attractive target for selectively inhibiting the immune system without also inhibiting the proliferation of other cells.

Inhibitors of IMPDH have also been described in the art. WO 97/40028 and U.S. Pat. No. 5,807,876 describe a class of urea derivatives that possess a common urea backbone. WO 98/40381 describes a series of heterocyclic substituted anilines as inhibitors of IMPDH.

Tiazofurin, ribavirin and mizoribine also inhibit IMPDH. These nucleoside analogs are competitive inhibitors of IMPDH; however, these agents inhibit other NAD dependent enzymes. This low level of selectivity for IMPDH limits the therapeutic application of tiazofurin, ribavirin and mizoribine. Thus, new agents which have improved selectivity for IMPDH would represent a significant improvement over the nucleoside analogs.

U.S. Pat. Nos. 5,380,879 and 5,444,072 and PCT publications WO 94/01105 and WO 94/12184 describe mycophenolic acid ("MPA") and some of its derivatives as potent, uncompetitive, reversible inhibitors of human IMPDH type I and type II. MPA has been demonstrated to block the response of B and T-cells to mitogen or antigen. Immunosuppressants, such as MPA and derivatives of MPA, are useful drugs in the treatment of transplant rejection and autoimmune disorders, psoriasis, inflammatory diseases, including rheumatoid arthritis, tumors and for the treatment of allograft rejection. These are described in U.S. Pat. Nos. 4,686,234, 4,725,622, 4,727,069, 4,753,935, 4,786,637, 4,808,592, 4,861,776, 4,868,153, 4,948,793, 4,952,579, 4,959,387, 4,992,467, and 5,247,083.

Mycophenolate mofetil, sold under the trade name CELLCEPT, is a prodrug which liberates MPA in vivo. It is approved for use in preventing acute renal allograft rejection following kidney transplantation. The side effect profile limits the therapeutic potential of this drug. MPA is rapidly metabolized to the inactive glucuronide in vivo. In humans, the blood levels of glucuronide exceed that of MPA. The glucuronide undergoes enterohepatic recycling causing accumulation of MPA in the bile and subsequently in the gastrointestinal tract. This together with the production of the inactive glucuronide effectively lowers the drug's in vivo potency, while increasing its undesirable gastrointestinal side effects.

The combination of agents for prevention and/or treatment of IMPDH-associated disorders, especially allograft rejection, has been investigated. In one study, it was observed that cyclic AMP agonists, such as the Type 4 Phosphodiesterase (PDE4) inhibitor Rolipram [4-[3-(cyclopentyloxy)-4-methoxy-phenyl]-2-pyrrolidinone] (Schering A G), synergized with IMPDH inhibitor MPA by a cAMP- and IMPDH-dependent mechanism. (P. A. Canelos et al., *J. Allergy and Clinical Immunology*, 107:593 (2001)). The investigators found that cyclic AMP agonists, such as the PDE4 inhibitor Rolipram (Rol), markedly downregulated antigen-specific T lymphocyte responses through their effects on a variety of signaling pathways. The study defined the potential to use a low concentration of Rol ($10^{-7}$ M, approximate $IC_{10}$) to synergize with a variety of immunosuppressive agents for the prevention and/or treatment of allograft rejection. While little or no synergistic effect on inhibition of antigen-induced proliferation (assessed by $^3$H Thymidine incorporation) could be demonstrated with calcineurin antagonists (cyclosporine and tacrolimus), sirolimus, or corticosteroids, a marked synergistic effect was demonstrated with MPA, the active metabolite of mycophenolate mofetil (CellCept, Roche). This effect was statistically significant over 4 orders of magnitude ($10^{-6}$ to $10^{-9}$ M). This synergism was recapitulated with dibuteryl-cAMP ($2\times10^{-6}$ M, approximate $IC_{10}$) and inhibited with the use of H-9, suggesting a mechanism involving both cAMP and protein kinase A.

Since MPA is a selective, uncompetitive, and reversible inhibitor of IMPDH, a key enzyme in the purine salvage pathway, the potential for cAMP-mediated cross-talk at this locus was further investigated. It was found that gene expression for IMPDH types I and II (assessed by RT-PCR) remained unaffected by the administration of rolipram, MPA, or both at low and high concentrations. However, functional reversal of the synergistic effect was demonstrated with the use of deoxyguanosine, a specific antagonist of MPA on IMPDH (% inhibition of proliferation 81±16 vs. 35±12, p<0.05). Finally, despite a marked synergistic effect on inhibition of proliferation, no significant downregulation in the generation of proinflammatory cytokines (IL-2, IL-4, and IFN, each assessed by RT-PCR), could be detected with the administration of Ro1 $10^{-7}$ M, MPA $10^{-8}$ M, or the combination. It was concluded that Ro1 demonstrates marked synergy with MPA by a cAMP- and IMPDH-dependent mechanism. The utility of this combination of agents for the induction of T cell tolerance was suggested by the specificity of the observed effect for proliferation, without the abrogation of cytokine generation and early signaling processes.

Unlike type I, type II mRNA is preferentially upregulated in human leukemic cell lines K562 and HL-60. Weber, *J. Biol. Chem.*, 266: 506-509 (1991). In addition, cells from human ovarian tumors and leukemic cells from patients with chronic granulocytic, lymphocytic and acute myeloid leukemias also display an up regulation type II mRNA. This disproportionate increase in IMPDH activity in malignant cells may be addressed through the use of an appropriate IMPDH inhibitor. IMPDH has also been shown to play a role in the proliferation of smooth muscle cells, indicating that inhibitors of IMPDH may be useful in preventing restenosis or other hyperproliferative vascular diseases.

IMPDH has been shown to play a role in viral replication in some viral cell lines. Carr, *J. Biol. Chem.*, 268:27286-27290 (1993). The IMPDH inhibitor VX-497, is currently being evaluated for the treatment of hepatitis C virus in humans. Ribavirin has also been used in the treatment of hepatitis C and B viruses and when used in combination with interferon an enhancement in activity was observed. The IMPDH inhibitor ribavirin is limited by its lack of a sustained response in monotherapy and broad cellular toxicity.

There remains a need for potent selective inhibitors of IMPDH with improved pharmacological properties, physical properties and fewer side effects. Such inhibitors would have therapeutic potential as immunosuppressants, anti-cancer agents, anti-vascular hyperproliferative agents, anti-inflammatory agents, antifungal agents, antipsoriatic and anti-viral agents. The compounds of the present invention are effective inhibitors of IMPDH. Inhibitors of IMPDH enzyme are also described in U.S. patent application Ser. No. 10/325,009, titled "Heterocyclic Acridone Inhibitors of IMPDH Enzyme," having the same assignee as the present invention and filed concomitantly herewith, the entire contents of which is incorporated herein by reference. Said application also claims priority to U.S. patent application Ser. No. 60/343,234, filed Dec. 21, 2001.

SUMMARY OF THE INVENTION

The present invention provides compounds of the following formula (I), their enantiomers, diastereomers, tautomers and pharmaceutically acceptable salts and solvates thereof, for use as IMPDH inhibitors:

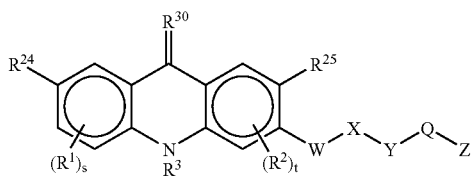

(I)

wherein:

$R^1$ and $R^2$ are the same or different and at each occurrence are independently selected from halogen, cyano, alkyl, substituted alkyl, alkenyl, substituted alkenyl, alkynyl, substituted alkynyl, —O—$R^7$, —(C=O)$R^7$, —(C=O)—O—$R^7$, —$NR^8R^9$, —(C=O)$NR^8R^9$, —$SR^{20}$, —$S(=O)R^{20}$, —$SO_2R^{20}$ and —C≡C—Si$(C_{1-4}alkyl)_3$;

$R^{24}$ and $R^{25}$ are the same or different and at each occurrence are independently selected from hydrogen, halogen, nitro, cyano, alkyl, substituted alkyl, alkenyl, substituted alkenyl, alkynyl, substituted alkynyl, —O—$R^7$, —(C=O)$R^7$, —(C=O)—O—$R^7$, —$NR^8R^9$, —(C=O)$NR^8R^9$, —$SR^{20}$, —$S(=O)R^{20}$, —$SO_2R^{20}$, —$SO_3H$, —$SO_3R^{20}$, —$SO_2NR^8R^9$, and —C≡C—Si$(C_{1-4}alkyl)_3$;

$R^3$ is selected from H, OH and $NH_2$;

$R^{30}$ is selected from =O and =S;

W is —C(=O)—, —S(=O)—, or —S(O)$_2$—; or W may be —$CH_2$— if X is —C(=O)—;

X is selected from —$CH_2$—, —N($R^4$)—, and —O—, except that when W is —$CH_2$—, X is —C(=O)—;

Y is a bond or —C($R^{40}$)($R^{45}$)—;

Q is selected from a bond, —C($R^{26}$)($R^{46}$)—, —C(=O)—, —$CH_2$—O—, —$CH_2$—O—$CH_2$—, —$CH_2$—$CO_2$—$NR^4$—, —$CH_2$—$CO_2$—, —C(=O)$NR^4$—, and —CH=C($R^{26}$)—;

Z is selected from alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclyl and substituted heterocyclyl, and when Y is —C($R^{40}$)($R^{45}$)— and Q is a bond or —C($R^{26}$)($R^{46}$)—, Z may be $CO_2H$ or $CO_2alkyl$;

$R^4$ is selected from H, OH and $C_{1-4}$ alkyl;

$R^7$ is selected from hydrogen, alkyl, substituted alkyl, alkenyl, alkynyl, C(=O)alkyl, C(=O)substituted alkyl, C(=O)cycloalkyl, C(=O)substituted cycloalkyl, C(=O)aryl, C(=O)substituted aryl, C(=O)heterocyclo, C(=O) substituted heterocyclo, C(=O)heteroaryl, C(=O)substituted heteroaryl, C(=O)O-alkyl, C(=O)O-substituted alkyl, —C(=O)—$NR^8R^9$, aryl, substituted aryl, cycloalkyl, substituted cycloalkyl, heterocyclo, substituted heterocyclo, heteroaryl, and substituted heteroaryl;

$R^8$ and $R^9$ are independently selected from hydrogen, hydroxy, O(alkyl), O(substituted alkyl), alkyl, substituted alkyl, alkenyl, alkynyl, C(=O)alkyl, C(=O)substituted alkyl, C(=O)cycloalkyl, C(=O)substituted cycloalkyl, C(=O)aryl, C(=O)substituted aryl, C(=O)O-alkyl, C(=O)O-substituted alkyl, C(=O)heterocyclo, C(=O)heteroaryl, cycloalkyl, substituted cycloalkyl, aryl, substituted aryl, heterocyclo, substituted heterocyclo, heteroaryl and substituted heteroaryl, or $R^8$ and $R^9$ are taken together with the nitrogen atom to which they are attached to form a substituted or unsubstituted heterocyclo ring of 3 to 8 atoms or substituted or unsubstituted heteroaryl ring;

$R^{20}$ is selected from alkyl and substituted alkyl;

$R^{26}$ and $R^{46}$ are independently selected from hydrogen, $C_{1-4}$alkyl, hydroxy, halogen, hydroxy$C_{1-4}$alkyl, halo$C_{1-4}$alkyl, and heterocyclo$C_{1-4}$alkyl, or taken together form a $C_{3-7}$ cycloalkyl ring;

$R^{40}$ and $R^{45}$ are independently selected from hydrogen, cyano, alkyl, substituted alkyl, alkenyl, substituted alkenyl, alkynyl, substituted alkynyl, cycloalkyl, substituted cycloalkyl, aryl, substituted aryl, heterocyclo, substituted heterocyclo, heteroaryl and substituted heteroaryl, or $R^{40}$ and $R^{45}$ are taken together to form a substituted or unsubstituted cycloalkyl ring of 3 to 8 atoms or a substituted or unsubstituted heterocyclo ring of 3 to 8 atoms;

s is 0, 1, 2 or 3; and t is 0, 1, or 2.

The present invention also relates to pharmaceutical compositions containing compounds of formula (I), and methods for treating IMPDH-associated disorders using the compounds of formula (I), alone or in combination with PDE4 inhibitors.

DETAILED DESCRIPTION OF THE INVENTION

The following are definitions of the terms as used throughout this specification and claims. The initial definition provided for a group or term herein applies to that group or term throughout the present specification, individually or as part of another group, unless otherwise indicated.

The term "alkyl" refers to straight or branched chain hydrocarbon groups having 1 to 12 carbons atoms, preferably 1 to 8 carbon atoms, and most preferably 1 to 4 carbon atoms. The term "lower alkyl" refers to an alkyl group of 1 to 4 carbon atoms.

The term "substituted alkyl" refers to an alkyl group as defined above having one, two, or three substituents selected from the group consisting of halo, cyano, O—$R^5$, S—$R^5$, $NR^6R^{6a}$, nitro, oxo, cycloalkyl, substituted cycloalkyl, aryl, substituted aryl, heterocyclo, substituted heterocyclo, heteroaryl, substituted heteroaryl, $CO_2R^5$, $S(O)R^5$, $SO_2R^5$, $SO_3R^5$, $SO_2NR^6R^{6a}$, $C(=O)NR^6R^{6a}$, $NR^6CO_2R^{6a}$, $CO_2NR^6R^{6a}$ and $C(=O)R^5$.

The term "alkenyl" refers to straight or branched chain hydrocarbon groups having 2 to 12 carbon atoms and one, two or three double bonds, preferably 2 to 6 carbon atoms and one double bond.

The term "substituted alkenyl" refers to an alkenyl group as defined above having one, two, or three substituents selected from the group consisting of halo, cyano, O—$R^5$, S—$R^5$, $NR^6R^{6a}$, nitro, oxo, cycloalkyl, substituted cycloalkyl, aryl, substituted aryl, heterocyclo, substituted heterocyclo, heteroaryl, substituted heteroaryl, $CO_2R^5$, $S(O)R^5$, $SO_2R^5$, $SO_3R^5$, $SO_2NR^6R^{6a}$, $C(=O)NR^6R^{6a}$, $NR^6CO_2R^{6a}$, $CO_2NR^6R^{6a}$ and $C(=O)R^5$.

The term "alkynyl" refers to straight or branched chain hydrocarbon group having 2 to 12 carbon atoms and one, two or three triple bonds, preferably 2 to 6 carbon atoms and one triple bond.

The term "substituted alkynyl" refers to an alkynyl group as defined above having one, two or three substituents selected from the group consisting of halo, cyano, O—$R^5$, S—$R^5$, $NR^6R^{6a}$, nitro, cycloalkyl, substituted cycloalkyl, oxo, aryl, substituted aryl, heterocyclo, heteroaryl, $CO_2R^5$, $S(O)R^5$, $SO_2R^5$, $SO_3R^5$, $SO_2NR^6R^{6a}$, $C(=O)NR^6R^{6a}$, and $C(=O)R^5$.

The term "halo" refers to chloro, bromo, fluoro, and iodo, with chloro, bromo and fluoro being preferred.

The term "cycloalkyl" refers to fully saturated and partially unsaturated monocyclic hydrocarbon rings of 3 to 9, preferably 3 to 7 carbon atoms. Also included in this definition are bicyclic rings where the cycloalkyl ring as defined above has a bridge of one, two or three carbon atoms in the bridge, or a second ring attached in a fused or spiro fashion, i.e., a fused aryl, substituted aryl, cycloalkyl, substituted cycloalkyl, heterocyclo, substituted heterocyclo, heteroaryl or substituted heteroaryl ring, or a spirocycloalkyl or spiroheterocycloalkyl ring, provided that the point of attachment is in the cycloalkyl ring.

Thus, the term "cycloalkyl" includes cyclopropyl, cyclobutyl, cyclopentyl, cyclohexyl, cycloheptyl, cyclooctyl, etc., as well as the following ring systems,

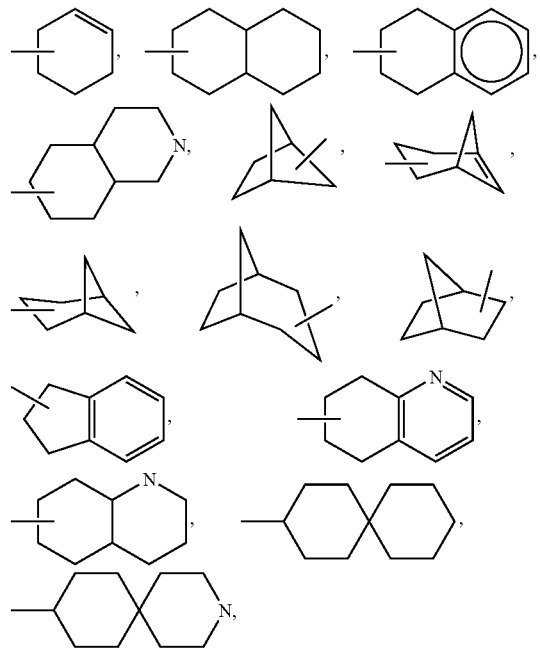

and so forth.

The term "substituted cycloalkyl" refers to such cycloalkyl groups as defined above having one, two or three substituents attached to any available carbon atom of a monocyclic ring or any available carbon or nitrogen atom of a bicyclic ring, wherein said substituents are selected from the group consisting of halogen, nitro, alkyl, substituted alkyl, alkenyl, cyano, cycloalkyl, aryl, heterocyclo, heteroaryl, oxo (=O), —$OR^5$, —$CO_2R^5$, —$C(=O)NR^6R^{6a}$, —$OC(=O)R^5$, —$OC(=O)OR^5$, —$OC(=O)NR^6R^{6a}$, —$OCH_2CO_2R^5$, —$C(=O)R^5$, $NR^6R^{6a}$, —$NR^{10}C(=O)R^5$, —$NR^{10}C(=O)OR^5$, —$NR^{10}C(=O)C(=O)OR^5$, —$NR^{10}C(=O)C(=O)NR^6R^{6a}$, —$NR^{10}C(=O)C(=O)$alkyl, —$NR^{10}C(NCN)OR^5$, $NR^{10}C(=O)NR^6R^{6a}$, —$NR^{10}C(NCN)NR^6R^{6a}$, —$NR^{10}C(NR^{11})NR^6R^{6a}$, —$NR^{10}SO_2NR^6R^{6a}$, —$NR^{10}SO_2R^5$, —$SR^5$, —$S(O)R^5$, —$SO_2R^5$, —$SO_3R^5$, —$SO_2NR^6R^{6a}$, —$NHOR^5$, —$NR^{10}NR^6R^{6a}$, —$N[C(=O)R^5][OR^{10}]$, —$N(CO_2R^5)OR^{10}$, —$C(=O)NR^{10}(CR^{12}R^{13})_rR^5$, —$C(=O)(CR^{12}R^{13})_pO(CR^{14}R^{15})_qCO_2R^5$, —$C(=O)(CR^{12}R^{13})_rOR^5$, —$C(=O)(CR^{12}R^{13})_pO(CR^{14}R^{15})_qR^5$, —$C(=O)(CR^{12}R^{13})_rNR^6R^{6a}$, —$OC(=O)O(CR^{12}R^{13})_mNR^6R^{6a}$, —$OC(=O)N(CR^{12}R^{13})_rR^5$, —$O(CR^{12}R^{13})_mNR^6R^{6a}$, —$NR^{10}C(=O)(CR^{12}R^{13})_rR^5$, —$NR^{10}C(=O)(CR^{12}R^{13})_rOR^5$, —$NR^{10}C(=NC)(CR^{12}R^{13})_rR^5$, —$NR^{10}C(=O)(CR^{12}R^{13})_rNR^6R^{6a}$, —$NR^{10}(CR^{12}R^{13})_mOR^5$, —$NR^{10}(CR^{12}R^{13})_rCO_2R^5$, —$NR^{10}(CR^{12}R^{13})_mNR^6R^{6a}$, —$NR^{10}(CR^{12}R^{13})_pSO_2(CR^{14}R^{15})_qR^5$, —$C(=O)NR^{10}(CR^{12}R^{13})_nSO_2(CR^{14}R^{15})_qR^5$, —$SO_2NR^{10}(CR^{12}R^{13})_nCO(CR^{14}R^{15})_qR^5$, —$SO_2NR^{10}(CR^{12}R^{13})_mOR^5$, and —$SO_2NR^{10}(CR^{12}R^{13})_nSi(alkyl)_3$.

When a substituted cycloalkyl is substituted with a second ring, including an aryl, heterocyclo, or heteroaryl ring, or a second cycloalkyl ring, said second ring in turn is optionally substituted with one to three $R^{17}$ groups as defined below.

It should be understood that a "substituted cycloalkyl" may have a substituent attached to any atom of the cycloalkyl ring, including its point of attachment to another group. Thus, for example, a cycloalkyl group substituted with a group "R" may comprise,

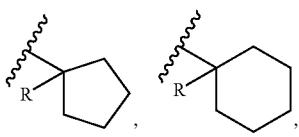

and so forth, where R is a substituent on a cycloalkyl group as defined above.

The term "aryl" refers to the phenyl, 1-naphthyl, and 2-naphthyl, preferably phenyl, as well as an aryl ring having a fused cycloalkyl, substituted cycloalkyl, heterocyclo, substituted heterocyclo, heteroaryl, or substituted heteroaryl ring, provided that the point of attachment is in the aryl ring. Thus, examples of aryl groups include Thus, examples of aryl groups include:

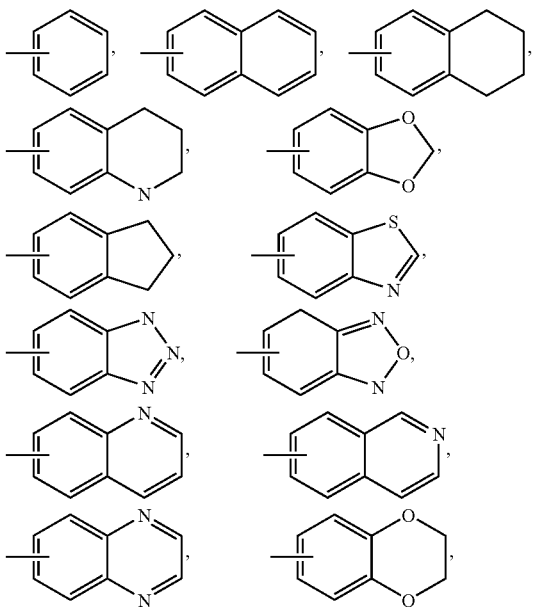

and so forth.

The term "substituted aryl" refers to such aryl groups as defined above having one, two, or three substituents selected from the group consisting of halogen, nitro, alkyl, substituted alkyl, alkenyl, cyano, cycloalkyl, aryl, heterocyclo, heteroaryl, —OR$^5$, —CO$_2$R$^5$, —C(=O)NR$^6$R$^{6a}$, —OC(=O)R$^5$, —OC(=O)OR$^5$, —OC(=O)NR$^6$R$^{6a}$, —OCH$_2$CO$_2$R$^5$, —C(=O)R$^5$, NR$^6$R$^{6a}$, —NR$^{10}$C(=O)R$^5$, —NR$^{10}$C(=O)OR$^5$, —NR$^{10}$C(=O)C(=O)OR$^5$, —NR$^{10}$C(=O)C(=O)NR$^6$R$^{6a}$, —NR$^{10}$C(=O)C(=O)alkyl, —NR$^{10}$C(NCN)OR$^5$, NR$^{10}$C(=O)NR$^6$R$^{6a}$, —NR$^{10}$C(NCN)NR$^6$R$^{6a}$, —NR$^{10}$C(NR$^{11}$)NR$^6$R$^{6a}$, —NR$^{10}$SO$_2$NR$^6$R$^{6a}$, —NR$^{10}$SO$_2$R$^5$, —SR$^5$, —S(O)R$^5$, —SO$_2$R$^5$, —SO$_3$R$^5$, —SO$_2$NR$^6$R$^{6a}$, —NHOR$^5$, —NR$^{10}$NR$^6$R$^{6a}$, —N[C(=O)R$^5$][OR$^{10}$], —N(CO$_2$R$^5$)OR$^{10}$, —C(=O)NR$^{10}$(CR$^{12}$R$^{13}$)$_r$R$^5$, —C(=O)(CR$^{12}$R$^{13}$)$_p$O(CR$^{14}$R$^{15}$)$_q$CO$_2$R$^5$, —C(=O)(CR$^{12}$R$^{13}$)$_r$OR$^5$, —C(=O)(CR$^{12}$R$^{13}$)$_p$O(CR$^{14}$R$^{15}$)$_q$R$^5$, —C(=O)(CR$^{12}$R$^{13}$)$_r$NR$^6$R$^{6a}$, —OC(=O)O(CR$^{12}$R$^{13}$)$_m$NR$^6$R$^{6a}$, —OC(=O)N(CR$^{12}$R$^{13}$)$_r$R$^5$, —O(CR$^{12}$R$^{13}$)$_m$NR$^6$R$^{6a}$, —NR$^{10}$C(=O)(CR$^{12}$R$^{13}$)$_r$R$^5$, —NR$^{10}$C(=O)(CR$^{12}$R$^{13}$)$_r$OR$^5$, —NR$^{10}$C(=NC)(CR$^{12}$R$^{13}$)$_r$R$^5$, —NR$^{10}$C(=O)(CR$^{12}$R$^{13}$)$_r$NR$^6$R$^{6a}$, —NR$^{10}$(CR$^{12}$R$^{13}$)$_m$OR$^5$, —NR$^{10}$(CR$^{12}$R$^{13}$)$_r$CO$_2$R$^5$, —NR$^{10}$(CR$^{12}$R$^{13}$)$_m$NR$^6$R$^{6a}$, —NR$^{10}$(CR$^{12}$R$^{13}$)$_n$SO$_2$(CR$^{14}$R$^{15}$)$_q$R$^5$, —C(=O)NR$^{10}$(CR$^{12}$R$^{13}$)$_n$SO$_2$(CR$^{14}$R$^{15}$)$_q$R$^5$, —SO$_2$NR$^{10}$(CR$^{12}$R$^{13}$)$_n$CO(CR$^{14}$R$^{15}$)$_q$R$^5$, —SO$_2$NR$^{10}$(CR$^{12}$R$^{13}$)$_m$OR$^5$, and —SO$_2$NR$^{10}$(CR$^{12}$R$^{13}$)$_n$Si(alkyl)$_3$, as well as pentafluorophenyl.

When a substituted aryl is substituted with a second ring, including a cycloalkyl, heterocyclo, or heteroaryl ring, or a second aryl ring, said second ring in turn is optionally substituted with one to three R$^{16}$ groups as defined below.

The term "heterocyclo" refers to saturated or partially saturated monocyclic rings of 3 to 7 members and bicyclic rings of 7 to 11 members having one or two O or S atoms and/or one to four N atoms, provided that the total number of heteroatoms is four or less and that the heterocyclo ring contains at least one carbon atom. The nitrogen and sulfur atoms may optionally be oxidized, and the nitrogen atoms may optionally be quaternized. The bicyclic heterocyclo ring may also contain a bridge of one, two or three carbon atoms between available carbon or nitrogen atoms. The bicyclic heterocyclo rings may also have a cycloalkyl, substituted cycloalkyl, aryl, substituted aryl, heterocyclo, substituted heterocyclo, heteroaryl, or substituted heteroaryl ring fused to the monocyclic ring provided that the point of attachment is through an available carbon or nitrogen atom of the heterocyclo ring. Also included are heterocyclo rings having a second ring attached thereto in a spiro fashion The term "substituted heterocyclo" refers to a heterocyclo ring or ring system as defined above having one, two or three substituents on available carbon or nitrogen atom(s) selected from the group consisting of halogen, nitro, alkyl, substituted alkyl, alkenyl, cyano, cycloalkyl, aryl, heterocyclo, heteroaryl, oxo (=O), —OR$^5$, —CO$_2$R$^5$, —C(=O)NR$^6$R$^{6a}$, —OC(=O)R$^5$, —OC(=O)OR$^5$, —OC(=O)NR$^6$R$^{6a}$, —OCH$_2$CO$_2$R$^5$, —C(=O)R$^5$, NR$^6$R$^{6a}$, —NR$^{10}$C(=O)R$^5$, —NR$^{10}$C(=O)OR$^5$, —NR$^{10}$C(=O)C(=O)OR$^5$, —NR$^{10}$C(=O)C(=O)NR$^6$R$^{6a}$, —NR$^{10}$C(=O)C(=O)alkyl, —NR$^{10}$C(NCN)OR$^5$, NR$^{10}$C(=O)NR$^6$R$^{6a}$, —NR$^{10}$C(NCN)NR$^6$R$^{6a}$, —NR$^{10}$C(NR$^{11}$)NR$^6$R$^{6a}$, —NR$^{10}$SO$_2$NR$^6$R$^{6a}$, —NR$^{10}$SO$_2$R$^5$, —SR$^5$, —S(O)R$^5$, —SO$_2$R$^5$, —SO$_3$R$^5$, —SO$_2$NR$^6$R$^{6a}$, —NHOR$^5$, —NR$^{10}$NR$^6$R$^{6a}$, —N[C(=O)R$^5$][OR$^{10}$], —N(CO$_2$R$^5$)OR$^{10}$, —C(=O)NR$^{10}$(CR$^{12}$R$^{13}$)$_r$R$^5$, —C(=O)(CR$^{12}$R$^{13}$)$_p$O(CR$^{14}$R$^{15}$)$_q$CO$_2$R$^5$, —C(=O)(CR$^{12}$R$^{13}$)$_r$OR$^5$, —C(=O)(CR$^{12}$R$^{13}$)$_p$O(CR$^{14}$R$^{15}$)$_q$R$^5$, —C(=O)(CR$^{12}$R$^{13}$)$_r$NR$^6$R$^{6a}$, —OC(=O)O(CR$^{12}$R$^{13}$)$_m$NR$^6$R$^{6a}$, —OC(=O)N(CR$^{12}$R$^{13}$)$_r$R$^5$, —O(CR$^{12}$R$^{13}$)$_m$NR$^6$R$^{6a}$, —NR$^{10}$C(=O)(CR$^{12}$R$^{13}$)$_r$R$^5$, —NR$^{10}$C(=O)(CR$^{12}$R$^{13}$)$_r$OR$^5$, —NR$^{10}$C(=NC)(CR$^{12}$R$^{13}$)$_r$R$^5$, —NR$^{10}$C(=O)(CR$^{12}$R$^{13}$)$_r$NR$^6$R$^{6a}$, —NR$^{10}$(CR$^{12}$R$^{13}$)$_m$OR$^5$, —NR$^{10}$(CR$^{12}$R$^{13}$)$_r$CO$_2$R$^5$, —NR$^{10}$(CR$^{12}$R$^{13}$)$_m$NR$^6$R$^{6a}$, —NR$^{10}$(CR$^{12}$R$^{13}$)$_n$SO$_2$(CR$^{14}$R$^{15}$)$_q$R$^5$, —C(=O)NR$^{10}$(CR$^{12}$R$^{13}$)$_n$SO$_2$(CR$^{14}$R$^{15}$)$_q$R$^5$, —SO$_2$NR$^{10}$(CR$^{12}$R$^{13}$)$_n$CO(CR$^{14}$R$^{15}$)$_q$R$^5$, —SO$_2$NR$^{10}$(CR$^{12}$R$^{13}$)$_m$OR$^5$, and —SO$_2$NR$^{10}$(CR$^{12}$R$^{13}$)$_n$Si(alkyl)$_3$.

When a substituted heterocyclo is substituted with a second ring, including an aryl, cycloalkyl, or heteroaryl ring, or a heterocyclo ring, said second ring in turn is optionally substituted with one to three R$^{17}$ groups as defined below.

Exemplary monocyclic heterocyclo groups include pyrrolidinyl, pyrrolinyl, pyrazolinyl, pyrazolidinyl, oxetanyl, imidazolinyl, imidazolidinyl, oxazolidinyl, isothiazolidinyl, isoxazolinyl, thiazolidinyl, tetrahydrofuryl, piperidinyl, piperazinyl, tetrahydrothiopyranyl, tetrahydropyranyl, morpholinyl, thiamorpholinyl, thiamorpholinyl sulfoxide, thiamorpholinyl sulfone, tetrahydrothiopyranylsulfone, 1,3-dioxolanyl, tetrahydro-1,1-dioxothienyl, dioxanyl, thietanyl, thiiranyl, triazolinyl, triazolidinyl, etc.

Exemplary bicyclic heterocyclo groups include indolinyl, quinuclidinyl, tetrahydroisoquinolinyl, benzimidazolinyl, chromanyl, dihydrobenzofuran, dihydrofuro[3,4-b]pyridinyl, dihydroisoindolyl, dihydroquinazolinyl (such as 3,4-dihydro-4-oxo-quinazolinyl), benzofurazanyl, benzotriazolinyl, dihydrobenzofuryl, dihydrobenzothienyl, dihydrobenzothiopyranyl, dihydrobenzothiopyranyl sulfone, dihydrobenzopyranyl, isoindolinyl, isochromanyl, benzodioxolyl, tetrahydroquinolinyl, etc.

Exemplary spirocyclic heterocyclo groups include 1-aza[4.5]spirodecane, 2-aza[4.5]spirodecane, 1-aza[5.5]spiroundecane, 2-aza[5.5]spiroundecane, 3-aza[5.5]spiroundecane, etc.

The term "heteroaryl" refers to aromatic 5 or 6 membered monocyclic groups and 9 or 10 membered bicyclic groups which have at least one heteroatom (O, S or N) in at least one of the rings. Each ring of the heteroaryl group containing a heteroatom can contain one or two O and S atoms and/or from one to four N atoms, provided that the total number of heteroatoms in each ring is four or less. The bicyclic heteroaryl rings are formed by fusing a cycloalkyl, substituted cycloalkyl, aryl, substituted aryl, heterocyclo, substituted heterocyclo, heteroaryl or substituted heteroaryl group to the monocyclic heteroaryl ring as defined above. The heteroaryl group is attached via an available carbon or nitrogen atom in the aromatic heteroaryl ring. The nitrogen and sulfur atoms may optionally be oxidized and the nitrogen atoms may optionally be quaternized.

The term "substituted heteroaryl" refers to a heteroaryl ring or ring system as defined above having one, two or three substituents on available carbon or nitrogen atom(s) selected from the group consisting of halogen, nitro, alkyl, substituted alkyl, alkenyl, cyano, cycloalkyl, aryl, heterocyclo, heteroaryl, —$OR^5$, —$CO_2R^5$, —C(=O)$NR^6R^{6a}$, —OC(=O)$R^5$, —OC(=O)$OR^5$, —OC(=O)$NR^6R^{6a}$, —$OCH_2CO_2R^5$, —C(=O)$R^5$, $NR^6R^{6a}$, —$NR^{10}$C(=O)$R^5$, —$NR^{10}$C(=O)$OR^5$, —$NR^{10}$C(=O)C(=O)$OR^5$, —$NR^{10}$C(=O)C(=O)$NR^6R^{6a}$, —$NR^{10}$C(=O)C(=O)alkyl, —$NR^{10}$C(NCN)$OR^5$, $NR^{10}$C(=O)$NR^6R^{6a}$, —$NR^{10}$C(NCN)$NR^6R^{6a}$, —$NR^{10}$C($NR^{11}$)$NR^6R^{6a}$, —$NR^{10}SO_2NR^6R^{6a}$, —$NR^{10}SO_2R^5$, —$SR^5$, —S(O)$R^5$, —$SO_2R^5$, —$SO_3R^5$, —$SO_2NR^6R^{6a}$, —$NHOR^5$, —$NR^{10}NR^6R^{6a}$, —N[C(=O)$R^5$][$OR^{10}$], —N($CO_2R^5$)$OR^{10}$, —C(=O)$NR^{10}(CR^{12}R^{13})_rR^5$, —C(=O)$(CR^{12}R^{13})_pO(CR^{14}R^{15})_qCO_2R^5$, —C(=O)$(CR^{12}R^{13})_rOR^5$, —C(=O)$(CR^{12}R^{13})_pO(CR^{14}R^{15})_qR^5$, —C(=O)$(CR^{12}R^{13})_rNR^6R^{6a}$, —OC(=O)O$(CR^{12}R^{13})_mNR^6R^{6a}$, —OC(=O)N$(CR^{12}R^{13})_rR^5$, —O$(CR^{12}R^{13})_mNR^6R^{6a}$, —$NR^{10}$C(=O)$(CR^{12}R^{13})_rR^5$, —$NR^{10}$C(=O)$(CR^{12}R^{13})_rOR^5$, —$NR^{10}$C(=NC)$(CR^{12}R^{13})_rR^5$, —$NR^{10}$C(=O)$(CR^{12}R^{13})_rNR^6R^{6a}$, —$NR^{10}(CR^{12}R^{13})_mOR^5$, —$NR^{10}(CR^{12}R^{13})_rCO_2R^5$, —$NR^{10}(CR^{12}R^{13})_mNR^6R^{6a}$, —$NR^{10}(CR^{12}R^{13})_nSO_2(CR^{14}R^{15})_rR^5$, —C(=O)$NR^{10}(CR^{12}R^{13})_nSO_2(CR^{14}R^{15})_rR^5$, —$SO_2NR^{10}(CR^{12}R^{13})_nCO(CR^{14}R^{15})_rR^5$, —$SO_2NR^{10}(CR^{12}R^{13})_mOR^5$, and —$SO_2NR^{10}(CR^{12}R^{13})_nSi(alkyl)_3$.

When a substituted heteroaryl is substituted with a second ring, including an aryl, cycloalkyl, or heterocyclo ring, or a second heteroaryl ring, said second ring in turn is optionally substituted with one to three $R^{16}$ groups as defined below.

Exemplary monocyclic heteroaryl groups include pyrrolyl, pyrazolyl, imidazolyl, oxazolyl, isoxazolyl, thiazolyl, thiadiazolyl, isothiazolyl, pyridinyl, furyl, thienyl, oxadiazolyl, 2-oxazepinyl, azepinyl, pyrazinyl, pyrimidinyl, pyridazinyl, triazinyl, triazolyl, etc.

Exemplary bicyclic heteroaryl groups include benzothiazolyl, benzoxazolyl, benzothienyl, benzofuryl, quinolinyl, quinolinyl-N-oxide, isoquinolinyl, benzimidazolyl, benzopyranyl, indolizinyl, cinnolinyl, quinoxalinyl, indazolyl, pyrrolopyridyl, furopyridinyl (such as furo[2,3-c]pyridinyl, furo[3,1-b]pyridinyl or furo[2,3-b]pyridinyl), benzisothiazolyl, benzisoxazolyl, benzodiazinyl, benzothiopyranyl, benzotriazolyl, benzpyrazolyl, naphthyridinyl, phthalazinyl, purinyl, pyridopyridyl, quinazolinyl, thienofuryl, thienopyridyl, thienothienyl, etc.

In the above definitions for substituted alkyl, substituted alkenyl, substituted cycloalkyl, substituted aryl, substituted heterocyclo, and substituted heteroaryl, the groups $R^5$, $R^6$, $R^{6a}$, $R^{10}$, $R^{11}$, $R^{12}$, $R^{13}$, $R^{14}$, $R^{15}$, $R^{16}$, and $R^{17}$, have the definitions set forth below:

$R^5$, $R^{10}$, and $R^{11}$ are independently selected from hydrogen, alkyl, alkenyl, alkynyl, —C(=O)alkyl, —C(=O)cycloalkyl, —C(=O)aryl, —C(=O)heterocyclo, C(=O)heteroaryl, —$CO_2$alkyl, cycloalkyl, aryl, heterocyclo and heteroaryl, wherein each alkyl, cycloalkyl, aryl, heterocyclo, and/or heteroaryl group of each $R^5$, $R^{10}$, and $R^{11}$ in turn is optionally substituted, where valence allows, with one, two or three groups selected from the group $R^{18}$ as defined below;

$R^6$ and $R^{6a}$ are independently selected from hydrogen, alkyl, —C(=O)alkyl, —C(=O)cycloalkyl, —C(=O)aryl, —C(=O)heterocyclo, C(=O)heteroaryl, —$CO_2$alkyl, cycloalkyl, aryl, heterocyclo and heteroaryl, or $R^6$ and $R^{6a}$ taken together with the nitrogen atom to which they are attached complete a heterocyclo or heteroaryl ring, wherein each alkyl, cycloalkyl, aryl, heterocyclo, and/or heteroaryl group of each $R^6$ and $R^{6a}$ (taken alone or together) in turn is optionally substituted, where valence allows, with one, two or three groups selected from the group $R^{16}$ as defined below;

$R^{12}$ and $R^{14}$ are independently selected from hydrogen and alkyl of 1 to 4 carbons;

$R^{13}$ and $R^{15}$ are independently selected from hydrogen, alkyl of 1 to 4 carbons, and alkyl of 1 to 4 carbons substituted with one, two or three $R^{18}$ groups;

$R^{16}$ at each occurrence is independently selected from the group consisting of —$(CH_2)_q$-halo, —$(CH_2)_q$-cyano, —$(CH_2)_q$—$CF_3$, —$(CH_2)_q$—$OR^{19}$, —$(CH_2)_q$—$OCF_3$, —$(CH_2)_q$—$SR^{19}$, —$(CH_2)_q$-nitro, —$(CH_2)_q$—$NR^{19a}R^{19b}$, —$(CH_2)_q$—$NR^{19}$—$(CH_2)_n NR^{19a}R^{19b}$, —$(CH_2)_q$—$NR^{19}$(cycloalkyl), —$(CH_2)_q$—NHC(=O)alkyl, —$(CH_2)_q$—$NHCO_2$(alkyl), —$(CH_2)_q$-cycloalkyl, —$(CH_2)_q$-aryl, —$(CH_2)_q$-heterocyclo, —$(CH_2)_q$-heteroaryl, —$(CH_2)_q$—$CO_2R^{19b}$, —$(CH_2)_q$—S(O)(alkyl), —$(CH_2)_q$—$SO_2$(alkyl), —$(CH_2)_q$—$SO_3$(alkyl), —$(CH_2)_q$—$SO_2NR^{19a}R^{19b}$, —$(CH_2)_q$—C(=O)$NR^{19a}R^{19b}$, and/or —$(CH_2)_q$—C(=O)$R^{19}$;

$R^{17}$ at each occurrence is independently selected from the group consisting of —$(CH_2)_q$-halo, —$(CH_2)_q$-cyano, —$(CH_2)_q$—$CF_3$, —$(CH_2)_q$—$OR^{19}$, —$(CH_2)_q$—$OCF_3$, —$(CH_2)_q$—$SR^{19}$, —$(CH_2)_q$-nitro, oxo, (=O), —$(CH_2)_q$—$NR^{19a}R^{19b}$, —$(CH_2)_q$—$NR^{19}$—$(CH_2)_n NR^{19a}R^{19b}$, —$(CH_2)_q$—$NR^{19}$(cycloalkyl), —$(CH_2)_q$—NHC(=O)alkyl, —$(CH_2)_q$—$NHCO_2$(alkyl), —$(CH_2)_q$-cycloalkyl, —$(CH_2)_q$-aryl, —$(CH_2)_q$-heterocyclo, —$(CH_2)_q$-heteroaryl, —$(CH_2)_q$—$CO_2R^{19b}$, —$(CH_2)_q$—S(O)(alkyl), —$(CH_2)_q$—$SO_2$(alkyl), —$(CH_2)_q$—$SO_3$(alkyl), —$(CH_2)_q$—$SO_2NR^{19a}R^{19b}$, —$(CH_2)_q$—C(=O)$NR^{19a}R^{19b}$, and/or —$(CH_2)_q$—C(=O)$R^{19}$;

$R^{18}$ at each occurrence is independently selected from the group consisting of halo, cyano, $CF_3$, OH, O(alkyl), $OCF_3$, SH, S(alkyl), nitro, $NH_2$, NH(alkyl), N(alkyl)$_2$, NH(cycloalkyl), NHC(=O)alkyl, $NHCO_2$(alkyl), cycloalkyl, aryl, heterocyclo, heteroaryl, $CO_2H$, $CO_2$(alkyl), S(O)(alkyl), $SO_2$(alkyl), $SO_3$(alkyl), $SO_2NH_2$, $SO_2NH$(alkyl), $SO_2N$ (alkyl)$_2$, C(=O)NH$_2$, C(=O)NH(alkyl), C(=O)N(alkyl)$_2$, C(=O)H, and/or C(=O)($_6$alkyl);

$R^{19}$, $R^{19a}$ and $R^{19b}$ are at each occurrence independently selected from hydrogen and alkyl;

m is an integer from 2 to 6;
n is zero or an integer from 1 to 4;
p is an integer from 1 to 3;
q is zero or an integer from 1 to 3; and
r is zero or an integer from 1 to 6.

Preferred Compounds

Preferred compounds are those having the formula (Ib),

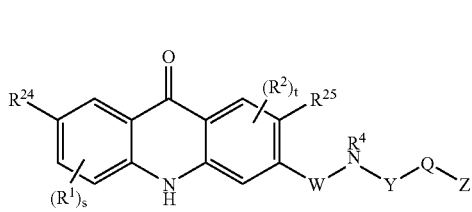

(Ib)

their enantiomers, diastereomers, tautomers, or pharmaceutically-acceptable salts, solvates, or prodrugs thereof, wherein:

W is —C(=O)—, —S(=O)—, or —S(O)$_2$—;

$R^1$ and $R^2$ are the same or different and at each occurrence are independently selected from halogen, cyano, C$_{1-4}$alkyl, C$_{2-4}$alkenyl, hydroxy, —O—C$_{1-4}$alkyl, CF$_3$, —O—CF$_3$, C(=O)H, C(=O)C$_{1-4}$alkyl, —(C=O)—OH, —C(=O)O—C$_{1-4}$alkyl, —NH$_2$, —NHC$_{1-4}$alkyl, N(C$_{1-4}$alkyl)$_2$, —SH, —S(C$_{1-4}$alkyl), —S(=O)(C$_{1-4}$alkyl), —SO$_2$NH$_2$, —SO$_2$NHC$_{1-4}$alkyl, —SO$_2$N(C$_{1-4}$alkyl)$_2$, and —SO$_2$(C$_{1-4}$alkyl);

$R^4$ is H or C$_{1-4}$alkyl;

$R^{24}$ is hydrogen, halogen, cyano, —C$_{1-4}$alkyl, —O—C$_{1-4}$alkyl, CF$_3$, —O—CF$_3$, NHC$_{1-4}$alkyl, N(C$_{1-4}$alkyl)$_2$, —S(C$_{1-4}$alkyl), —S(=O)(C$_{1-4}$alkyl), and —SO$_2$CH$_3$;

$R^{25}$ is selected from hydrogen, halogen, cyano, C$_{1-4}$alkyl, C$_{2-4}$alkenyl, hydroxy, —O—C$_{1-4}$alkyl, CF$_3$, —O—CF$_3$, NHC$_{1-4}$alkyl, N(C$_{1-4}$alkyl)$_2$, —S(C$_{1-4}$alkyl), —S(=O)(C$_{1-4}$alkyl), and —SO$_2$CH$_3$;

Y is a bond or —C(R$^{40}$)(R$^{45}$)—;

Q is selected from a bond, —C(R$^{26}$)(R$^{46}$)—, —C(=O)—, —CH$_2$—O—, —CH$_2$—O—CH$_2$—, —CH$_2$—CO$_2$—NR$^4$—, —CH$_2$—CO$_2$—, —C(=O)NR$^4$—, and —CH=C(R$^{26}$)—;

Z is selected from alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclyl and substituted heterocyclyl, and when Y is —C(R$^{40}$)(R$^{45}$)— and Q is a bond, Z may be CO$_2$H or CO$_2$alkyl;

$R^{26}$ and $R^{46}$ are independently selected from hydrogen, C$_{1-4}$alkyl, hydroxy, halogen, hydroxyC$_{1-4}$alkyl, haloC$_{1-4}$alkyl, and heterocycloC$_{1-4}$alkyl, or taken together form a C$_{3-7}$ cycloalkyl ring;

$R^{40}$ and $R^{45}$ are independently selected from hydrogen, cyano, alkyl, substituted alkyl, alkenyl, substituted alkenyl, alkynyl, substituted alkynyl, cycloalkyl, substituted cycloalkyl, aryl, substituted aryl, heterocyclo, substituted heterocyclo, heteroaryl, substituted heteroaryl, or R$^{40}$ and R$^{45}$ are taken together to form a substituted or unsubstituted cycloalkyl ring of 3 to 8 atoms or a substituted or unsubstituted heterocyclo ring of 3 to 8 atoms; and s and t are independently 0 or 1.

Preferred compounds are those wherein, when $R^{25}$ is hydrogen, X—Y-Q-Z taken together are not —CO$_2$H, —CO$_2$(alkyl), —CO$_2$(substituted alkyl), —CO$_2$(alkenyl), —CO$_2$(substituted alkenyl), —CO$_2$(alkynyl), or —CO$_2$(substituted alkynyl).

More preferred are compounds as immediately defined above, wherein:

Q-Z taken together comprise a group selected from:
C$_{1-4}$alkyl optionally substituted with up to two R$^{31}$;

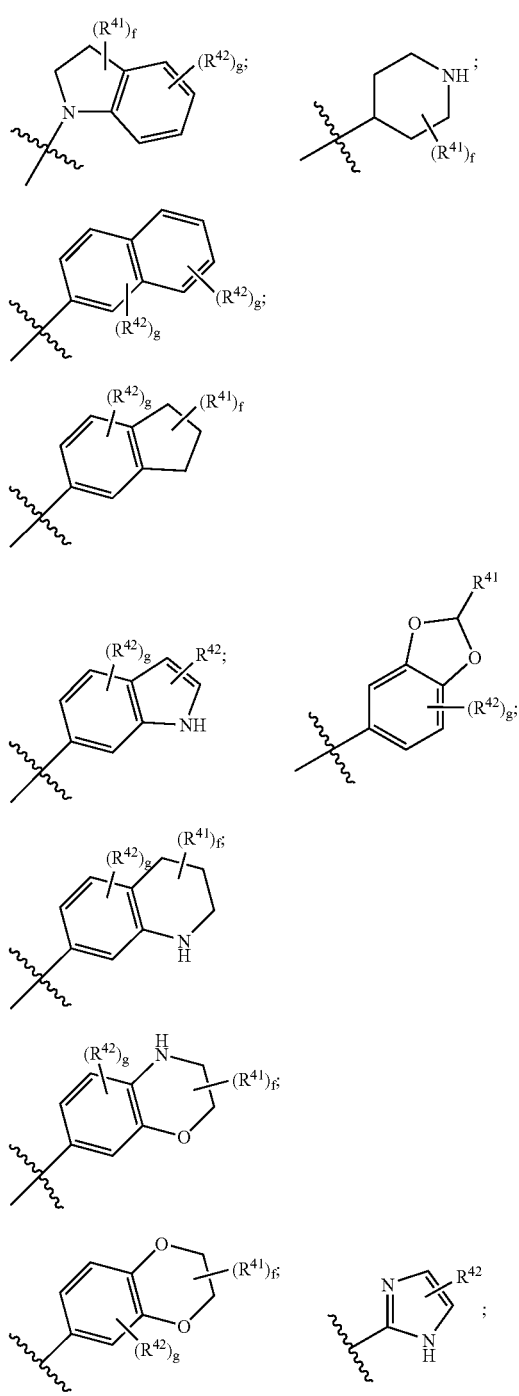

-continued

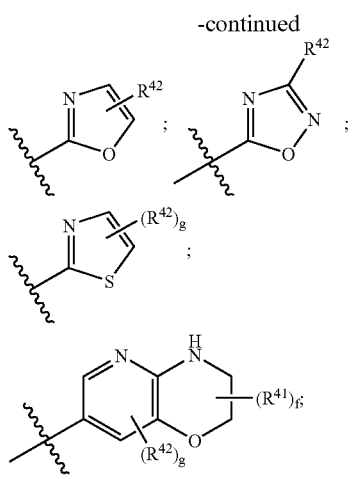

or, Q is selected from a bond, —CH(R$^{26}$)—, —CH$_2$—O—, —CH$_2$—O—CH$_2$—, and —CH$_2$—CO$_2$—NH—, and Z is selected from

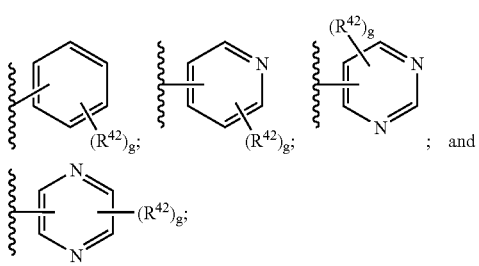

R$^{26}$ is selected from hydrogen, hydroxy, halogen, hydroxyC$_{1-4}$alkyl, and haloC$_{1-4}$alkyl;

R$^{31}$ and R$^{41}$ are at each occurrence independently selected from =O, =CH$_2$, halogen, trifluoromethyl, C$_{2-4}$alkenyl, C$_{2-4}$alkynyl, S(alkyl), cyano, S(=O)alkyl, SO$_2$(alkyl), CO$_2$(alkyl), SO$_2$NR$^{50}$R$^{51}$, NR$^{50}$R$^{51}$, OR$^{60}$; or a group R$^{62}$; or a C$_{1-6}$alkyl optionally substituted with up to two groups selected from R$^{62}$, NH$_2$, NH(C$_{1-4}$alkyl), N(C$_{1-4}$alkyl)$_2$, OR$^{60}$, and SO$_2$(alkyl);

R$^{42}$ is at each occurrence independently selected from halogen, trifluoromethyl, C$_{2-4}$alkenyl, C$_{2-4}$alkynyl, S(alkyl), cyano, S(=O)alkyl, SO$_2$(alkyl), CO$_2$(alkyl), SO$_2$NR$^{50}$R$^{51}$, NR$^{50}$R$^{51}$, OR$^{60}$ or a group R$^{62}$; or a C$_{1-6}$alkyl optionally substituted with up to two groups selected from R$^{62}$, NH$_2$, NH(C$_{1-4}$alkyl), N(C$_{1-4}$alkyl)$_2$, OR$^{60}$, and SO$_2$(alkyl);

R$^{50}$ and R$^{51}$ are independently selected from hydrogen, hydroxy, alkyl, —(CH$_2$)$_d$-cycloalkyl, —(CH$_2$)$_d$-heterocyclo, O(alkyl), O(Si)(C$_{1-4}$alkyl)$_3$, or C$_{1-6}$alkyl substituted with O(alkyl), NH$_2$, NH(C$_{1-4}$alkyl), or N(C$_{1-4}$alkyl)$_2$, or R$^{50}$ and R$^{51}$ together form a four to six membered heterocyclo ring, wherein when R$^{50}$ or R$^{51}$ is a heterocyclo, said heterocyclo in turn is optionally substituted with lower alkyl, NH$_2$, NH(C$_{1-4}$alkyl), or N(C$_{1-4}$alkyl)$_2$;

R$^{60}$ is hydrogen, alkyl, pyridyl or pyrimidinyl in turn optionally substituted with C$_{1-4}$alkyl, S(alkyl), NH$_2$, NH(C$_{1-4}$ alkyl), N(C$_{1-4}$alkyl)$_2$, or C$_{1-6}$alkyl substituted with O(alkyl), NH$_2$, NH(C$_{1-4}$alkyl), N(C$_{1-4}$alkyl)$_2$, or five or six membered heterocyclo;

R$^{62}$ is selected from phenyl, tetrahydrofuryl, azetidinyl, morpholinyl, thiamorpholinyl, piperazinyl, pyrrolidinyl, diazapinyl, seven membered bicyclic heterocyclo having at least one nitrogen atom and zero or one oxygen atom, wherein each R$^{62}$ in turn is optionally substituted with one to two of OH, SO$_2$(alkyl), CH$_2$—OH, CH$_2$—OCH$_3$, NHC(=O)CH$_3$, NH$_2$, NH(C$_{1-4}$alkyl), and/or N(C$_{1-4}$alkyl)$_2$;

d is 0, 1, or 2;

f is 0, 1, 2 or 3; and g is 0, 1 or 2.

In compounds of formula (I) and (Ib), recited above, preferably W is C(=O) and

Z is selected from: methyl, ethyl,

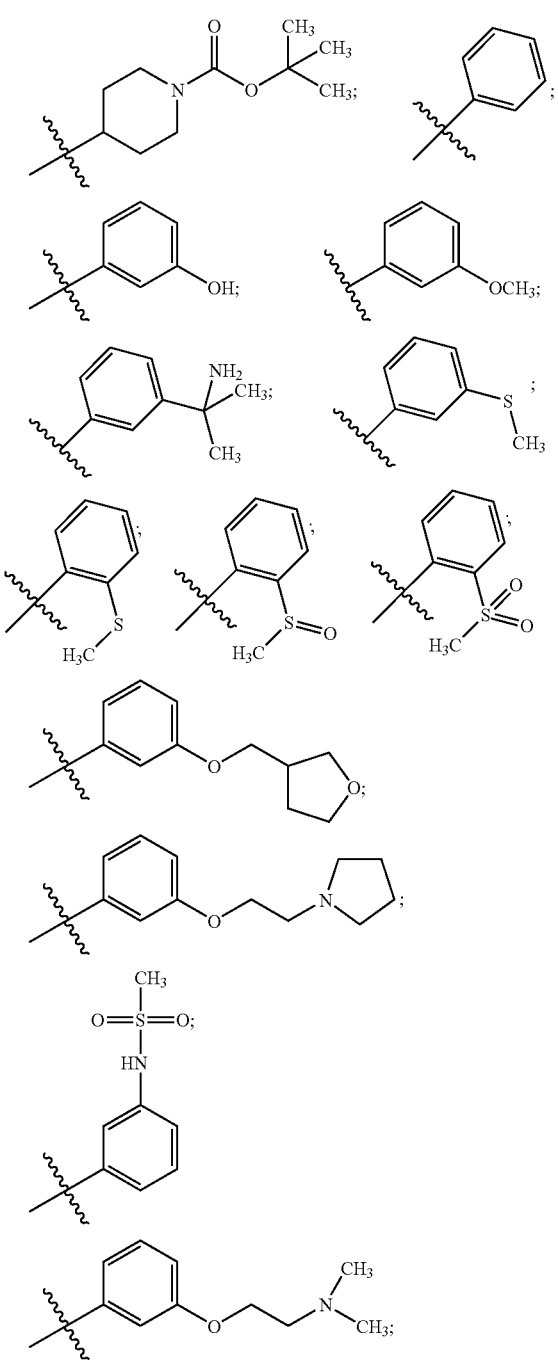

-continued
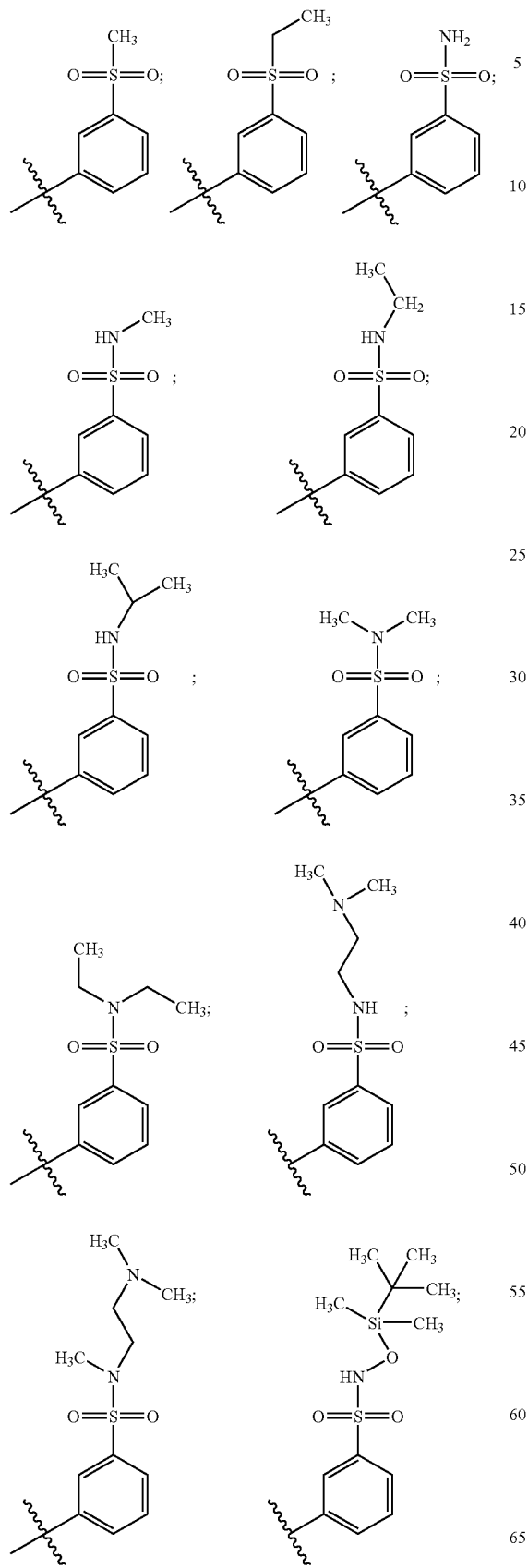
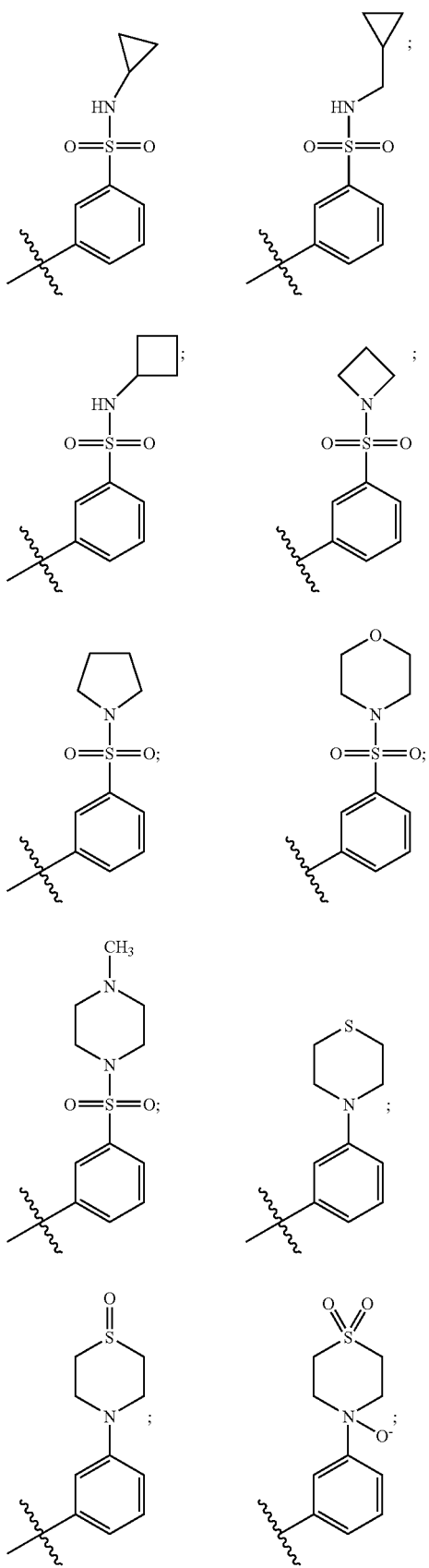

-continued
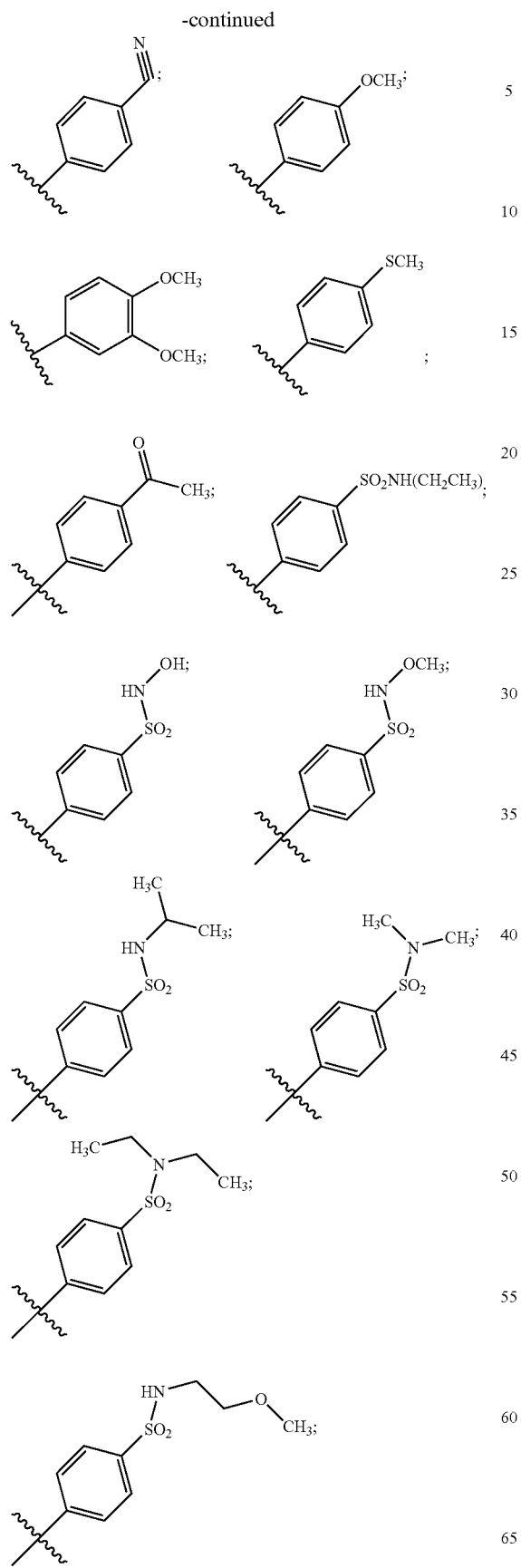
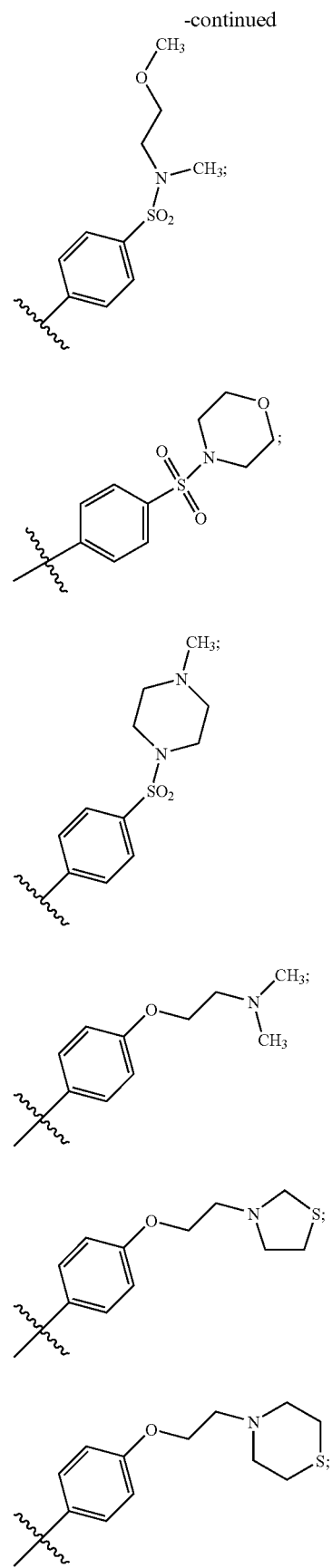

-continued
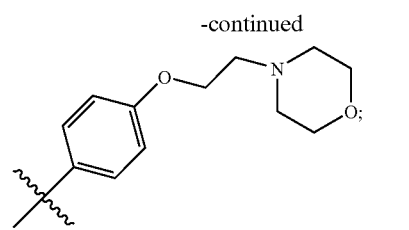
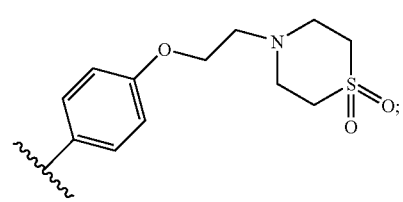
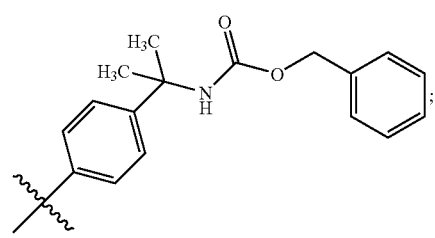
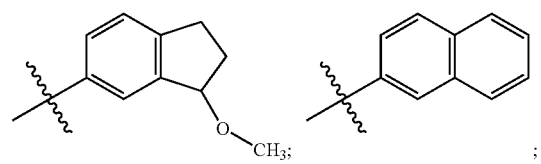
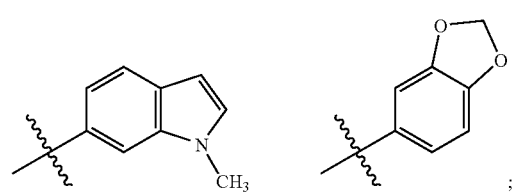
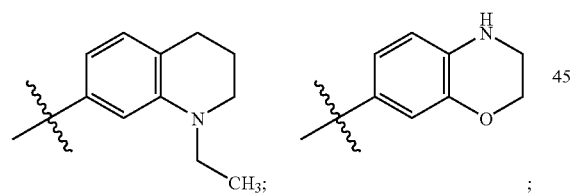
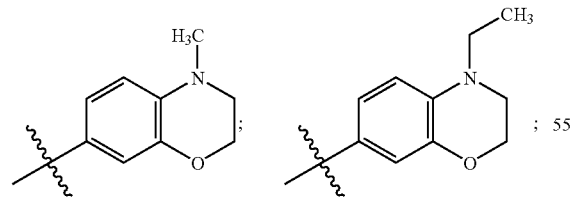
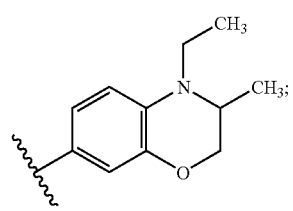
-continued
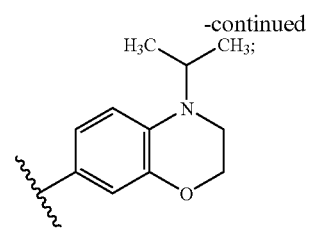
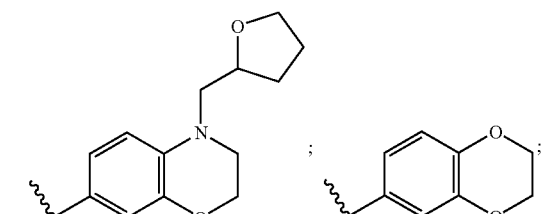
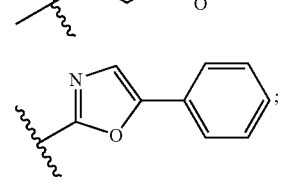
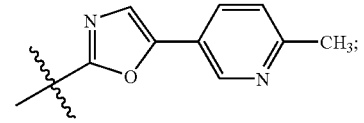
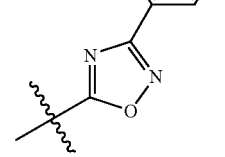
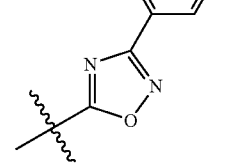
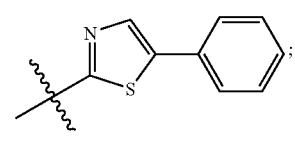
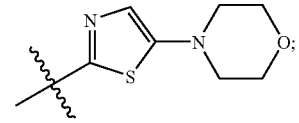
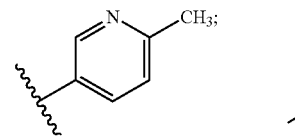

-continued

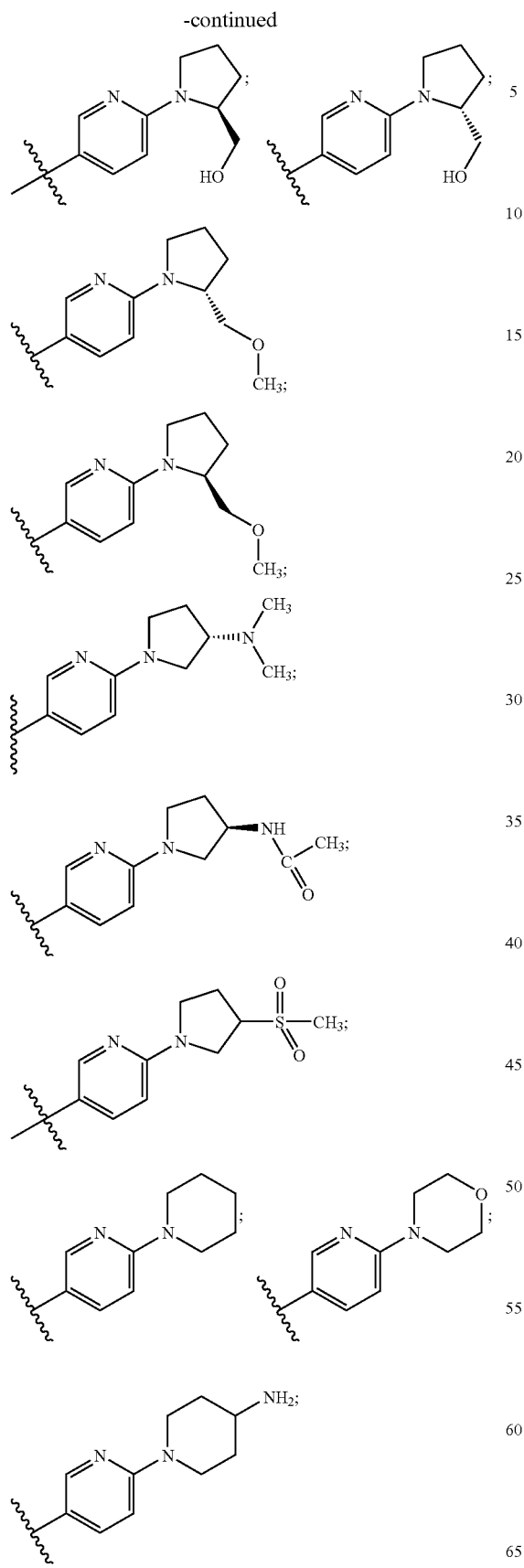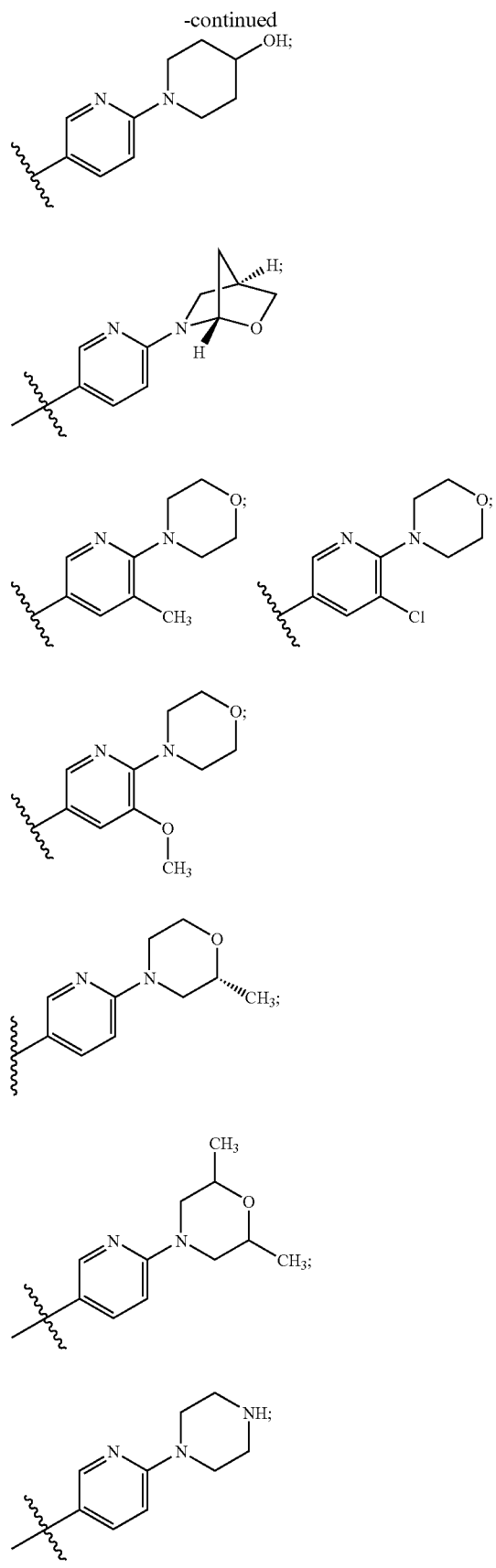

-continued
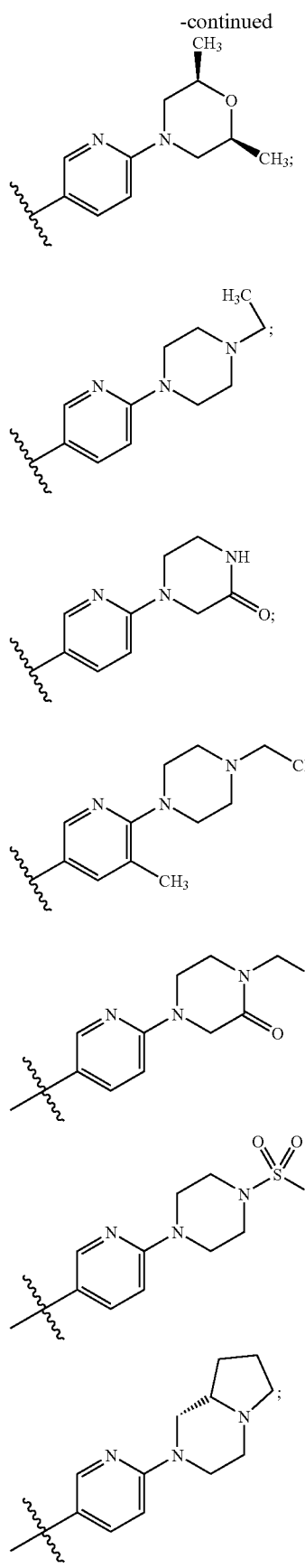
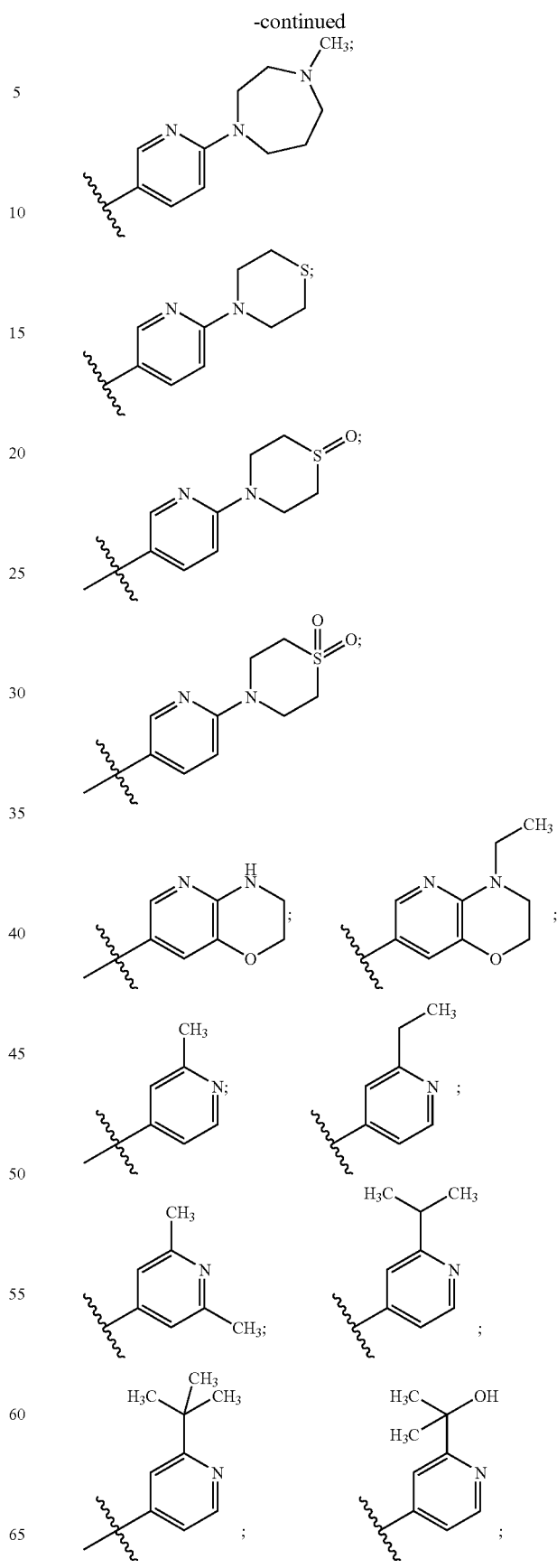

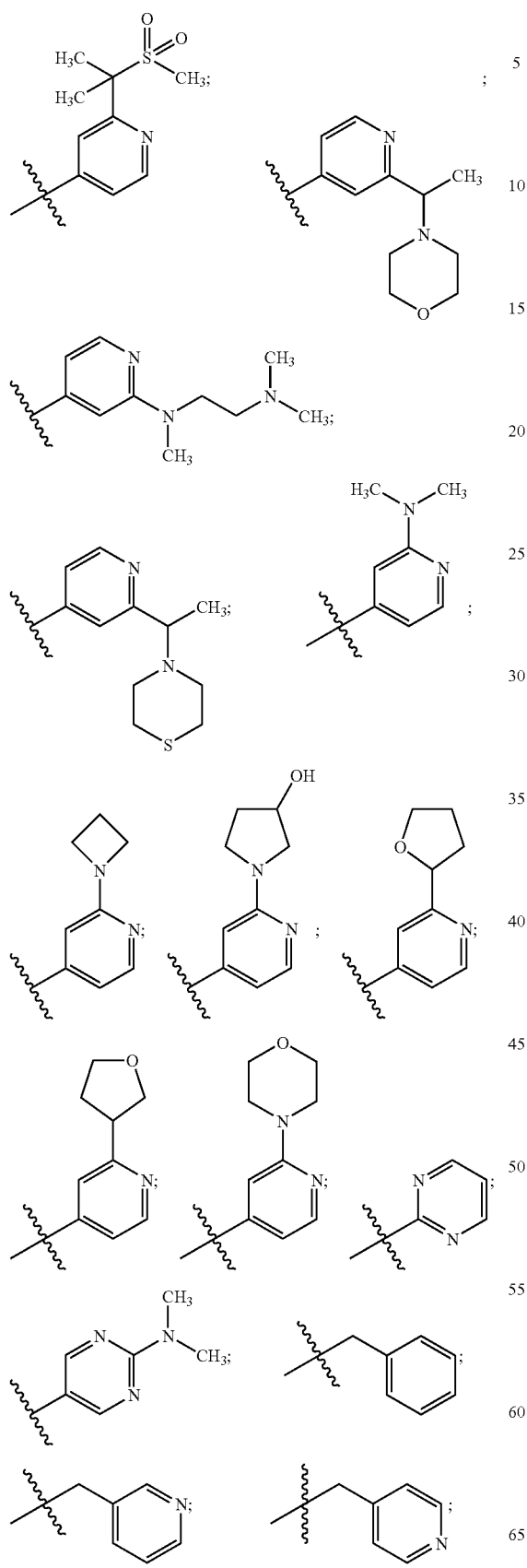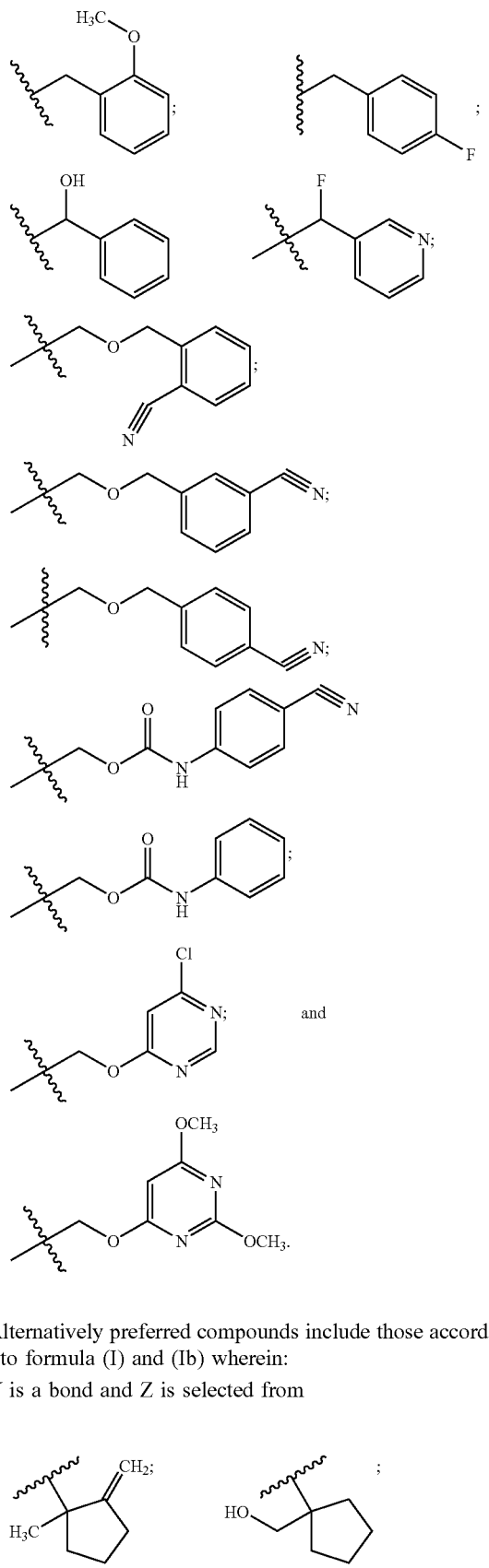
Alternatively preferred compounds include those according to formula (I) and (Ib) wherein:
Y is a bond and Z is selected from
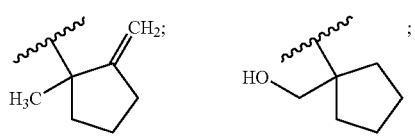

-continued
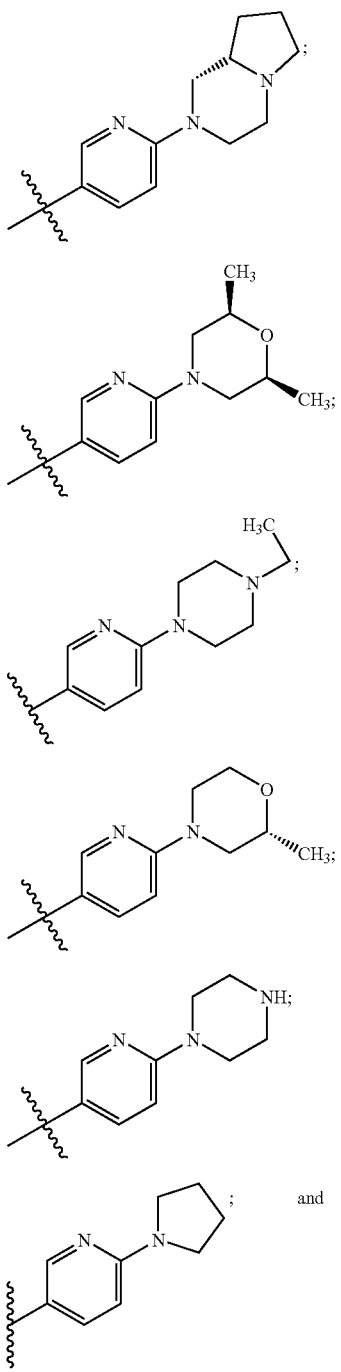
Most preferred are compounds having the formula:
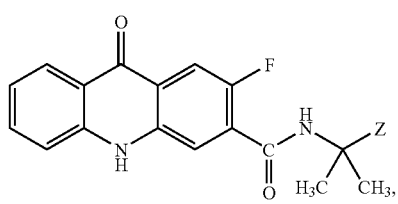
or enantiomers, diastereomers, tautomers, or pharmaceutically-acceptable salts, solvates, or prodrug thereof, wherein Z is slected from one of:
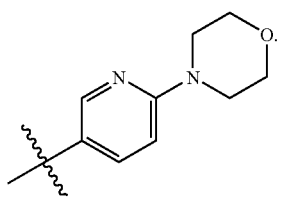

Utility

The compounds of the present invention inhibit IMPDH enzyme and are thus useful in the treatment of disorders which are affected by cells that are sensitive to IMPDH inhibition. The present invention thus provides methods for the treatment of IMPDH-associated disorders, comprising administering to a subject in need thereof at least one compound of Formula (I) in an amount effective therefor. As used herein, the term "treating" includes both prophylactic and therapeutic (responsive) uses and thus includes the alleviation of symptoms of an IMPDH-associated condition in a patient, the improvement of an ascertainable measurement associated with such a condition, or the prevention of such a condition or its symptoms. The term "patient" refers to a mammal, preferably a human.

In view of the inventive compounds' activity in inhibiting the IMPDH enzyme, the compounds may be used to treat hyperproliferative diseases and conditions. Below are non-limiting examples of particular diseases and conditions the inventive compounds may be used to treat.

The compounds of the present invention may be used to treat transplant rejection, such as, for example, kidney, liver, heart, lung, pancreas (e.g., islet cells), skin allografts, skin homografts (such as employed in burn treatment), bone marrow, small bowel and/or cells derived from any of these organs. The inventive compounds also may be used to treat conditions associated with and/or developed as a consequence of transplant rejections, such as, for example, serum sickness, graft vs. host disease, and ischemic or reperfusion injury.

The compounds of the present invention may be used to treat inflammatory and/or autoimmune diseases and conditions, such as rheumatoid arthritis, psoriatic arthritis, multiple sclerosis, diabetes (type 1) inflammatory bowel disease, (such as Crohn's disease and ulcerative colitus), pyoderma gangrenosum, lupus (systemic lupus erythematosis), myasthenia gravis, uveitis, Behcet's or Sjogren's syndrome (dry eyes/mouth), pernicious or immunohemolytic anemia, glomerulonephritis, Guillain-Barre syndrome, osteoarthritis, acute pancreatitis, chronic pancreatitis, and vascular diseases which have an inflammatory and/or a proliferative component such as restenosis, stenosis and atherosclerosis.

The inventive compounds may be used to treat autoimmune endocrine disorders, such as, for example, autoimmune thyroiditis, Grave's disease, Hashimoto's thyroiditis, autoimmune polyglandular syndrome (e.g., Addison's disease), hypoparathyroidism, autoimmune testicular failure, autoimmune ovarian failure, and autoimmune hypopituitarism.

The inventive compounds may be used to treat inflammatory conditions of the skin having internal or external etiology, such as, for example, psoriasis, dermatomyositis, Sezary's syndrome, and mycosis fungiodes; eczema, atopic dermatitis, contact dermatitis, urticaria, seborrhea, scleroderma, morphea, lichen planus, vitiligo (depigmentation of the skin), alopecia areata, autoimmune alopecia, and T-cell mediated hypersensitivity diseases, including contact hypersensitivity, delayed-type hypersensitivity, uticaria, and contact dermatitis (including that due to poison ivy).

The compounds also may be used to treat respiratory allergies and conditions, such as, for example, asthma, pulmonary fibrosis, alveolitis, allergic rhinitis, hayfever, oxygen toxicity, emphysema, chronic bronchitis, gluten-sensitive enteropathy (Celiac disease), acute respiratory distress syndrome (ARDs), and any chronic obstructive pulmonary disease (COPD).

Additionally, the inventive compounds may be used to treat infectious diseases, including viral, bacterial, and fungal infections. For example, the inventive compounds may be used in the treatment of DNA or RNA viral replication diseases, such herpes simplex type 1 (HSV-1), herpes simplex type 2 (HSV-2), hepatitis (including hepatitis B and hepatitis C), cytomegalovirus, Epstein-Barr, and human immunodeficiency virus (HIV).

The inventive compounds may be used in the treatment of cancer and tumor disorders, such as solid tumors, lymphomas and leukemia; the compounds of the present invention are useful in treating tumor growth, as an adjunct to chemotherapy, and for treating cancer, more particularly cancer of the lung, prostate, colon, breast, ovaries, and bone.

The term "pharmaceutically acceptable carrier, adjuvant or vehicle" refers to a carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β- and γ-cyclodextrin, or chemically modified derivatives such as hydroxyalkylcyclodextrins, including 2- and 3-hydroxypropyl-β-cyclodextrins, or other solubilized derivatives may also be used to enhance delivery of the compounds of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the Formula I may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to IMPDH-associated disorders.

The present invention also provides pharmaceutical compositions comprising at least one of the compounds of Formula I, or a pharmaceutically-acceptable salt thereof, capable of treating an IMPDH-associated disorder in an amount effective therefor, alone or in combination with at least one additional therapeutic agent, and a pharmaceutically acceptable carrier, adjuvant or vehicle. "Additional therapeutic agent" encompasses, but is not limited to, an agent selected from the group consisting of an immunosuppressant, an anti-cancer agent, an anti-viral agent, an anti-inflammatory agent, an anti-fungal agent, an antibiotic, or an anti-vascular hyperproliferative compound. These other therapeutic agent(s) may be administered prior to, simultaneously with, or following the administration of the compound(s) of the present invention.

Examples of suitable other anti-inflammatory agents with which the inventive compounds may be used include aspirin, cromolyn, nedocromil, theophylline, zileuton, zafirlukast, monteleukast, pranleukast, indomethacin, and lipoxygenase inhibitors; non-steroidal antiinflammatory drugs (NSAIDs) (such as ibuprofen, celecoxib, rofecoxib, and naproxin); TNF-α inhibitors (such as tenidap and rapamycin or derivatives thereof), or TNF-α antagonists (e.g., infliximab, Enbrel®, D2E7, OR1384), cytokine modulators (e.g. TNF-alpha converting enzyme [TACE] inhibitors, Interleukin-1 converting enzyme (ICE) inhibitors, Interleukin-1 receptor antagonists), prednisone, dexamethasone, cyclooxygenase inhibitors (i.e., COX-1 and/or COX-2 inhibitors such as Naproxen®, Celebrex®, or Vioxx®), CTLA4 and/or B7 agonists/antagonists (LEA29Y), CD40 ligand antagonists, other IMPDH inhibitors (such as mycophenolate [CellCept®] and VX-497 [merimepodib]), methotrexate (FK506), leflunomide, integrin antagonists (e.g., alpha-4 beta-1, alpha-V-beta-3), cell adhesion inhibitors, interferon gamma antagonists, prostaglandin synthesis inhibitors, budesonide, clofazimine, CNI-1493, p38 mitogen-activated protein kinase inhibitors, protein tyrosine kinase (PTK) inhibitors, IKK inhibitors, therapies for the treatment of irritable bowel syndrome (e.g., Zelmac®, Zelnorm®, and Maxi-K® openers such as those disclosed in U.S. Pat. No. 6,184,231 B1), or NF-κB inhibitors (such calphostin, CSAIDs, and quinoxalines as disclosed in U.S. Pat. No. 4,200,750); disassociated steroids; chemokine receptor modulators (including CCR1, CCR2, CCR3, CCR4, and CXCR2 receptor antagonists); secretory and cytosolic phospholipase A2 inhibitors, glucocorticoids, salicylates, nitric oxide, and other immunosuppressants; and nuclear translocation inhibitors, such as deoxyspergualin (DSG). Exemplary other therapeutic agents also include cyclosporins (e.g., cyclosporin A), antibodies such as anti-ICAM-3, anti-IL-2 receptor (Anti-Tac), CD4 antagonists (e.g., priliximab), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, and fusion proteins constructed from CD40 and/or CD154/gp39 (e.g., CD40Ig and CD8gp39).

The inventive compounds may be used in combination with other agents used to treat respiratory conditions such as asthma, COPD, and allergic rhinitis, such as β-adrenergic agonists (such as albuterol, terbutaline, formoterol, salbutamol, salmeterol, bitolterol, pilbuterol, and fenoterol); corticosteroids (such as beclomethasone, triamcinolone, budesonide, fluticasone, flunisolide, dexamethasone, prednisone, and dexamethasone); leukotriene antagonists (e.g., Accolate [Zafirlukast®], and Singulair [Montelukast®]); MJ cholinergic antagonists (e.g., Spiriva®), PDE 4 inhibitors (e.g. rolipram, cilomilast, piclamilast, or roflumilast [Airoflo®]), histamine $H_1$ antagonists, Allegra® (hexohenadine), Claritin® (loratidone), and/or Clarinex® (deskratidine).

Examples of suitable antiviral agents for use with the inventive compounds include abacavir, nucleoside-based inhibitors, protease-based inhibitors, and viral-assembly inhibitors.

Examples of suitable anti-osteoporosis agents for use in combination with the compounds of the present invention include alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1 inhibitors.

Examples of suitable anti-oxidants for use in combination with the compounds of the present invention include lipid peroxidation inhibitors such as probucol, BO-653, Vitamin A, Vitamin E, AGI-1067, and α-lipoic acid.

The inventive compounds also may be used in combination with anti-diabetic agents, such as biguanides (e.g. metformin), glucosidase inhibitors (e.g. acarbose), insulins (including insulin secretagogues or insulin sensitizers), meglitinides (e.g. repaglinide), sulfonylureas (e.g., glimepiride, glyburide and glipizide), biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), glucagon phosphorylase, and dipeptidyl peptidase IV (DP4) inhibitors.

In addition, the compounds may be used with agents that increase the levels of cAMP or cGMP in cells for a therapeutic benefit. For example, the compounds of the invention may have advantageous effects when used in combination with phosphodiesterase inhibitors, including PDE1 inhibitors (such as those described in Journal of Medicinal Chemistry, Vol. 40, pp. 2196-2210 [1997]), PDE2 inhibitors, PDE3 inhibitors (such as revizinone, pimobendan, or olprinone), PDE4 inhibitors (referenced above), PDE7 inhibitors, or other PDE inhibitors such as dipyridamole, cilostazol, sildenafil, denbutyline, theophylline (1,2-dimethylxanthine), ARIFLO™ (i.e., cis-4-cyano-4-[3-(cyclopentyloxy)-4-methoxyphenyl]cyclohexane-1-carboxylic acid), arofyline, C-11294A, CDC-801, BAY-19-8004, cipamfylline, SCH351591, YM-976, PD-189659, mesiopram, pumafentrine, CDC-998, IC-485, and KW-4490.

In view of their usefulness in treating ischemia (e.g., post-operative), the inventive compounds may be used in combination with agents for inhibiting $F_1F_0$-ATPase, including efrapeptin, oligomycin, autovertin B, azide, and compounds described in U.S. patent application Ser. No. 60/339, 108, filed Dec. 10, 2001 and assigned to the present assignee; -alpha- or beta-adrenergic blockers (such as propranolol, nadolol, carvedilol, and prazosin), antianginal agents such as nitrates, for example, sodium nitrates, nitroglycerin, isosorbide mononitrate, isosorbide dinitrate, and nitrovasodilators; antiarrhythmic agents including Class I agents (such as propafenone); Class II agents (propranolol); Class III agents (such as sotalol, dofetilide, amiodarone, azimilide and ibutilide); Class IV agents (such as ditiazem and verapamil); K⁺ channel modulators such as $I_{Ach}$ inhibitors and inhibitors of the $K_v1$ subfamily of K⁺ channel openers such as $I_{Kur}$ inhibitors (e.g., compounds disclosed in U.S. application Ser. No. 09/729,731, filed Dec. 5, 2000); and gap-junction modulators such as connexions; anticoagulant or antithrombotic agents including aspirin, warfarin, ximelagtran, low molecular weight heparins (such as lovenox, enoxaparain, and dalteparin), anti-platelet agents such as GPIIb/GPIIIa blockers, (e.g., abciximab, eptifibatide, and tirofiban), thromboxane receptor antagonists (e.g., ifetroban), $P2Y_1$ and $P2Y_{12}$ antagonists (e.g., clopidogrel, ticlopidine, CS-747, and aspirin/clopidogrel combinations), and Factor Xa inhibitors (e.g., fondaprinux); and diuretics such as sodium-hydrogen exchange inhibitors, chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, and amiloride.

The inventive compounds may also be used with lipid-lowering agents, lipid profile modulators and/or antiatherosclerotic agents including HMG-CoA reductase inhibitors (e.g., pravastatin, simvastatin, atorvastatin, fluvastatin, cerivastatin, AZ4522, itavastatin [Nissan/Kowa]), ZD-4522 (a.k.a. rosuvastatin, atavastatin or visastatin), squalene synthetase inhibitors, fibrates, bile acid sequestrants (such as questran), niacin and niacin/statin combinations, ACAT1 inhibitors, ACAT2 inhibitors, dual ACAT1/2 inhibitors, microsomal triglyceride transport protein inhibitors (such as disclosed in U.S. Pat. Nos. 5,739,135, 5,712,279 and 5,760, 246), cholesterol absorption inhibitors, cholesterol ester transfer protein inhibitors (e.g., CP-529414), PPAR-delta agonists, PPAR-alpha agonists, dual PPAR-alpha/delta agonists, LXR-alpha agonists, LXR-beta agonists, LXR dual alpha/beta agonists, and SCAP modulators.

The inventive compounds may also be useful in combination with antiangiogenic agents, such as compounds that are inhibitors of VEGF receptors, or in conjunction with antitumor agents such as paclitaxel, adriamycin, epithilones, cisplatin, and carboplatin. Examples of anticancer and other cytotoxic agents that may be used in combination with the inventive compounds include azathiaprine, cyclophosphamide, and epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416; and prenyl-protein transferase inhibitors as found in WO 97/30992 and WO 98/54966.

The combination of the inventive compounds with other therapeutic agents may prove to have additive and synergistic effects. The combination may be advantageous to increase the efficacy of the administration or decrease the dosage to reduce possible side-effects.

Another useful application for the inventive compounds is in methods of inhibiting smooth muscle cell proliferation in a patient and as a coating material in making medical devices, e.g., stent devices, catheters, and other transluminal devices. Methods for coating stents are described in U.S. Pat. Nos. 5,356,433, 5,213,898, 5,049,403, 4,807,784 and 4,565,740, each of which is incorporated herein by reference.

The above other therapeutic agents, when employed in combination with the compounds of the present invention, may be used, for example, in those amounts indicated in the Physicians' Desk Reference (PDR) or as otherwise determined by one of ordinary skill in the art.

Compounds disclosed herein are capable of targeting and inhibiting IMPDH enzyme. Inhibition can be measured by various methods, including, for example, IMP dehydrogenase HPLC assays (measuring enzymatic production of XMP and NADH from IMP and NAD) and IMP dehydrogenase spectrophotometric assays (measuring enzymatic production of NADH from NAD). See, e.g., Montero et al., *Clinica Chimica Acta* 238:169-178 (1995). Additional assays known in the art can be used in ascertaining the degree of activity of a compound ("test compound") as an IMPDH inhibitor. The inventors used the following assay to determine the degree of activity of the compounds disclosed herein as IMPDH inhibitors:

Activity of IMPDH I and IMPDH II was measured following an adaptation of the method described in WO 97/40028. The reaction mixture was prepared containing 0.1M Tris pH 8.0, 0.1 M KCl, 3 mM EDTA, 2 mM DTT, 0.4 mM IMP and 40 nM enzyme (IMPDH I or IMPDH II). The reaction was started by the addition of NAD to a final concentration of 0.4 mM. The enzymatic reaction was followed by measuring the increase in absorbance at 340 nM that results from the formation of NADH. For the analysis of potential inhibitors of the enzyme, compounds were dissolved in DMSO to a final concentration of 10 mM and added to the assay mixture such that the final concentration of DMSO was 2.5%. The assay was carried out in a 96-well plate format, with a final reaction volume of 200 μl.

Compounds disclosed herein are capable of inhibiting the enzyme IMPDH at a measurable level, under the above-described assay or an assay which can determine an effect of inhibition of the enzyme IMPDH.

Methods of Preparation

The compounds of the present invention may be synthesized using conventional techniques known in the art. Advantageously, these compounds are conveniently synthesized from readily available starting materials. Following are general synthetic schemes for manufacturing compounds of the present invention. These schemes are illustrative and are not meant to limit the possible techniques one skilled in the art may use to manufacture compounds disclosed herein. Different methods will be evident to those skilled in the art. Additionally, the various steps in the synthesis may be performed in an alternate sequence or order to give the desired compound(s). All documents cited herein are incorporated herein by reference in their entirety.

Compounds of the present invention can be made by many methods, which will be known to one skilled in the art of organic chemistry. In general, the time taken to complete a reaction procedure will be judged by the person performing the procedure, preferably with the aid of information obtained by monitoring the reaction by methods such as HPLC or TLC. A reaction does not have to go to completion to be useful to this invention. Methods for preparing heterocycles useful to this invention are described in the literature, including Katritzky, A. R., Rees, C. W. Eds, *Comprehensive Heterocyclic Chemistry, The Structure, Reactions, Synthesis and Uses of Heterocyclic Compounds*, Pergamon Press New York (First edition 1984), and Katritzky, A. R., Rees, C. W. and Scriven, E., F. Eds, *Comprehensive Heterocyclic Chemistry II, A Review of the Literature 1982-1995: The Structure, Reactions, Synthesis and Uses of Heterocyclic Compounds*, Pergamon Press New York (1996).

Amines such as anilines or heterocyclic amines, useful for preparing compounds according to the invention may be commercially available or readily prepared by many methods known to one skilled in the art of organic chemistry. For example, such methods are described in Richard C. Larock, *Comprehensive Organic Transformations A Guide to Functional Group Preparation*, pp 385-439 (VCH Publishers, Inc. 1989). Examples include but are not limited to reduction of a nitro group, and reduction of an azide.

A general method for the synthesis of the anilines useful in this invention can be performed by metal catalyzed cross-coupling methods known in the literature. The simplest case is a Suzuki-type cross coupling of an aryl boronic acid or ester with an appropriate bromoheterocycle in the presence of a suitable catalyst such as tetrakis(triphenylphosphine)palladium. (See, e.g., Miyaura et al., *Synth. Comm.* 11(7):513-519 (1981); A. Suzuki et. al., *J. Am. Chem. Soc.* 111:513 (1989); and V. N. Kalinin, *Russ. Chem. Rev.* 60:173 (1991)). After the cross coupling has been performed, the product may be deprotected. The choice of protecting group and the method of removal will be readily apparent to one skilled in the art of organic chemistry. Such considerations and methods are, for example, described by Greene and Wuts, *Protective Groups in Organic Synthesis*, John Wiley and Sons, Inc., New York, N.Y. ($2^{nd}$ Ed. 1991).

Schemes 1-10 describe various methods for the synthesis of acridones and acridone acids that may be used to prepare compounds described in this invention. Various modifications to these methods may be envisioned by those skilled in the art to achieve similar results to that of the authors given below. For example, in scheme 1, LDA is used as a base and it is anticipated that other bases would also be effective for this transformation.

Scheme 1 (See, e.g., MacNeil et al., *Synlett*, Vol. 4 (1998), at p. 419):

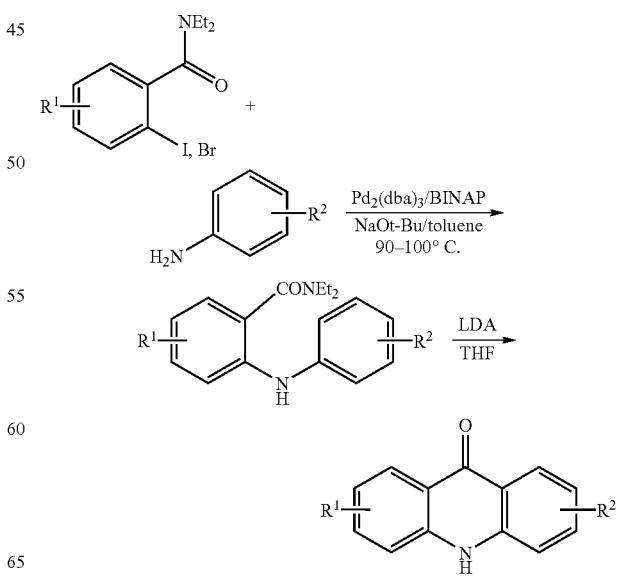

Scheme 2 (See, e.g., Kato, *Chem. Pharm. Bull.*, Vol. 41 (1993), at p. 445):
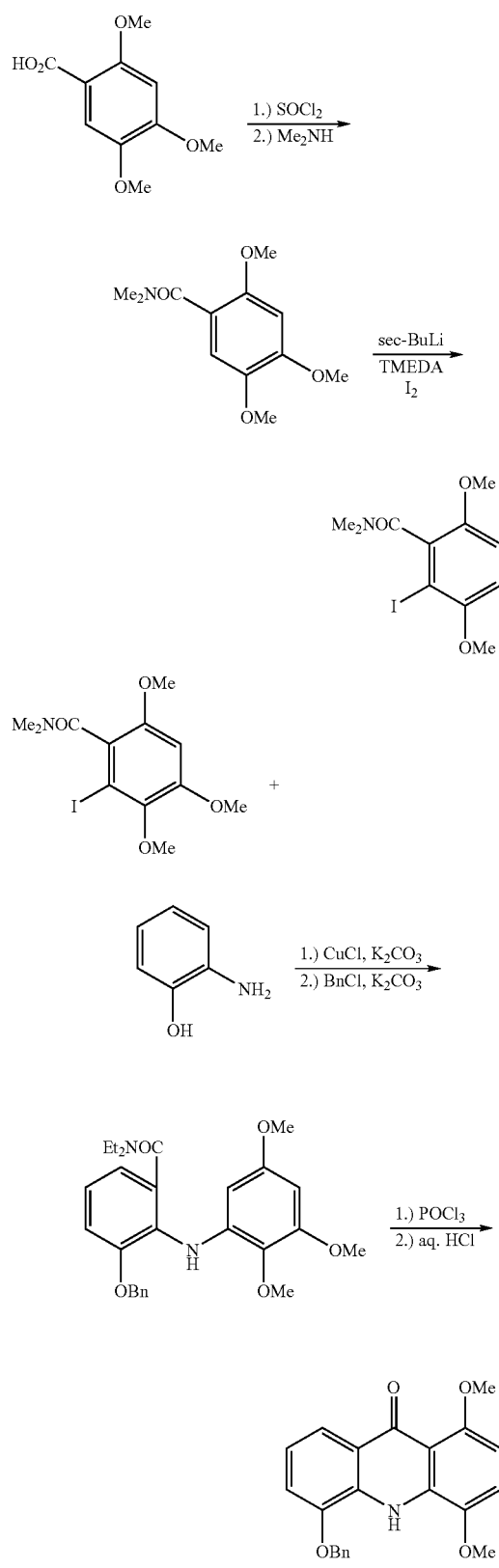
Scheme 3 (See, e.g., Rewcastle et al., *J. Med. Chem.*, Vol. 29 (1986), at p. 472):
Scheme 4 (See, e.g., Rewcastle et al., *Synthetic Comm.* (1987), at 309):
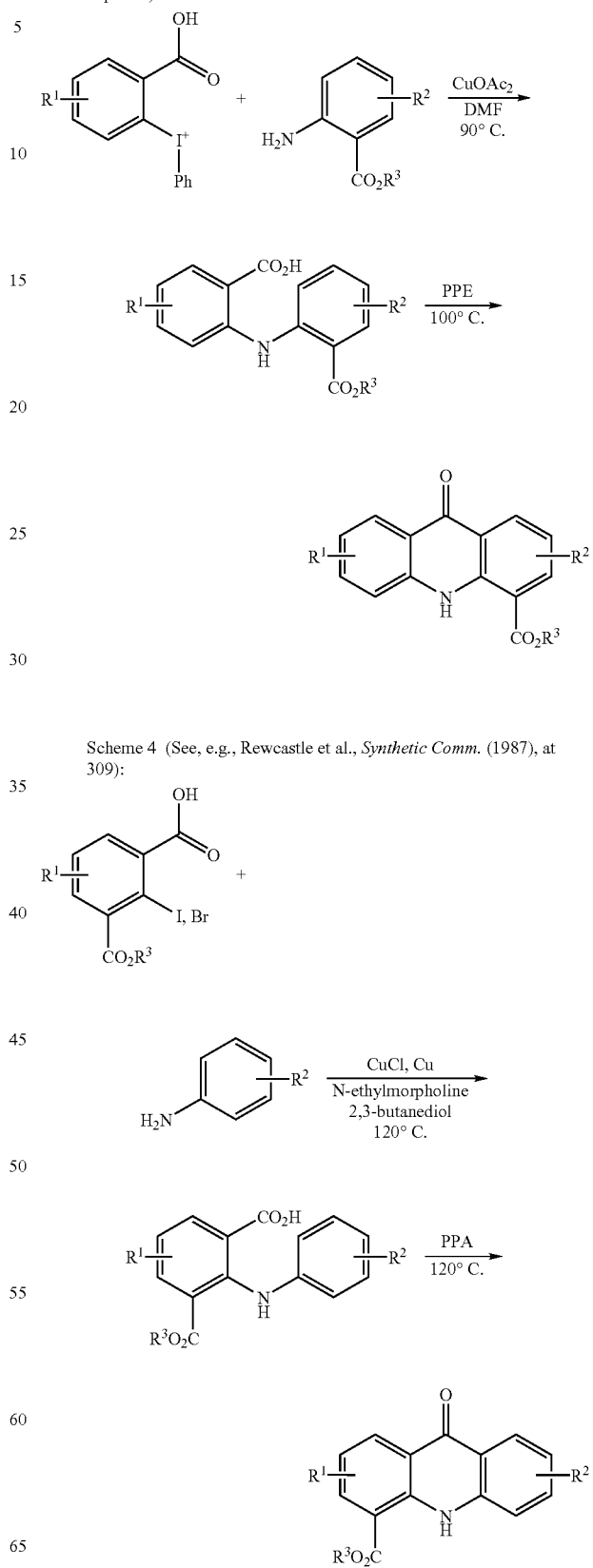

Scheme 5 (See, e.g., Horiguchi, et al., *Heterocycles*, Vol. 53 (2000), at 1305).
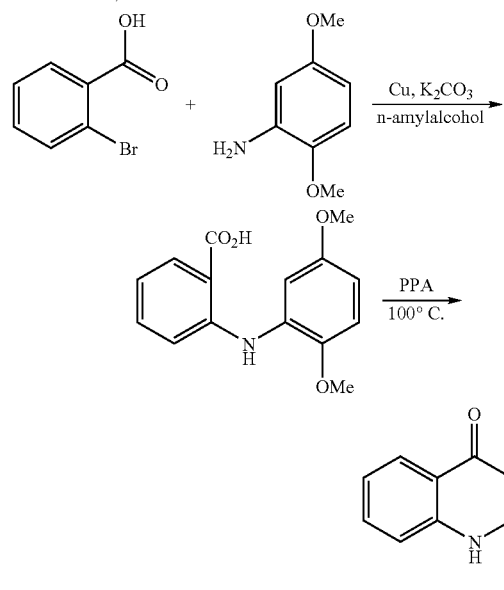
Scheme 6 (See, e.g., Sharp, et al., WO 98/52923 (1998)).
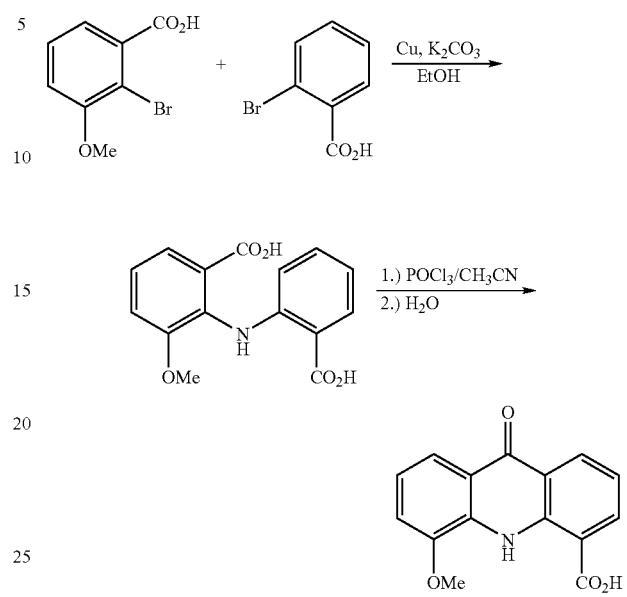
Scheme 7:
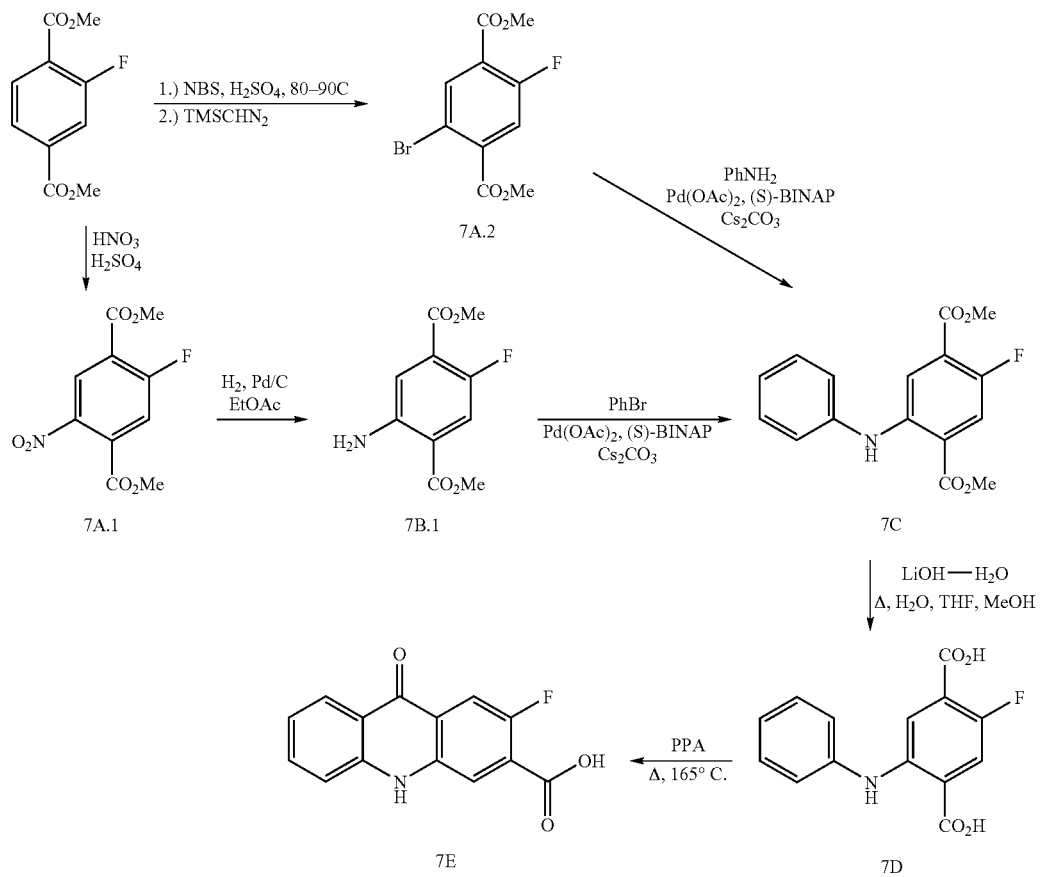

Scheme 7 shows two alternative methods for the synthesis of 7E. This procedure is general and has been used to prepare various acridones described in this application. Individuals skilled in the art may anticipate other reaction conditions for each of the steps outlined in this scheme. For example, the conversion of 7A.1 to 7B.1 may be achieved via reduction with stannous chloride dihydrate.

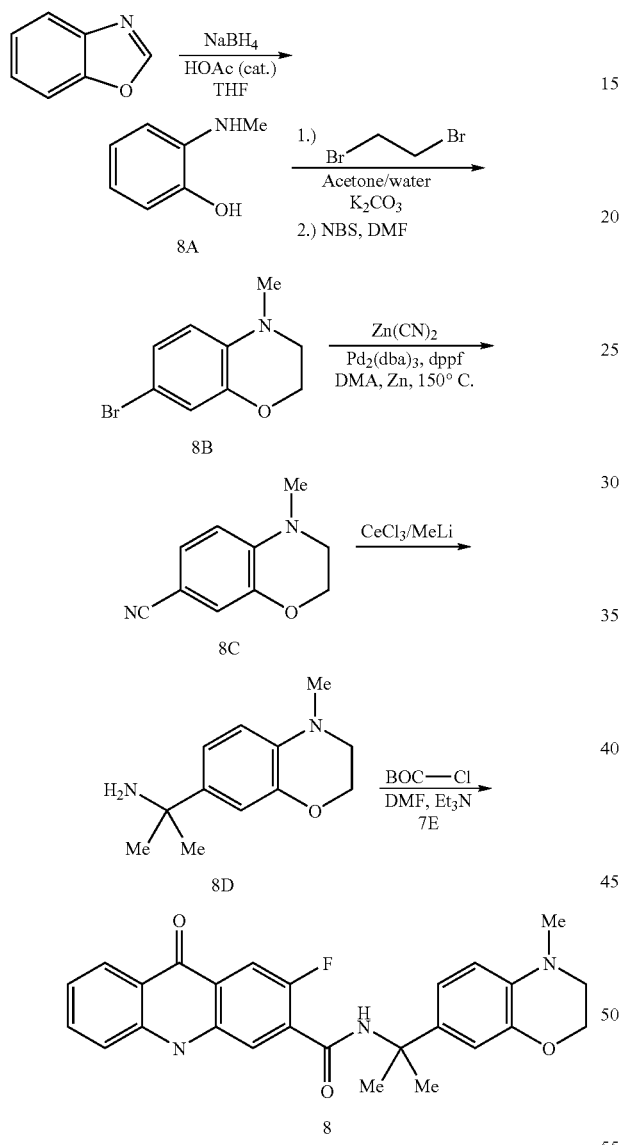

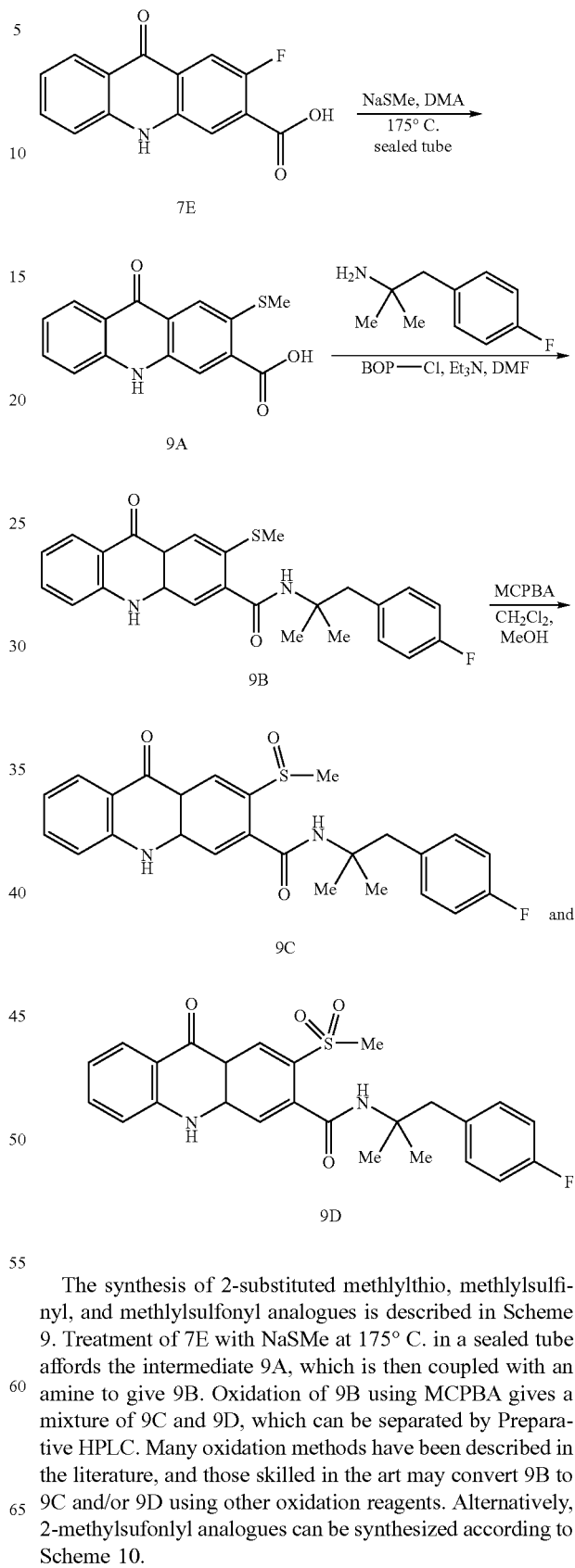

Scheme 8 describes the synthesis of 8. Of particular note is the conversion of 8C to 8D through the use of MeLi/CeCl₃. This procedure is general and has been used widely to prepare many example described herein. This scheme also describes the formation of an amide bond, i.e. the conversion of 8D to 8 using compound 7E. Many methods have been described in the literature to prepare amides. Those skilled in the art may convert 8D to a more reactive species such as the corresponding acid chloride and use this to prepare the amide linkage.

The synthesis of 2-substituted methlylthio, methlylsulfinyl, and methlylsulfonyl analogues is described in Scheme 9. Treatment of 7E with NaSMe at 175° C. in a sealed tube affords the intermediate 9A, which is then coupled with an amine to give 9B. Oxidation of 9B using MCPBA gives a mixture of 9C and 9D, which can be separated by Preparative HPLC. Many oxidation methods have been described in the literature, and those skilled in the art may convert 9B to 9C and/or 9D using other oxidation reagents. Alternatively, 2-methylsufonlyl analogues can be synthesized according to Scheme 10.

Scheme 10:

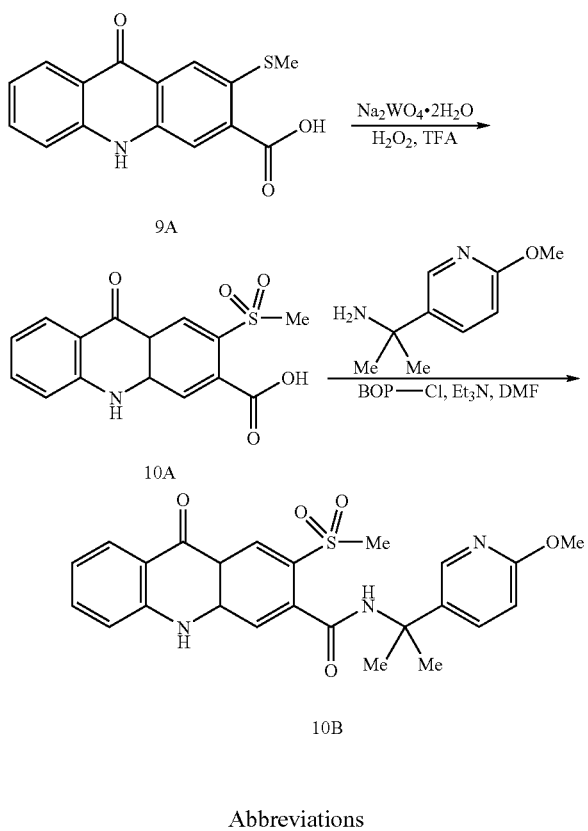

Abbreviations

The following abbreviations are used in the Examples herein, for ease of reference.

| | |
|---|---|
| Ac | Acetyl |
| AcOH | Acetic acid |
| aq. | Aqueous |
| CDI | Carbonyldiimidazole |
| Bn | Benzyl |
| Boc | tert-butoxycarbonyl |
| BOP-Cl | Bis(2-oxo-3-oxazolidinyl)phosphinic chloride |
| DCM | dichloromethane |
| DMAP | Dimethylaminopyridine |
| DMF | dimethylformamide |
| DMSO | Dimethylsulfoxide |
| EDC | 1-(3-Dimethylaminopropyl)-3-ethylcarbodiimide hydrochloride |
| EtOAc | Ethyl acetate |
| Et | Ethyl |
| EtOH | Ethanol |
| h | Hours |
| i | iso |
| HMPA | hexamethyl phosphoric amide |
| HPLC | High pressure liquid chromatography |
| HOAc | Acetic acid |
| Lawesson's Reagent | [2,4-bis(4-methoxyphenyl)-1,3-dithia-2, 4-diphosphetane-2-4-disufide |
| LC | liquid chromatography |
| LDA | Lithium diisopropylamide |
| MCPBA | 3-Chloroperoxybenzoic acid |
| Me | Methyl |
| MeOH | Methanol |
| min. | Minutes |
| $M^+$ | $(M + H)^+$ |
| $M^{+1}$ | $(M + H)^+$ |
| MS | Mass spectrometry |
| n | Normal |
| Pd/C | Palladium on carbon |
| Ph | Phenyl |
| PPA | polyphosphoric acid |
| PPTS | Pyridinium p-toluenesulfonate |
| Pr | Propyl |
| p-TsOH | para-Toluenesulonic acid |
| Ret Time | Retention time |
| rt or RT | Room temperature |
| sat. | Saturated |
| TBAF | tetra-n-Butylammonium fluoride |
| TBDMS | t-Butyldimethylsilane |
| TBTU | O-(1H-benzotriazol-1-yl)-N, N, N', N'-tetramethyluronium tetrafluoroborate |
| TBDMSCl | t-Butyldimethylsilyl chlordie |
| THF | Tetrahydrofuran |
| TFA | Trifluoroacetic acid |
| THF | Tetrahydrofuran |
| TOSMIC | Tosylmethyl isocyanide |
| YMC | YMC Inc, Wilmington, NC 28403 |

Abbreviations for HPLC Conditions:
A: YMC ODS column; 4.6×50 mm (4 min. gradient); Solvent A=10% MeOH, 90% $H_2O$, 0.1% TFA; solvent B=90% MeOH, 10% $H_2O$, 0.1% TFA.
B: YMC ODS column; 4.6×50 mm (4 min. gradient); Solvent A=10% MeOH, 90% $H_2O$, 0.2% $H_3PO_4$; solvent B=90% MeOH, 10% $H_2O$, 0.2% $H_3PO_4$.
C: YMC ODS column; 4.6×50 mm (2 min. gradient); Solvent A=10% MeOH, 90% $H_2O$, 0.1% TFA; solvent B=90% MeOH, 10% $H_2O$, 0.1% TFA.
D: YMC ODS column 4.6×33 mm (2 min. gradient); Solvent A=10% MeOH, 90% $H_2O$, 0.1% TFA; solvent B=90% MeOH, 10% $H_2O$, 0.1% TFA.
E: Phenomenex column; 4.6×30 mm (2 min. gradient); Solvent A=10% MeOH, 90% $H_2O$, 0.1% TFA; solvent B=90% MeOH, 10% $H_2O$, 0.1% TFA.
F: YMC ODS column; 4.6×30 mm (2 min. gradient); Solvent A=10% MeOH, 90% $H_2O$, 0.1% TFA; solvent B=90% MeOH, 10% $H_2O$, 0.1% TFA.

EXAMPLES

The invention will now be further described by the following working examples, which are preferred embodiments of the invention. HPLC conditions were as set forth in the above Abbreviations. These examples are illustrative rather than limiting. There may be other embodiments that fall within the spirit and scope of the invention as defined by the appended claims.

Example 1

9-Oxo-4a,9,9a,10-tetrahydro-acridine-3-carboxylic acid, [1-methyl-1-(4-py-ridinyl)ethyl]amide

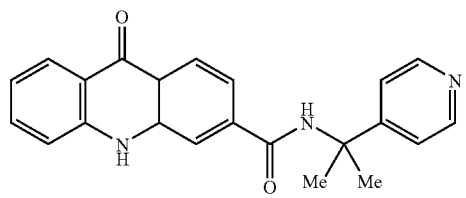

1A. 5-phenylamino-terephthalic acid dimethyl ester

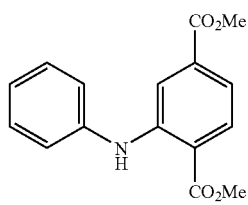

To a mixture of dimethyl bromoterephthalate (4.5 g, 16.0 mmol), aniline (2.2 mL, 24.0 mmol), (S)-(−)-2,2'-bis(diphenylphosphino)-1,1'-binaphthyl (922 mg, 1.48 mmol), and toluene (50 mL) was added cesium carbonate (7.53 g, 23.1 mmol), followed by palladium(II) acetate (0.22 g, 1.0 mmol). The mixture was heated to 100° C. for 24 h. HPLC indicated that the reaction was complete. The reaction mixture was cooled to room temperature, diluted with diethyl ether and filtered under reduced pressure through a pad of Celite. The filtrate was concentrated under reduced pressure and purified by silica gel chromatography using a 1:10 mixture of EtOAc and hexane to give 4.58 (97%) of 1A as a bright yellow solid. HPLC retention time=3.74 min. (Condition A) and LC/MS M$^+$+1=286$^+$. $^1$H-NMR (400 MHz, CDCl$_3$): δ 9.50 (bs, 1H), 8.01 (d, J=8.30, 1H), 7.91 (d, J=1.50, 1H), 7.32-7.40 (m, 4H), 7.25 (m, 1H), 7.13 (m, 1H), 3.93 (s, 3H), 3.88 (s, 3H).

1B. 5-phenylamino-terephthalic acid

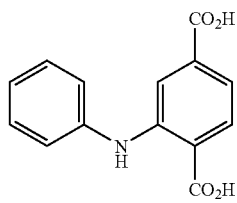

A mixture of compound 1A (4.56 g, 16.0 mmol) and lithium hydroxide monohydrate (2.0 g, 48.0 mmol) in MeOH (32 mL), THF (32 mL) and water (16 mL) was heated to reflux for 0.5 h. HPLC indicated that the reaction was complete. The organic solvents were removed under reduced pressure, and the aqueous residue was diluted with water. The pH was adjusted to 3.0 with 6N aqueous hydrochloric acid. The resulting precipitate was collected by vacuum filtration, rinsed with water and dried under reduced pressure to provide 3.95 g (96%) of 1B as a bright yellow solid. HPLC retention time=2.75 min. (Condition A) and LC/MS M$^+$+1=258$^+$.

1C. 9-Oxo-9,10-dihydro-acridine-3-carboxylic acid

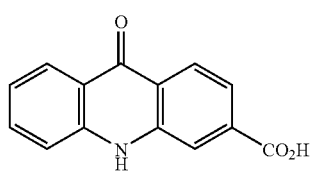

To a round bottom flask containing polyphosphoric acid (35 g) at 165° C. was added finely ground compound 1B (3.0 g, 1.17 mmol) over 10 min. After the addition was complete, the reaction mixture was stirred for 30 min at 165° C. HPLC indicated that the reaction was complete. While at 165° C., the mixture was slowly added to a mixture of ice and sodium hydroxide. The pH was adjusted to 3.0 with additional sodium hydroxide, and the resulting mixture was filtered through a medium porosity fritted funnel to give a yellow paste which was rinsed with MeOH and DCM into a round bottom flask. The organic solvents were removed under reduced pressure and the residue was azeotripic evaporated several times with MeOH and DCM to give 2.75 g (98%) of compound 1C as a yellow solid. HPLC retention time=2.45 min. (Condition A) and LC/MS M$^+$+1=240$^+$. $^1$H-NMR (500 MHz, DMSO-d$_6$) δ 13.13 (bs, 1H), 11.96 (s, 1H), 8.31 (d, J=8.42 Hz, 1H), 8.24 (d, J=8.20 Hz, 1H), 8.18 (s, 1H), 7.77 (t, J=7.55 Hz, 1H), 7.72 (d, J=8.42 Hz, 1H), 7.55 (d, J=8.20 Hz, 1H), 7.30 (t, J=7.55 Hz, 1H).

1D. 1-methyl-1-(4-pyridinyl)ethylamine

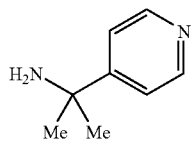

To a flame-dried flask under nitrogen was added cerium chloride (2.47 g, 10.0 mmol), followed by anhydrous THF (20 mL). The mixture was stirred vigorously for 2 h, during which time the cerium chloride became finely suspended. The suspension was cooled to −78° C., and methyl lithium (7.14 mL, 10.0 mmol, 1.4 M in ether) was added dropwise. After the addition was complete, the reaction mixture was stirred for 0.5 h at −78° C. A solution of 4-cyanopyridine (0.347 g, 3.3 mmol) in THF (3 mL) was added via cannula to the −78° C. solution. The dry-ice bath was removed, and the reaction mixture was stirred at room temperature overnight. The mixture was quenched with concentrated aqueous ammonium hydroxide (5 mL) and the mixture was stirred vigorously for 1 h. The mixture was filtered through Celite and rinsed with DCM. The combined filtrates were concentrated under reduced pressure. Further purification using silica gel chromatography (CH$_2$Cl$_2$-MeOH-NH$_4$OH:95:5:0.5) gave 264 mg (59%) of compound 1D as a colorless oil. HPLC retention time=0.187 min. (Condition A) and LC/MS M$^+$+1=137$^+$. $^1$H-NMR (400 MHz, CDCl$_3$) δ 8.55 (d,J=6.22 Hz, 2H), 7.41 (d, J=6.22 Hz, 2H), 1.51 (s, 6H).

1E. Example 1

To compound 1C (24 mg, 0.1 mmol) was sequentially added compound 1D (14 mg, 0.1 mmol), Et$_3$N (0.028 mL, 0.2 mmol), anhydrous DMF (0.5 mL), and BOP-Cl (26 mg, 0.1 mmol). The reaction mixture was stirred for 18 h at 50° C., then cooled to room temperature and concentrated under reduced pressure. The crude residue was purified by preparative HPLC on a reversed C$_{18}$ column to give Example 1 as a yellow solid. HPLC retention time=2.05 min. (Condition A); MS (M+H)$^+$=358$^+$.

Example 2

9-Oxo-4a,9,9a,10-tetrahydro-acridine-3-carboxylic acid, [1-methyl-1-(3-methoxyphenly)ethyl]amide

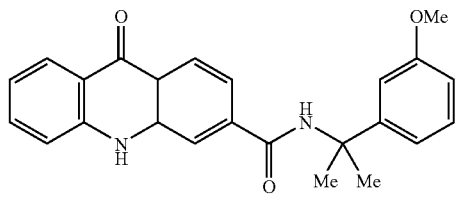

Example 2 was prepared from compound 1C, following the same procedure as described above for Example 1, using 1-methyl-1-(3-methoxyphenyl) ethyl amine in Step E in place of compound 1D.

Examples 3-22

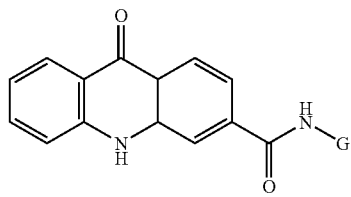

Compounds having the above formula, wherein G has the values listed in Table 1, were prepared from acridone acid 1C, by a route analogous to that used for the preparation of Example 1, replacing amine 1D with the corresponding $H_2N$-G. The corresponding amines were prepared by a route analogous to that used for the preparation of 1D. If the products carry basic moieties, they were purified by preparative HPLC.

TABLE 1

| Ex. No | —G | HPLC time (min) | $M^+ + H$ |
|---|---|---|---|
| 3 | —C(Me)(Me)-(3-pyridyl) | 2.03 A | 358 |
| 4 | —C(Me)(Me)-(2-pyridyl) | 2.04 A | 358 |
| 5 | —(1-phenylcyclopropyl) | 2.92 A | 355 |
| 6 | —(1-phenylcyclobutyl) | 3.16 A | 369 |
| 7 | (S)-1-indanyl | 3.09 A | 355 |
| 8 | (R)-1-indanyl | 3.10 A | 355 |
| 9 | (1S,2R)-2-hydroxy-1-indanyl | 2.86 A | 371 |
| 10 | (1R,2S)-2-hydroxy-1-indanyl | 2.86 A | 371 |
| 11 | —CH$_2$-(3-pyridyl) | 1.91 A | 330 |
| 12 | (S)-1-phenylpropyl | 3.03 A | 357 |
| 13 | (R)-1-phenylpropyl | 3.02 A | 357 |

TABLE 1-continued

| Ex. No | —G | HPLC time (min) | M⁺ + H |
|---|---|---|---|
| 14 | 2-MeO-C6H4-C(Me)2- | 3.04 A | 387 |
| 15 | 3-MeO-C6H4-C(Me)2- | 2.93 A | 387 |
| 16 | 4-MeO-C6H4-C(Me)2- | 2.94 A | 387 |
| 17 | 3,4-(MeO)2-C6H3-C(Me)2- | 2.75 A | 417 |
| 18 | 2,3-dihydro-benzo[1,4]dioxin-6-yl-C(Me)2- | 2.92 A | 415 |
| 19 | benzo[1,3]dioxol-5-yl-C(Me)2- | 2.95 A | 401 |
| 20 | 6-methyl-pyridin-3-yl-C(Me)2- | 2.05 A | 372 |
| 21 | naphthalen-1-yl-C(Me)2- | 3.44 A | 407 |
| 22 | naphthalen-2-yl-C(Me)2- | 3.53 A | 407 |

Example 23

9-Oxo-4a,9,9a,10-tetrahydro-acridine-3-carboxylic acid, [1-methyl-1-(3-hydroxyphenly)ethyl]amide

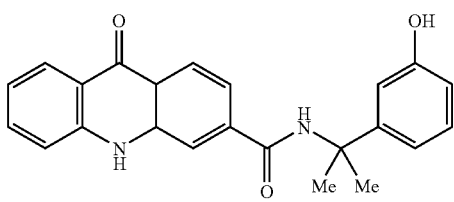

To a suspension of Example 15 (26 mg, 0.066 mmol) in dry DCM (2 mL) cooled at 0° C., was added BBr₃ (neat, 0.02 mL, 0.2 mmol). After stirring for 15 min at 0° C., the ice-bath was removed and the mixture (yellow paste) was diluted with DCM (1 mL) and stirred for another 1.0 h. Ether (2 mL) and DCM (1 mL) were added and the yellow precipitate was collected by filtration. After trituration with water, the yellow solid was collected by filtration and dried under high vacuum to give 23.6 mg of Example 23 as a bright yellow solid. HPLC retention time=2.603 min. (Condition A) and LC/MS M⁺+1=373⁺.

Example 24

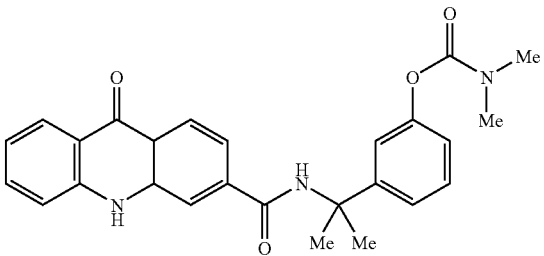

To a solution of Example 23 (19 mg, 0.05 mmol) in dry pyridine (1 mL) was added N,N-dimethyl carbamyl chloride (0.01 mL, 0.1 mmol). After 12 h, water was added and the reaction mixture was extracted with DCM (×2). The combined organic extracts were dried over anhydrous Na₂SO₄. Further purification by flash chromatography (CH₂Cl₂-MeOH:98:2) on silica gel afforded Example 24. HPLC retention time=2.946 min. (Condition A) and LC/MS M⁺+1=444⁺.

Example 25

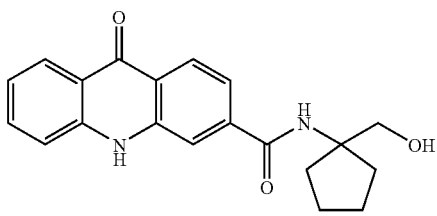

To a mixture of acridone acid 1C (0.250 g, 1.05 mmol), 1-amino-1-cyclopentanemethanol (0.120 g, 1.05 mmol), and triethylamine (0.44 mL, 3.15 mmol) in 12 mL of anhydrous DMF was added BOP-Cl (0.267 g, 0.105 mmol). The reaction mixture was stirred overnight at room temperature. The mixture was diluted with DCM, washed with water, and dried over anhydrous sodium sulfate. Concentration under reduced pressure followed by purification by silica gel chromatography afforded 121 mg of Example 25 as a pale yellow solid. HPLC retention time=2.81 min. (Condition B) and LC/MS $M^{+1}$=337.

Examples 26-36

Compounds having the above formula, wherein G has the values listed in Table 2, were prepared from acid 1C, by a route analogous to that described for Example 1, replacing amine 1D with the corresponding amine $H_2N$-G as set forth in Table 2.

TABLE 2

| Ex. # | G | Amine | HPLC Ret. Time (min) (Condition) | M+ |
|---|---|---|---|---|
| 26 | (C(CH3)2CH2-C6H4-F) | 1-(4-fluorophenyl)-2-methyl-2-propylamine | 3.28 (A) | 390 |
| 27 | (C(Me)2CH2-Ph) | 1-phenyl-2-methyl-2-propylamine | 1.8 (D) | 371 |
| 28 | (C(Me)(CN)-Ph) | 2-amino-2-phenyl-propionitrile (Organic synthesis 3, p. 88). | 2.78 (A) | 368 |
| 29 | (C(Me)3) | tert-butylamine | 2.56 (A) | 309 |
| 30 | (C(Me)2CH2-2-pyridyl) | From 2-picoline as outlined in Example 260, infra. | 1.90 (A) | 372 |
| 31 | (C(Me)2CH2-3-pyridyl) | From 3-picoline as outlined in Example 260, infra, except n-BuLi is replaced by LDA. | 1.20 (A) | 372 |
| 32 | (CH2-C(cyclopropyl)-C6H4-Cl) | 1-(p-chlorophenyl)-cyclopropyl-methylamine | 3.47 (A) | 403 |
| 33 | (Me, CO2Me on cyclopentane) | 2-amino-2-methyl-cyclopentane carboxylic acid ethyl ester (Tetrahedron, 54, 5–6 [1998], 1013–1020). | 1.65 (A) | 379 |

TABLE 2-continued

| Ex. # | G | Amine | HPLC Ret. Time (min) (Condition) | M+ |
|---|---|---|---|---|
| 34 | (Me, cyclopentyl-CH2OH structure) | (2-amino-2-methyl-cyclopentyl)methanol (Tetrahedron, 54, 5–6 ]1998] 1013–1020). | 1.53 (E) | 351 |
| 35 | (Me, pyrrolidine-N-benzyl structure) | 1-benzyl-3-methyl-pyrrolidin-3-yl amine (Chem. Pharm. Bull 44, 7 [1996], 1376–1386). | 1.32 (E) | 412 |
| 36 | (cyclopentyl-C(Me)(Me)-CH2OH structure) | 1-amino-1-cyclopentane-methanol | 2.91 (A) | 337 |

Example 37

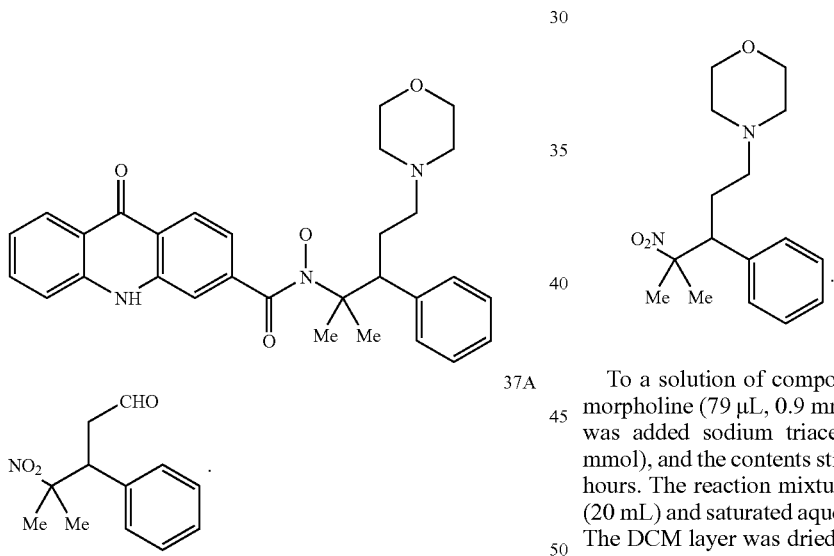

To 2-nitropropane (1.35 mL, 5.15 mmol) in EtOH (15 mL) was added potassium methoxide (0.206 g, 3.03 mmol), and the contents were stirred at room temperature for five minutes. Cinnmaldehyde (2.0 g, 15.15 mmol) was added, and the reaction mixture was stirred at room temperature for twenty four hours, quenched by the slow addition of AcOH (1 mL) and concentrated. The residue was partitioned between EtOAc (50 mL) and water (20 mL). The EtOAc layer was washed with saturated aqueous sodium bicarbonate (20 mL), brine (20 mL), dried over sodium sulfate, concentrated and purified by silica gel column chromatography using hexane and EtOAc to afford compound 37A. Yield: 2.25 g (67%). Retention time=2.74 min (Condition A).

To a solution of compound 37A (0.2 g, 0.90 mmol) and morpholine (79 μL, 0.9 mmol) in 1,2-dichloroethane (1 mL) was added sodium triacetoxyborohydride (0.268 g, 1.26 mmol), and the contents stirred at room temperature for sixty hours. The reaction mixture was partitioned between DCM (20 mL) and saturated aqueous sodium bicarbonate (10 mL). The DCM layer was dried over sodium sulfate and concentrated to yield the above compound 37B as an oil. Yield: 0.25 g, (95%). Retention time=1.47 min (Condition A).

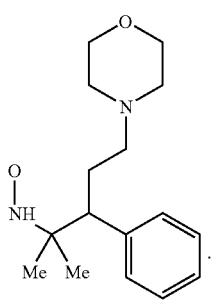

37C

To a solution of compound 37B 0.2 g, 0.68 mmol) in THF (10 mL) was added lithium aluminum hydride (0.052 g, 1.36 mmol) at room temperature over a period of three minutes. The reaction mixture was stirred at room temperature for eighteen hours and quenched by the slow addition of water (0.06 mL), 15% sodium hydroxide (0.06 mL) and water (0.2 mL). The contents in the flask were stirred for fifteen minutes at room temperature, the THF layer decanted, dried over sodium sulfate and concentrated. The syrup that was obtained was used for the next step without further purification.

37D. Example 37

Example 37 was prepared as described for Example 1 using acridone acid 1C and compound 37C. The compound was purified by preparative HPLC and isolated as its TFA salt. Retention time=2.94 min (Condition A), $M^+$ 500.54.

Examples 38 and 39

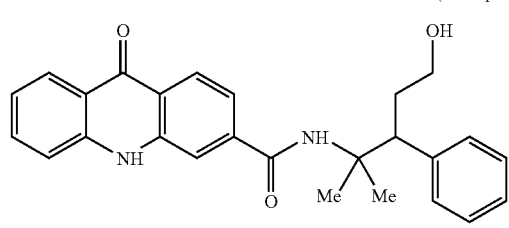
(Example 38)

and

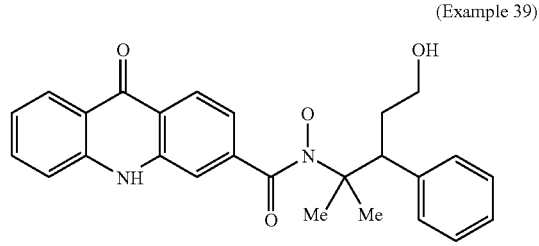
(Example 39)

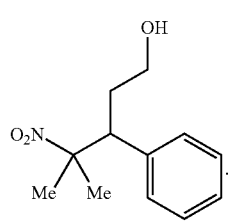
38A

To a solution of compound 37A (0.1 g, 0.45 mmol) in MeOH (5 mL) was added sodium borohydride (0.017 g, 0.45 mmol), and the contents were stirred at room temperature for ten minutes. The reaction mixture was concentrated and partitioned between EtOAc (20 mL) and brine (20 mL). The EtOAc layer was dried over sodium sulfate and concentrated to yield the above compound 38A as an oil which solidified on standing. Retention time=2.7 min (Condition A).

38B and 39B.

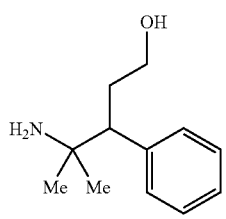
(38B)

and

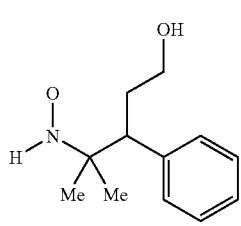
(39B)

To a solution of compound 38A (0.085 g, 0.38 mmol) in AcOH (5 mL) was added zinc (0.175 g, 2.66 mmol), and the contents were stirred at room temperature for three hours. An additional amount of AcOH (5 mL) and zinc (0.175 g, 2.66 mmol) were added and the contents stirred at room temperature for eighteen hours. The reaction mixture was filtered and the filter pad was washed with AcOH (3×10 mL). The filtrate was concentrated under reduced pressure and partitioned between 1N sodium hydroxide and EtOAc (30 mL). The EtOAc layer was washed with brine (20 mL), dried over sodium sulfate, and concentrated to yield an oil which was used as such for the subsequent step without further purification. Yield 0.048 g.

38C and 39C. Examples 38 and 39

Examples 38 and 39 having the above formulae were prepared as described for Example 1 using acridone acid 1C and compounds 38B and 39B. The compounds were purified by preparative HPLC. Retention time (Example 38)=3.02 min; $M^+$ 415.45; Retention time (Example 39)=1.86 min. $M^+$ 431.16 (Condition A).

Example 40

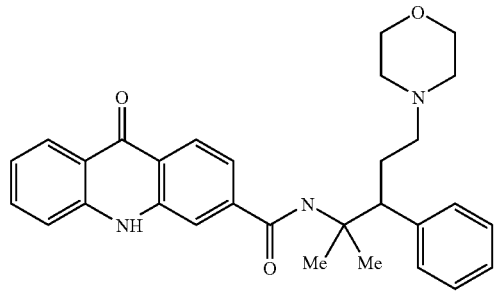

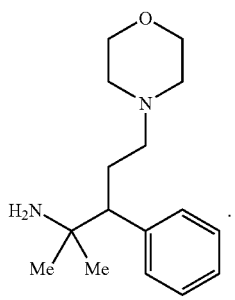

40A

To a solution of compound 37C (0.155 g) in EtOH (5 mL) and 6N HCl (5 mL) was added platinum oxide (0.07 g) and the contents hydrogenated at 40 psi for three hours. The reaction mixture was filtered and the filtrate concentrated. The resultant residue was partitioned between EtOAc (20 mL) and water (30 mL). The aqueous layer was separated, made basic using 1N sodium hydroxide and extracted into EtOAc (2×20 mL). The EtOAc layer was dried over sodium sulfate and concentrated to yield an oil which was used as such for the subsequent step without further purification.

40B. Example 40

Example 40 above was prepared as described for Example 1 using acridone acid 1C and compound 40A. The compound was purified by preparative HPLC. Retention time=1.8 min (Condition A). M⁺ 484.48

Example 41

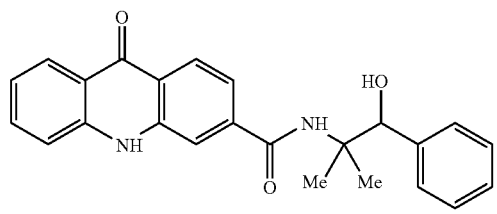

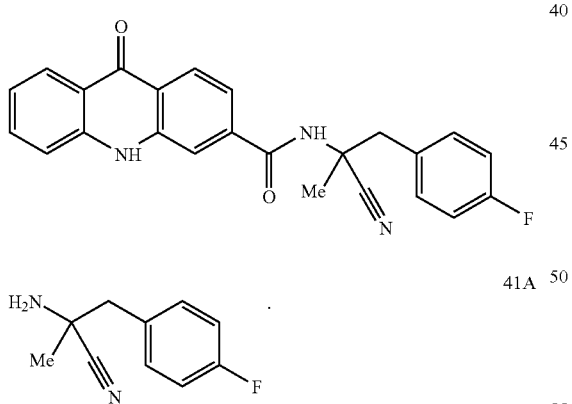

41A

To a solution of sodium cyanide (0.225 g, 4.6 mmol) in water (1 mL) were sequentially added 4-fluorophenylacetone (0.7 g, 4.6 mmol), ammonium chloride (0.244 g, 4.6 mmol), aqueous ammonia (0.6 mL, 9.2 mmol), EtOH (3 mL) and water (1 mL), and the reaction mixture was heated at 60° C. for three hours. The reaction mixture was cooled to room temperature and partitioned between water (20 mL) and EtOAc (30 mL). The EtOAc layer was separated and made acidic using 1N HCl (10 mL) and extracted into EtOAc (2×20 mL). To the EtOAc layer was added aqueous ammonia (20 mL) and the solution was extracted into EtOAc (30 mL), dried over sodium sulfate, and concentrated to yield the above compound 41A as an oil. Yield: 0.660 g (81%). ¹H NMR (DMSO-d6): 7.3 (2H, m), 7.15 (2H, t), 2.9 (2H, d), 1.3 (3H, s).

41B. Example 41

Example 41 above was prepared as described for Example 1 using acridone acid 1C and compound 41A. Retention time=3.08 min (Condition A). M⁺ 400.41

Example 42

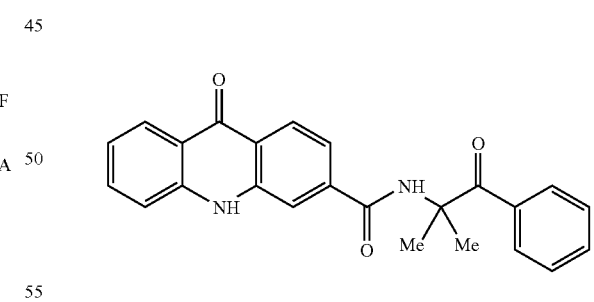

A solution of 2-azido-2-methyl-1-phenyl-propan-1-one (*JACS*, 75 [1953], 1642) (0.16 g) in MeOH (10 mL) was hydrogenated at atmospheric pressure for three hours. The reaction mixture was filtered and the filter pad was washed with MeOH (2×5 mL). The filtrate was concentrated under reduced pressure to yield an amino alcohol solid which was coupled without further purification with acridone acid 1C as described for Example 1 to provide Example 42. Retention time=3.2 min. (Condition A). M⁺ 387.39

Example 43

A solution of 2-azido-2-methyl-1-phenyl-propan-1-one (*JACS*, 75 [1953], 1642) (0.16 g) in EtOAc (10 mL) was hydrogenated at atmospheric pressure for eighteen hours. The reaction mixture was filtered and the filter pad was washed with EtOAc (2×5 mL). The filtrate was concentrated under reduced pressure to afford an amino ketone which was coupled without further purification with the acridone acid 1C as described for Example 1 to afford Example 43. Retention time=1.54 min. (Condition A). M⁺ 385.17

Example 44

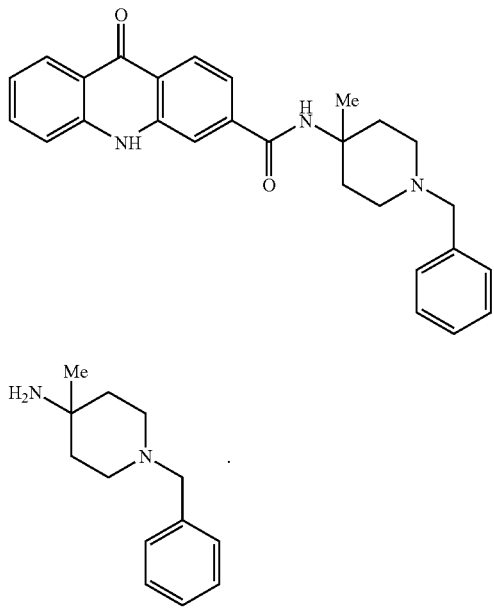

44A

To N-(1-benzyl-4-methyl-piperidin-4-yl)-acetamide (*Tet. Lett.* 37(8) [1996], 1297-1300) (1.0 g) was added concentrated HCl (20 mL) and the contents heated at 140° C. for twenty hours. The reaction mixture was concentrated and made basic with 30% potassium hydroxide and extracted into EtOAc (2×25 mL). The EtOAc layer was dried over sodium sulfate and concentrated to yield Compound 44A, above. More of compound 44A was obtained by extracting the aqueous layer with chloroform. Total yield: 0.375 g (45%). $^1$H NMR (CDCl$_3$): 7.3 (5H, m), 3.5 (2H, s), 2.5 (4H, m), 1.8 (2H, brs), 1.6 (2H, m), 1.5 (2H, m), 1.1 (s, 3H).

44B. Example 44

Example 44 was prepared as described for Example 1 using acridone acid 1C and compound 44A. Retention time=1.51 min. (Condition D). M$^+$ 426.44

Example 45

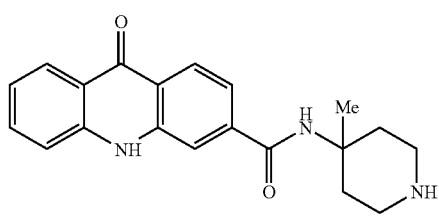

A solution of Example 44 (0.02 g) in MeOH (15 mL) was hydrogenated over Pd(OH)$_2$ (0.010 g) at 30 psi for eighteen hours. The reaction mixture was filtered and the filter cake washed with MeOH. The filtrate was concentrated under reduced pressure and purified by preparative HPLC to yield Example 45 as a TFA salt. Yield: 0.04 g. Retention time=1.1 min. (Condition D). M$^+$ 336.21.

Example 46

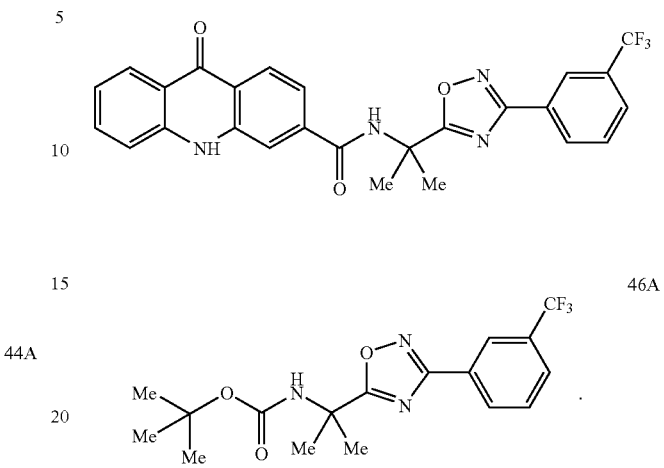

46A

To a solution of BOC-2-aminoisobutyric acid (0.5 g, 2.46 mmol) in DMF (5 mL) was sequentially added HOBT (0.066 g, 0.5 eq), diisopropylethyl amine (2.26 mL, 12.3 mmol), and TBTU (2.46 mmol), and the contents were stirred at room temperature for five minutes. Then N-Hydroxy-3-trifluoromethyl-benzamidine (0.5 g, 2.46 mmol) was added and the contents heated at 110° C. for eighteen hours. The reaction mixture was partitioned between EtOAc (25 mL) and 1N HCl (20 mL). The EtOAc layer was washed with 1N sodium hydroxide (20 mL), brine (20 mL), dried over sodium sulfate, concentrated and purified by silica gel column chromatography using hexane and EtOAc to afford compound 46A. Yield: 0.72 g (79%). Retention time=3.54 min. (Condition A).

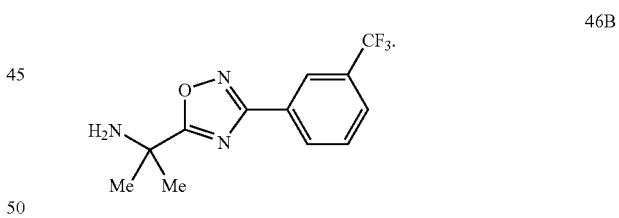

46B

To compound 46A (0.76 g, 2 mmol) at 0° C. was added TFA over a ten minute period. The reaction mixture was stirred at 0° C. for ten minutes and at room temperature for ten minutes. The reaction mixture was concentrated and partitioned between EtOAc (20 mL) and saturated aqueous sodium bicarbonate (20 mL). The EtOAc layer was dried over sodium sulfate and concentrated to yield compound 46B as an oil. Yield: 0.5 g (90%). Retention time=2.36 min. (Condition A).

46C. Example 46

Example 46 was prepared as described for Example 1 using acridone acid 1C and compound 46B. Retention time=3.51 min. (Condition A). M$^+$ 493.19

Example 47

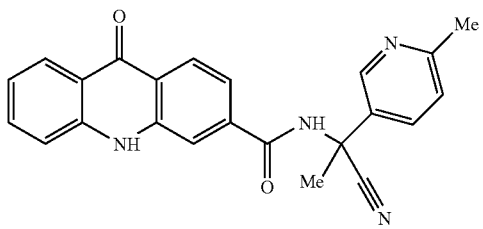

Example 47 was made using the procedure described for Example 41, using 5-acetyl-2-methyl pyridine in place of 4-fluorophenylacetone, and coupling the resultant amine with acridone 1C. Retention time=1.12 min. (Condition A). M+ 401.3

Example 48

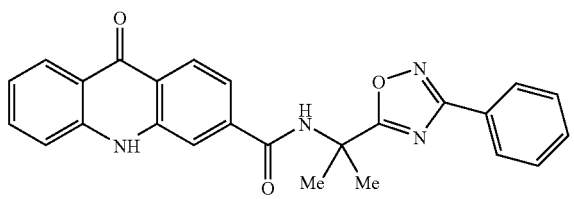

Example 48 was prepared as described for Example 46 using acridone acid 1C and benzamidoxime. Retention time=1.67 min. (Condition E). M+ 425.13.

Example 49

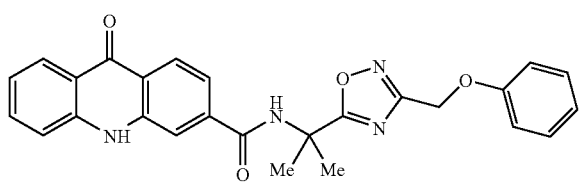

Example 49 was prepared as described for Example 46 using acridone acid 1C and N'-hydroxy-2-phenoxyethanimidamide. Retention time=1.68 min. (Condition E). M+ 455.17.

Example 50

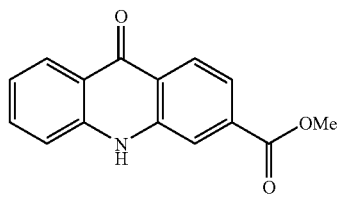

To a solution of acridone acid 1C (0.036 g, 0.150 mmol) in MeOH was added a catalytic amount of sulfuric acid. The reaction mixture was refluxed for 1 h. Purification by preparative HPLC afforded Example 50 as a bright yellow solid. HPLC retention time=2.28 min. (Condition B) and LC/MS M+=254.

Example 51

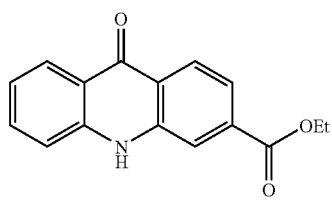

To a solution of acridone acid 1C (0.075 g, 0.314 mmol) in EtOH (8 ml) was added 5 drops of sulfuric acid. The reaction mixture was heated at 70° C. overnight. The solvent was removed under reduced pressure, and the residue was suspended in dilute NaOH. Vacuum filtration of the bright yellow precipitate afforded Example 51. HPLC retention time=3.16 min. (Condition B) and LC/MS M+=268.

Example 52

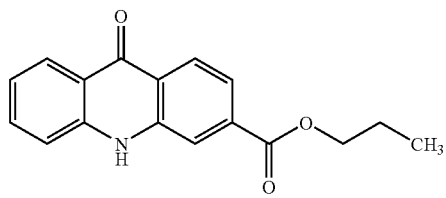

To a solution of acridone acid 1C (0.050 g, 0.209 mmol) in n-propanol was added 5 drops of sulfuric acid. The reaction mixture was heated at 50° C. overnight. The solvent was removed under reduced pressure, and the residue was purified by silica gel chromatography to give Example 52 as a yellow solid. HPLC retention time=3.16 min. (Condition B) and LC/MS M+=268.

Example 53

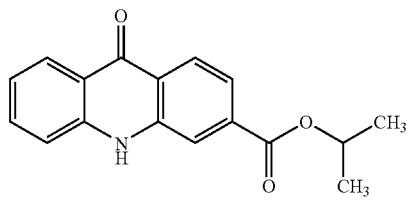

To a solution of acridone acid 1C (0.050 g, 0.209 mmol) in iso-propanol was added 5 drops of sulfuric acid. The reaction mixture was heated at 50° C. overnight. The solvent was removed under reduced pressure, and the residue was purified by silica gel chromatography to give Example 53 as a bright yellow solid. HPLC retention time=3.32 min. (Condition B) and LC/MS M+=282.

Example 54

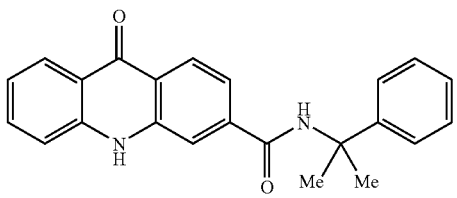

A 4 dram vial containing acridone acid 1C (0.025 g, 0.105 mmol), dimethylaminopyridine (0.014, 0.115 mmol), and 1-[3-dimethylamino)propyl]-3-ethylcarbodiimide hydrochloride (0.022 g, 0.115 mmol) in 1.5 mL of anhydrous DMF was placed in a shaker at 235 rpm and heated overnight at 70° C. The mixture was diluted with ~2 mL of EtOAc, washed with 1M HCl, washed with 1 M NaOH, and washed with water. The organic layer was dried over anhydrous sodium sulfate, concentrated under reduced pressure, and purified by preparative HPLC to give Example 54 as a yellow solid. HPLC retention time=3.13 min. (Condition B) and LC/MS $M^+$=357.

Examples 55-77

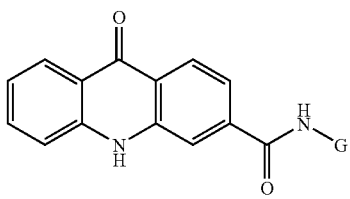

Compounds having the above formula wherein G has the values listed in Table 3 were prepared using a method analogous to that described for Example 54, using commercially available amines. The compounds were submitted after work up or purified by preparative HPLC.

TABLE 3

| Ex. No | —G | HPLC time (min.)/ Condition $M^+$ |
|---|---|---|
| 55 | —Me | 2.28/B 253 |
| 56 | —CH₂Me | 2.43/B 267 |
| 57 | —(CH₂)₂Me | 2.65/B 281 |
| 58 | —(CH₂)₃Me | 2.94/B 295 |
| 59 | —CH₂CH₂CH(Me)Me | 3.18/B 309 |
| 60 | —CH₂CH(Me)CH₂Me | 3.12/B 309 |
| 61 | —CH(Me)CH₂CH₂Me | 3.04/B 309 |
| 62 | —cyclopentyl | 2.91/B 307 |
| 63 | —(CH₂)₅Me | 3.42/B 323 |
| 64 | —(CH₂)₃OMe | 2.54/A 311 |
| 65 | —CH₂-(2-pyridyl) | 1.83/A 330 |
| 66 | —(CH₂)₂-(2-pyridyl) | 1.79/A 344 |
| 67 | —CH₂-(5-methyl-2-furyl) | 2.93/A 333 |
| 68 | —C(Me)₃ | 2.82/A 295 |
| 69 | —(4-methylcyclohexyl) | 3.35/A 335 |
| 70 | —CH₂-(2-furyl) | 2.69/A 319 |
| 71 | —CH₂CH(Me)Me | 2.87/A 295 |
| 72 | —CH₂-(4-(2-methyl-2-propyl)phenyl) | 3.72/A 385 |

TABLE 3-continued

| Ex. No | —G | HPLC time (min.)/ Condition M+ |
|---|---|---|
| 73 | 4-pyridylmethyl | 1.75/A 330 |
| 74 | benzyl | 2.98/A 329 |
| 75 | 1-phenylethyl | 3.04/A 343 |
| 76 | (R)-1-phenylethyl | 3.03/A 343 |
| 77 | (S)-1-phenylethyl | 3.02/A 343 |

Example 78

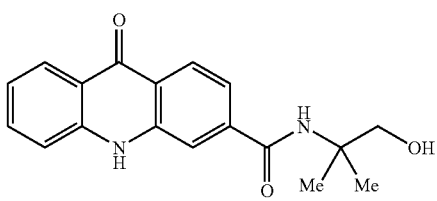

To a mixture of acridone acid 1C (0.282 g, 1.18 mmol) and 2-amino-2-propanol (0.17 mL, 1.77 mmol) in 3 mL of anhydrous DMF was added triethylamine followed by BOP-Cl (0.450 g, 1.77 mmol). The reaction mixture was stirred at room temperature for 2.5 h. Water was added, and the precipitated product was collected by vacuum filtration and purified by preparative HPLC to give 0.280 g (77%) of Example 78 as a bright yellow solid. HPLC retention time=2.48 min. (Condition B) and LC/MS $M^{+1}$=311.

Example 79

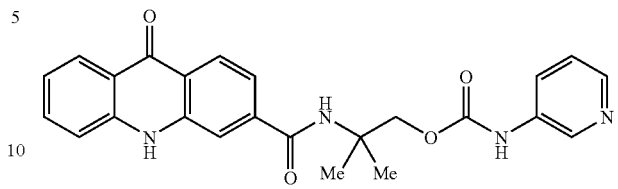

A mixture of 3-aminopyridine (0.006 g, 0.064 mmol) and carbondiimidazole (0.010 g, 0.064 mmol) in 1 mL of DCM was stirred for 1 h at room temperature. The DCM was removed under reduced pressure, and Example 78 (0.020 g, 0.064 mmol), triethylamine (0.02 mL, 0.129 mmol), and 1 mL of DMF were added. The reaction mixture was heated at 70° C. overnight. Concentration followed by purification by silica gel chromatography gave 5.6 mg of Example 79 as a pale yellow solid. HPLC retention time=2.25 min. (Condition B) and LC/MS $M^{+1}$=431.

Example 80

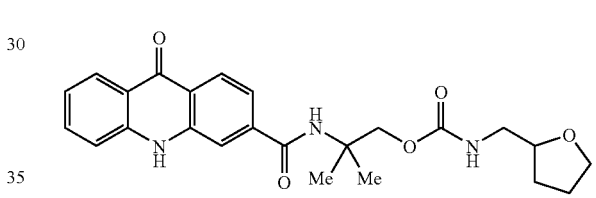

Example 80 was prepared using a method analogous to that described for Example 79. HPLC retention time=2.81 min. (Condition B) and LC/MS $M^{+1}$=438.

Example 81

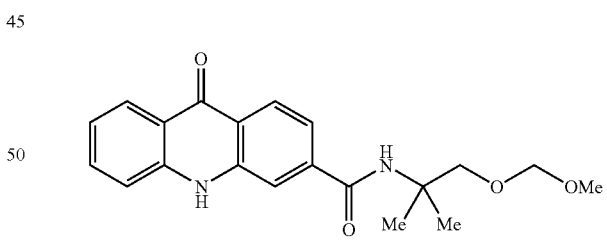

To a mixture of Example 78 (0.010 g, 0.032 mmol) and 60% sodium hydride (1.3 mg, 0.032 mmol) in 4 mL of anhydrous THF at room temperature was added chloromethyl methyl ether (2.5 µL, 0.032 mmol). The reaction mixture was heated at 45-55° C. for 4 h, quenched with water, and extracted with EtOAc. The organic layer was washed with water, washed with dilute sodium hydroxide, and dried over anhydrous sodium sulfate. Concentration under reduced pressure followed by purification by silica gel chromatography afforded Example 81 as a yellow solid. HPLC retention time=2.79 min. (Condition B) and LC/MS $M^{+1}$=355.

Example 82

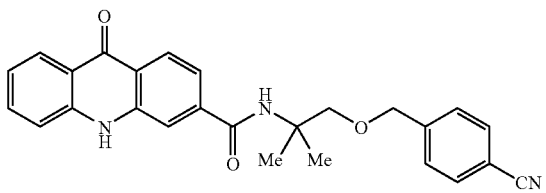

A mixture of Example 78 (0.020 g, 0.064 mmol) and 60% sodium hydride (2.8 mg, 0.071 mmol) in 3 mL of anhydrous THF (or DMF) was stirred at room temperature for 15 min. 4-cyano-benzylbromide (0.014 g, 0.071 mmol) was added, and the mixture was stirred at room temperature for 2 h, quenched with a saturated solution of ammonium chloride, and extracted with EtOAc. The organic layer was collected and dried over anhydrous sodium sulfate. Concentration under reduced pressure followed by purification by silica gel chromatography afforded 8.8 mg of Example 82 as a bright yellow solid. HPLC retention time=3.18 min. (Condition B) and LC/MS $M^{+1}$=426.

Examples 83-85

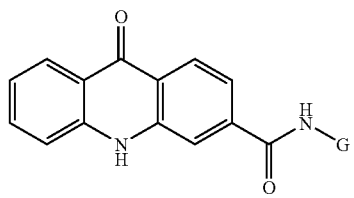

Compounds having the above formula wherein G has the values listed in Table 4 were prepared using a method analogous to the method described for Example 82 using commercially-available bromides and Example 78. The compounds were purified by silica gel chromatography or by preparative HPLC.

TABLE 4

| Ex. No | —G | HPLC time (min.)/ Condition $M^+$ |
|---|---|---|
| 83 | ![Me Me O-CH2-Ph] | 3.49/B 402 |
| 84 | ![Me Me O-CH2-Ph-CN (ortho)] | 3.26/B 426 |
| 85 | ![Me Me O-CH2-Ph-CN (meta)] | 3.20/B 426 |

Example 86

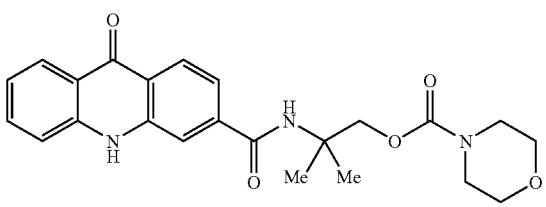

A mixture of Example 78 (0.020 g, 0.064 mmol), morpholine carbonyl chloride (8.2 μL, 0.071 mmol), and triethylamine (9.9 mL, 0.071 mmol) in anhydrous THF was stirred for 30 min. No reaction was observed. An additional equivalent of the morpholine carbonyl chloride and 60% sodium hydroxide (0.071 mmol) was added. The mixture was stirred at room temperature for 40 min and quenched with water (2-3 drops). Concentration under reduced pressure followed by purification by silica gel chromatography afforded 12.1 mg of Example 86 as a yellow solid. HPLC retention time=2.73 min. (Condition B) and LC/MS $M^{+1}$=424.

Example 87

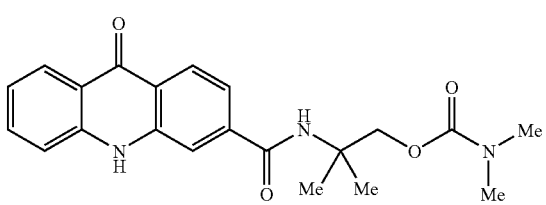

Example 87 was prepared using a method analogous to the method described for Example 86 using a commercially available isocyanate and Example 78. HPLC retention time=2.82 min. (Condition B) and LC/MS $M^{+1}$=382.

Example 88

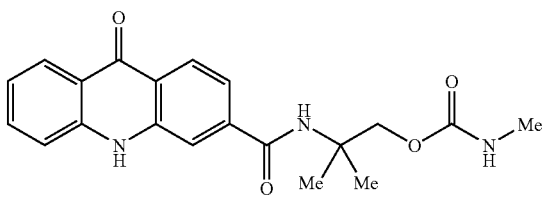

A mixture of Example 78 (0.026 g, 0.084 mmol), potassium carbonate (0.013 g, 0.092 mmol), and methyl isocyanate (5.3 mg, 0.092 mol) in a mixture of acetonitrile (4 mL) and DMF (0.5 mL) was heated at 50° C. overnight. The reaction was only 30% complete by analytical HPLC, so an additional 1.5 equivalents of the isocyanate was added. The reaction mixture was heated for an additional 1 h, at which point the reaction was complete. The mixture was filtered, the filtrated was concentrated under reduced pressure, and the residue was purified by silica gel chromatography to give 7.6 mg of Example 88 as a bright yellow solid. HPLC retention time=2.63 min. (Condition B) and LC/MS $M^{+1}$=368.

Example 89-92

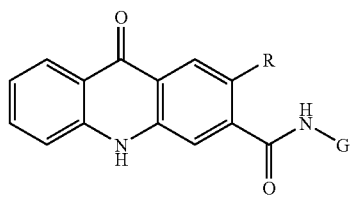

Examples 89-92 having the above formula wherein G has the values listed in Table 5, were prepared using a method analogous to that described for Example 88 using commercially-available isocyanates and Example 78. The compounds were purified by silica gel chromatography or by preparative HPLC.

TABLE 5

| Ex. No | —G | HPLC time (min.)/Condition $M^+$ |
|---|---|---|
| 89 | ![structure] | 3.18/B 430 |
| 90 | ![structure with CN] | 3.18/B 455 |
| 91 | ![structure with Me] | 3.32/B 444 |
| 92 | ![structure with OMe] | 3.17/B 460 |

Example 93

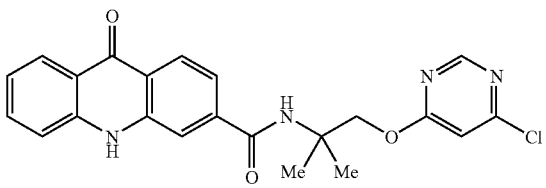

To a suspension of 60% sodium hydride (0.008 g, 0.209 mmol) in 3 mL of anhydrous DMF was added Example 78. The mixture was stirred for 10 min. at room temperature. 4,6-dichloropyrimidine was added, and the reaction mixture was heated at 60° C. overnight, diluted with DCM, and quenched with ammonium chloride. Water was added, and the organic layer was collected, washed with a 1N aqueous sodium hydroxide solution, and dried over anhydrous sodium sulfate. Concentration followed by purification by silica gel chromatography provided 50 mg of Example 93 as a bright yellow solid. HPLC retention time=3.12 min. (Condition B) and LC/MS $M^{+1}$=423.

Example 94

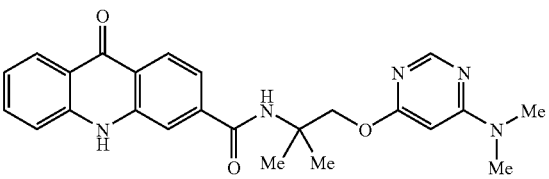

A mixture of Example 93 (0.029 g, 0.069 mmol) and 4 mL of a 2.0 M solution of dimethylamine in THF in a sealed tube was heated at 75° C. overnight. The solvent was removed under reduced pressure and the residue was purified by silica gel chromatography to give 12 mg of Example 94 as a bright yellow solid. HPLC retention time=2.40 min. (Condition B) and LC/MS $M^{+1}$=432.

Examples 95-102

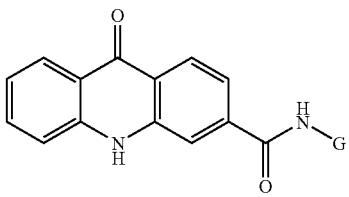

Compounds having the above formula wherein G has the values listed in Table 6 were prepared using a method analogous to that described for Example 93, using commercially-available heterocyclic chlorides and Examples 25 and 78. The compounds were purified by silica gel chromatography or by preparative HPLC.

TABLE 6

| Ex. No | —G | HPLC time (min.)/Condition M+ |
|---|---|---|
| 95 | pyrimidine-OCH2C(Me)2- with 2-Cl | 3.05/B 423 |
| 96 | pyrimidine-OCH2C(Me)2- | 2.82/B 389 |
| 97 | pyrazine-OCH2C(Me)2- | 2.91/B 389 |
| 98 | pyridine-OCH2C(Me)2- | 3.02/B 388 |
| 99 | 6,7-dimethoxy-2-chloroquinazoline-4-OCH2C(Me)2- | 3.48/B 534 |
| 100 | 4,6-dimethoxypyrimidine-2-OCH2C(Me)2- | 3.32/B 449 |
| 101 | pyrimidine-2-OCH2-(cyclopentyl)- | 3.05/B 415 |
| 102 | 6-chloropyrimidine-4-OCH2-(cyclopentyl)- | 3.29/B 449 |

Example 103

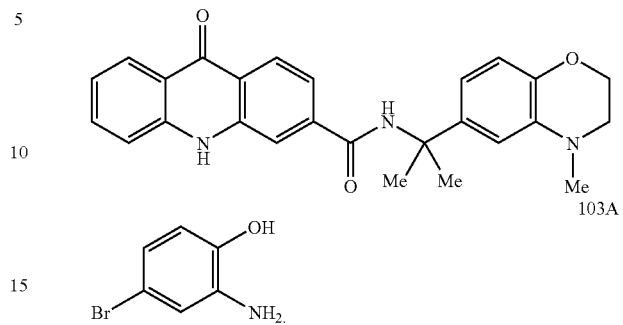

103A

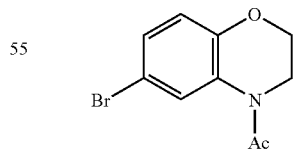

To a mixture of stannous chloride dihydrate (0.025 g, 110.0 mmol and concentrated hydrochloric acid (55 mL) in 100 mL of MeOH at ~15° C. was added 4-bromo-2-nitrophenol. The reaction mixture was stirred overnight at room temperature. The mixture was diluted with EtOAc, and the pH was adjusted to 7.0 with saturated sodium bicarbonate. The mixture was filtered through Celite, and the organic layer was collected, dried over anhydrous sodium sulfate, and concentrated under reduced pressure to give 3.49 g (81%) of 103A as a white solid. HPLC retention time=0.657 min. (Condition B)and LC/MS $M^{+1}$=189.

103B

A mixture of 103A (2.70 g, 14.4 mmol) and several drops of pyridine in 75 mL of acetic anhydride was heated at reflux for 5 min., stirred for an additional 5 min., and cooled to 0° C. The resulting precipitate was filtered under reduced pressure and washed with hexane to the bis-acetate. The solid was then stirred in a 1M aqueous solution of sodium hydroxide (39 mL) until the mixture became homogeneous. The solution was poured into a mixture of crushed ice (19 g) and 6 M aqueous hydrochloric acid (8 mL). The resulting solid was collected by vacuum filtration to give 103B (3.11 g, 94%) as a white solid.

103C.

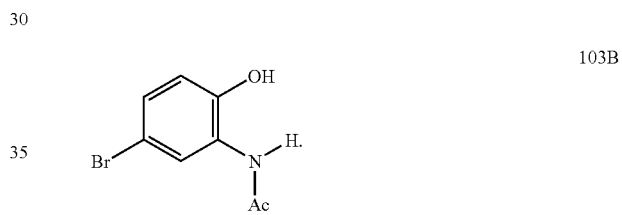

A mixture of 103B (2.21 g, 9.61 mmol), 1,2-dibromoethane (3.3 mL, 38.4 mmol), sodium hydroxide (1.54 g, 38.4 mmol), and Aliquat 336 (0.50 g) in 20 mL of DCM and 12 mL of acetonitrile was stirred at room temperature for 3 days. The reaction mixture was filtered, and the precipitate was washed with ether. The filtrate was concentrated under reduced pressure, and the residue was purified by silica gel chromatography to give 2.20 g (89%) of 103C as a white solid. HPLC retention time=2.74 min. (Condition B) and LC/MS M$^{+1}$=256.

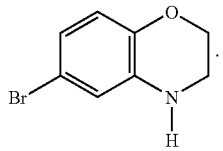

103D

A mixture of the bromobenzoxazine (1.0 g, 3.90 mmol) and potassium hydroxide (1.40 g, 25.0 mmol) in 5 mL of MeOH and 2.5 mL of water was heated at 55° C. for 30 min. The reaction mixture was poured over crushed ice and extracted with ether. The organic layer was collected, washed with brine, and dried over anhydrous sodium sulfate. Concentration under reduced pressure afforded 0.734 g of 103D as an off-white solid. HPLC retention time=2.63 min. (Condition B) and LC/MS M$^{+1}$=214/216.

103E.

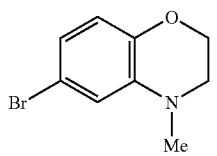

To a mixture of 103D (0.734 g, 3.43 mmol) and aqueous formaldehyde (0.51 mL of a 37% solution, 6.86 mmol) in 30 mL of acetonitrile at room temperature was added sodium cyanoborohydride (0.345 g, 5.49 mmol). The reaction mixture was stirred at room temperature for 25 min., and 3-4 drops of acetic acid was added. The mixture was stirred overnight, poured into ether, and washed with 1M aqueous sodium hydroxide followed by brine. The organic layer was collected, dried over anhydrous sodium sulfate, and concentrated under reduced pressure. HPLC indicated that the crude mixture contained a 2:1 mixture of 103E:103D. Purification of a portion of the crude product afforded 0.300 g of 103E as a white semi-solid. HPLC retention time=3.36 min. (Condition B) and LC/MS M$^{+1}$=229/230.

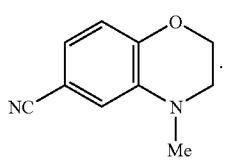

103F

A mixture of 103E (0.210 g, 0.921 mmol), tris(dibenzylideneacetone)dipalladium(0) (0.051 g, 0.056 mmol), 1,1'-bis(diphenylphosphino)ferrocene (0.061 g, 0.111 mmol), zinc powder (0.007 g, 0.134 mmol), and zinc cyanide (0.065 g, 0.553 mmol) was flushed with nitrogen. Dimethyl acetamide (3.0 mL) was added, and the resulting mixture was heated at 150° C. overnight. HPLC indicated that the reaction was complete. The reaction mixture was cooled to room temperature, diluted with EtOAc, and washed with 2N aqueous ammonium hydroxide, washed with brine, and dried over anhydrous sodium sulfate. Concentration under reduced pressure followed by purification by silica gel chromatography using a 30% mixture of EtOAc and hexane afforded 103F (0.80 g) as a white solid. HPLC retention time=2.54 min. (Condition B) and LC/MS M$^{+1}$=175.

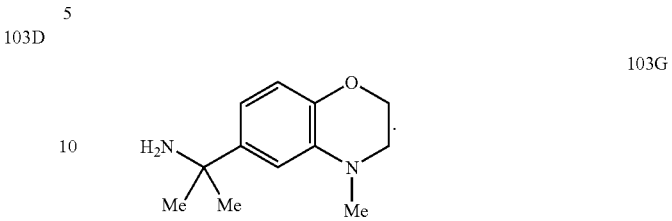

103G

To a flame-dried flask under nitrogen was added cerium chloride (0.226 g, 0.918 mmol) followed by anhydrous THF (7 mL). The mixture was stirred vigorously for 2 h, during which time the cerium chloride became suspended. The suspension was cooled to −78° C., and methyl lithium (0.99 mL, 1.38 mmol, 1.4 M in ether) was added dropwise. After the addition was complete, the reaction mixture was stirred for 0.5 h at −78° C. Compound 103F (0.080 g, 0.459 mmol) in THF (5 mL) was added via cannula to the −78° C. solution. The dry-ice bath was removed, and the reaction mixture was stirred at room temperature overnight. The mixture was quenched with a few drops of a saturated aqueous solution of ammonium chloride, and a 2M aqueous solution of ammonium hydroxide was added dropwise until a precipitate formed and settled to the bottom of the flask. The mixture was filtered through Celite under reduced pressure, diluted with DCM, washed with water, and dried over anhydrous sodium sulfate. Concentration under reduced pressure afforded 103G (0.94 g) as an oil. HPLC retention time=1.47 min. (Condition B) and LC/MS M$^{+1}$=191 (M$^{+1}$-CH$_3$).

103H. Example 103

To a mixture of acridone acid 1C (0.025 g, 0.105 mmol), 103G (0.022 g, 0.105 mmol), and triethylamine (0.03 mL, 0.210 mmol) was added BOP-Cl (0.027 g, 0.105 mmol) in 4 mL of anhydrous DMF at room temperature. The reaction mixture was stirred at room temperature overnight. The mixture was diluted with DCM, washed with water, washed with 1N aqueous sodium hydroxide (3×), and dried over anhydrous sodium sulfate. Concentration under reduced pressure followed by purification by silica gel chromatogrpahy afforded Example 103 (0.012 g) as a bright yellow solid. HPLC retention time=3.10 min. (Condition B) and LC/MS M$^{+1}$=428.

Example 104

9-oxo-9,10-dihydro-acridine-3-carboxylic acid [1-methyl-1-(4-methyl-3,4-dihydro-2H-benzo[1,4] oxazin-7-yl)-ethyl]-amide

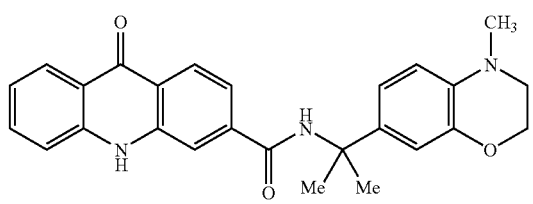

104A. 2-Methylamino-phenol

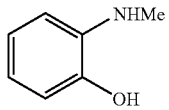

To a stirred suspension of sodium borohydride (4.77 g, 126.0 mmol) and benzoxazole (5.00 g, 42.0 mmol) in THF (150 mL) was added ~1 mL of acetic acid. The reaction mixture was stirred overnight at room temperature and concentrated to dryness under reduced pressure. The excess sodium borohydride was decomposed with saturated aqueous ammonium chloride and extracted with EtOAc. The organic layer was collected, washed with water, washed with brine, and dried over anhydrous sodium sulfate. Concentration under reduced pressure afforded 104A in near quantitative yield. HPLC retention time=0.34 min. (Condition B). $^1$H-NMR (500 MHz, d$^6$-DMSO) δ 2.69 (s, 3H), 4.70 (brs, 1H), 6.40-6.42 (m, 2H), 6.63-6.66 (m, 2H), and 9.12 (brs, 1H).

104B. 4-Methyl-3,4-dihydro-2H-benzo[1,4]oxazine

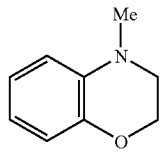

To a mixture of 104A (2.33 g, 18.9 mmol) and dibromoethane (6.5 mL, 75.7 mmol) in a mixture of acetone (80 mL) and water (20 mL) at room temperature was added potassium carbonate (10.46 g, 75.7 mmol). The mixture was heated at reflux for 3 days. HPLC indicated that the reaction was complete, and the acetone was removed under reduced pressure. The aqueous residue was extracted with DCM, washed with water, and dried over anhydrous sodium sulfate. Concentration under reduced pressure followed by purification by silica gel chromatography afforded 104B (2.22 g, 79%). HPLC retention time=2.07 min. (Condition B) and LC/MS M$^{+1}$=150.08. $^1$H-NMR (500 MHz, CDCl$_3$) δ 2.91 (s, 3H), 3.28 (t, 2H), 4.33 (t, 2H), 6.70 (t, 1H, J=7.5 Hz), 6.72 (d, 1H, J=7.5 Hz), 6.82 (d, 1H, J=7.5 Hz), and 6.89 (t, 1H, J=7.5 Hz).

104C. 7-Bromo-4-methyl-3,4-dihydro-2H-benzo[1,4]oxazine

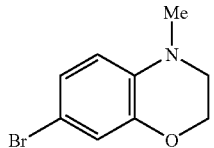

A mixture of the 104B (0.225 g, 1.51 mmol) and N-bromosuccinimide (0.269 g, 1.51 mmol) in DMF (10 mL) was heated at 80° C. overnight. The reaction mixture was dissolved in DCM and washed with water several times. The organic layer was collected, dried over anhydrous sodium sulfate, and concentrated under reduced pressure. The residue was purified by silica gel chromatography to give 0.267 g (78%) of 104C. HPLC retention time=3.32 min. (Condition B) and LC/MS M$^{+1}$=230.03 (d). $^1$H-NMR (500 MHz, CDCl$_3$) δ 2.83 (s, 3H), 3.22 (t, 2H), 4.26 (t, 2H), 6.49 (d, 1H, J=8.8 Hz), 6.87 (s, 1H), and 6.90 (d, 1H, J=8.8 Hz).

104D. 4-Methyl-3,4-dihydro-2H-benzo[1,4]oxazine-7-carbonitrile

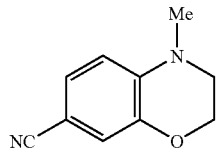

A mixture of 104C (0.255 g, 1.12 mmol), tris(dibenzylideneacetone)dipalladium(0) (0.061 g, 0.067 mmol), 1,1'-bis(diphenylphosphino)ferrocene (0.075 g, 0.134 mmol), zinc powder (0.009 g, 0.134 mmol), and zinc cyanide (0.079 g, 0.672 mmol) was flushed with nitrogen. Dimethyl acetamide (3.5 mL) was added, and the resulting mixture was heated at 150° C. overnight. HPLC indicated that the reaction was complete. The reaction mixture was cooled to room temperature, diluted with EtOAc, and washed with 2N aqueous ammonium hydroxide, washed with brine, and dried over anhydrous sodium sulfate. Concentration under reduced pressure followed by purification by silica gel chromatography using a 30% mixture of EtOAc and hexane afforded 104D (0.107 g, 55%) as a white solid. HPLC retention time=2.48 min. (Condition B) and LC/MS M$^{+1}$=175. $^1$H-NMR (500 MHz, CDCl$_3$) δ 2.94 (s, 3H), 3.37 (t, 2H), 4.23 (t, 2H), 6.55 (d, 1H, J=10.5 Hz), 6.95 (s, 1H), and 7.10 (d, 1H, J=10.5 Hz).

104E. 1-Methyl-1-(4-methyl-3,4-dihydro-2H-benzo[1,4]oxazin-7-yl)-ethylamine

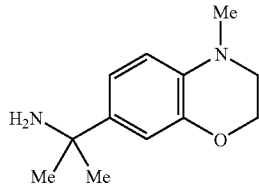

To a flame-dried flask under nitrogen was added cerium chloride (0.294 g, 1.19 mmol) followed by anhydrous THF (9 mL). The mixture was stirred vigorously for 2 h, during which time the cerium chloride became suspended. The suspension was cooled to −78° C., and methyl lithium (1.28 mL, 1.79 mmol, 1.4 M in ether) was added dropwise. After the addition was complete, the reaction mixture was stirred for 0.5 h at −78° C. Compound 104D (0.104 g, 0.597 mmol) in THF (5 mL) was added via cannula to the −78° C. solution. The dry-ice bath was removed, and the reaction mixture was stirred at room temperature overnight. The mixture was quenched with a few drops of a saturated aqueous solution of ammonium chloride, and a 2M aqueous solution of ammonium hydroxide was added dropwise until a precipitate formed and settled to the bottom of the flask. The mixture was filtered through Celite under reduced pressure, diluted with DCM, washed with water, and dried over anhydrous sodium sulfate. Concentration under reduced pressure afforded 104E (0.112 g, 91%) as an oil. HPLC retention time=1.44 min. (Condition B) and LC/MS M$^{+1}$=191.15 (M$^{+1}$-CH$_3$).

104F. Example 104

To a mixture of 104E (0.022 g, 0.105 mmol), acridone acid 1C (0.025 g, 0.105 mmol), and triethylamine (0.03 mL, 0.210 mmol) was added N,N-N,N-bis(2-oxo-3-oxazolidinyl)phosphorodiamidic chloride (0.027 g, 0.105 mmol) in 4 mL of anhydrous DMF at room temperature. The reaction mixture was heated at 50° C. overnight. The mixture was cooled, diluted with DCM, washed with water, washed with 1N aqueous sodium hydroxide (3x), and dried over anhydrous sodium sulfate. Concentration under reduced pressure followed by purification by preparative HPLC afforded 18 mg of Example 104 as a yellow solid. HPLC retention time=3.03 min (condition B) LC/MS $M^{+1}$=428.

Example 105

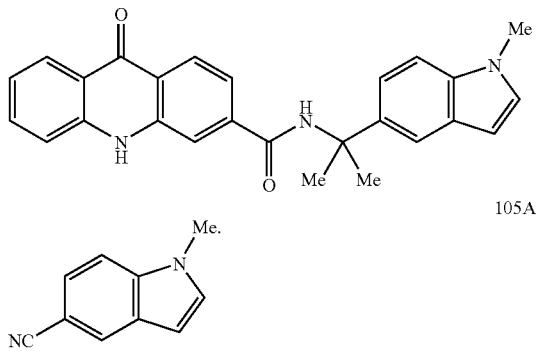

105A

To mixture of 5-cyanoindole (0.500 g, 3.52 mmol) in THF at 0° C. was added 60% sodium hydride (0.155 g; 3.87 mmol). After 4 min., iodomethane (0.26 mL, 4.22 mmol) was added, and the reaction mixture was warmed to room temperature. The reaction was quenched and worked up to give a quantitative yield of compound 105A. HPLC retention time=2.27 min. (Condition B).

105B. Example 105

Example 105 was prepared using a reaction sequence analogous to the procedure described for Example 104 starting with compound 105A. HPLC retention time=3.27 min. (Condition B) and LC/MS $M^{+1}$=410.

Example 106

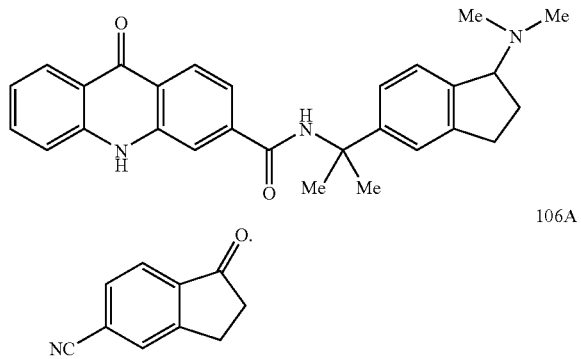

106A

To a flame-dried flask under nitrogen containing 5-bromoindanone (0.500 g, 2.37 mmol) and anhydrous DMF was added tetrkis(triphenylphosphine)-palladium(0) (0.137 g, 0.118 mmol), zinc cyanide (0.167 g, 1.42 mmol), and copper iodide (0.045 g, 0.237 mmol), with vigorous stirring. The reaction mixture was heated at 85° C. overnight, quenched with 3 drops of water, and diluted with toluene (100 mL). The mixture was washed with 2N aqueous ammonium hydroxide, washed with water, washed with brine and dried over anhydrous sodium sulfate. Concentration under reduced pressure afforded 0.345 g (93%) of compound 106A.

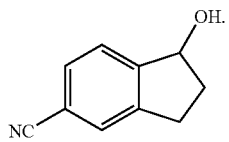

106B

A mixture of compound 106A (0.340 g, 2.16 mmol) and sodium borohydride (0.021 g, 0.541 mmol) in EtOH was stirred for 4 h at room temperature. The mixture was diluted with ether and washed with water. The organic layer was collected, dried over magnesium sulfate, and concentrated under reduced pressure to give a quantitative yield of 106B.

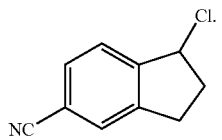

106C

To a solution of compound 106B (0.167, 1.05 mmol) in DCM at 0° C. was added thionyl chloride (0.38 mL, 5.25 mmol) slowly. After the addition was complete, the reaction mixture was stirred at 0° C. for 5 min. and was then allowed to warm to room temperature. The reaction was quenched with water, and the organic layer was collected, dried, and concentrated to give compound 106C.

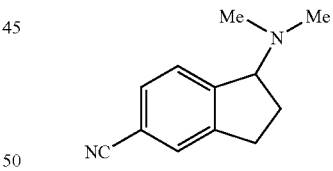

A mixture of compound 106C (110 g, 0.619 mmol) and dimethylamine (3.0 mL of a 2M solution in MeOH) in toluene in a sealed tube was heated at 100° C. for 1 h. The excess amine and MeOH were removed under reduced pressure, and the remaining residue was diluted with ether and extracted with 1N aqueous hydrochloric acid. The aqueous layer was made basic with 1N aqueous sodium hydroxide and extracted with DCM. The organic layer was collected, dried, and concentrated to give 55 mg of compound 106D.

106E. Example 106

Example 106 was prepared using a reaction sequence analogous to the procedure described for Example 105 using nitrile 106D. HPLC retention time=2.30 min. (Condition B) and LC/MS $M^{+1}$=440.

Example 107

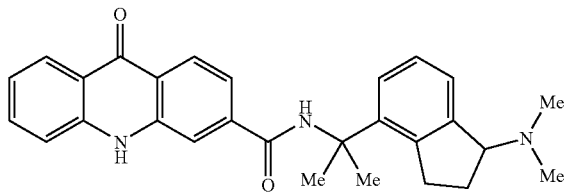

Example 107 was prepared using a reaction sequence analogous to the procedure described for Example 106 starting with 4-bromoindanone. HPLC retention time=2.23 min. (Condition B) and LC/MS $M^{+1}$=424 ($M^{+1}$-Me).

Example 108

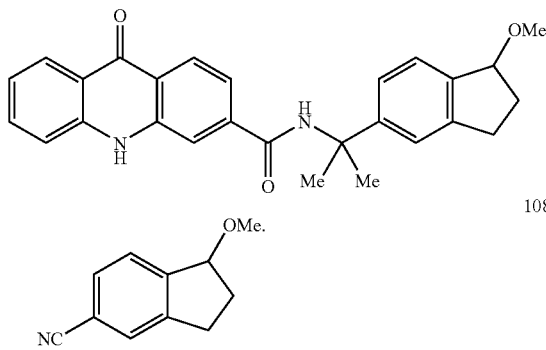

To a suspension of 60% sodium hydride (0.281 g, 7.04 mmol) in THF at room temperature was added compound 106B (0.500 g, 2.34 mmol). The mixture was stirred until hydrogen evolution ceased. Iodomethane (0.73 mL, 11.7 mmol) was added, and the reaction mixture was stirred for 4 h and quenched with water. The solvent was removed under reduced pressure, and the residue was dissolved in DCM, washed with water, dried, and concentrated to give compound 108A.

108B. Example 108

Example 108 was prepared using a reaction sequence analogous to that described for Example 105 using nitrile 108A. HPLC retention time=3.22 min. (Condition B) and LC/MS $M^{+1}$=427.

Example 109

9,10-Dihydro-N-[1-(4-hydroxy)phenyl]-1-methylethyl]-9-oxo-3-acridinecarboxamide

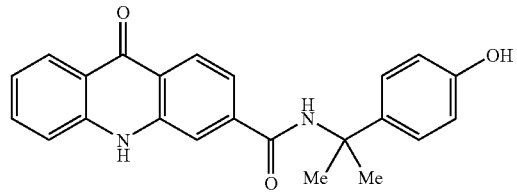

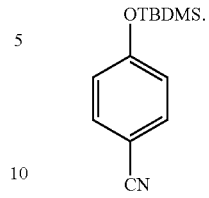

To a solution of 4-cyanophenol (3.57 g, 30 mmol) and TBDMSCl (4.97 g, 33 mmol) in DMF (30 ml) was added imidazole (3.06 g, 45 mmol). The reaction mixture was stirred overnight, water was added, and white solid product precipitated, which was filtered, washed with water and dried to give 6.3 g (90%) of compound 109A. HPLC retention time=3.88 min. (Condition A) $^1$H-NMR (400 MHz, CDCl$_3$) δ 7.44 (d, J=8.79 Hz, 2H), 6.78 (d, J=8.79 Hz, 2H), 0.88 (s, 9H), 0.13 (s, 6H)

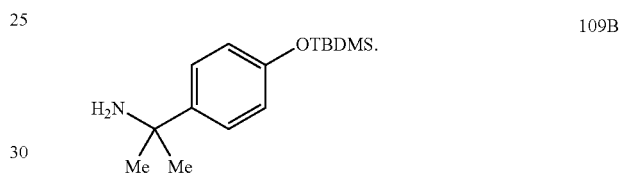

Using the cerium chloride procedure described for making compound 1D and nitrile 109A, the corresponding amine 109B was prepared as a yellow solid. (HPLC retention time=3.21 min. (Condition A). $^1$H-NMR (400 MHz, CDCl$_3$) δ 7.25 (d, J=8.79 Hz, 2H), 6.69 (d, J=8.79 Hz, 2H), 1.40 (s, 6H), 0.88 (s, 9H), 0.096 (s, 6H)

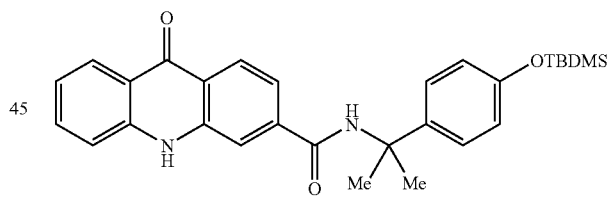

Using acridone acid 1C with compound 109B and a route analogous to that described for Example 1, Compound 109C was prepared as a yellow solid. HPLC retention time=4.04 min. (Condition A) and LC/MS $M^+$+1=487.

109D. Example 109

To a solution of compound 109C (240 mg, 0.49 mmol) in THF (10 ml) was added a solution of 1.0 M TBAF in THF (0.59 ml, 0.59 mmol). The mixture was stirred at room temperature overnight. THF was removed and water was added. A yellow solid precipitated and was filtered, washed with water and Et$_2$O, and dried to give 170 mg of Example 109. HPLC retention time=2.62 min. (Condition A) and LC/MS $M^+$+1=373. Alternatively, Example 109 can be prepared from Example 16, following the method described for making Example 23 from Example 15.

Example 110

9,10-Dihydro-N-[1-[4-(2-methoxyethoxy)phenyl]-1-methylethyl]-9-oxo-3-acridinecarboxamide

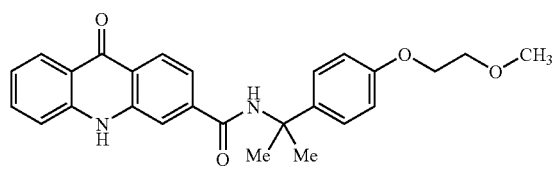

To a solution of Example 109 (15 mg, 0.04 mmol) and PPh$_3$ (21 mg, 0.08 mmol) in THF (1 ml) was added 2-methoxyethanol (6.1 mg, 0.08 mmol) followed by DEAD (14 mg, 0.08 mmol). The reaction mixture was stirred overnight. Solvent was removed, the residue was purified by silica gel column eluting with EtOAc, and 8 mg of Example 110 was obtained as a yellow solid. HPLC retention time=2.94 min. (Condition A) and LC/MS M$^+$+1=431.

Examples 111-115

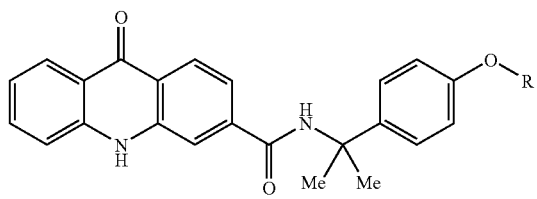

Compounds having the above formula wherein R has the values listed in Table 7 were prepared from Example 109 using a route analogous to that described above for Example 110, using the corresponding alcohol R—OH, in place of 2-methoxyethanol. If the products carry basic moieties, they were purified by preparative HPLC.

TABLE 7

| Ex. No | —R | Compound name | HPLC time (min)/ Condition | M$^+$ |
|---|---|---|---|---|
| 111 | Me-N(Me)-CH$_2$CH$_2$- | N-[1-[4-[2-(Dimethylamino)ethoxy]phenyl]-1-methylethyl]-9,10-dihydro-9-oxo-3-acridinecarboxamide | 2.39/A | 444 |
| 112 | (2S)-1-methyl-2-pyrrolidinylmethyl | 9,10-Dihydro-N-[1-methyl-1-[4-[((2S)-1-methyl-2-pyrrolidinyl)methoxy]phenyl]ethyl]-9-oxo-3-acridinecarboxamide | 2.49/A | 470 |
| 113 | 1-methyl-3-piperidinyl | 9,10-Dihydro-N-[1-methyl-1-[4-[(1-methyl-3-piperidinyl)oxy]phenyl]ethyl]-9-oxo-3-acridinecarboxamide | 2.48/A | 470 |
| 114 | Me$_2$N(Me)-CH(Me)-CH$_2$CH$_2$- | 9,10-Dihydro-N-[1-methyl-1-[4-[2-[methyl(1-methylethyl)amino]ethoxy]phenyl]ethyl]-9-oxo-3-acridinecarboxamide | 2.46/A | 472 |
| 115 | 1-pyrrolidinyl-CH$_2$CH$_2$- | 9,10-Dihydro-N-[1-methyl-1-[4-[2-(1-pyrrolidinyl)ethoxy]phenyl]ethyl]-9-oxo-3-acridinecarboxamide | 2.44/A | 470 |

Examples 116-118

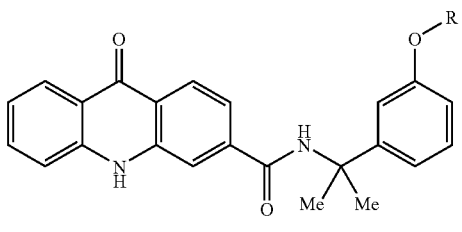

Compounds having the above formula wherein R has the values listed in Table 8 were prepared from Example 23 using a route analogous to that described above for Example 110, using the corresponding alcohol R—OH, in place of 2-methoxyethanol. If the products carry basic moieties, they were purified by preparative HPLC.

TABLE 8

| No | —R | Compound name | HPLC time (min)/ Condition | M$^+$ |
|---|---|---|---|---|
| 116 | Me-N(Me)-CH$_2$CH$_2$- | N-[1-[3-[2-(Dimethylamino)ethoxy]phenyl]-1-methylethyl]-9,10-dihydro-9-oxo-3-acridinecarboxamide | 2.40/A | 444 |
| 117 | (2S)-1-methyl-2-pyrrolidinylmethyl | 9,10-Dihydro-N-[1-methyl-1-[3-[((2S)-1-methyl-2-pyrrolidinyl)methoxy]phenyl]ethyl]-9-oxo-3-acridinecarboxamide | 2.50/A | 470 |
| 118 | tetrahydro-3-furanyl | 9,10-Dihydro-N-[1-methyl-1-[3-[(tetrahydro-3-furanyl)methoxy]phenyl]ethyl]-9-oxo-3-acridinecarboxamide | 3.09/A | 457 |

Example 119

Dimethylcarbamic acid, 4-[1-[[(9,10-dihydro-9-oxo-3-acridinyl)carbonyl]amino]-1-methylethyl]phenyl ester

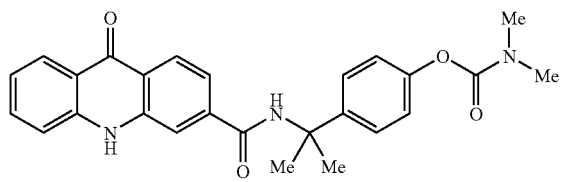

Using the method described above for the making of Example 24 but using Example 109 in place of Example 23, the above Example 119 was prepared as a yellow solid. HPLC retention time=2.96 min. (Condition A) and LC/MS $M^++1=444$.

Examples 120-127

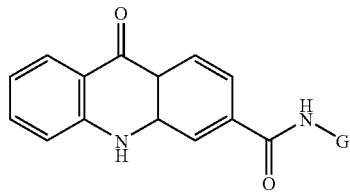

Compounds having the above formula wherein G has the values listed in Table 9 were prepared from acridone acid 1C as described above for Example 1, using the corresponding amines in place of compound 1D in Step E. Amines used to prepare Examples 124 and 126 were prepared in an analogous manner as described below for Examples 299 and 300, below, and the corresponding sulfonyl groups prepared as described for Example 301.

TABLE 9

| Ex. No | —G | Compound name | HPLC time (min)/ Condition | $M^+$ |
|---|---|---|---|---|
| 120 | | 9,10-Dihydro-N-[1-methyl-1-[6-(1-pyrrolidinyl)-3-pyridinyl]ethyl]-9-oxo-3-acridinecarboxamide | 2.24/A | 427 |
| 121 | | N-[1-[6-(1-Azetidinyl)-3-pyridinyl]-1-methylethyl]-9,10-dihydro-9-oxo-3-acridinecarboxamide | 2.18/A | 413 |
| 122 | | N-[1-[2-(1-Azetidinyl)-4-pyridinyl]-1-methylethyl]-9,10-dihydro-9-oxo-3-acridinecarboxamide | 2.18/A | 413 |
| 123 | | 9,10-Dihydro-N-[1-methyl-1-[6-(4-morpholinyl)-3-pyridinyl]ethyl]-9-oxo-3-acridinecarboxamide | 2.08/A | 443 |

TABLE 9-continued

| Ex. No | —G | Compound name | HPLC time (min)/ Condition | M+ |
|---|---|---|---|---|
| 124 | (4-SMe-phenyl-C(Me)₂-) | 9,10-Dihydro-N-[1-methyl-1-[4-(methylthio)phenyl]ethyl]-9-oxo-3-acridinecarboxamide | 3.20/A | 403 |
| 125 | (4-SO₂Me-phenyl-C(Me)₂-) | 9,10-Dihydro-N-[1-methyl-1-[4-(methylsulfonyl)phenyl]ethyl]-9-oxo-3-acridinecarboxamide | 2.51/A | 435 |
| 126 | (2-SMe-phenyl-C(Me)₂-) | 9,10-Dihydro-N-[1-methyl-1-[2-(methylthio)phenyl]ethyl]-9-oxo-3-acridinecarboxamide | 3.06/A | 403 |
| 127 | (2-SO₂Me-phenyl-C(Me)₂-) | 9,10-Dihydro-N-[1-methyl-1-[2-(methylsulfonyl)phenyl]ethyl]-9-oxo-3-acridinecarboxamide | 2.68/A | 435 |

Example 128

N-[(9,10-Dihydro-9-oxo-3-acridinyl)carbonyl]-2-methyl-alanine, methyl ester

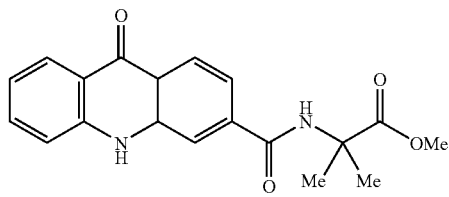

Example 128 was prepared from compound 1C by a route analogous to that used for the preparation of Example 1, replacing the amine in Step E with 2-Amino-2-methyl-propionic acid methyl ester. HPLC retention time=2.453 min./condition A.

Example 129

N-[(9,10-Dihydro-9-oxo-3-acridinyl)carbonyl]-2-methylalanine

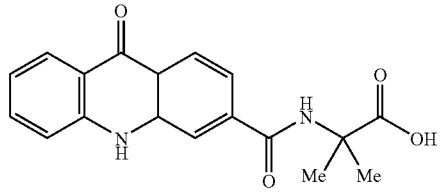

Example 129 was prepared from Example 128 by a route analogous to that used for the preparation of compound 1B. M+=325.

Examples 130-135

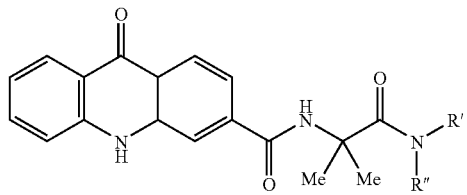

Compounds having the above formula wherein the group NR'R" has the values listed in Table 10, were prepared from Example 129 by a route analogous to that used for the preparation of Example 1, replacing the amine with the required HNR'R". The desired compounds may be further purified by preparative HPLC.

Example 136

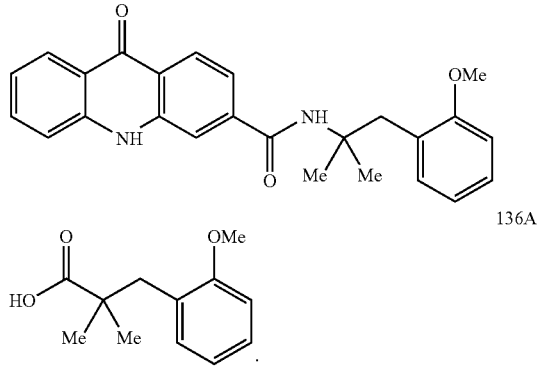

To a solution of LDA (2.0M solution, 6.4 mL, 12.8 mmol) in anhydrous THF (20 mL) at −76° C. was added isobutyric acid (0.618 g, 7.02 mmol) followed by the addition of HMPA (1.1 mL, 6.39 mmol). The reaction mixture was

TABLE 10

| No | —NR'R" | Compound name | HPLC time (min)/ Condition | M+ |
|---|---|---|---|---|
| 130 | N(CH₃)₂ | N-[2-(Dimethylamino)-1,1-dimethyl-2-oxoethyl]-9,10-dihydro-9-oxo-3-acridinecarboxamide | 2.23/A | 352 |
| 131 | NH-phenyl | N-[1,1-Dimethyl-2-oxo-2-(phenylamino)ethyl]-9,10-dihydro-9-oxo-3-acridinecarboxamide. | 2.98/A | 400 |
| 132 | 2,3-dihydroindol-1-yl | N-[2-(2,3-Dihydro-1H-indol-1-yl)-1,1-dimethyl-2-oxoethyl]-9,10-dihydro-9-oxo-3-acridinecarboxamide. | 2.97/A | 426 |
| 133 | morpholinyl | N-[1,1-Dimethyl-2-(4-morpholinyl)-2-oxoethyl]-9,10-dihydro-9-oxo-3-acridinecarboxamide. | 2.19/A | 394 |
| 134 | 4-methylpiperazin-1-yl | N-[1,1-Dimethyl-2-(4-methyl-1-piperazinyl)-2-oxoethyl]-9,10-dihydro-9-oxo-3-acridinecarboxamide. | 1.98/A | 407 |
| 135 | isoindolin-2-yl | N-[2-(1,3-Dihydro-2H-isoindol-2-yl)-1,1-dimethyl-2-oxoethyl]-9,10-dihydro-9-oxo-3-acridinecarboxamide. | 2.87/A | 426 | warmed to room temperature and 2-methoxybenzyl chloride (1.0 g, 6.39 mmol) was added. The reaction mixture was stirred at room temperature for eighteen hours, quenched by the addition of 1N HCl and extracted into EtOAc. The EtOAc layer was washed with water, brine, dried over sodium sulfate, concentrated under reduced pressure and purified by silica gel chromatography using EtOAc and hexane. Yield: 0.53 g (40%). $^1$H NMR (CDCl$_3$): 7.2 (1H, t), 7.1 (1H, d), 6.8 (1H, m), 3.8 (3H, s), 3.0 (2H, s), 1.2 (3H, s), 1.25 (3H, s).

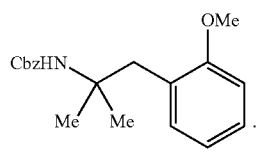

136B

To a solution of the compound 136A (0.53 g, 2.55 mmol) in acetone (1 mL) and water (0.5 mL) was added triethylamine (390 μL, 2.80 mmol). This was followed by the addition of ethyl chloroformate (292 μL, 3.06 mmol) and sodium azide (0.215 g, 3.32 mmol). The reaction mixture was stirred at room temperature for forty minutes and concentrated under reduced pressure. To the residue was added anhydrous toluene (50 mL) and the contents refluxed for three hours. Benzyl alcohol (2 mL) was added and the contents refluxed for a further three hours. The reaction mixture was cooled to room temperature and concentrated under reduced pressure. The residue was partitioned between EtOAc and brine. The EtOAc layer was dried over sodium sulfate and concentrated to yield an oil, which was used as such for the subsequent step without further purification.

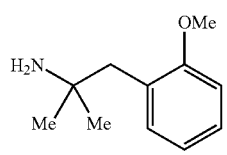

To a solution of compound 136B (0.8 g) was added MeOH (20 mL) followed by 10% Pd—C (0.1 g) at 0° C. under a nitrogen atmosphere. The contents were hydrogenated at 50 psi for 3.5 hours. The reaction mixture was filtered and the filtrate was concentrated under reduced pressure. The residue was partitioned between 1N HCl and EtOAc. The HCl layer was separated, made basic using iN NaOH and extracted into EtOAc. The EtOAc layer was dried over sodium sulfate and concentrated under reduced pressure to yield compound 136C as an oil. Yield: 0.05 g. $^1$H NMR (CDCl$_3$): 7.15 (1H, t), 7.05 (1H, d), 6.8 (1H, m), 3.7 (3H, s), 2.6 (2H, s), 1.0 (6H, s).

136D.

Example 136 was prepared in a fashion analogous to Example 1 starting from acridone acid 1C and amine 136C. HPCL Retention time=3.5 min. (Condition A). M$^+$ 401.46.

Example 137

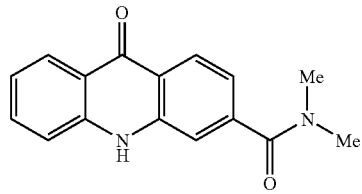

Example 137 was prepared using a method similar to the method described for Example 54 and purified by preparative HPLC. HPLC retention time=3.17 min. (Condition B) and LC/MS M$^{+1}$=267.

Example 138

9,10-Dihydro-7-methyl-N-(1-methyl-1-phenylethyl)-9-oxo-3-acridine Carboxamide

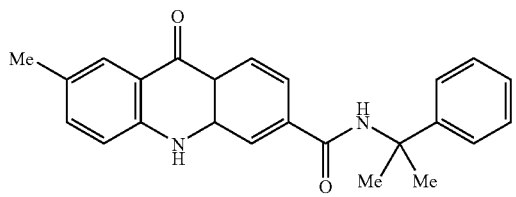

138A. 2-p-Tolylamino-terephthalic acid

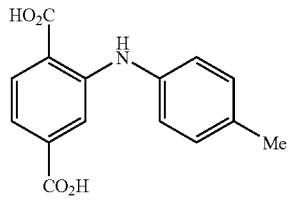

To a mixture of 2-amino-terephthalic acid (2.5 g, 23.8 mmol) and 1-iodo-4-methyl-benzene (7.78 g, 35.7 mmol) in butane-2,3-diol (38 mL) was added Cu (24 mg, 0.016 mmol), CuCl (950 mg, 9.6 mmol), and n-methyl morpholine (6.5 mL) under argon. The mixture was heated at 150° C. for 18 h. The reaction mixture was cooled to room temperature and HCl (0.1 N, 100 mL) was added. The resulting yellow precipitate was collected by filtration and triturated in a mixture of Et$_2$O and EtOAc (1:1, 50 mL) for 1 h. The yellow solid was filtered, washed with ether (25 mL), and dried in vacuo to give 2.4 of 138A. HPLC retention time=3.046 min., condition A.

138B. 9,10-Dihydro-7-methyl-9-oxo-3-acridinecarboxylic acid

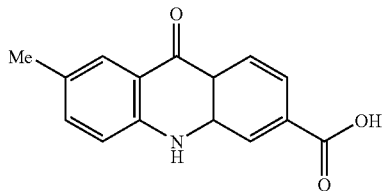

To a round bottom flask equipped with a condenser was added compound 138A (2.0 g), polyphosphoric acid (15 g) and CHCl$_3$ (50 mL), and the mixture was heated to 100° C. for 18 h. LC/MS indicated that the reaction was complete. The reaction mixture was cooled to room temperature, diluted with MeOH (25 mL), and H$_2$O (50 mL) was added. The resulting mixture was filtered through a medium porosity fritted funnel, washed with MeOH:1% Et$_3$N in H$_2$O (1:1, 30 mL) two times, and dried in air to give a yellow paste which was then dispersed in dioxane (10 mL) with sonication and dried over lyophlyzer to give compound 138B as a yellow solid (2.0 g). HPLC retention time: 2.76 min., condition A. M+: 254.

138C. Example 138

Example 138 was prepared from acid 138B by a route analogous to that used for Example 1, replacing the amine in Step E with 1-methyl-1-phenyl ethylamine. The amine is commercially-available or can be prepared as described in Example 1, Step 1D, starting with 4-cyanobenzene in place of 4-cyanopyridine. HPLC retention time: 3.17 min., condition A. M+: 370.

Examples 139-141

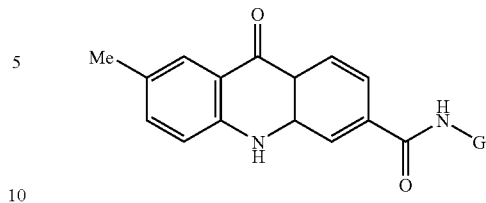

Compounds having the above formula, wherein G has the values listed in Table 11 were prepared from 138B by a route analogous to that used for the preparation of Example 138, replacing the amine with the required H$_2$N-G. The desired compounds may be further purified by preparative HPLC.

TABLE 11

| Ex. No | —G | Compound name | HPLC time (min)/ Condition | M+ |
|---|---|---|---|---|
| 139 | -CH(Me)$_2$ | 9,10-Dihydro-7-methyl-N-(1-methylethyl)-9-oxo-3-acridinecarboxamide. | 2.75/A | 295 |
| 140 | -C(Me)$_3$ | N-(1,1-Dimethylethyl)-9,10-dihydro-7-methyl-9-oxo-3-acridinecarboxamide | 3.01/A | 309 |
| 141 | -C(Me)$_2$CH$_2$-C$_6$H$_4$-F | N-[2-(4-Fluorophenyl)-1,1-dimethylethyl]-9,10-dihydro-7-methyl-9-oxo-3-acridinecarboxamide | 3.42/A | 403 |

Example 142

9,10-Dihydro-7-methyl-9-oxo-3-acridinecarboxylic acid, methyl ester

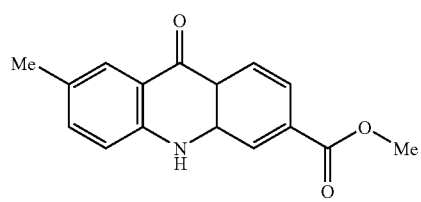

A mixture of compound 138B (50 mg), MeOH (12 mL), Conc. H$_2$SO$_4$ (2 drops), and DMF (2 drops) was heated to reflux over 18 h. LC/MS indicated the reaction was complete. The reaction mixture was concentrated in vacuo to give a brown oil (47.5 mg). HPLC retention time: 3.05 min., condition: A. M+: 268.

Examples 143-144

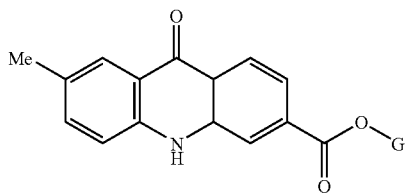

Examples 143-144 having the above formula wherein G is as set forth in Table 12, were prepared from 138B by a route analogous to that used for the preparation of Example 142, using the corresponding alcohol HO-G in place of MeOH. The desired compounds may be further purified by preparative HPLC.

TABLE 12

| Ex. No | —G | Compound name | HPLC time (min)/ Condition | M+ |
|---|---|---|---|---|
| 143 | ⸺CH₂Me | 9,10-Dihydro-7-methyl-9-oxo-3-acridinecarboxylic acid, ethyl ester. | 3.30/A | 282 |
| 144 | ⸺CH(Me)(Me) / 1-methylethyl | 9,10-Dihydro-7-methyl-9-oxo-3-acridinecarboxylic acid, 1-methylethyl ester. | 3.45/A | 296 |

Example 145

N-(1,1-Dimethylethyl)-2-ethyl-9,10-dihydro-9-oxo-3-acridinecarboxamide

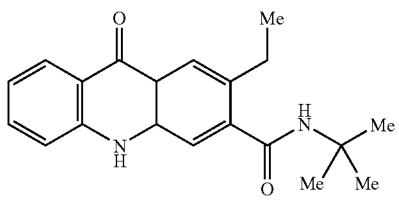

145A. N-(1,1-Dimethylethyl)-2-trimethylsilanylethynyl-9,10-dihydro-9-oxo-3-acridinecarboxamide

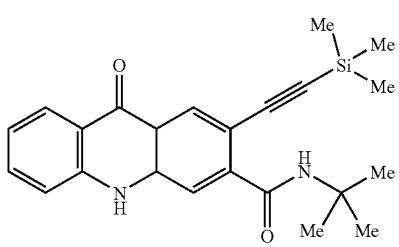

A one dram vial was charged with Br-acridone-t-butyl amide (50 mg, 0.13 mmol), DMF (0.7 mL), PdCl$_2$(PPh$_3$)$_2$ (5 mg, 0.053 mmol), Et$_3$N (0.1 mL), and ethynyl-trimethylsilane (27 µL, 0.19 mmol) under argon. The reaction mixture was stirred at 85° C. for 5 h, then cooled to RT, and concentrated in vacuo. Preparative HPLC gave 145A (16 mg). HPLC retention time=3.67 min./condition A, M+=391.

145B. N-(1,1-Dimethylethyl)-2-ethynyl-9,10-dihydro-9-oxo-3-acridinecarboxamide

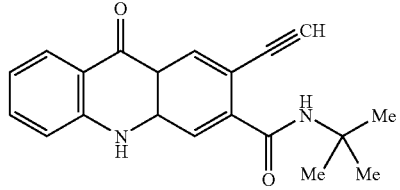

A one dram vial was charged with compound 145A (13 mg, 0.033 mmol), THF (0.5 mL) and TBAF (33 L, 0.033 mmol) under argon. The reaction mixture was stirred at RT for 20 min., and then diluted with EtOAc (10 mL), washed with sat. NaHCO$_3$ (10 mL), water (10 mL) and brine (10 mL). The organic layer was dried over MgSO$_4$ and concentrated in vacuo to give 145B as a yellow solid (12 mg). HPLC retention time=2.74 min. (Condition A), M+=319.

145C. Example 145

A 15 mL pear-shaped flask was charged with compound 145B (5.7 mg), Pd/C (2.5 mg), and DMF (0.6 mL). The reaction mixture was stirred at RT under hydrogen (1 atmosphere) for 30 min. The resulting mixture was then filtered through celite and washed with EtOAc (10 mL). The filtrate was concentrated in vacuo to give Example 145 as a reddish-brown solid (5 mg). HPLC retention time=2.63 min. (Condition A), M+=323.

Example 146

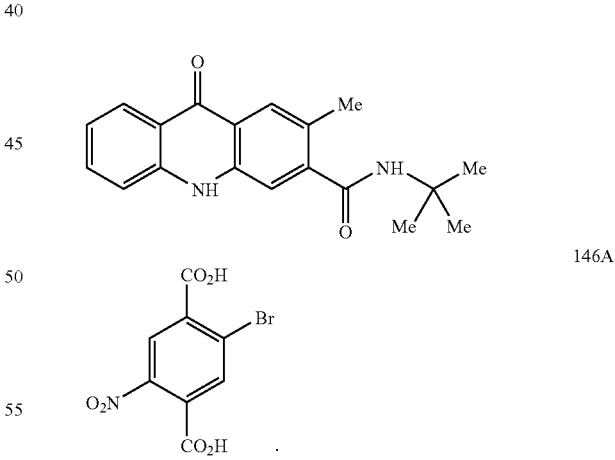

To 2-bromoterphthalic acid (5.0 g, 20 mmol) at 0° C. was slowly added concentrated sulfuric acid (25 mL). Then a 1:1 mixture of concentrated sulfuric acid and concentrated nitric acid (2.1:2.1 mL) was added dropwise over a period of twenty minutes. After the addition was complete, the reaction mixture was heated at 100° C. for two hours and then stirred at room temperature for eighteen hours. The reaction was cooled to room temperature and poured into 300 mL of ice/water. The solid that separated out was filtered and dried to afford compound 146A (4.85 g, 82%). Retention time=1.21 min. (Condition A).

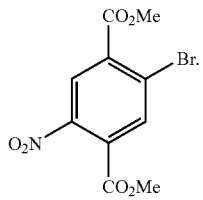

146B

To compound 146A (3.0 g, 10.34 mmol) in a mixture of DCM (20 mL) and MeOH (7 mL) was added (trimethylsilyl)diazomethane (2.0 M solution in hexanes, 23 mL) at 0° C. The reaction mixture was stirred at 0° C. for fifteen minutes, quenched by the slow addition of acetic acid (approximately 6 mL) and partitioned between DCM (30 mL) and brine (2×20 mL). The DCM layer was dried over sodium sulfate and concentrated to yield compound 146B (2.8 g, 85%). $^1$H NMR (CDCl$_3$): 8.4 (1H, s), 8.0 (1H, s), 4.0 (3H, s), 3.95 (3H, s).

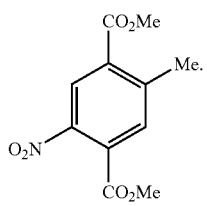

146C

To a solution of compound 146B (0.5 g, 1.57 mmol) in toluene (2 mL) was sequentially added cesium carbonate (1.5 g, 4.71 mmol), trimethylboroxine (0.22 mL, 1.57 mmol) and tetrakis(triphenylphosphine)palladium (0.18 g, 0.16 mmol). The reaction mixture was purged with nitrogen gas for ten minutes and heated at 100° C. in a sealed tube for eighteen hours. The reaction mixture was cooled to room temperature and filtered over a thin pad of celite and the celite pad was washed with EtOAc. The filtrate was concentrated under reduced pressure and purified by silica gel flash chromatography employing hexane and EtOAc to yield compound 146C (0.210 g, 53%). $^1$H NMR (CDCl$_3$): 8.5 (1H, s), 7.5 (1H, s), 4.0 (3H, s), 3.95 (3H, s), 2.7 (3H, s).

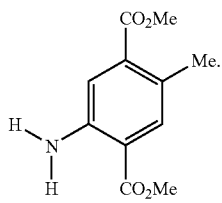

146D

To a solution of compound 146C (0.2 g, 0.79 mmol) in MeOH (15 mL) was added 10% palladium on carbon (0.05 g) at 0° C. and the contents hydrogenated at 25 psi for three hours. The reaction mixture was filtered and the filter pad washed with MeOH (3×10 mL). The filtrate was concentrated under reduced pressure to yield compound 146D as a solid (0.175 g, 100%). Retention time=2.94 min (Condition A).

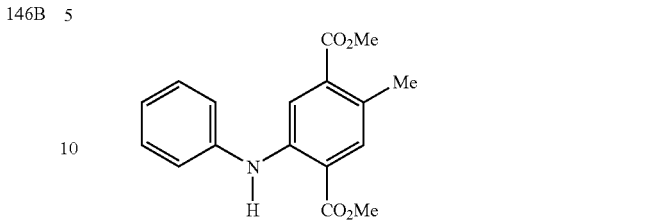

146E

To compound 146D (0.17 g, 0.76 mmol) in toluene (5 mL) was sequentially added bromobenzene (80 μL, 0.76 mmol) cesium carbonate (0.745 g, 2.28 mmol), (±) BINAP (0.142 g, 0.23 mmol) and palladium acetate (0.034 g, 0.15 mmol). The reaction mixture was purged with nitrogen gas for ten minutes and heated at 100° C. in a sealed tube for eighteen hours. The reaction mixture was cooled to room temperature and filtered over a thin pad of celite and the celite pad was washed with EtOAc. The filtrate was concentrated under reduced pressure and purified by silica gel flash chromatography employing hexane and EtOAc to yield compound 146E (0.156 g, 68%). $^1$H NMR (CDCl$_3$): 9.25 (1H, s), 7.8 (s, 1H), 7.75 (1H, s), 7.3 (2H, t), 7.2 (2H, t), 7.1 (1H, t), 3.9 (3H, s), 3.8 (3H, s), 2.5 (3H, s).

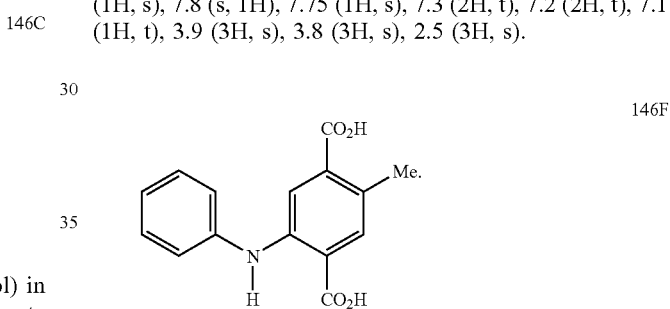

146F

To a solution of compound 146E (0.152 g, 0.51 mmol) in a mixture of THF:MeOH and water (2:2:1 mL) was added lithium hydroxide (0.064 g, 0.45 mmol), and the contents heated at 80° C. for one hour. The reaction mixture was cooled to room temperature and acidified with 6N hydrochloric acid. The solid that separated out was filtered, washed with water (2×10 mL) and dried to yield compound 146F (0.13 g, 94%). Retention time=3.14 min (Condition A).

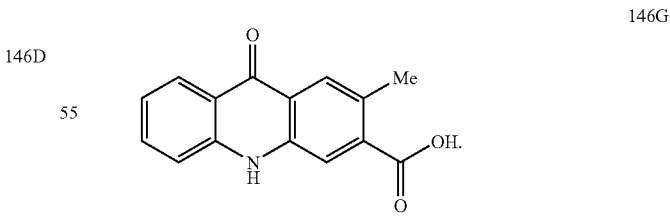

146G

PPA (approximately 6 g) in a 50 mL round bottomed flask was immersed in a pre-heated 160° C. oil bath and stirred for fifteen minutes. Then compound 146F (0.130 g, 0.48 mmol) was added as a solid and the contents heated at 160° C. for ninety minutes. The reaction mixture was cooled to room temperature and water (10 mL) was added. The pH of the solution was adjusted to approximately 4 using 50% sodium hydroxide (aqueous) and the contents allowed to stand at room temperature for sixty four hours. The reaction mixture was filtered, washed with water (2×10 mL), MeOH (5 mL) and dried to afford compound 146G (0.108 g, 89%). $^1$H NMR (DMSO-d6): 12.0 (1H, s), 8.2 (1H,s), 8.1 (1H, S), 8.0 (1H, S), 7.75 (1H, t), 7.5 (1H, d), 7.25 91H, t), 2.55 (3H, s).

146H. Example 146

Example 146 was prepared following the same or similar procedure described in Example 1, Step E, using acridone acid 146G and tert-butylamine. Retention time=2.56 min. (Condition A). M+ 309.40

Examples 147-172

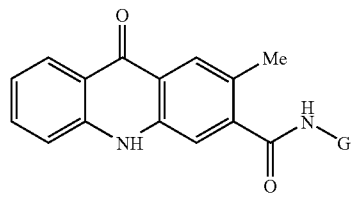

Compounds having the above formula, wherein G has the values listed in Tables 13 and 14, were prepared following the same or similar method described in Example 1, Step E, using compound 146G as the acridone acid and the appropriate amine NH$_2$-G. The amines are commercially-available and/or may be prepared as described in other Examples herein (see, e.g., Examples 1, 42, 43, 44, 46, 103, 104 etc.), and/or as described in the literature. See, e.g., *Tetrahedron*, Vol. 54, 5-6 [1998], at pp. 1013-1020 (2-amino-2-methyl-cyclopentanecarboxylic acid ethyl ester, Ex. 156; and 2-amino-2-methyl-cyclopentylmethanol, Ex. 157).

TABLE 13

| Ex. No. | G | HPLC Retention time (min.) (Condition) | MS (M+) |
|---|---|---|---|
| 147 | | 2.87 (A) | 429 |
| 148 | | 3.2 (A) | 403 |
| 149 | | 1.51 (D) | 399 |
| 150 | | 2.72 (A) | 351 |

TABLE 13-continued

| Ex. No. | G | HPLC Retention time (min.) (Condition) | MS (M+) |
|---|---|---|---|
| 151 | | 1.28 (D) | 440 |
| 152 | | 3.44 (A) | 507 |
| 153 | | 2.04 (A) | 454 |
| 154 | | 2.86 (C) | 401 |
| 155 | | 2.08 (C) | 386 |
| 156 | | 2.42 (A) | 393 |
| 157 | | 2.78 (A) | 365 |
| 158 | | 1.63 (E) | 439 |

TABLE 13-continued

| Ex. No. | G | HPLC Retention time (min.) (Condition) | MS (M+) |
|---|---|---|---|
| 159 | 3-(phenoxymethyl)-1,2,4-oxadiazol-5-yl with C(Me)₂ linker | 1.63 (E) | 469 |
| 160 | 5-phenyloxazol-2-yl with C(Me)₂ linker | 2.97 (A) | 439 |
| 161 | 4-methoxyphenyl with C(Me)₂ linker | 2.862 (A) | 401 |
| 162 | benzo[1,3]dioxol-5-yl with C(Me)₂ linker | 2.819 (A) | 415 |
| 163 | 3,4-dimethoxyphenyl with C(Me)₂ linker | 2.656 (A) | 431 |
| 164 | phenyl with C(Me)₂ linker | 2.862 (A) | 371 |
| 165 | 6-methylpyridin-3-yl with C(Me)₂ linker | 1.936 (A) | 386 |
| 166 | 4-methyl-3,4-dihydro-2H-benzo[1,4]oxazin-7-yl with C(Me)₂ linker | 2.96 (B) | 442 |
| 167 | 4-methyl-3,4-dihydro-2H-benzo[1,4]oxazin-6-yl with C(Me)₂ linker | 2.99 (B) | 442 |
| 168 | phenyl with C(Me)₂ linker | 2.98 (A) | 371 |

TABLE 14

| Ex. No | G | Compound name | HPLC time (min.) (Condition) | M+ |
|---|---|---|---|---|
| 169 | 6-(1-pyrrolidinyl)pyridin-3-yl with C(Me)₂ linker | 9,10-Dihydro-2-methyl-N-[1-methyl-1-[6-(1-pyrrolidinyl)-3-pyridinyl]ethyl]-9-oxo-3-acridinecarboxamide | 2.14 (A) | 441 |
| 170 | 6-(1-azetidinyl)pyridin-3-yl with C(Me)₂ linker | N-[1-[6-(1-Azetidinyl)-3-pyridinyl]-1-methylethyl]-9,10-dihydro-2-methyl-9-oxo-3-acridinecarboxamide | 2.05 (A) | 427 |

TABLE 14-continued

| Ex. No | G | Compound name | HPLC time (min.) (Condition) | M+ |
|---|---|---|---|---|
| 171 | ![azetidinyl-pyridinyl group with gem-dimethyl linker] | N-[1-[2-(1-Azetidinyl)-4-pyridinyl]-1-methylethyl]-9,10-dihydro-2-methyl-9-oxo-3-acridinecarboxamide | 2.08 (A) | 427 |
| 172 | ![morpholinyl-pyridinyl group with gem-dimethyl linker] | 9,10-Dihydro-2-methyl-N-[1-methyl-1-[6-(4-morpholinyl)-3-pyridinyl]ethyl]-9-oxo-3-acridinecarboxamide | 1.97 (A) | 457 |

Example 173

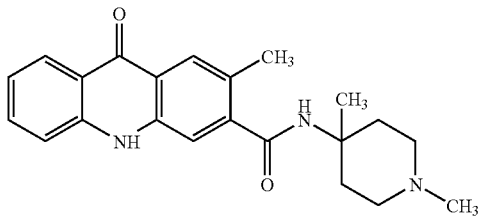

A solution of Example 151 (0.02 g) in MeOH (20 mL) was hydrogenated over 10% Pd on carbon at 50 psi for eighteen hours. The reaction mixture was filtered and the filter cake washed with MeOH. The filtrate was concentrated under reduced pressure and purified by preparative HPLC to yield Example 173 as a TFA salt (0.004 g). Retention time=1.97 min (Condition A). M+ 364.24

Example 174

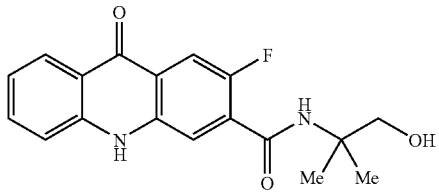

174A. 2-Fluoro-5-nitro-terephthalic acid dimethyl ester

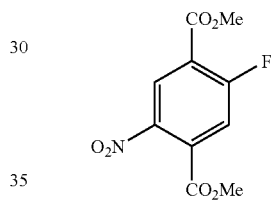

To a mixture of dimethyl 2-fluoroterephthalate (42.0 g, 0.198 mol) in concentrated sulfuric acid (200 mL) at 0° C. was added 36 mL of a 1:1 mixture of nitric acid and sulfuric acid dropwise. The mixture was stirred at 0° C. for 15 min., the ice-bath was removed, and the reaction mixture was stirred for an additional 45 min. HPLC indicated that the starting material had been consumed. The reaction mixture was poured over ice and extracted with EtOAc. The organic layer was collected, washed with brine, and dried over anhydrous sodium sulfate. Concentration under reduced pressure followed by recrystallization from MeOH afforded 48.5 g (95%) of 174A as a white solid. HPLC retention time=2.69 min. (Condition B). $^1$H-NMR (500 MHz, CDCl$_3$) δ 3.95 (s, 3H), 3.98 (s, 3H), 7.44 (d, 1H), and 8.59 (d, 1H).

174B. 2-Amino-5-fluoro-terephthalic acid dimethyl ester

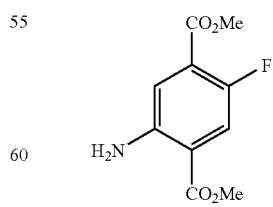

A mixture of 174A (48.5 g, 0.178 mol) and palladium/carbon (4.6 g) in EtOAc (450 mL) was evacuated under reduced pressure and charged with hydrogen (3×). The reaction mixture was subsequently stirred under a steady stream of nitrogen for 1 h. The reaction mixture was filtered through a pad of Celite, concentrated, and recrystallized form a mixture of MeOH and DCM to provide 36.2 g (90%) of 174B as a bright yellow solid. HPLC retention time=2.68 min. (Condition B), and LC/MS M$^{+1}$=228. $^1$H-NMR (500 MHz, CDCl$_3$) δ 3.89 (s, 3H), 3.92 (s, 3H), 7.20 (d, 1H), and 7.61 (d, 1H).

174C. 2-Fluoro-5-phenylamino-terephthalic acid dimethyl ester

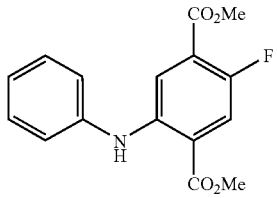

To a mixture of 174B (10.0 g, 44.0 mmol), bromobenzene (4.6 mL, 44.0 mmol), (S)-(−)-2,2'-Bis(diphenylphosphino)-1,1'-binaphthyl (2.06 g, 3.30 mmol), and toluene (250 mL) was added cesium carbonate (20.0 g, 44.0 mmol) followed by palladium(II) acetate (0.494 g, 2.20 mmol). The mixture was heated at 90° C. for 24 h. HPLC indicated that the reaction was complete. The reaction mixture was cooled to room temperature, and filtered under reduced pressure through a pad of Celite topped with a pad of silica gel, and the Celite/Silica gel pad was rinsed with EtOAc. The filtrate was concentrated under reduced pressure and purified by silica gel chromatography using a 1:10 mixture of EtOAc and hexane to give 10.7 g (80%) of compound 174C as a pale yellow solid. HPLC retention time=3.72 min. (Condition A). $^1$H-NMR (400 MHz, CDCl$_3$) δ 3.89 (s, 3H), 3.93 (s, 3H), 7.12 (m, 1H), 7.22 (m, 2H), 7.37 (m, 2H), 7.74 (m, 2H), and 9.22 (br s, 1H).

174D. 2-Fluoro-5-phenylamino-terephthalic acid

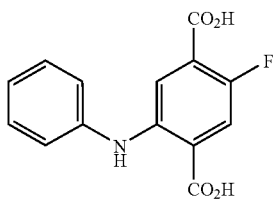

A mixture of 174C (30.0 g, 9.89 mmol) and lithium hydroxide monohydrate (12.5 g, 29.7 mmol) in MeOH (200 mL), THF (200 mL) and water (100 mL) was heated at 75° C. for 0.5 h. HPLC indicated that the reaction was complete. The organic solvents were removed under reduced pressure, and the aqueous residue was diluted with water. The pH was adjusted to 3.0 with 6N aqueous hydrochloric acid which resulted in a precipitate. The solid was collected by vacuum filtration and dried under reduced pressure to provide a quantitative yeild of compound 174D as an orange-yellow solid. HPLC retention time=3.02 min. (Condition B). $^1$H-NMR (400 MHz, DMSO) δ7.11 (m, 1H), 7.25 (m, 2H), 7.39 (m, 2H), 7.60 (m, 1H), 7.68 (m, 1H), 9.32 (br s, 1H), and 13.55 (br s, 2H).

174E. 2-Fluoro-9-oxo-9,10-dihydro-acridine-3-carboxylic acid

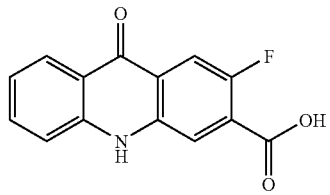

To a round bottom flask containing polyphosphoric acid (254 g) at 165-172° C. was added finely ground compound 174D (15.0 g, 55.6 mmol) over 30 min. After the addition was complete, the reaction mixture was stirred for 10 min at 165° C. HPLC indicated that the reaction was complete. While at 165° C., the mixture was slowly added to a mixture of ice and sodium bicarbonate. The pH was adjusted to 3.0 with additional solid sodium bicarbonate, and the resulting mixture was filtered through a medium porosity fritted funnel to give a greenish-yellow paste which was washed with water (3×) and air-dried under vacuum. The resulting paste was rinsed with MeOH into a flask. The paste/MeOH mixture was then sonicated to disperse the paste. DCM was added, and the mixture was concentrated under reduced pressure. The azeotrope procedure was repeated 2× to give 12.0 g (84%) of acridone acid 174E as a yellow solid. HPLC retention time=2.35 min. (Condition A) and LC/MS M$^{+1}$=258.03. $^1$H-NMR (500 MHz, DMSO) δ 7.30 (t, 1H, J=7.6 Hz), 7.56 (d, 1H, J=7.6 Hz), 7.78 (t, 1H, J=7.6 Hz), 7.93 (d, 1H, J=11.0 Hz), 8.11 (d, 1H, J=6.1 Hz), 8.22 (d, 1H, J=7.6 Hz), and 12.06 (s, 1H).

174F. Example 174

To a mixture of acridone acid 174E (0.200 g, 0.778 mmol) and 2-amino-2-propanol (0.089 mL, 0.934 mmol) in 10 mL of anhydrous DMF was added triethylamine (0.33 mL, 2.33 mmol) followed by BOP-Cl (0.218 g, 0.856 mmol). The reaction mixture was stirred at 55° C. overnight. The mixture was diluted with DCM, washed with water, and dried over anhydrous sodium sulfate. Concentration under reduced pressure followed by purification by silica gel chromatography afforded 160 mg of Example 174 as a bright yellow solid. HPLC retention time=2.60 min. (Condition B) and LC/MS M$^{+1}$=329.

Examples 175-176

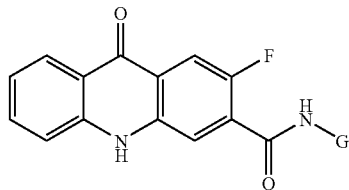

Examples 175-176 (Table 15) were prepared using a method analogous to the method described for the preparation of Example 93 using commercially available heterocyclic chlorides and Example 174. The compounds were purified by silica gel chromatography or by preparative HPLC.

TABLE 15

| Ex. No. | G | HPLC Retention time (min) (Condition) | MS M+ |
|---|---|---|---|
| 175 | 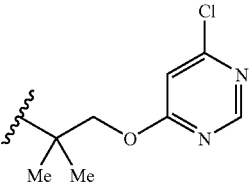 | 3.23 (A) | 441 |
| 176 | 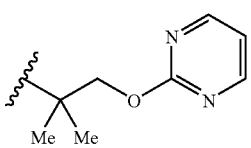 | 2.86 (A) | 467 |

Example 177

2-Fluoro-9-oxo-9,10-dihydro-acridine-3-carboxylic acid [1-methyl-1-(4-methyl-3,4-dihydro-2H-benzo[1,4]oxazin-7-yl)-ethyl]-amide

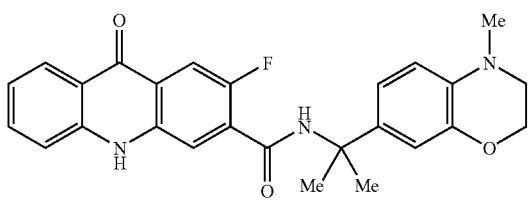

To a mixture of 104E (0.022 g, 0.105 mmol), acridone acid 174E (0.013 g, 0.051 mmol), and triethylamine (0.03 mL, 0.210 mmol) was added N,N-bis(2-oxo-3-oxazolidinyl)phosphorodiamidic chloride (0.027 g, 0.105 mmol) in 2 mL of anhydrous DMF at room temperature. The reaction mixture was heated at 50° C. overnight. The mixture was cooled, diluted with DCM, washed with water, washed with 1N aqueous sodium hydroxide (3×), and dried over anhydrous sodium sulfate. Concentration under reduced pressure followed by purification by preparative HPLC afforded Example 177 (0.015 g, 68%) as a yellow solid. HPLC retention time=3.26 min. (Condition B) and LC/MS M$^{+1}$=446.12.

Example 178

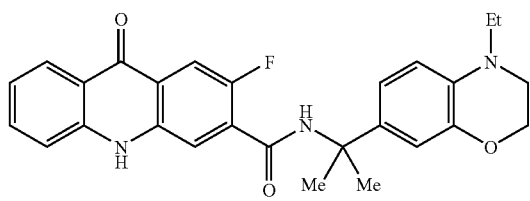

Example 178 was prepared using a reaction sequence analogous to the procedure described for the preparation of Example 177 starting with 2-methylbenzoxazole in the reaction sequence for the preparation of the amine (Steps A-E, Example 104). HPLC retention time=3.89 min. (Condition B) and LC/MS M$^{+1}$=460.

Example 179

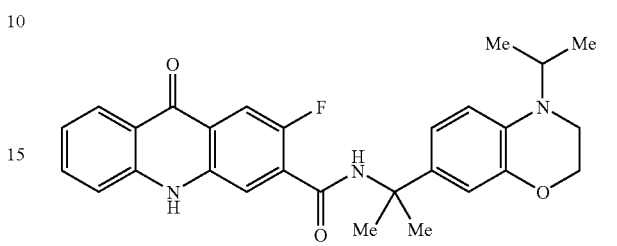

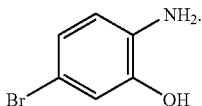

179A

A mixture of 3-bromo-6-nitrophenol (0.910 g, 4.17 mmol) and stannous chloride dihydrate (3.39 g, 15.0 mmol) in 20 mL of EtOAc was heated at reflux for 3 h. The reaction mixture was stirred overnight at room temperature and poured into 75 mL of a 1:1:1 mixture of ice, sodium bicarbonate, and water. The mixture was extracted with EtOAc, and the organic layer was collected, washed with water, washed with brine, and dried over anhydrous sodium sulfate. Concentration under reduced pressure afforded 0.654 g (83%) of 179A as a white solid. HPLC retention time 0.587 min. (Condition B) and LC/MS M$^{+1}$=189.

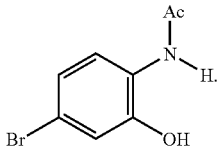

179B

A mixture of 179A (0.645 g, 3.48 mmol) and several drops of pyridine in 18 mL of acetic anhydride was heated at reflux for 5 min., stirred for an additional 5 min., and cooled to 0° C. The resulting precipitate was filtered under reduced pressure and washed with hexane to give the bis-acetate. The solid was then stirred in a 1M aqueous solution of sodium hydroxide (9.5 mL) until the mixture became homogeneous. The solution was poured into a mixture of crushed ice (4.6 g) and 6 M aqueous hydrochloric acid (1.9 mL). The aqueous mixture was extracted with DCM, washed with water, and dried over anhydrous sodium sulfate to give 179B (0.623 g, 78%) as an off-white solid. HPLC retention time=2.27 min. (Condition B) and LC/MS M$^{+1}$=231.

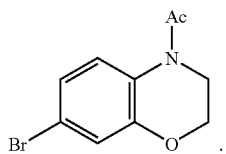

179C

A mixture of 179B (0.478 g, 2.08 mmol), 1,2-dibromoethane (0.72 mL, 8.32 mmol), sodium hydroxide (0.333 g, 8.32 mmol), and Aliquat 336 (0.11 g) in 4.3 mL of DCM and 2.6 mL of acetonitrile was stirred at room temperature for 2 days. The reaction mixture was filtered, and the precipitate was washed with ether. The filtrate was concentrated under reduced pressure, and the residue was purified by silica gel chromatography to give 0.514 g (96%) of 179C as a white solid. HPLC retention time=3.03 min. (Condition B) and LC/MS $M^{+1}$=257.

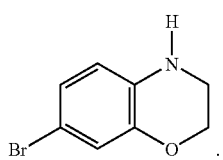

179D

A mixture of the bromobenzoxazine (0.514 g, 2.01 mmol) and potassium hydroxide (0.722 g, 12.9 mmol) in 3 mL of MeOH and 1.5 mL of water was heated at 55° C. for 35 min. The reaction mixture was poured over crushed ice and extracted with DCM. The organic layer was collected, washed with water, and dried over anhydrous sodium sulfate. Concentration under reduced pressure afforded 0.382 g (89%) of 179D as a white solid. HPLC retention time=2.65 min. (Condition B) and LC/MS $M^{+1}$=215.

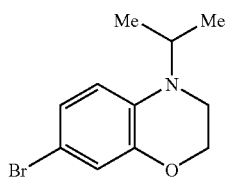

179E

To a mixture of 179D (0.176 g, 0.822 mmol) and acetone (0.30 mL, 4.11 mmol) in 2 mL of MeOH at room temperature was added sodium cyanoborohydride (0.077 g, 1.23 mmol) followed by 1.25 mL of a 2.25M solution of hydrochloric acid in MeOH. The reaction mixture was stirred overnight at 50° C. HPLC indicated that there was still additional starting material remaining, so additional acetone, sodium cyanoborohydride, and hydrochloric acid were added. The reaction mixture was stirred for 7 h, poured into ether, and washed with 1M aqueous sodium hydroxide followed by brine. The organic layer was collected, dried over anhydrous sodium sulfate, and concentrated under reduced pressure. Purification by silica gel chromatography afforded 0.141 g (67%) of 179E as a solid. HPLC retention time=3.94 min. (Condition B) and LC/MS $M^{+1}$=256.

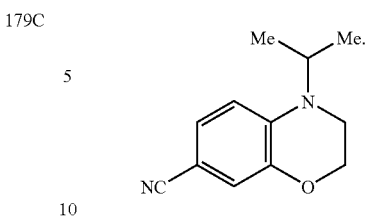

179F

A mixture of 179E (0.141 g, 0.550 mmol), tris(dibenzylideneacetone)dipalladium(0) (0.030 g, 0.033 mmol), 1,1'-bis(diphenylphosphino)ferrocene (0.037 g, 0.066 mmol), zinc powder (4.3 mg, 0.066 mmol), and zinc cyanide (0.039 g, 0.330 mmol) was flushed with nitrogen. Dimethyl acetamide (2.5 mL) was added, and the resulting mixture was heated at 150° C. overnight. HPLC indicated that the reaction was complete. The reaction mixture was cooled to room temperature, diluted with EtOAc, and washed with 2N aqueous ammonium hydroxide, then with brine, and dried over anhydrous sodium sulfate. Concentration under reduced pressure followed by purification by silica gel chromatography afforded 179F (0.057 g, 51%) as a solid. HPLC retention time=3.10 min. (Condition B) and LC/MS $M^{+1}$=203.

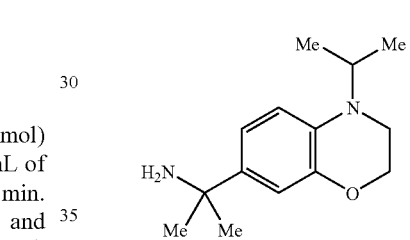

To a flame-dried flask under nitrogen was added cerium chloride (0.209 g, 0.846 mmol) followed by anhydrous THF (6 mL). The mixture was stirred vigorously for 45 min., during which time the cerium chloride became suspended. The suspension was cooled to −78° C., and methyl lithium (0.81 mL, 1.13 mmol, 1.4 M in ether) was added dropwise. After the addition was complete, the reaction mixture was stirred for 0.5 h at −78° C. Compound 179F (0.046 g, 0.0.227 mmol) in THF (4 mL) was added via cannula to the −78° C. solution. The dry-ice bath was removed, and the reaction mixture was stirred at room temperature overnight. The mixture was quenched with a few drops of a saturated aqueous solution of ammonium chloride, and a 2M aqueous solution of ammonium hydroxide was added dropwise until a precipitate formed and settled to the bottom of the flask. The mixture was filtered through Celite under reduced pressure, diluted with DCM, washed with water, and dried over anhydrous sodium sulfate. Concentration under reduced pressure afforded 179G (0.046 g, 87%). HPLC retention time=1.97 min. (Condition B) and LC/MS $M^{+1}$=218 ($M^{+1}$-$CH_3$).

179. Example 179

To a mixture of acridone acid 174E (0.042 g, 0.164 mmol), 179G (0.046 g, 0.196 mmol), and triethylamine (0.07 mL, 0.492 mmol) was added N,N-bis[2-oxo-3-oxazolidinyl]phosphorodiamidic chloride (0.050 g, 0.105 mmol) in 6 mL of anhydrous DMF at room temperature. The reaction mixture was stirred at room temperature overnight. The mixture was diluted with DCM, washed with water, washed with 1N aqueous sodium hydroxide (3×), and dried over anhydrous sodium sulfate. Concentration under reduced pressure followed by purification by preparative HPLC afforded Example 179 (0.012 g) as a bright yellow solid. HPLC retention time=2.70 min. (Condition B) and LC/MS $M^{+1}$=474.

Example 180

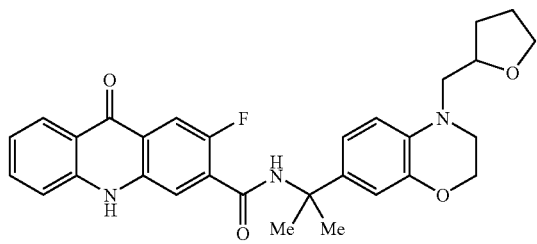

Example 180 was prepared using a reaction sequence analogous to the procedure described for the preparation of example 179. HPLC retention time=3.57 min. (Condition B) and LC/MS $M^{+1}$=516.

Example 181

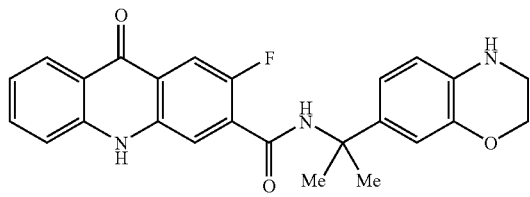

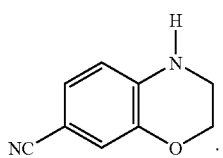

A mixture of 179D (0.069 g, 0.322 mmol), tris(dibenzylideneacetone)dipalladium(0) (0.018 g, 0.019 mmol), 1,1'-bis(diphenylphosphino)ferrocene (0.021 g, 0.039 mmol), zinc powder (3.0 mg, 0.039 mmol), and zinc cyanide (0.023 g, 0.193 mmol) was flushed with nitrogen. Dimethyl acetamide (1.5 mL) was added, and the resulting mixture was heated at 150° C. overnight. HPLC indicated that the reaction was complete. The reaction mixture was cooled to room temperature, diluted with EtOAc, and washed with 2N aqueous ammonium hydroxide, washed with brine, and dried over anhydrous sodium sulfate. Concentration under reduced pressure followed by purification by silica gel chromatography afforded 181A (0.030 g) as a solid. HPLC retention time=2.01 min. (Condition B) and LC/MS $M^{+1}$=161.

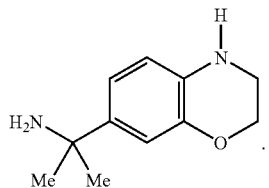

To a flame-dried flask under nitrogen was added cerium chloride (0.238 g, 0.967 mmol) followed by anhydrous THF (7 mL). The mixture was stirred vigorously for 45 min., during which time the cerium chloride became suspended. The suspension was cooled to −78° C., and methyl lithium (0.92 mL, 1.29 mmol, 1.4 M in ether) was added dropwise. After the addition was complete, the reaction mixture was stirred for 0.5 h at −78° C. Compound 181A (0.034 g, 0.0.227 mmol) in THF (3 mL) was added via cannula to the −78° C. solution. The dry-ice bath was removed, and the reaction mixture was stirred at room temperature overnight. The mixture was quenched with a few drops of a saturated aqueous solution of ammonium chloride, and a 2M aqueous solution of ammonium hydroxide was added dropwise until a precipitate formed and settled to the bottom of the flask. The mixture was filtered through Celite under reduced pressure, diluted with DCM, washed with water, and dried over anhydrous sodium sulfate. Concentration under reduced pressure afforded 181B (0.030 g, 73%). The amine was used without any further purification.

181. Example 181

To a mixture of acridone acid 174E (0.020 g, 0.778 mmol), 181G (0.030 g, 0.156 mmol), and triethylamine (0.03 mL, 0.233 mmol) was added N,N-bis[2-oxo-3-oxazolidinyl]phosphorodiamidic chloride (0.024 g, 0.093 mmol) in 4 mL of anhydrous DMF at room temperature. The reaction mixture was stirred at room temperature overnight. The mixture was diluted with DCM, washed with water, washed with 1N aqueous sodium hydroxide (3×), and dried over anhydrous sodium sulfate. Concentration under reduced pressure followed by purification by silica gel chromatogrpahy afforded Example 181 (8.0 mg) as a bright yellow solid. HPLC retention time=2.74 min. (Condition B) and LC/MS $M^{+1}$=432.

Example 182

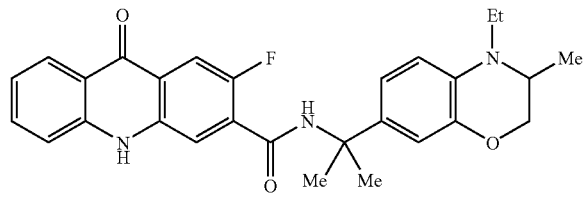

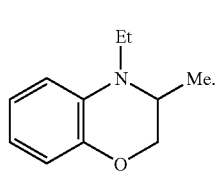

A mixture of 3-methyl-3,4-dihydro-2H-1,4-benzoxazine (0.500 g, 3.35 mmol), sodium cyanoborohydride (0.337 g, 5.36 mmol), and acetaldehyde (0.37 mL, 6.70 mmol) in 25 mL of acetonitrile at room temperature was stirred for 25 min. To the mixture was added 6 drops of AcOH, and the reaction mixture was stirred overnight. The mixture was diluted with EtOAc, washed with 1M aqueous sodium hydroxide, washed with brine, and dried over anhydrous sodium sulfate. Concentration under reduced pressure followed by purification by silica gel chromatography provided 0.573 g (96%) of 182A as an off-white solid. HPLC retention time=2.88 min. (Condition B) and LC/MS $M^{+1}$=178.

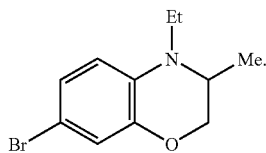

182B

A mixture of 182A (0.573 g, 3.23 mmol) and N-bromosuccinimide (0.575 g, 3.23 mmol) in 10 mL of DMF was heated at 75° C. for 2 h. The solvent was removed under reduced pressure, and the residue was dissolved in DCM, washed with water, and dried over anhydrous sodium sulfate. Concentration under reduced pressure followed by purification by silica gel chromatography afforded 0.810 g (98%) of 182B as an off-white solid. HPLC retention time=3.92 min. (Condition B) and LC/MS $M^{+1}$=257.

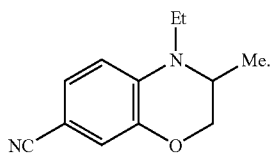

182C

Following the procedure outline in 181A, nitrile 182C was prepared from compound 182B as a pale yellow oil. HPLC retention time=3.03 min. (Condition B) and LC/MS $M^{+1}$=203.

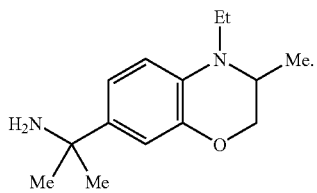

182D

Following the procedure outline in 181B, nitrile 182D was prepared from 182C. HPLC retention time=1.97 min. (Condition B) and LC/MS $M^{+1}$=218 ($M^{+1}$-Me).

182E. Example 182

To a mixture of acidone acid 174E (0.100 g, 0.389 mmol), 182D (0.100 g, 0.428 mmol), and triethylamine (0.163 mL, 1.17 mmol) was added N,N-bis[2-oxo-3-oxazolidinyl]phosphorodiamidic chloride (0.109 g, 0.428 mmol) in 10 mL of anhydrous DMF at room temperature. The reaction mixture was stirred at room temperature overnight. The mixture was diluted with DCM, washed with water, washed with 1N aqueous sodium hydroxide (3×), and dried over anhydrous sodium sulfate. Concentration under reduced pressure followed by purification by silica gel chromatography afforded Example 182 (55.0 mg) as a yellow solid. HPLC retention time=3.67 min. (Condition B) and LC/MS $M^{+1}$=474.

Example 183

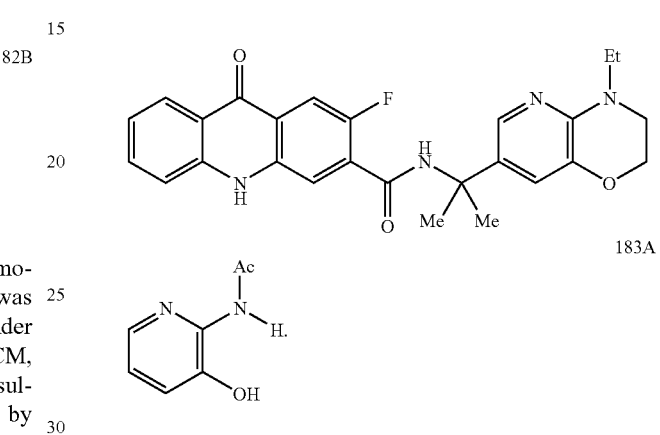

183A

A mixture of 2-amino-3-hydroxypyridine (3.0 g, 27.2 mmol) and 2 mL of pyridine in 141 mL of acetic anhydride was heated at reflux for 5 min., cooled to room temperature, and concentrated under reduced pressure. The oily residue was then stirred in a 1M aqueous solution of sodium hydroxide (75 mL) until the mixture became homogeneous. The solution was poured into a mixture of crushed ice and 6 M aqueous hydrochloric acid, and the pH was adjusted to ~4.0. The aqueous mixture was extracted with DCM, washed with water, dried over anhydrous sodium sulfate, and concentrated to give 183A (3.70 g, 89%) as an off-white solid. HPLC retention time=0.193 min. (Condition B) and LC/MS $M^{+1}$=153.

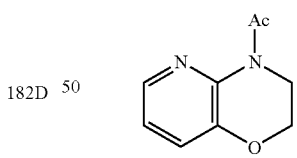

To a mixture of 183A (3.70 g, 24.3 mmol), 1,2-dibromoethane (8.4 mL, 97.2 mmol), water (30 mL), and acetone (120 mL) was added potassium carbonate (13.4 g, 97.2 mmol). The reaction mixture was heated at reflux overnight and concentrated. The residue was dissolved in DCM, washed with water, dried over anhydrous sodium sulfate, and concentrated under reduced pressure. The crude solid was dissolved in ether, and the undissolved material was removed by vacuum filtration. The filtrate was concentrated to give 4.28 g (99%) of 183B as an off-white solid. HPLC retention time=0.720 min. (Condition B) and LC/MS $M^{+1}$=179.

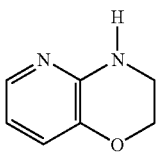

A mixture of 183B (0.289 g, 1.62 mmol) and potassium hydroxide (0.582 g, 10.4 mmol) in 4 mL of MeOH and 2 mL of water was heated at 55° C. for 45 min. The reaction mixture was poured over crushed ice and extracted with DCM. The organic layer was collected, washed with water, and dried over anhydrous sodium sulfate. Concentration under reduced pressure afforded 0.215 g (97%) of 183D as a white solid. HPLC retention time=0.293 min. (Condition B) and LC/MS $M^{+1}$=137.

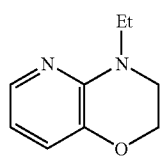

A mixture of 183C (0.215 g, 1.58 mmol), sodium cyanoborohydride (0.159 g, 2.53 mmol), and acetalde (0.18 mL, 3.16 mmol) in 14 mL of acetonitrile at room temperature was stirred for 30 min. To the mixture was added 4 drops of AcOH, and the reaction mixture was stirred overnight. The mixture was diluted with EtOAc, washed with 1M aqueous sodium hydroxide, with brine, and dried over anhydrous sodium sulfate. Concentration under reduced pressure followed by purification by silica gel chromatogrpahy provided 183D (0.090 g) as a white solid. HPLC retention time=2.00 min. (Condition B) and LC/MS $M^{+1}$=165.

A mixture of 183D (0.090 g, 0.548 mmol) and N-bromosuccinimide (0.098 g, 0.548 mmol) in 3.6 mL dMF was heated at 75° C. for 1 h. The solvent was removed under reduced pressure, and the residue was dissolved in DCM, washed with water, and dried over anhydrous sodium sulfate. Concentration under reduced pressure followed by purification by silica gel chromatography afforded 0.102 g of 183E (77%) as an off-white solid. HPLC retention time=1.81 min. (Condition B) and LC/MS $M^{+1}$=242/244.

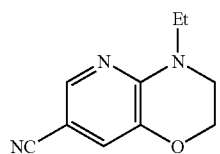

A mixture of 183E (0.102 g, 0.420 mmol), tris(dibenzylideneacetone)dipalladium(0) (0.023 g, 0.025 mmol), 1,1'-bis(diphenylphosphino)ferrocene (0.028 g, 0.050 mmol), zinc powder (3.0 mg, 0.050 mmol), and zinc cyanide (0.030 g, 0.025 mmol) was flushed with nitrogen. Dimethyl acetamide (2 mL) was added, and the resulting mixture was heated at 150° C. overnight. HPLC indicated that the reaction was complete. The reaction mixture was cooled to room temperature, diluted with EtOAc, washed with 2N aqueous ammonium hydroxide, washed with brine, and dried over anhydrous sodium sulfate. Concentration under reduced pressure followed by purification by silica gel chromatography afforded 183F (0.061 g, 77%) as a white solid. HPLC retention time=2.16 min. (Condition B) and LC/MS $M^{+1}$=190.

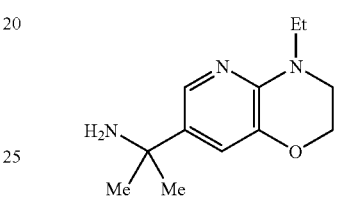

To a flame-dried flask under nitrogen was added cerium chloride (0.238 g, 0.967 mmol) followed by anhydrous THF (6 mL). The mixture was stirred vigorously for 45 min., during which time the cerium chloride became suspended. The suspension was cooled to −78° C., and methyl lithium (0.92 mL, 1.29 mmol, 1.4 M in ether) was added dropwise. After the addition was complete, the reaction mixture was stirred for 0.5 h at −78° C. Compound 183F (0.061 g, 0.322 mmol) in THF (2 mL) was added via cannula to the −78° C. solution. The dry-ice bath was removed, and the reaction mixture was stirred at room temperature overnight. The mixture was quenched with a few drops of a saturated aqueous solution of ammonium chloride, and a 2M aqueous solution of ammonium hydroxide was added dropwise until a precipitate formed and settled to the bottom of the flask. The mixture was filtered through Celite under reduced pressure, diluted with DCM, washed with water, and dried over anhydrous sodium sulfate. Concentration under reduced pressure afforded 183G (0.036 g). The amine was used without any further purification. HPLC retention time=0.115 min. (Condition B) and LC/MS $M^{+1}$=222.

183. Example 183

To a mixture of compound 174E (0.035 g, 0.136 mmol), 183G (0.036 g, 0.163 mmol), and triethylamine (0.06 mL, 0.408 mmol) was added N,N-bis[2-oxo-3-oxazolidinyl]phosphorodiamidic chloride (0.0.041 g, 0.163 mmol) in 5 mL of anhydrous DMF at room temperature. The reaction mixture was stirred at room temperature overnight. The mixture was diluted with DCM, washed with water, washed with 1N aqueous sodium hydroxide (3×), and dried over anhydrous sodium sulfate. Concentration under reduced pressure followed by purification by preparative HPLC afforded Example 183 (40.0 mg) as a bright yellow solid. HPLC retention time=2.24 min. (Condition B) and LC/MS $M^{+1}$=461.

Example 184

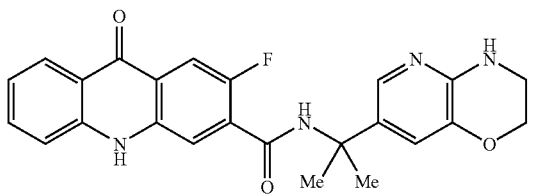

184A

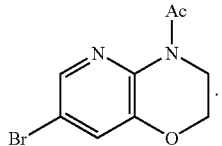

A mixture of 183B (0.438 g, 2.46 mmol) and N-bromosuccinimide (0.438 g, 2.46 mmol) in 6 mL of DMF was heated at 75° C. for 1 h. The solvent was removed under reduced pressure, and the residue was dissolved in DCM, washed with water, and dried over anhydrous sodium sulfate. Concentration under reduced pressure followed by purification by silica gel chromatography afforded 0.315 g of 184A as a white solid. HPLC retention time=2.99 min. (Condition B) and LC/MS $M^{+1}$=258.

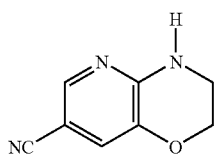

A mixture of 184A (0.290 g, 1.13 mmol), tris(dibenzylideneacetone)dipalladium(0) (0.062 g, 0.068 mmol), 1,1'-bis(diphenylphosphino)ferrocene (0.075 g, 0.136 mmol), zinc powder (9.0 mg, 0.136 mmol), and zinc cyanide (0.080 g, 0.678 mmol) was flushed with nitrogen. Dimethyl acetamide (4 mL) was added, and the resulting mixture was heated at 150° C. overnight. HPLC indicated that the reaction was complete. The reaction mixture was cooled to room temperature, diluted with EtOAc, washed with 2N aqueous ammonium hydroxide, washed with brine, and dried over anhydrous sodium sulfate. Concentration under reduced pressure followed by purification by silica gel chromatography afforded 184B (0.183 g, 80%) as an off-white solid. HPLC retention time=0.997 min. (Condition B) and LC/MS $M^{+1}$=162.

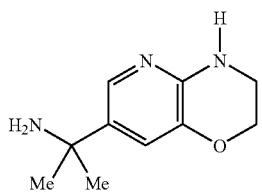

To a flame-dried flask under nitrogen was added cerium chloride (0.918 g, 3.73 mmol) followed by anhydrous THF (11 mL). The mixture was stirred vigorously for 45 min., during which time the cerium chloride became suspended. The suspension was cooled to −78° C., and methyl lithium (2.66 mL, 3.73 mmol, 1.4 M in ether) was added dropwise. After the addition was complete, the reaction mixture was stirred for 0.5 h at −78° C. Compound 184B (0.120 g, 0.745 mmol) in THF (4 mL) was added via cannula to the −78° C. solution. The dry-ice bath was removed, and the reaction mixture was stirred at room temperature overnight. The mixture was quenched with a few drops of a saturated aqueous solution of ammonium chloride, and a 2M aqueous solution of ammonium hydroxide was added dropwise until a precipitate formed and settled to the bottom of the flask. The mixture was filtered through Celite under reduced pressure, diluted with DCM, washed with water, and dried over anhydrous sodium sulfate. Concentration under reduced pressure afforded 184C. The amine was used without any further purification. HPLC retention time=0.197 min. (Condition B) and LC/MS $M^{+1}$=194.

184. Example 184

To a mixture of compound 174E (0.020 g, 0.078 mmol), 184C (0.017 g, 0.086 mmol), and triethylamine (0.033 mL, 0.233 mmol) was added N,N-bis[2-oxo-3-oxazolidinyl]phosphorodiamidic chloride (0.024 g, 0.093 mmol) in 4 mL of anhydrous DMF at room temperature. The reaction mixture was stirred at room temperature overnight. The mixture was diluted with DCM, washed with water, washed with 1N aqueous sodium hydroxide (3×), and dried over anhydrous sodium sulfate. Concentration under reduced pressure followed by purification by preparative HPLC afforded Example 184 (17.0 mg) as a bright yellow solid. HPLC retention time=2.34 min. (Condition B) and LC/MS $M^{+1}$=433.

Example 185

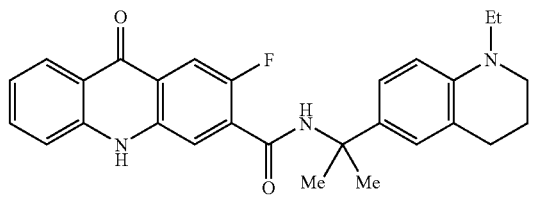

Example 185 was prepared as a yellow solid using a reaction sequence analogous to the procedure described for the preparation of example 182 starting with tetrahydroquinoline. HPLC retention time=2.72 min. (Condition B) and LC/MS $M^{+1}$=458.

Example 186

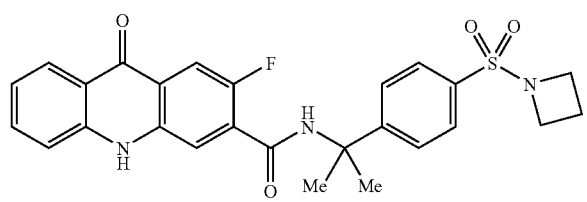

-continued

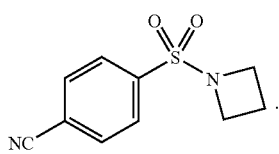

186A

To 4-cyano-sulfonyl chloride (0.100 g, 0.496 mmol) in DCM at 0° C. was added azetidine-HCl followed by triethylamine (0.152 mL, 1.09 mmol). The ice-bath was removed, and the reaction was warmed to room temperature, diluted with DCM, washed with water, and dried over anhydrous magnesium sulfate. Concentration under reduced pressure afforded 0.105 g (95%) of 186A as a white solid. HPLC retention time=1.87 min. (Condition B).

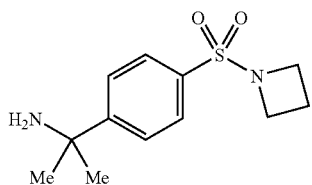

To a flame-dried flask under nitrogen was added cerium chloride (0.468 g, 1.89 mmol) followed by anhydrous THF. The mixture was stirred vigorously for 45 min., during which time the cerium chloride became suspended. The suspension was cooled to −78° C., and methyl lithium (1.69 mL, 2.30 mmol, 1.4 M in ether) was added dropwise. After the addition was complete, the reaction mixture was stirred for 0.5 h at −78° C. Compound 186A (0.105 g, 0.472 mmol) in THF was added via cannula to the −78° C. solution. The dry-ice bath was removed, and the reaction mixture was stirred at room temperature overnight. The mixture was quenched with a few drops of a saturated aqueous solution of ammonium chloride, and a 2M aqueous solution of ammonium hydroxide was added dropwise until a precipitate formed and settled to the bottom of the flask. The mixture was filtered through Celite under reduced pressure, diluted with DCM, washed with water, and dried over anhydrous sodium sulfate. Concentration under reduced pressure afforded 0.115 g (96%) 186B as a tan solid.

186. Example 186

To a mixture of 174E (0.090 g, 0.348 mmol), 186B (0.115 g, 0.452 mmol), and triethylamine (0.097 mL, 0.696 mmol) was added N,N-bis[2-oxo-3-oxazolidinyl]phosphorodiamidic chloride (0.106 g, 0.417 mmol) in 8 mL of anhydrous DMF at room temperature. The reaction mixture was stirred at room temperature overnight. The mixture was diluted with DCM, washed with water, washed with 1N aqueous sodium hydroxide (3×), and dried over anhydrous sodium sulfate. Concentration under reduced pressure followed by purification by preparative HPLC afforded compound 186 a yellow solid. HPLC retention time=3.10 min. (Condition B) and LC/MS $M^{+1}$=494.

Examples 187-190

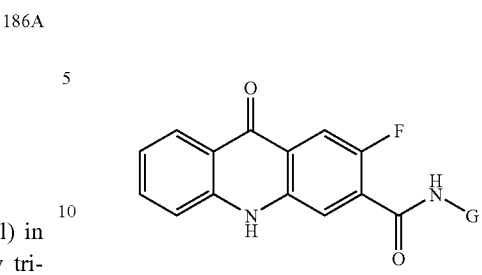

Examples 187-190 (Table 16) were prepared using a method analogous to the method described for the preparation of Example 186 using acridone acic 174E. The compounds were either purified by silica gel chromatography or by preparative HPLC.

TABLE 16

| Ex. No. | —G | HPLC time (min.) Condition | MS ($M^+$) |
| --- | --- | --- | --- |
| 187 | ![structure with SO2N(Me)CH2CH2OMe on dimethylmethylene-phenyl] | 2.85 (A) | 526 |
| 188 | ![structure with SO2-piperazine-Me on dimethylmethylene-phenyl] | 2.37 (B) | 537 |
| 189 | ![structure with SO2N(Me)OMe on dimethylmethylene-phenyl] | 3.01 (B) | 498 |
| 190 | ![structure with SO2NH-OMe on dimethylmethylene-phenyl] | 3.06 (B) | 484 |

Example 191

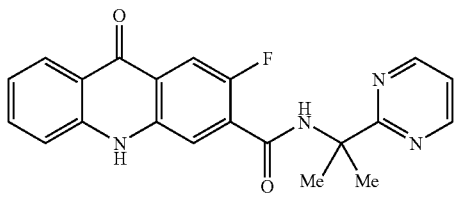

Example 191 was prepared using a method analogous to the method described for the preparation of Example 186 using 2-cyanopyrimidine. HPLC retention time=2.97 min. (Condition B) and LC/MS $M^{+1}$=377.

Example 192

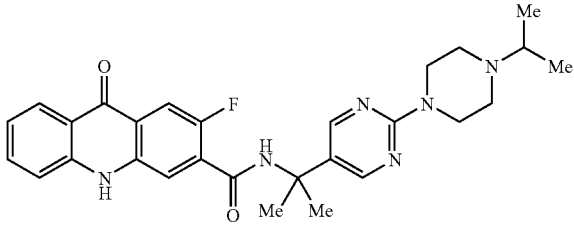
192A

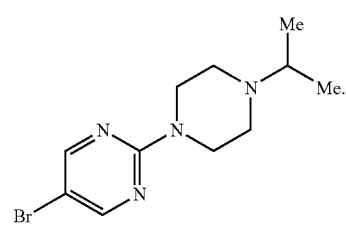

A mixture of 5-bromo-2-chloropyrimidine (0.300 g, 1.55 mmol) and 1-isopropylpiperazine (0.20 mL) in MeOH was heated at 70° C. for 3 h. The solvent was removed under reduced pressure to give a quantitative yield of compound 192A as a cream colored solid.

192B.

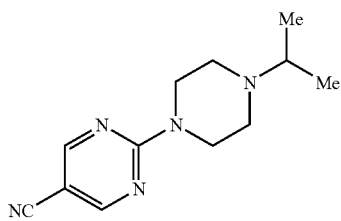

A mixture of 192B (0.440 g, 1.54 mmol), tris(dibenzylideneacetone)dipalladium(0) (0.085 g, 0.093 mmol), 1,1'-bis(diphenylphosphino)ferrocene (0.103 g, 0.185 mmol), zinc powder (12.0 mg, 0.185 mmol), and zinc cyanide (0.109 g, 0.926 mmol) was flushed with nitrogen. Dimethyl acetamide (4 mL) was added, and the resulting mixture was heated at 150° C. overnight. HPLC indicated that the reaction was complete. The reaction mixture was cooled to room temperature, diluted with EtOAc, and washed with 2N aqueous ammonium hydroxide, washed with brine, and dried over anhydrous sodium sulfate. Concentration under reduced pressure followed by purification by silica gel chromatography afforded 192B (0.250 g, 70%) as a tan solid.

192. Example 192

Example 192 was prepared using a method analogous to the method described for the preparation of example 186 using nitrile 192B. HPLC retention time=2.38 min. (Condition B) and LC/MS $M^{+1}$=503.

Example 193

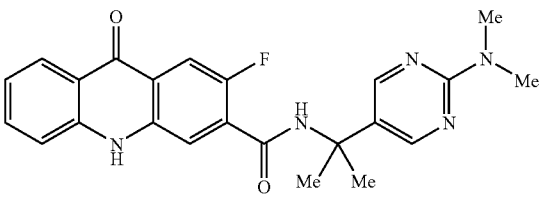

Example 193 was prepared using a method analogous to the method described for the preparation of Example 193. HPLC retention time=2.99 min. (Condition B) and LC/MS $M^{+1}$=420.

Example 194

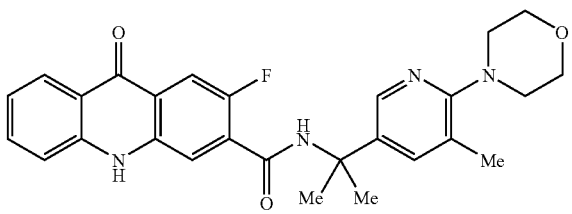
194A

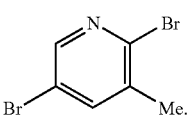

To a heterogeneous suspension of 2-amino-5-bromo-3-methylpyridine (5.0 g, 26.7 mmol) in 17 mL of hydrobromic acid at 0° C. was added bromine (4.25 mL). To this mixture was added sodium nitrite (5.25 g) in 7.5 mL of water slowly via pipet. The mixture was stirred for 15 min., and 11.3 g of sodium hydroxide in 29 mL of water was slowly added. The resulting oil was extracted with ether, and the organic layer was collected, dried over anhydrous sodium sulfate, and concentrated under reduced pressure to give 194A as a yellowish-orange solid. HPLC retention time=3.19 min. (Condition B) and LC/MS $M^{+1}$=250.

194B.

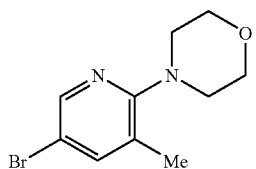

A mixture of the 2,5-bromo-3-methylpyridine (0.491 g, 1.96 mmol) and morpholine (6 mL) in a sealed tube was heated at 140° C. for 5 h. The reaction mixture was cooled to room temperature, diluted with water, and extracted with DCM. The organic layer was collected, washed with water, and dried over anhydrous sodium sulfate. Concentration under reduced pressure afforded a quantitative yield of 194B. HPLC retention time=3.26 min. (Condition B) and LC/MS $M^{+1}$=257.

194C.

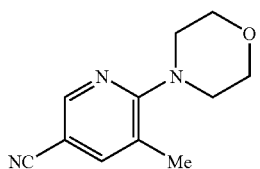

A mixture of 194B (0.558 g, 2.17 mmol), tris(dibenzylideneacetone)dipalladium(0) (0.119 g, 0.130 mmol), 1,1'-bis(diphenylphosphino)ferrocene (0.144 g, 0.260 mmol), zinc powder (17.0 mg, 0.260 mmol), and zinc cyanide (0.153 g, 1.30 mmol) was flushed with nitrogen. Dimethyl acetamide (7.5 mL) was added, and the resulting mixture was heated at 150° C. overnight. HPLC indicated that the reaction was complete. The reaction mixture was cooled to room temperature, diluted with EtOAc, washed with 2N aqueous ammonium hydroxide, washed with brine, and dried over anhydrous sodium sulfate. Concentration under reduced pressure followed by purification by silica gel chromatography afforded 194C (0.341 g, 77%) as an off-white solid. HPLC retention time=2.33 min. (Condition B) and LC/MS $M^{+1}$=204.

194D.

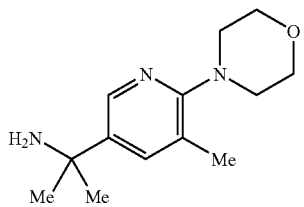

To a flame-dried flask under nitrogen was added cerium chloride (2.07 g, 8.39 mmol) followed by 25 mL of anhydrous THF. The mixture was stirred vigorously for 45 min., during which time the cerium chloride became suspended. The suspension was cooled to −78° C., and methyl lithium (6.0 mL, 8.39 mmol, 1.4 M in ether) was added dropwise. After the addition was complete, the reaction mixture was stirred for 0.5 h at −78° C. Compound 194C (0.341 g, 1.68 mmol) in THF was added via cannula to the −78° C. solution. The dry-ice bath was removed, and the reaction mixture was stirred at room temperature overnight. The mixture was quenched with a few drops of a saturated aqueous solution of ammonium chloride, and a 2M aqueous solution of ammonium hydroxide was added dropwise until a precipitate formed and settled to the bottom of the flask. The mixture was filtered through Celite under reduced pressure, diluted with DCM, washed with water, and dried over anhydrous sodium sulfate. Concentration under reduced pressure afforded 0.376 g (95%) 194D as a yellowish-orange oil. HPLC retention time=0.39 min. (Condition B) and LC/MS $M^{+1}$=236.

194. Example 194

To a mixture of acridone acid 174E (0.019 g, 0.074 mmol), 194D (0.21 g, 0.089 mmol), and triethylamine (0.03 mL, 0.223 mmol) was added N,N-bis[2-oxo-3-oxazolidinyl]phosphorodiamidic chloride (0.023 g, 0.223 mmol) in 4 mL of anhydrous DMF at room temperature. The reaction mixture was stirred at room temperature overnight. The mixture was diluted with DCM, washed with water, washed with 1N aqueous sodium hydroxide (3×), and dried over anhydrous sodium sulfate. Concentration under reduced pressure followed by purification by preparative HPLC afforded 16 mg of compound 194 as a bright yellow solid. HPLC retention time=2.27 min. (Condition B) and LC/MS $M^{+1}$=475.

Example 195-198

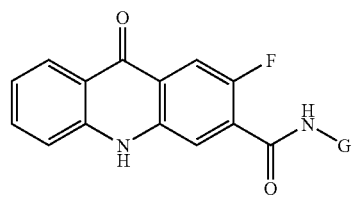

Examples 195-198 (Table 17) were prepared using a method analogous to the method described for the preparation of Example 194. The compounds were purified by silica gel chromatography or by preparative HPLC.

TABLE 17

| Ex. No. | —G | HPLC time (min.) Condition | $M^+$ |
|---|---|---|---|
| 195 | ![structure] | 2.11 (B) | 502 |
| 196 | ![structure] | 2.33 (B) | 459 |

TABLE 17-continued

| Ex. No. | —G | HPLC time (min.) Condition | M+ |
|---|---|---|---|
| 197 | pyridine with Br, Me, and C(Me)₂ substituents | 3.26 (B) | 469 |
| 198 | pyridine with Cl, Me, and C(Me)₂ substituents | 3.01 (B) | 410 |

Examples 199-204

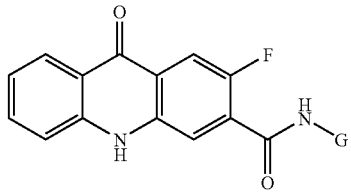

Examples 199-204 were prepared according to this general procedure: A mixture of bromide 197 or chloride 198 (1 equivalent), the amine (1 equivalent), Pd₂(dba)₃ (0.25 equivalents), dicyclohexyphosphodiphenyl (0.25 equivalents), t-BuOK (2.5 equivalents), and DMA (50 mg of 198/1 mL) under nitrogen was stirred overnight. The reaction mixture was filtered, and the filtrate was concentrated under reduced pressure and purified by preparative HPLC to give acridones 199-204.

TABLE 18

| Ex. No | —G | HPLC time (min.) Condition | M+ |
|---|---|---|---|
| 199 | 2-methylpyrrolidinyl-pyridine substituent | 2.58 (B) | 473 |
| 200 | 2-(hydroxymethyl)pyrrolidinyl-pyridine substituent | 2.21 (B) | 489 |
| 201 | 3-(dimethylamino)pyrrolidinyl-pyridine substituent | 1.82 (B) | 502 |

TABLE 18-continued

| Ex. No | —G | HPLC time (min.) Condition | M+ |
|---|---|---|---|
| 202 | ![structure with pyrrolidine-pyridine-CMe2] | 2.28 (B) | 489 |
| 203 | ![structure with ethyl-piperazinone-pyridine-CMe2] | 2.16 (B) | 502 |
| 204 | ![structure with methoxybenzyl-piperazine-pyridine-CMe2] | 2.22 (B) | 580 |

Example 205

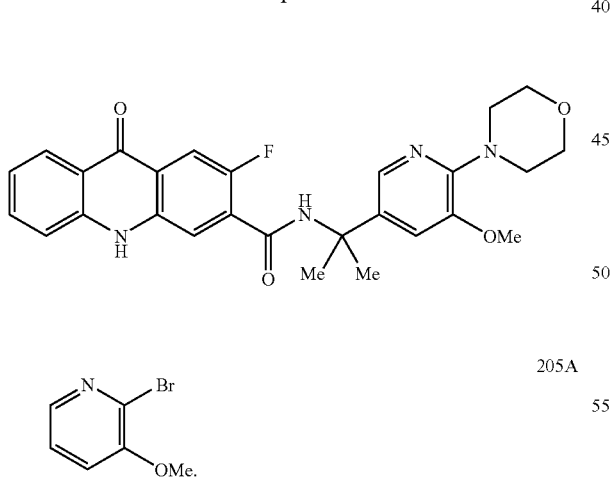

205A

To 2-bromo-3-methoxypyridine (1.00 g, 5.75 mmol) in 20 mL of DCM and 10 mL of MeOH was added trimethylsilyl diazomethane dropwise (5.76 mL, 11.5 mmol). The reaction mixture was stirred for 30 min. at room temperature. The solvent was removed under reduced pressure to give a quantitative yield of 205A as a light-brown solid. HPLC retention time=1.81 min. (Condition B) and LC/MS M+1=189.

205B.

A mixture of 205A (0.453 g, 2.41 mmol) and morpholine (6 mL) in a sealed tube was heated at 125° C. for 3 h. The reaction mixture was diluted with DCM, washed with water, and dried over anhydrous sodium sulfate. Concentration under reduced pressure afforded 0.411 g (88%) of 205B as a brownish oil. HPLC retention time=0.603 min. (Condition B) and LC/MS M+1=195.

205C.

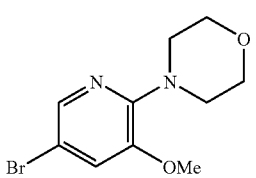

A mixture of 205B (0.411 g, 2.12 mmol) and N-bromosuccinimide (0.377 g, 2.12 mmol) in 6 mL of DMF was heated at 75° C. for 1.5 h. The solvent was removed under reduced pressure, and the residue was dissolved in DCM, washed with water, and dried over anhydrous sodium sulfate. Concentration under reduced pressure followed by purification by silica gel chromatography afforded 0.326 g of 205C as a white solid. HPLC retention time=2.72 min. (Condition B) and LC/MS $M^{+1}$=274.

205D.

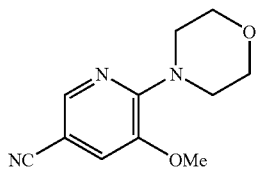

A mixture of 205C (0.326 g, 1.19 mmol), tris(dibenzylideneacetone)dipalladium(0) (0.065 g, 0.071 mmol), 1,1'-bis(diphenylphosphino)ferrocene (0.079 g, 0.143 mmol), zinc powder (9.3 mg, 0.143 mmol), and zinc cyanide (0.084 g, 0.714 mmol) was flushed with nitrogen. Dimethyl acetamide (4.0 mL) was added, and the resulting mixture was heated at 150° C. overnight. HPLC indicated that the reaction was complete. The reaction mixture was cooled to room temperature, diluted with EtOAc, and washed with 2N aqueous ammonium hydroxide, washed with brine, and dried over anhydrous sodium sulfate. Concentration under reduced pressure followed by purification by silica gel chromatography afforded 205D (0.226 g, 87%) as an off-white solid. HPLC retention time=2.26 min. (Condition B) and LC/MS $M^{+1}$=220.

205E.

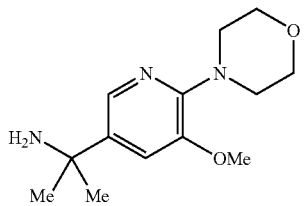

To a flame-dried flask under nitrogen was added cerium chloride (1.19 g, 4.83 mmol) followed by 20 mL of anhydrous THF. The mixture was stirred vigorously for 45 min., during which time the cerium chloride became suspended. The suspension was cooled to −78° C., and methyl lithium (3.5 mL, 4.83 mmol, 1.4 M in ether) was added dropwise. After the addition was complete, the reaction mixture was stirred for 0.5 h at −78° C. Compound 205D (0.212 g, 0.967 mmol) in THF was added via cannula to the −78° C. solution. The dry-ice bath was removed, and the reaction mixture was stirred at room temperature overnight. The mixture was quenched with a few drops of a saturated aqueous solution of ammonium chloride, and a 2M aqueous solution of ammonium hydroxide was added dropwise until a precipitate formed and settled to the bottom of the flask. The mixture was filtered through Celite under reduced pressure, diluted with DCM, washed with water, and dried over anhydrous sodium sulfate. Concentration under reduced pressure afforded 205E (0.242 g) as a yellowish-orange oil. HPLC retention time=0.620 min. (Condition B) and LC/MS $M^{+1}$=252.

205. Example 205

To a mixture of 174E (0.025 g, 0.097 mmol), compound 205E (0.029 g, 0.117 mmol), and triethylamine (0.04 mL, 0.292 mmol) was added N,N-bis[2-oxo-3-oxazolidinyl] phosphorodiamidic chloride (0.030 g, 0.117 mmol) in 5 mL of anhydrous DMF at room temperature. The reaction mixture was stirred at room temperature overnight. The mixture was diluted with DCM, washed with water, washed with 1N aqueous sodium hydroxide (3×), and dried over anhydrous sodium sulfate. Concentration under reduced pressure followed by purification by preparative HPLC afforded 16 mg of compound 205 as a bright yellow solid. HPLC retention time=2.32 min. (Condition B) and LC/MS $M^{+1}$=491.

Example 206

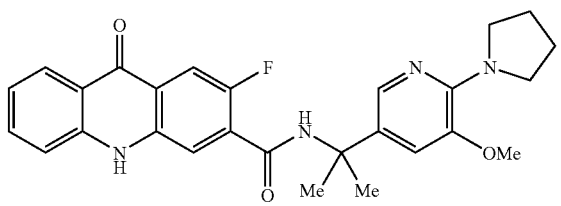

Example 206 was prepared using a method analogous to the method described for the preparation of Example 205. HPLC retention time=2.42 min. (Condition B) and LC/MS $M^{+1}$=475.

Example 207

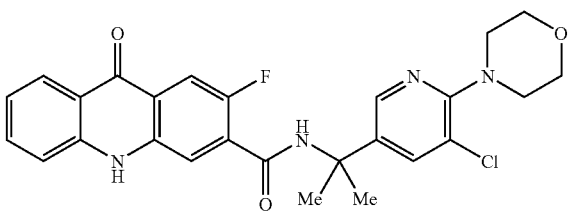

Example 207 was prepared using a method analogous to the method described for the preparation of Example 206 starting with 2,3-dichloropyridine. HPLC retention time=3.33 min. (Condition B) and LC/MS $M^{+1}$=495/497.

Example 208

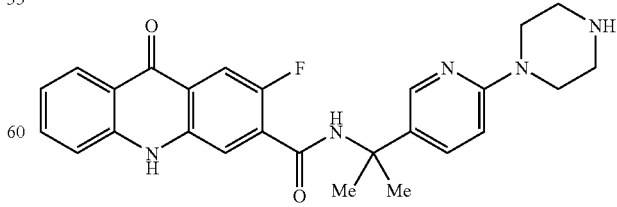

To a mixture of 204 (0.100 g, 0.17 mmol) and 10 mL of DCM was at 0° C. was added 1-chloroethyl chhloroformate (0.123 g, 0.86 mmol). The reaction mixture was stirred for 10 at 0° C., stirred at room temperature for 3.5 h., and refluxed for 1 h. The solvent was removed under reduced pressure, and the residue was dissolved in MeOH (5 mL) and 3N aqueous HCl(0.5 mL). The mixture was stirred at room temperature for 1 h. Concentration under reduced pressure followed by purification by preparative HPLC afforded 36 mg (46%) of Example 208. HPLC retention time=1.91 min. (Condition B) and LCMS $M^{+1}$=460.

Examples 209-216

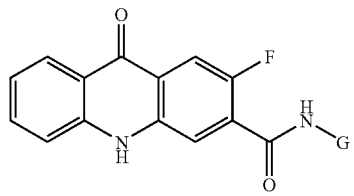

Examples 209-216 (Table 19) were prepared using methods analogous to those described in Examples 1 using corresponding amines and acridone 174E. The amines were made from commercially-available nitrile starting materials and the cerium chloride procedure described for making compound 1D. The compounds were either purified by silica gel chromatography or by preparative HPLC.

TABLE 19

| Ex. No. | —G | HPLC time (min.) (Condition) | MS ($M^+$) |
|---|---|---|---|
| 209 | (2-pyridyl)C(Me)(Me)– | 2.13 (A) | 376 |
| 210 | (3-SMe-phenyl)C(Me)(Me)– | 3.30 (A) | 421 |
| 211 | (3-S(=O)Me-phenyl)C(Me)(Me)– | 2.62 (A) | 437 |
| 212 | (3-SO$_2$Me-phenyl)C(Me)(Me)– | 2.58 (A) | 453 |
| 213 | (2-CF$_3$-pyridin-5-yl)C(Me)(Me)– | 2.92 (A) | 444 |
| 214 | (2-Me-pyridin-4-yl)C(Me)(Me)– | 2.14 (A) | 390 |
| 215 | (2,6-diMe-pyridin-4-yl)C(Me)(Me)– | 2.14 (A) | 404 |
| 216 | (pyridin-3-yl)CHF–C(Me)(Me)– | 2.29 (A) | 408 |

Example 217

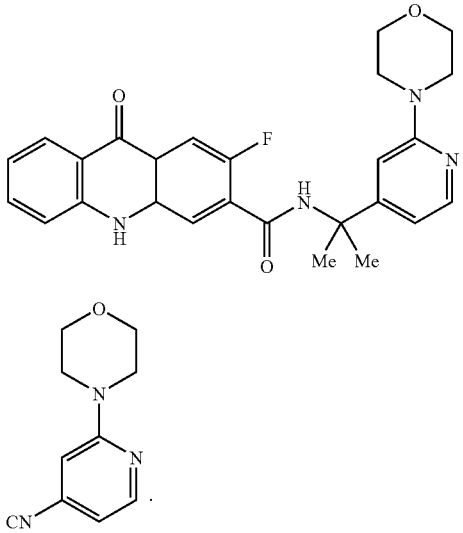

217A

To an oven-dried Schlenk flask was charged with palladium(II) acetate (11 mg, 5 mol %), 2-(di-t-butylphosphino)biphenyl (30 mg, 10 mol %), and NaOt-Bu (135 mg, 1.4 mmol), followed by 2-chloropyridine-4-carbonitrile (139 mg, 1.0 mmol) and toluene (2.0 mL). After the Schlenk flask was evacuated and backfilled with argon, the mixture was heated to 100° C. for 2 h. After cooling to room temperature, ether was added, and the reaction mixture was filtered through Celite and concentrated in vacuo. The crude product was purified by flash chromatography (100% CH$_2$Cl$_2$) on silica gel to afford compound 217A as a pale yellow solid. HPLC retention time=1.256 min. (Condition A) and LC/MS $M^+$+1=190$^+$.

217B.

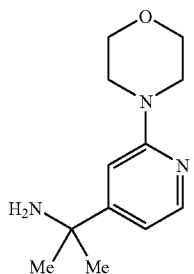

Using compound 217A and a route analogous to that described for the preparation of compound 1D, compound 217B was prepared as a pale yellow semi-solid. HPLC retention time=0.195 min. (Condition A) and LC/MS M$^+$+1=222$^+$.

217. Example 217

Following the same or similar procedure as described for making Example 1 but using 217B and acridone acid 174E, Example 217 was prepared as a pale yellow solid. HPLC retention time=2.189 min. (Condition A) and LC/MS M$^+$+1=461$^+$.

Example 218

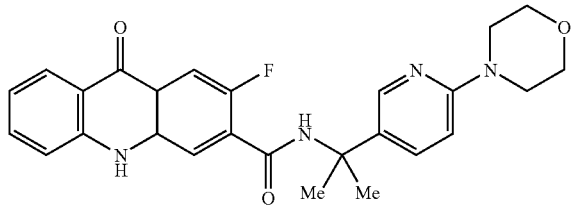

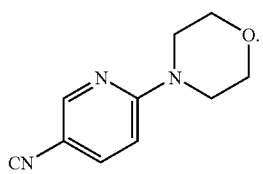

218A

A mixture of 6-chloronicotinonitrile (139 mg, 1.0 mmol) and morpholine (0.35 mL, 4.0 mmol) in 2 mL of EtOH was heated to reflux for 1 h. Upon cooling to room temperature, the solvent was removed under reduced pressure and the residue was diluted with water. The white solid was collected by filtration, rinsed thoroughly with water, and dried under high vacuum overnight to afford compound 218A as a white crystalline solid. HPLC retention time=1.59 min. (Condition A) and LC/MS M$^+$+1=190$^+$.

218B.

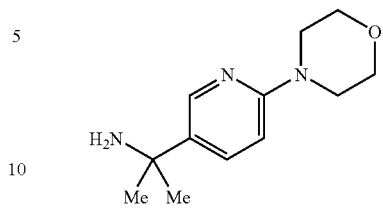

Compound 218B was prepared from 218A by a route analogous to that used for the preparation of compound 1D. Compound 218B is a pale yellow solid. HPLC retention time=0.203 min. (Condition A) and LC/MS M$^+$+1=222$^+$.

218C. Example 218

Following the same or similar procedure as described for making Example 1 but using 217B and acridone acid 174E, Example 217 was prepared as a pale yellow solid. HPLC retention time=2.146 min. (Condition A) and LC/MS M$^+$+1=461$^+$.

Examples 219-228

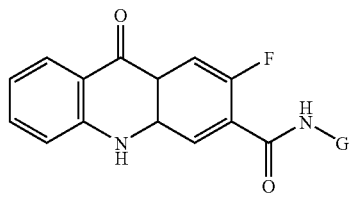

Examples 219-228 having the above formula wherein G has the values set forth in Table 20, were prepared from acridone acid 174E, by a route analogous to that used for the preparation of 217, replacing the amine 217B with the required H$_2$N-G. The corresponding amines were prepared by a route analogous to that used for the preparation of 217B or 218B. If the products carry basic moieties, they were purified by preparative HPLC.

TABLE 20

| Ex. No | —G | HPLC time (min) (Condition) | M$^+$ + H |
|---|---|---|---|
| 219 | 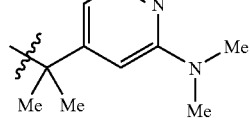 | 2.19 (A) | 419 |
| 220 | 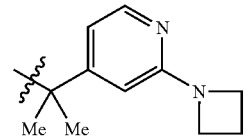 | 2.25 (A) | 431 |

TABLE 20-continued

| Ex. No | —G | HPLC time (min) (Condition) | M⁺ + H |
|---|---|---|---|
| 221 | [structure] | 2.09 (A) | 476 |
| 222 | [structure] | 1.97 (A) | 476 |
| 223 | [structure] | 2.19 (A) | 419 |
| 224 | [structure] | 2.24 (A) | 431 |
| 225 | [structure] | 2.31 (A) | 445 |
| 226 | [structure] | 2.30 (A) | 489 |
| 227 | [structure] | 2.30 (A) | 489 |
| 228 | [structure] | 2.92 (A) | 571 |

Example 229

[structure 229A]

Anhydrous cerium chloride (22 g, 89.3 mmol) was placed in a flame-dried three neck round bottom flask under argon. To this, was added 100 mL of dry THF and the mixture was stirred vigorously for 2 h. The off-white paste was cooled to −78° C. and a 1.6 M solution of MeLi (27 mL, 43.2 mmol) in ether was added dropwise via an additional funnel. After stirring at −78° C. for 0.5 h, a solution of 2-chloro-pyridine-5-carbonitrile (2.0 g, 14.4 mmol) in dry THF (10 mL) was added, and the mixture was stirred at ambient temperature overnight. Water (15 mL) was added slowly at 0° C. and the precipitate was removed by filtration through a pad of Celite (the Celite pad was rinsed thoroughly with THF). Combined filtrates were concentrated under reduced pressure and the resulting residue was taken into $CH_2Cl_2$. After being washed with 50% $NH_4OH$ (×2) and brine, the organic layer was dried over anhydrous $Na_2SO_4$ and concentrated to dryness under reduced pressure to give 1.67 g (68%) of Compound 229A as a yellow oil, which was used in the next reaction without further purification. HPLC retention time=0.610 min. (Condition A) and LC/MS M⁺+1=171⁺. $^1$H-NMR (400 MHz, $CDCl_3$) δ 8.48 (s, 1H), 7.75 (d, J=2.75 Hz, 1H), 7.20 (d, J=2.75 Hz, 1H), 1.43 (s, 6H).

229B. Example 229

Compound 229B was prepared from acid 174E and compound 229A by a route analogous to that used for the preparation of Example 1. Compound 229B is a yellow solid. HPLC retention time=3.013 min. (Condition A) and LC/MS M⁺+1=410⁺.

Example 230

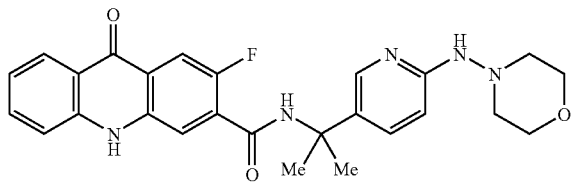

An oven-dried Schlenk flask was charged with tris(dibenzylideneacetone)dipalladium(0) (10 mg), ditricyclohexyl-2-biphenylphosphone (10 mg), and NaOt-Bu (15 mg), followed by 1,4-dioxane (1.0 mL), Example 229 (30 mg) and 4-aminomorpholine (9 mg). After the Schlenk flask was evacuated and backfilled with argon, the mixture was heated to 100° C. for 24 h. After being cooled to room temperature, ether was added and the reaction mixture was filtered through Celite and concentrated in vacuo. The crude product was purified by reversed-phase preparative HPLC to afford Example 230 as a pale yellow solid. HPLC retention time=2.120 min. (Condition A) an LC/MS $M^{+}+1=476^{+}$.

Examples 231-234

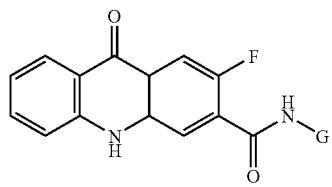

Examples 231-234 having the above formula wherein G is as set forth in Table 21 were prepared from compound 229 by a route analogous to that used for the preparation of 230, replacing the amine with the required $H_2N$-G. If the products carry basic moieties, they were purified by preparative HPLC.

TABLE 21

| Ex. No | —G | HPLC time (min) (Condition) | $M^+ + H$ |
|---|---|---|---|
| 231 | (pyridine-NH-pyrrolidine with gem-dimethyl linker) | 2.49 (A) | 460 |
| 232 | (pyridine-NH-N-(CH2OMe)-pyrrolidine with gem-dimethyl linker) | 2.31 (A) | 504 |
| 233 | (pyridine-N-pyrrolidine-C(O)N(Me)Me with gem-dimethyl linker) | 2.17 (A) | 516 |
| 234 | (pyridine-N-pyrrolidine-C(O)NH2 with gem-dimethyl linker) | 2.19 (A) | 488 |

Example 235

(structure of 235)

235A (structure of 235A: 4-(2-bromoethoxy)benzonitrile)

A mixture of 4-cyanophenol (3.0 g, 25.0 mmol), 1,2-dibromoethane (22 mL, 250 mmol) and potassium carbonate (8.64 g, 62.5 mmol) in 250 mL of dry DMF was heated to 80° C. for 3 h. After being cooled to room temperature, the solid was removed by filtration and the filtrate was concentrated under reduced pressure. The residue was directly purified by flash chromatography (hexane-EtOAc: 9:1) on silica gel to give 4.82 g of Compound 235A as a white crystalline solid. HPLC retention time=2.523 min. (Condition A). $^1$H-NMR (400 MHz, CDCl$_3$) δ 7.61 (d, J=8.87 Hz, 2H), 6.97 (d, J=8.87 Hz, 2H), 4.34 (t, J=6.14 Hz, 4H), 3.66 (t, J=6.14 Hz, 4H).

235B.

(structure of 235B)

Compound 235B was prepared from Compound 235A by a route analogous to that used for the preparation of compound 1D. Compound 235B is a pale yellow semi-solid. HPLC retention time=1.873 min. (Condition A). $^1$H-NMR (400 MHz, CDCl₃) δ 7.43 (d, J=8.82 Hz, 2H), 6.87 (d, J=8.82 Hz, 2H), 4.29 (t, J=6.36 Hz, 2H) 3.63 (t, J=6.36 Hz, 2H), 1.48 (s, 6H).

235C. Example 235

Example 235 was prepared from Compound 235B and acid 174E by a route analogous to that used for the preparation of compound 1E. Compound 235C is a light yellow solid. HPLC retention time=3.382 min. (Condition A).

Example 236

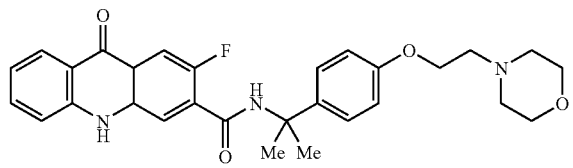

A solution of Example 235 (5 mg) and morpholine (0.009 mL) in a 2:1 mixture of CH₃CN-EtOH (1,0 mL) was heated to 130° C. for 2 h in a sealed tube. After being cooled to room temperature, the reaction mixture was concentrated in vacuo. Trituration with water and drying under high vacuum gave 5.6 mg of Example 236 as a yellow solid. HPLC retention time=2.516 min. (Condition A) and LC/MS M⁺+1=504⁺.

Examples 237-245

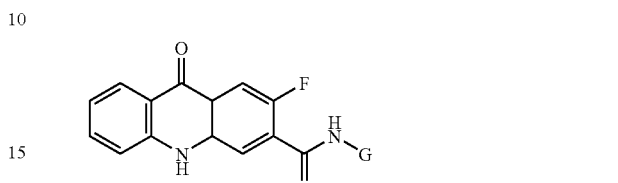

Examples 237-245 having the above formula wherein G has the values set forth in Table 22 were prepared from Example 235 by a route analogous to that used for the preparation of 236, replacing the amine with the required H₂N-G. If the products carry basic moieties, they were purified by preparative HPLC.

TABLE 22

| Ex. No | —G | HPLC time (min) | M⁺ + H |
|---|---|---|---|
| 237 | | 2.54 (A) | 462 |
| 238 | | 2.61 (A) | 490 |
| 239 | | 2.58 (A) | 488 |
| 240 | | 2.59 (A) | 520 |
| 241 | | 2.65 (A) | 502 |

TABLE 22-continued

| Ex. No | —G | HPLC time (min) | M⁺ + H |
|---|---|---|---|
| 242 | 4-methylpiperazinyl-ethoxy-phenyl-C(Me)₂- | 2.43 (A) | 517 |
| 243 | thiazolidinyl-ethoxy-phenyl-C(Me)₂- | 2.59 (A) | 506 |
| 244 | thiomorpholine-1,1-dioxide-ethoxy-phenyl-C(Me)₂- | 2.54 (A) | 552 |
| 245 | thiomorpholinyl-ethoxy-phenyl-C(Me)₂- | 2.59 (A) | 520 |

Example 246

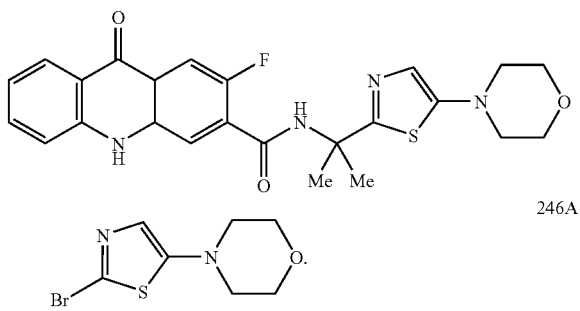

246A

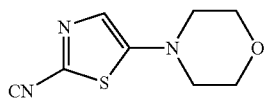

A mixture of 2,5-dibromothiazole (1.2 g, 5.0 mmol), morpholine (2.2 mL, 25 mmol) in 10 mL of EtOH was heated to reflux overnight. After being cooled to room temperature, the mixture was diluted with water and the precipitate collected by filtration. After being rinsed with water and dried under high vacuum, 0.98 g of Compound 246A was observed as a white solid. This material was directly used in the next step without further purification. $^1$H-NMR (400 MHz, DMSO-d$_6$) δ 7.09 (s, 1H), 3.78-3.82 (m, 4H), 3.41-3.46 (m, 4H).

246B.

A round-bottom flask was charged with Compound 246A (0.5 g, 2.0 mmol), tris(dibenzylideneacetone)dipalladium(0) (110 mg, 6 mol %), DPPF (133 mg, 12 mol %), Zn powder (16 mg, 12 mol %), Zn(CN)$_2$ (141 mg, 1.2 mmol) and 10 mL of dry DMF. After the flask was evacuated and backfilled with argon, the mixture was heated to 150° C. for 12 h. After cooling to room temperature, EtOAc was added and the reaction mixture was washed with 2N NH$_4$OH and filtered through a pad of Celite. The filtrate was dried over anhydrous Na$_2$SO$_4$. Concentration in vacuo followed by flash chromatography (hexane-EtOAc: 7:3) on silica gel gave 263 mg of Compound 246B as a pale green solid. $^1$H-NMR (400 MHz, CDCl$_3$) δ 7.71 (s, 1H), 3.81-3.84 (m, 4H), 3.55-3.58 (m, 4H).

246C.

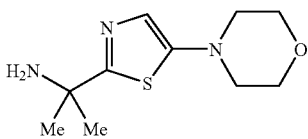

Compound 246C was prepared from Compound 246B by a route analogous to that used for the preparation of Compound 1D. Compound 246C is a light yellow semi-solid. $^1$H-NMR (400 MHz, CDCl$_3$) δ 3.79-3.82 (m, 4H), 3.41-3.43 (m, 4H), 1.51 (s, 6H).

246D. Example 246

Example 246 was prepared from Compound 246C and acridone acid 174E by a route analogous to that used for the preparation of compound 1E. Compound 246D is a light yellow solid. HPLC retention time=2.226 min. (Condition A) and LC/MS M⁺+1=467⁺.

Examples 247-259

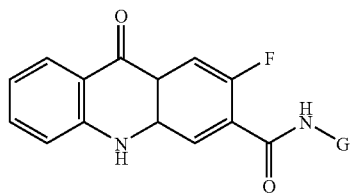

Examples 247-251 having the above formula wherein G has the values set forth in Table 23 were prepared in an manner analogous to that used for the preparation of Example 1 starting with acridone acid 174E, and the appropriate amine H₂N-G. The amines are commercially available and/or can be prepared as described in other Examples herein and/or as described in the literature. (See, e.g., *Tetrahedron*, Vol. 54, 5-6 [1998], pp. 1013-1020 [Ex. 252]; *Chem. Pharm. Bull.*, Vol. 44, 7 [1996], pp. 1376-1386 [Ex. 253]; *J. Nat. Prod.* Vol. 62, 7 [1999], at pp. 963-968 [Ex. 259]). If the products carry basic moieties, they were purified by preparative HPLC.

TABLE 23

| Ex. No | —G | HPLC Retention time (min.) Condition | MS M⁺ |
| --- | --- | --- | --- |
| 247 |  | 2.74 (A) | 355 |
| 248 |  | 2.57 (A) | 444 |
| 249 |  | 2.43 (A) | 444 |
| 250 |  | 2.64 (A) | 446 |
| 251 |  | 1.56 (A) | 363 |
| 252 |  | 1.55 (E) | 369 |

TABLE 23-continued

| Ex. No | —G | HPLC Retention time (min.) Condition | MS M⁺ |
| --- | --- | --- | --- |
| 253 |  | 1.34 (E) | 430 |
| 254 |  | 3.19 (F) | 444 |
| 255 |  | 1.16 (E) | 390 |
| 256 |  | 2.31 (A) | 473 |
| 257 |  | 2.35 (A) | 505 |
| 258 |  | 2.35 (A) | 505 |
| 259 |  | 2.76 (A) | 385 |

Example 260

N-[1,1-Dimethyl-2-(4-pyridinyl)ethyl]-2-fluoro-9,10-dihydro-9-oxo-3-acridinecarboxamide

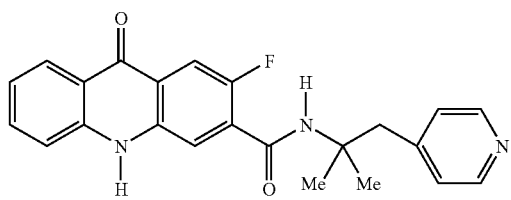

260A. 1,1'-Dimethyl-2-(4-pyridyl)-ethanol

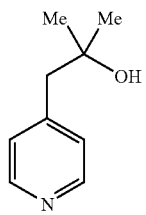

To a stirred solution of 2-picoline (1.4 g, 15 mmol) in THF (80 ml) was added n-BuLi (6.6 ml, 2.5 M in hexane) dropwise at −50° C. After stirring for 15 min at the same temperature, dried acetone (1.5 ml) was slowly added and reaction mixture was stirred for an additional 30 min at −50° C. The reaction was quenched with sat. ammonium chloride and extracted with EtOAc (2×25 mL). The EtOAc layer was washed with water (20 mL) brine (20 mL), dried over Na$_2$SO$_4$ and concentrated under reduced pressure to give 260A (1.3 g, 57%) as an oil. $^1$H NMR (CDCl$_3$) δ 8.45 (d, 2H), 7.16 (d, 2H), 2.75 (s, 2H), 2.4 (br s, 1H), 1.24 (s, 6H).

260B. 2-Chloro-N-[1,1-dimethyl-2-(4-pyridinyl)ethyl]acetamide

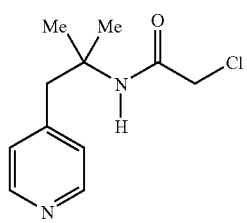

To a stirred solution of 260A (910 mg, 6.03 mmol) in acetic acid (2 ml) was added chloroacetonitrile (1.37 g, 18 mmol), followed by the addition of sulfuric acid (2 ml). The reaction mixture was stirred at RT for 3 hr, made basic using 2 N NaOH, and extracted with EtOAc (3×25 mL). The EtOAc layer was washed with water (20 mL), dried over Na$_2$SO$_4$ and concentrated under reduced pressure to give 260B (650 mg, 48%) as an oil. $^1$H NMR (CDCl$_3$) δ8.44 (d, 2H), 6.99 (d, 2H), 3.89 (s, 2H), 3.03 (s, 2H), 1.30 (s, 6H).

260C. □,□-Dimethyl-4-pyridineethanamine

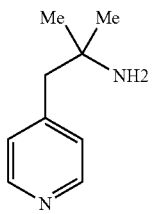

A mixture of 260B (1.30 g, 5.75 mmol), thiourea (524 mg, 6.90 mmol), acetic acid (2 ml) and EtOH (10 ml) was refluxed overnight. The reaction mixture was cooled to room temperature and the solid that separated out was filtered. The filtrate was concentrated and made acidic using 1N HCl. The aqueous solution was washed with EtOAc (2×25 mL), cooled to 0° C. and basified with 2N NaOH. The sodium hydroxide layer was re-extracted with EtOAc (2×25 mL), washed with water (25 mL), dried over Na$_2$SO$_4$ and concentrated under reduced pressure to give 260C (390 mg, 45%) $^1$NMR (CDCl$_3$) δ 8.45 (d, 2H), 7.06 (d, 2H), 2.58 (s, 2H), 1.06 (s, 6H)

260D. Example 260

To a mixture of 174E (13 mg, 0.05 mmol) and amine 260C (8 mg, 0.05 mmol) in DMF (1 ml) was sequentially added Et$_3$N (10 mg, 2 mmol) and BOP-Cl (13 mg, 0.05 mmol). The reaction mixture was stirred at room temperature for 20 min. and purified using preparative HPLC. The desired fractions were collected and concentrated under reduced pressure to yield Example 260 as a TFA salt (8 mg, 41%) HPLC Retention time=1.2 (Condition E). LC/MS: 390.

Example 261

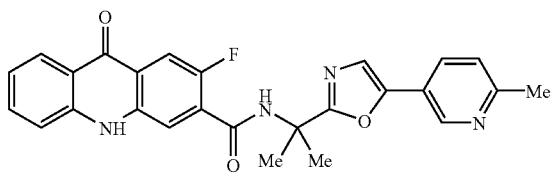

To a solution of 2-amino-1-(6-methyl-pyridin-3-yl)-ethanone hydrochloride (prepared according to *J. Antibiot.*, Vol. 48 [1995], at pp. 1336-1344) (0.54 g, 2.42 mmol) in DMF (10 mL) was sequentially added BOC-2-aminoisobutyric acid (0.491 g, 2.46 mmol), triethylamine (1.35 mL, 9.68 mL) and BOP-Cl (4.8 mmol), and the reaction mixture was stirred at room temperature for one hour. The reaction mixture was concentrated and partitioned between 1N sodium hydroxide (10 mL) and EtOAc (50 mL). The EtOAc layer was separated, dried over sodium sulfate, concentrated and purified by silica gel column chromatography using DCM and MeOH to afford compound 261A. Yield: 0.33 g (41%).

261B.

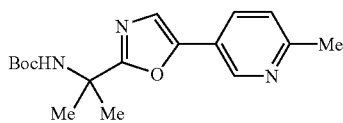

To a solution of triphenylphosphine (0.124 g, 0.45 mmol) in DCM (2 mL) was sequentially added hexachloroethane (0.94 g, 0.4 mmol) and triethylamine (0.13 mL, 0.95 mmol), followed by compound 261A (0.053 g, 0.158 mmol). The reaction mixture was stirred at room temperature for eighteen hours and partitioned between 1N HCl (6 mL) and DCM (2×10 mL). The HCl layer was made basic using 1N sodium hydroxide and extracted into EtOAc (2×15 mL). The EtOAc layer was dried over sodium sulfate and concentrated to yield an oil (0.025 g), which was used as such for the next step without further purification.

261C.

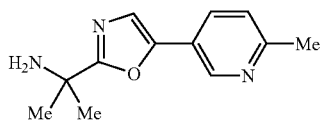

To compound 261B (0.025 g) at room temperature was added TFA over a ten minute period. The reaction mixture was stirred at room temperature for two hours, and concentrated and partitioned between DCM (20 mL) and 1N sodium hydroxide (5 mL). The DCM layer was dried over sodium sulfate and concentrated to yield an oil which was used as such for the next step without further purification.

261D. Example 261

Example 261 was prepared in a fashion analogous to Example 1 starting from acridone acid 174E and compound 261C. Retention time=2.19 min. (A). M+ 457.51

Example 262

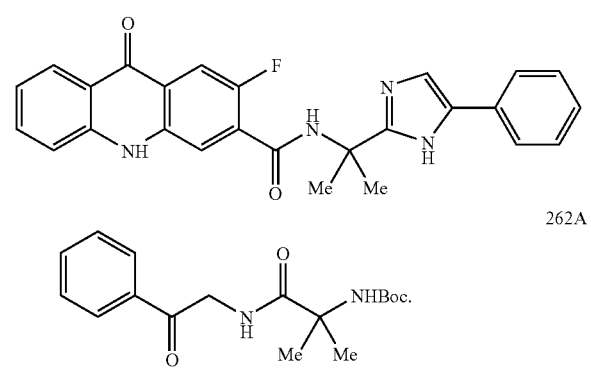

262A

This compound was prepared in a fashion analogous to the preparation of compound 261A, starting from BOC-2-aminoisobutyric acid and α-aminoacetophenone hydrochloride. The compound was used as such for the subsequent step without further purification.

262B.

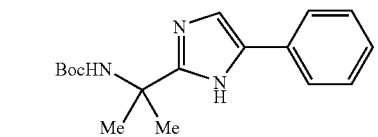

To a solution of compound 262A (0.45 g, 1.4 mmol) in AcOH (20 mL) was added ammonium acetate (10 g) and the contents heated at 110° C. for eighteen hours. The reaction mixture was concentrated and partitioned between 1N HCl (10 mL) and EtOAc (2×20 mL). The HCl layer was cooled to 0° C., made basic using 1N sodium hydroxide (20 mL) and extracted into DCM (2×25 mL). The DCM layer was dried over sodium sulfate, concentrated under reduced pressure and used as such for the next step without further purification. Yield 0.110 g.

262C.

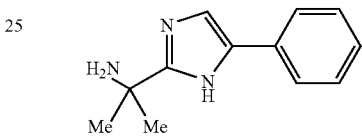

The method of Example 261, Step C was used to prepared compound 262C from 262B. This compound was used as such for the subsequent step without further purification. Yield: 0.06 g.

262D. Example 262

Example 262 was prepared in a fashion analogous to Example 1 starting from acridone acid 174E and compound 262C. The compound was purified using preparative HPLC and isolated as its TFA salt. Retention time=2.65 min. (Condition A). M+ 441.41

Example 263

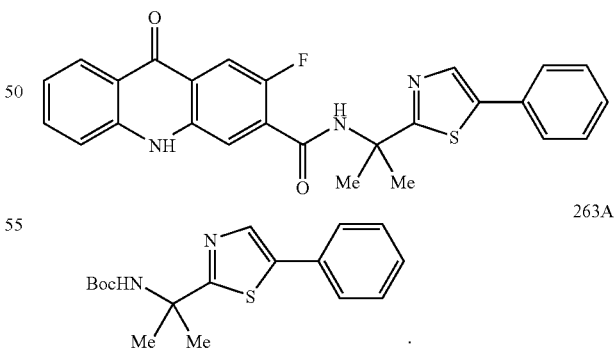

263A

To a solution of compound 262A (0.5 g, 1.56 mmol) in toluene (20 mL) was added Lawesson's reagent (1.9 g, 4.7 mmol), and the contents refluxed for twenty four hours. The reaction mixture was concentrated and purified by silica gel chromatography using hexane and EtOAc. Yield: 0.095 g (19%).

263B.

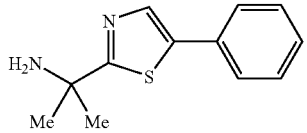

Compound 263A was processed in a fashion analogous to step C of Example 261, to afford compound 263B, which was used as such for the subsequent step without further purification. Yield: 0.04 g.

263C. Example 263

Example 263 was prepared in a fashion analogous to Example 1 starting from acridone acid 174E and compound 263B. The compound was purified using preparative HPLC. Retention time=3.57 min. (Condition A). M⁺ 458.36

Example 264

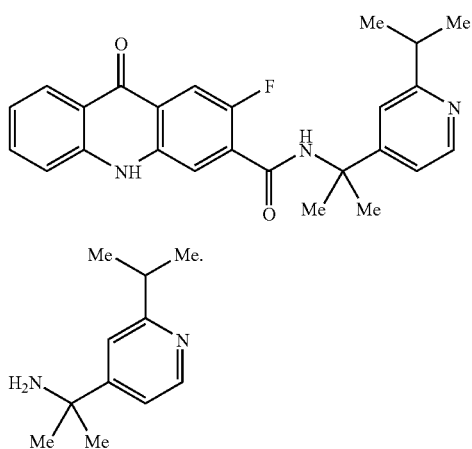

Compound 264A was prepared by treating 2-isopropyl-4-cyano pyridine (see, *Tetrahedron*, Vol. 27, [1971], pp. 3575-3579) with MeLi and cerium(III) chloride as outlined in Example 282A. $^1$H NMR (CDCl$_3$): 8.5 (1H, d), 7.3 (1H, s), 7.15 (1H, d), 3.1 (1H, m), 1.6 (6H, s), 1.3 (6H, d).

264B. Example 264

Compound 264B was prepared in a fashion analogous to Example 1 starting from acridone acid 174E and compound 264A. Retention time=2.19 min. (A). M⁺ 418.51

Example 265

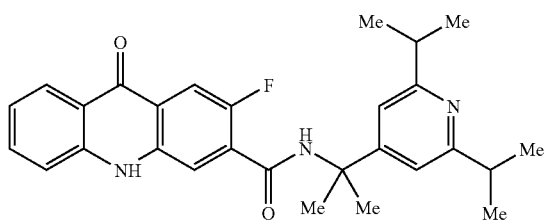

-continued

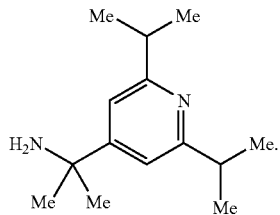

Compound 265A was prepared by treating 2-isopropyl-4-cyano pyridine (*Tetrahedron*, Vol. 27 [1971], pp. 3575-3579) with MeLi and cerium(III) chloride as outlined in Example 282A. $^1$H NMR (CDCl$_3$): 7.1 (2H, s), 3.1 (1H, m) 1.6 (6H, s), 1.3 (6H, d).

265B. Example 265

Example 265 was prepared in a fashion analogous to Example 1 starting from acridone acid 174E and compound 265A. Retention time=2.38 min. (Condition A). M⁺ 460.58

Example 266

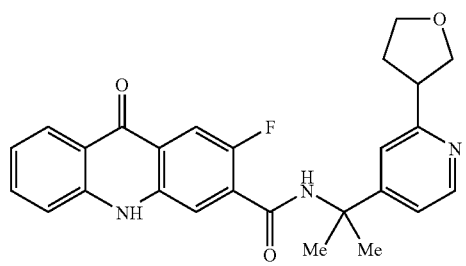

266A.

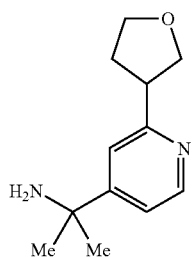

Compound 266A was prepared by treating 2-(3-tetrahydrofuranyl)-4-cyano pyridine (prepared using the general experimental protocol outlined in *Tetrahedron*, Vol. 27, [1971], pp. 3575-3579) with MeLi and cerium(III) chloride as outlined in Example 282A. $^1$H NMR (CDCl$_3$): 8.7 (1H, d), 7.4 (1H, s), 7.3 (1H, d), 4.2 (1H, t), 4.1 (1H, m), 3.95 (2H, m), 2.4 (1H, m), 2.2 (1H, m).

266B. Example 266

Example 266 was prepared in a fashion analogous to Example 1 starting from acridone acid 174E and compound 266A. Retention time=2.14 min. (Condition A). M⁺ 446.44

Example 267

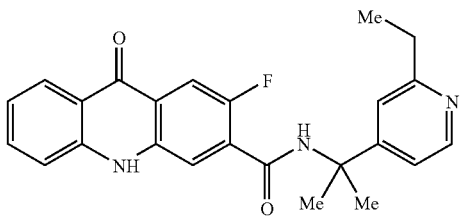

267A

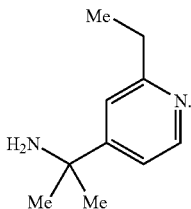

Compound 267A was prepared by treating 2-ethyl-4-cyano pyridine (see, *Tetrahedron*, Vol. 27, [1971], at pp. 3575-3579) with MeLi and cerium(III) chloride as outlined in Example 282A.

267B. Example 267

Example 267 was prepared in a fashion analogous to Example 1 starting from acridone acid 174E and compound 267A. Retention time=2.17 min. (A). M+ 404.46

Example 268

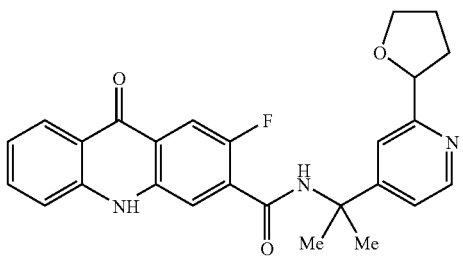

268A

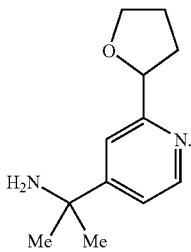

Compound 268A was prepared by treating 2-(3-tetrahydrofuranyl)-4-cyano pyridine (prepared using the general experimental protocol outlined in *Tetrahedron*, Vol. 27, [1971], at pp. 3575-3579) with MeLi and cerium(III) chloride as described for Example 282A.

268B. Example 268

Example 268 was prepared in a fashion analogous to Example 1 starting from acridone acid 174E and compound 268A. Retention time=2.22 min. (A). M+ 446.55

Example 269

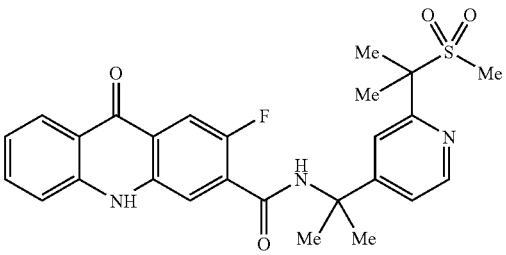

269A

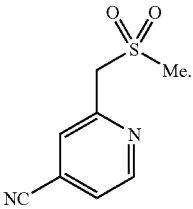

To a solution of 2-methylsulfanylmethyl-isonicotinonitrile (0.08 g, 0.48 mmol) (prepared from 4-cyanopyridine and (methylmercapto)acetic acid using the general experimental protocol outlined in *Tetrahedron*, Vol. 27 [1971], at pp. 3575-3579), in TFA (4 mL) was added trifluoroperacetic acid (4.0 M solution in TFA, 0.84 mL, 3.36 mmol) at 0° C., and the contents stirred at room temperature for one hour. The reaction mixture was partitioned between DCM (25 mL) and saturated aqueous sodium bicarbonate (15 mL). The DCM layer was dried over sodium sulfate and concentrated to yield compound 269A as a solid. Yield: 0.08 g (84%). $^1$H NMR (CD$_2$Cl$_2$): 8.7 (1H, d), 7.6 (1H, s), 7.5 (1H, d), 4.4 (2H, s), 2.8 (3H, s).

269B.

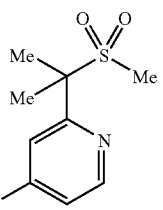

To a solution of compound 269A (0.36 g, 1.83 mmol) in THF (15 mL) at −20° C. was added lithium bis(trimethylsilyl)amide (2.2 mL, 2.2 mmol, 1.0M in THF) over a period of five minutes. The reaction mixture was stirred at −20° C. for fifteen minutes, iodomethane (0.17 mL, 2.75 mmol) was added in one lot, and the reaction mixture stirred at room temperature for fifteen minutes. The reaction mixture was recooled to −20° C., iodomethane (0.17 mL, 2.75 mmol) was added in one lot, and the mixture was stirred at room temperature for eighteen hours. The reaction mixture was concentrated and partitioned between DCM (2×25 mL) and brine (15 mL). The DCM layer was concentrated and the residue was purified by preparative HPLC and the desired fraction was collected. The free base was liberated by washing the desired HPLC fractions with saturated aqueous sodium bicarbonate. Yield: 0.055 g, (13%). $^1$H NMR (CDCl$_3$): 8.8 (1H, d), 7.6 (1H, s), 7.4 (1H, d), 2.7 (3H, s), 1.8 (3H, s).

269C.

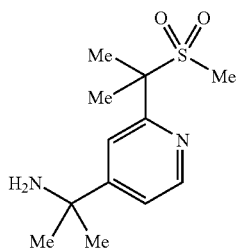

Compound 269C was prepared by treating compound 269B with MeLi and cerium(III) chloride as outlined in Example 282A.

269D. Example 269

Example 269 was prepared in a fashion analogous to Example 1 starting from acridone acid 174E and compound 269C. Retention time=2.47 min. (Condition A). M+ 496.02

Example 270

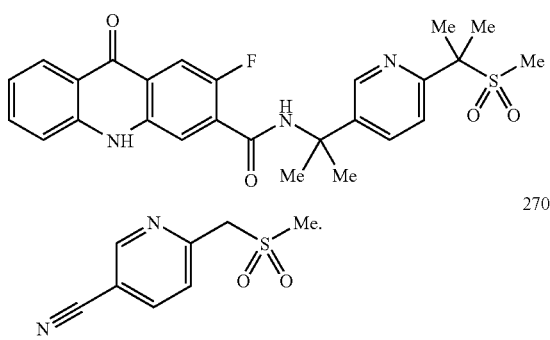

270A

To a solution of 6-chloromethylpyridine-3-carbonitrile (prepared according to *Aust. J. Chem*, Vol. 35, [1982] at pp. 1451-1468) in butanol (10 mL) was added methanesulphinic acid sodium salt (0.191 g, 1.9 mmol) and sodium acetate (2.9 mmol), and the contents heated at 120° C. for two hours. The reaction mixture was stirred at room temperature for eighteen hours and concentrated and partitioned between EtOAc (25 mL) and brine (25 mL). The EtOAc layer was dried over sodium sulfate, concentrated, and purified by silica gel column chromatography to yield the compound 270A as a solid. Yield: 0.162 g (57%). $^1$H NMR (CDCl$_3$) 8.85 (1H, s), 8.0 (1H, d), 7.6 (1H, d), 4.4 (2H, s), 2.9 (3H, s).

270B.

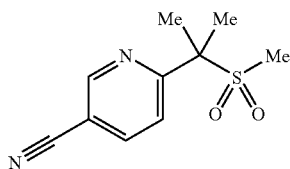

Compound 270B was prepared in a fashion analogous to compound 269B, starting from compound 270A. $^1$H NMR (CDCl$_3$): 8.85 (1H, s), 8.0 (1H, d), 7.6 (1H, d), 2.7 (3H, s), 1.8 (3H, s).

270C.

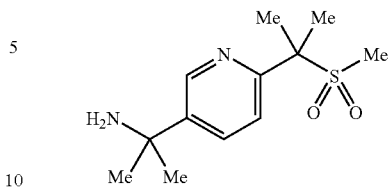

Compound 270C was prepared by treating compound 270B with MeLi and cerium(III) chloride as described for Example 282A.

270D. Example 270

Example 270 was prepared in a fashion analogous to Example 1, starting from acridone acid 174E and compound 270C. Retention time=2.57 min. (Condition A). M+ 496.11

Example 271

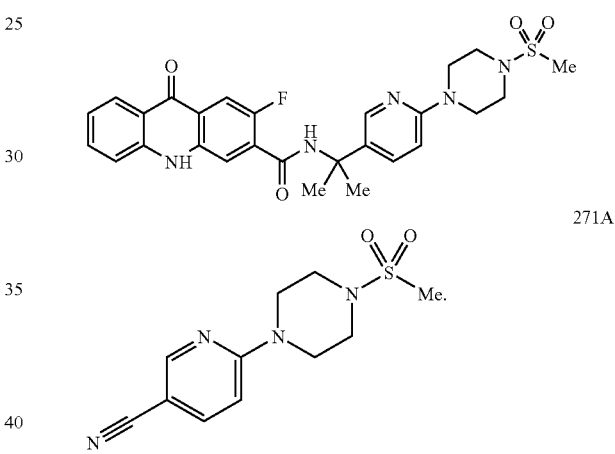

271A

To a solution of 2-chloro-4-cyanopyridine (0.25 g, 1.81 mmol) in EtOH (20 mL) was added 1-methanesulfonylpiperazine (1.2 g, 7.2 mmol), and the contents refluxed for twenty-four hours. The reaction mixture was concentrated and partitioned between 1N sodium hydroxide (10 mL) and DCM (25 mL). The DCM layer was washed with brine, dried over sodium sulfate, concentrated, and purified by silica gel column chromatography. Yield: 0.46 g (95%). $^1$H NMR (DMSO-d6): 8.7 (1H, s), 8.1 (1H, d), 7.15 (1H, d), 3.95 (4H, m), 3.3 (4H, m), 3.1 (3H, s).

271B.

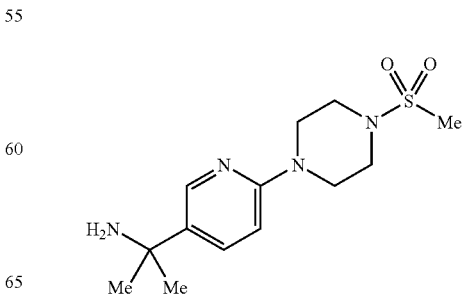

Ccompound 271B was prepared by treating the compound obtained in step A with MeLi and cerium(III) chloride as outlined in Example 282A.

271C. Example 271

Compound 271 was prepared in a fashion analogous to Example 1, starting from acridone acid 174E and compound 271B. Retention time=2.13 min. (Condition A). M+ 537.91

Example 272

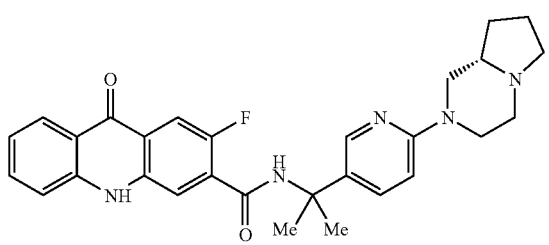

272A

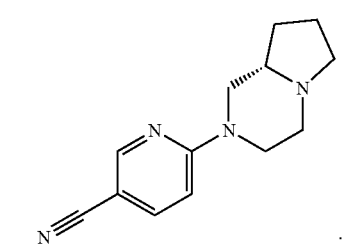

Compound 272A was made in a fashion analogous to compound 271A, starting from (S)-1,4-Diazabicyclo[4.3.0]nonane (*J. Med. Chem.*, Vol. 36, 16, [1993] at pp. 2311-2320) and 2-chloro-5-cyanopyridine. The compound was purified by preparative HPLC. Retention time=1.00 min. (Condition A). M+=229.

272B.

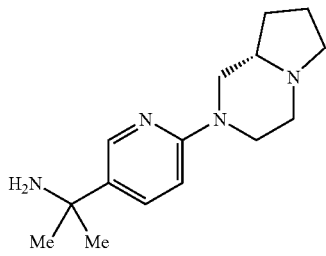

Compound 272B was prepared by treating the compound 272A with MeLi and cerium(III) chloride as outlined in Example 282A. Retention time=0.34 min. (Condition A). M+ 261.

272C. Example 272

Compound 272 was prepared in a fashion analogous to Example 1, starting from acridone acid 174E and compound 272B. Retention time=2.05 min. (Condition A). M+ 499.98

Example 273

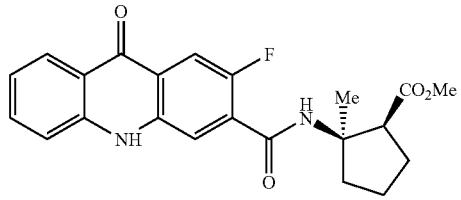

This compound was prepared in a fashion analogous to Example 1 starting from acridone acid 174E and 2-amino-2-methyl-cyclopentanecarboxylic acid ethyl ester (*Tetrahedron*, Vol. 54, 5-6, [1998], at pp. 1013-1020). Retention time=3.05 min. (Condition A). M+ 397.30.

Example 274

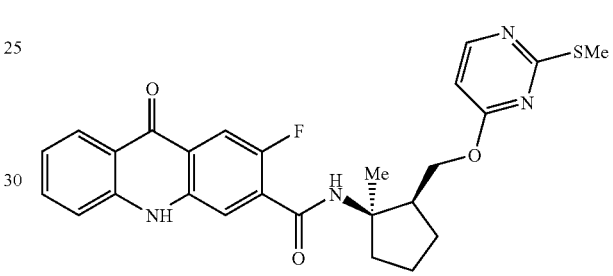

To a solution of Example 252 (0.05 g, 0.136 mmol) in DMF (2 mL) was added sodium hydride (0.005 g, 0.204 mmol). The reaction mixture was stirred at room temperature for fifteen minutes and 4-chloro-2-methylthiopyrimidine (0.026 g, 0.163 mmol) was added. After 40 minutes, the reaction mixture was partitioned between EtOAc and water. The EtOAc layer was dried over sodium sulfate, concentrated under reduced pressure and purified by prep. HPLC. Yield: 0.009 g (13%). Retention time=3.39 min. (Condition A). M+ 493.47.

Example 275

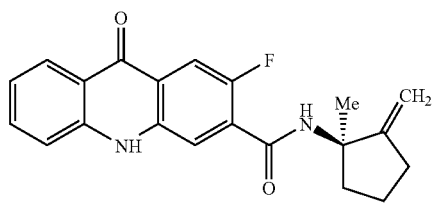

To a solution of Example 252 (0.02 g, 0.054 mmol) in THF (1 mL) was added triethylamine (9 μL, 0.065 mmol), followed by methanenesulfonyl chloride (5 μL). The reaction mixture was stirred at room temperature for thirty minutes. The reaction mixture was concentrated under reduced pressure and purified by prep. HPLC. Yield: 0.004 g, (21%). Retention time=1.32 min. (Condition E). M+ 351.34.

Example 276

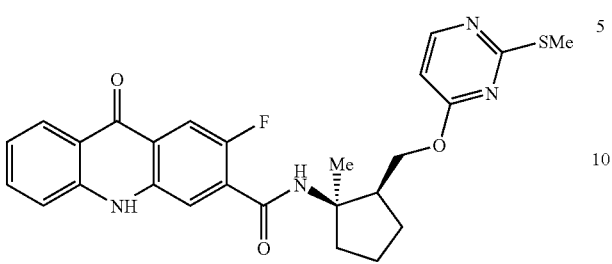

To a solution of Example 274 (0.03 g, 0.061 mmol) in AcOH (1 mL) was added sodium tungstate (0.006 g) and hydrogen peroxide (five drops). The reaction mixture was stirred at room temperature for 18 hours and partitioned between water and EtOAc. The EtOAc layer was dried over sodium sulfate and concentrated under reduced pressure to yield Example 276 as an oil.

Example 277

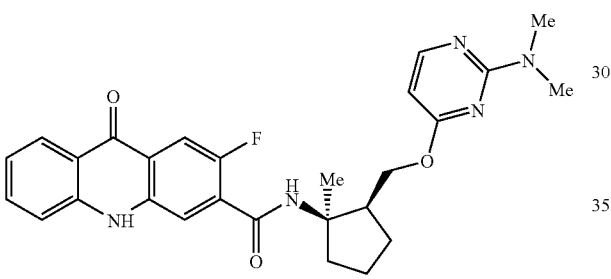

A solution of Example 276 (0.03 g) in dimethylamine (2 mL, 2.0 M in THF) was stirred at room temperature for ninety minutes. The reaction mixture was filtered and the residue dissolved in MeOH and purified by prep. HPLC. Yield: 0.009 g (32%). Retention time=1.50 min. (Condition E). $M^+$ 490.36.

Example 278

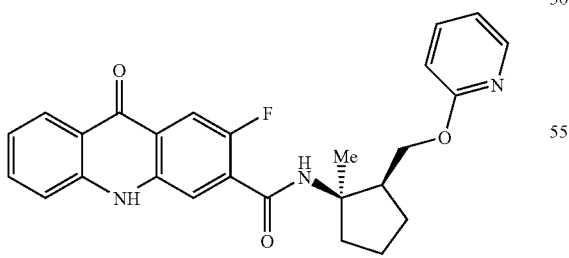

To a solution of Example 252 (0.03 g, 0.08 mmol) in DMF (1 mL) was added sodium hydride (0.003 g, 0.096 mmol). The reaction mixture was stirred at room temperature for fifteen minutes and 2-fluoropyridine (0.008 g, 0.08 mmol) was added. After 30 minutes, the reaction mixture was partitioned between EtOAc and water. The EtOAc layer was dried over sodium sulfate, concentrated under reduced pressure and purified by prep. HPLC. Yield: 0.008 g, (22%). Retention time=3.39 min. (Condition A). $M^+$ 493.47.

Examples 279-281

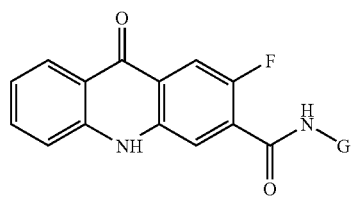

Examples 279-282 having the above formula wherein G has the values set forth in Table 24 were prepared in a fashion analogous to Example 278 starting from compound 278A and the appropriately-substituted 2-fluoro-methylpyridine.

TABLE 24

| Ex. No. | G | HPLC retention time (min.) (Condition) | MS $M^+$ |
|---|---|---|---|
| 279 | ![6-Me pyridine] | 1.58 (E) | 460 |
| 280 | ![5-Me pyridine] | 1.58 (E) | 460 |
| 281 | ![5-Me pyridine isomer] | 1.86 (E) | 460 |

Example 282

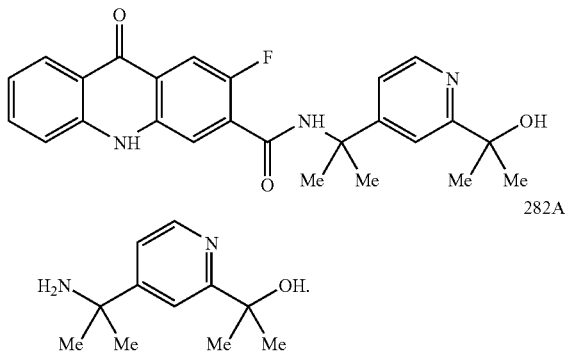

A solution of cerium(III) chloride (2.02 g, 8.22 mmol) in anhydrous THF (15 mL) was stirred at 0° C. The reaction mixture was cooled to −78° C. and methyl lithium (1.4M solution in diethyl ether, 5.9 mL, 8.22 mmol) was added over a 25 minute period. The reaction mixture was stirred at −78° C. for 45 minutes and a solution of 2-acetyl-4-cyanopyridine (0.2 g, 1.37 mmol, *J. Org. Chem.* Vol. 56 [1991], at pp. 2866-2869) in THF (15 mL) was added dropwise over a period of 15 minutes. The reaction was allowed to stir at −78° C. for fifty minutes, warmed to room temperature, and stirred at room temperature for thirty minutes. The reaction mixture was cooled to −78° C., quenched by the dropwise addition of ammonium hydroxide, filtered, and the filter pad washed with THF. The filtrate was concentrated under reduced pressure, the residue redissolved in DCM, washed with water, dried over sodium sulfate and concentrated. Yield: 0.190 g (71%).

282B. Example 282

Example 282 was prepared in a fashion analogous to Example 1 starting from acridone acid 174E and amine 282A. Retention time=1.2 min. (Condition E). M⁺ 434.

Example 283

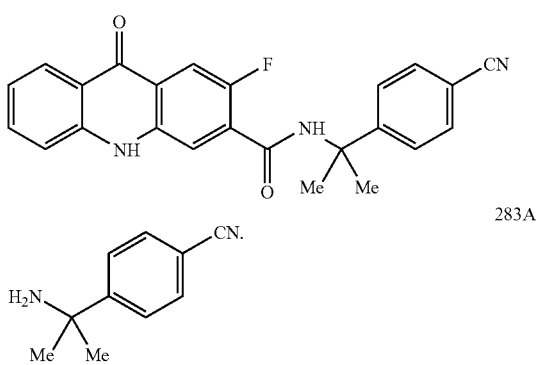

1,4-dicyanobenzene was processed in a fashion similar to that described in 282A to yield compound 283A. ¹H NMR (CDCl₃): 7.5 (4H, m), 1.4 (6H, s).

283B. Example 283

Example 283 was prepared in a fashion analogous to Example 1, starting from acridone acid 174E and amine 283A. Retention time=1.5 min. (Condition E). M⁺ 400.22.

Example 284

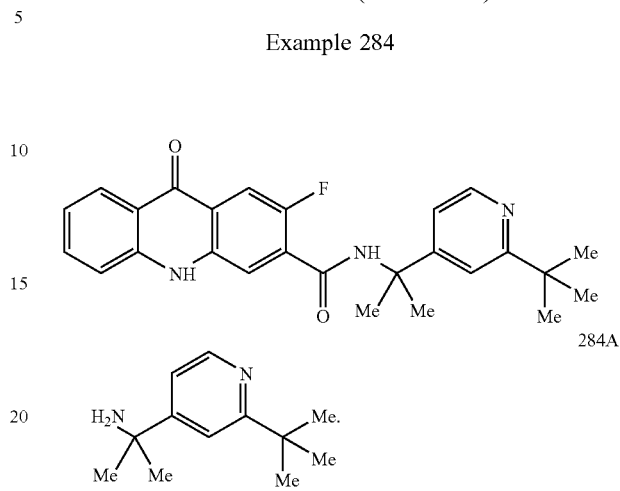

Example 284A was prepared by treating 2-tert-butyl-4-cyano pyridine (prepared using the general experimental protocol outlined in *Tetrahedron*, Vol. 27 [1971], at pp. 3575-3579) with MeLi and cerium(III) chloride as outlined in step A, Example 282.

284B. Example 284

Example 284 was prepared in a fashion analogous to Example 1 starting from acridone acid 174E and compound 284A. retention time=2.33 min. (Condition A). M⁺ 432.

Example 285

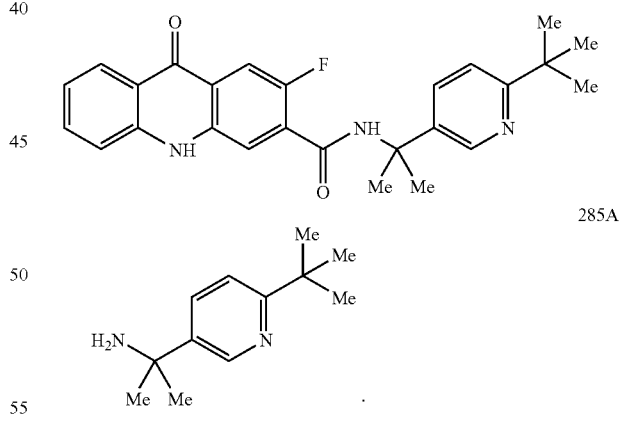

Compound 285A was prepared by treating 2-tert-butyl-5-cyano pyridine (prepared using the general experimental protocol outlined in *Tetrahedron*, Vol. 27 [1971], at pp. 3575-3579) with MeLi and cerium(III) chloride as outlined in step A, Example 282.

285B.

Compound 285B was prepared in a fashion analogous to Example 1, starting from acridone acid 174E and compound 285A. Retention time=2.36 min. (Condition A). M⁺ 432.

Example 286

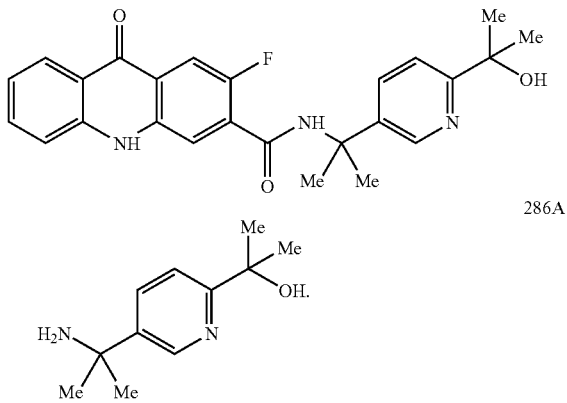

Compound 286A was prepared by treating 2-acetyl-5-cyano pyridine (prepared using the general experimental protocol outlined in *J. Org. Chem.*, Vol. 56 [1991], at pp. 2866-2869) with MeLi and cerium(III) chloride as outlined in step A, Example 282.

286B. Example 286

Example 286 was prepared in a fashion analogous to Example 1 starting from acridone acid 174E and compound 286A. Retention time=2.14 min. (Condition A). M⁺ 434.

Example 287

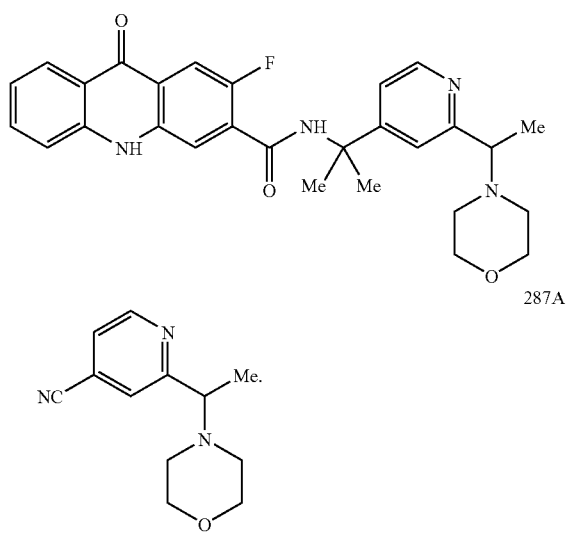

To a solution of 2-acetyl-4-cyanopyridine (*J. Org. Chem.* Vol. 56 [1991], at pp. 2866-2869)(0.09 g, 0.62 mmol) in EtOH (3 mL) was sequentially added morpholine (0.27 g, 3.08 mmol), 4N HCl in dioxane (0.3 mL0, 1.24 mmol), molecular sieves (~1.0 g) and sodium cyanoborohydride (0.04 g, 0.62 mmol). The reaction mixture was stirred at room temperature for 48 hours, filtered, and the filtrate concentrated under reduced pressure. The residue was made basic using 2N NaOH, extracted into DCM, washed with water, dried over sodium sulfate, concentrated under reduced pressure, and purified by prep. HPLC. Yield: 0.058 g (43%). ¹H NMR (CDCl3): 8.6 (1H, d), 7.8 (1H, s), 7.7 (1H, d), 3.8-2.9 (8H, m), 1.5 (3H, d).

287B.

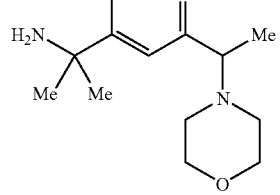

Compound 287B was prepared by treating the compound obtained in step A with MeLi and cerium(III) chloride as outlined in step A, Example 282.

287C. Example 287

Example 287 was prepared in a fashion analogous to Example 1, starting from acridone acid 174E and compound 287B. Retention time=1.26 min. (E). M⁺ 489.23.

Example 288

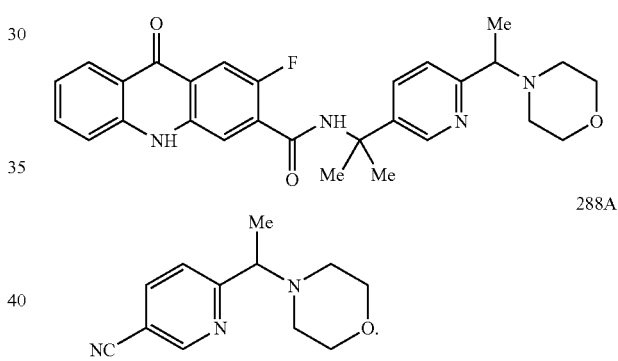

This compound was prepared in a fashion analogous to compound 286A, starting from 2-acetyl-5-cyanopyridine. ¹H NMR (CDCl3): 8.7 (1H, s), 7.8 (1H, d), 7.5 (1H, d), 3.6 (m, 4H), 2.4 (m, 4H), 1.2 (3H, d).

288B.

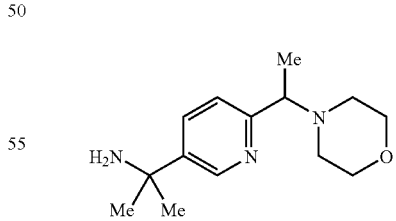

This compound was prepared by treating compound 288A with MeLi and cerium(III) chloride as outlined in step A, Example 282.

288C. Example 288

Example 288 was prepared in a fashion analogous to Example 1, starting from acridone acid 174E and compound 288B. Retention time=2.26 min. (Condition A). M⁺ 489.14.

Example 289

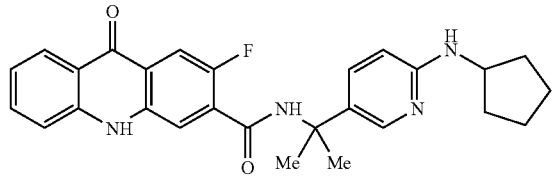

289A

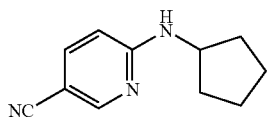

A mixture of 6-chloronicotinonitrile (0.2 g, 1.44 mmol), cyclopentylamine (0.147 g, 1.72 mmol), triethylamine (300 µL, 2.16 mmol) and dioxane (3 mL) was heated in a microwave at 120° C. for three hours. The reaction mixture was partitioned under reduced pressure and partitioned between DCM and water. The DCM layer was washed with saturated aqueous sodium bicarbonate, brine, dried over sodium sulfate and concentrated to yield compound 289A as an oil. Yield: 0.1 g (37%). $^1$H NMR (CDCl3): 8.25 (1H, s), 7.5 (1H, d), 6.3 (1H, d), 5.1 (1H, brs), 4.0 (1H, brs), 2.0 (2H, m), 1.6 (4H, m), 1.4 (2H, m).

289B.

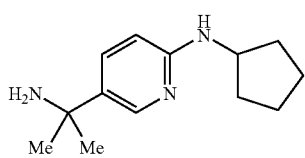

This compound was prepared by treating compound 289A with MeLi and cerium(III) chloride as outlined in step A, Example 282. The compound was used as such for the subsequent step without further purification.

289C. Example 289

Example 289 was prepared in a fashion analogous to Example 1 starting from acridone acid 174E and the compound 289B. Retention time=2.49 min. (Condition A). M$^+$ 459.04.

Example 290

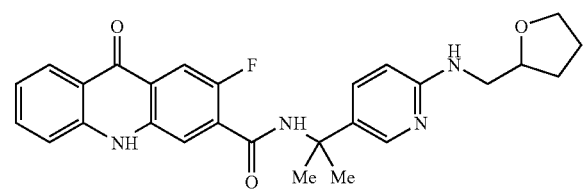

290A

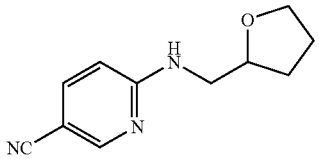

This compound was prepared in a fashion analogous to compound 288A, starting from 6-chloronicotinonitrile and tetrahydrofurfurylamine. $^1$H NMR (CDCl3): 8.2 (1H, s), 7.4 (1H, d), 6.3 (1H, d), 5.3 (1H, brs), 4.0 (1H, m), 3.85 (1H, m), 3.7 (1H, m), 3.5 (1H, brs), 3.2 (1H, m), 2.0 (1H, m), 1.9 (2H, m), 1.5 (1H, m).

290B.

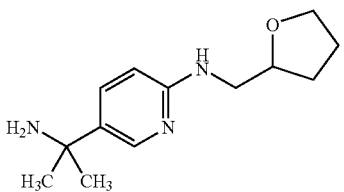

This compound was prepared by treating compound 290A with MeLi and cerium(III) chloride as outlined in step A, Example 282. The compound was used as such for the subsequent step without further purification.

290C. Example 290

Example 290 was prepared in a fashion analogous to Example 1, starting from acridone acid 174E and compound 290B. Retention time=2.37 min. (Condition A). M$^+$ 475.89.

Example 291

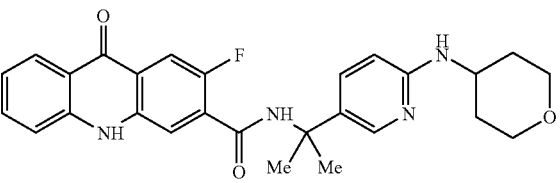

291A

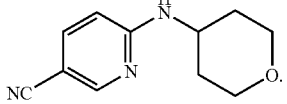

This compound was prepared in a fashion analogous to compound 289A, starting from 6-chloronicotinonitrile and morpholine. $^1$H NMR (CDCl3): 8.25 (1H, s), 7.4 (1H, d), 6.3 (1H, d), 4.9 (1H, brs), 3.9 (3H, m), 3.5 (2H, m), 2.0 (2H, m), 1.5 (1H, m).

291B.

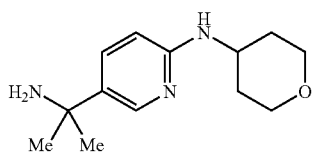

Compound 291B was prepared by treating the compound obtained in step A with MeLi and cerium(III) chloride as outlined in step A, Example 282. The compound was used as such for the subsequent step without further purification.

291C. Example 291

Example 291 was prepared in a fashion analogous to Example 1, starting from acridone acid 174E and compound 291B. Retention time=2.20 min. (Condition A). M$^+$ 474.97.

Example 292

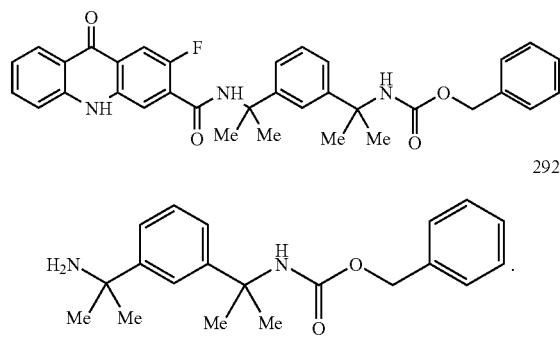

To a solution of 1-[3-(1-Amino-1-methyl-ethyl)-phenyl]-1-methyl-ethylamine (0.15 g, 0.78 mmol) (prepared according to JACS, Vol. 123 (16) [2001], at pp. 3706-3715) in THF (20 mL) was sequentially added sodium hydroxide (0.1 g, 2.34 mmol) and Cbz-Cl (0.13 g, 0.766 mmol). The reaction mixture was stirred at room temperature for two hours, concentrated under reduced pressure and extracted into DCM. The DCM layer was washed with water, brine, dried over sodium sulfate, and concentrated. The obtained residue was used as such for the subsequent step without further purification.

292B. Example 292

This compound was prepared in a fashion analogous to Example 1, starting from acridone acid 174E and compound 292A. Retention time=3.56 min. (Condition A). M$^+$ 566.04.

Example 293

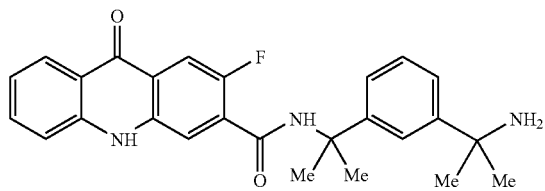

To a solution of Example 292 (0.028 g) in MeOH (20 mL) was added 10% Pd—C (3 mg) and the contents hydrogenated at 35 psi for three hours. The reaction mixture was filtered and the filtrate concentrated under reduced pressure to yield Example 293 as a solid. Yield: 0.011 g (51%). Retention time=2.44 min. (Condition A). (M–H) 429.9.

Example 294

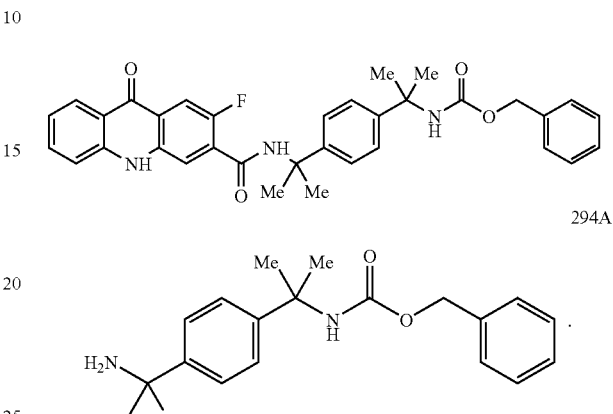

This compound was prepared in a fashion analogous to compound 292A, starting from 1-[4-(1-Amino-1-methyl-ethyl)-phenyl]-1-methyl-ethylamine (see JACS, Vol. 123 (16) [2001] at pp. 3706-3715). The crude product was used as such for the subsequent step without further purification.

294B. Example 294

Example 294 was prepared in a fashion analogous to Example 1 starting from acridone acid 174E and compound 294A. Retention time=3.41 min. (Condition A). M$^+$ 566.03.

Example 295

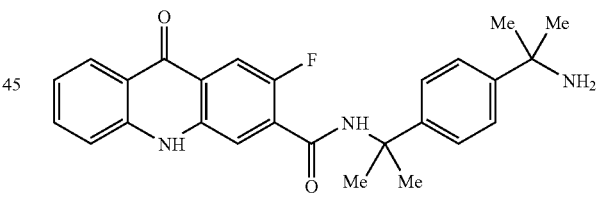

This compound was prepared in a fashion analogous to Example 293 starting from Example 294. Retention time=2.55 min. (Condition A).

Example 296

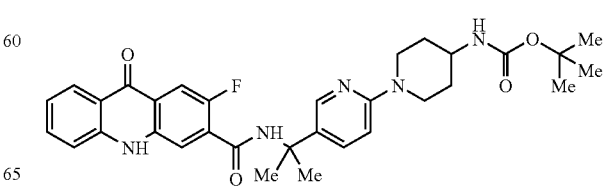

To a solution of Example 229 (0.02 g, 0.05 mmol) in anhydrous dimethylacetamide (1 mL) was sequentially added 4-N-Boc-aminopiperidine (0.015 g), Pd$_2$(dba)$_3$ (0.007 g), (Ph)$_2$P(Cy)$_2$ (0.006 g) and potassium tert-butoxide (0.0096 g). The reaction mixture was purged with nitrogen gas for 10 minutes and heated at 75-80° C. for eighteen hours. The reaction mixture was cooled, filtered and the filtrate concentrated under reduced pressure. The residue that was obtained was purified by preparative HPLC and the desired fractions were collected to afford Example 296. Yield: 0.010 g. Retention time=2.59 min. (Condition A). M$^+$ 573.

Example 297

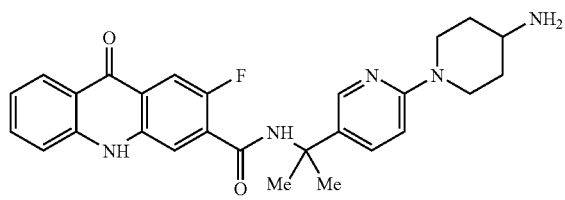

To Example 296 (0.010 g) was added TFA (1 mL) and the contents stirred at room temperature for fifty minutes. The reaction mixture was concentrated under reduced pressure to yield Example 297 as the TFA salt. Retention time=1.96 min. (Condition A). M$^+$ 473.95.

Example 298

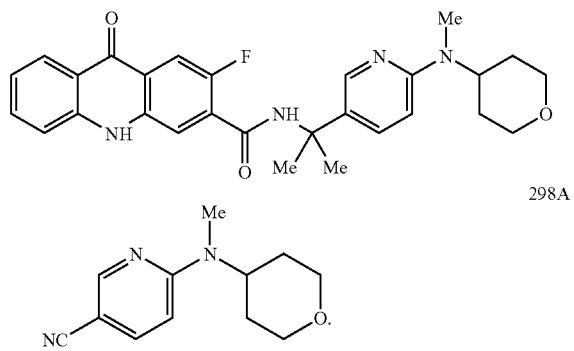

This compound was prepared in a fashion analogous to 289A, starting from 6-chloronicotinonitrile and N-methyl-N-(tetrahydropyran-4-yl)amine (prepared according to *Org. Process. Res and Dev.*, Vol. 6 [2002], at pp. 70-73).

298B.

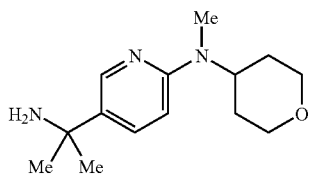

This compound was prepared by treating compound 298A with MeLi and cerium(III) chloride as outlined in step A, Example 282. The compound was used as such for the subsequent step without further purification.

298C. Example 298

This compound was prepared in a fashion analogous to Example 1, starting from acridone acid 174E and compound 298B. Retention time=2.26 min. (Condition A). M$^+$ 488.99.

Example 299

2-fluoro-9,10-dihydro-N-[1-methyl-1-[3-(methylthio)phenyl]ethyl]-9-oxo-3-acridinecarboxamide

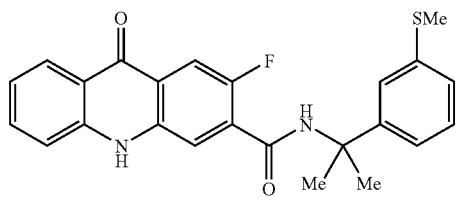

299A. 3-(methylthio)benzonitrile

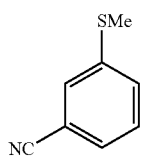

To a solution of 3-bromophenyl methylsulfide (1.624 g, 8.0 mmol) in DMF (30 ml) was added cuprous cyanide (0.788 g, 8.8 mmol). The mixture was heated at 150° C. overnight. DMF was removed under reduced pressure, then water was added, and the mixture was extracted with DCM. The combined organic layer was dried over Na$_2$SO$_4$ and evaporated. The resulting residue was purified by silica gel column to give compound 299A as a light yellow solid. 1H-NMR (400 MHz, CDCl3) δ 7.44 (m, 4H), 2.53 (s, 3H).

299B. 1-methyl-1-(3-methylthiophenyl)ethyl-amine

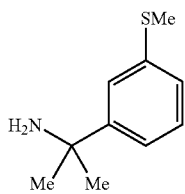

Compound 299B was prepared from 299A by a route analogous to that used for compound 1D. Example 299 is a colorless oil. 1H-NMR (400 MHz, CDCl3) δ 7.11-7.44 (m, 4H), 2.50 (s, 3H), 1.60 (brs, 2H), 1.48 (s, 6H).

299C. Example 299

Example 299 was prepared from 299B and acridone 174E by a route analogous to that used for the preparation of Example 1. Compound 299C is a yellow solid and had an analytical HPLC retention time=3.30 min. (Condition A) and LC/MS M$^+$+1=421.

Example 300

2-Fluoro-9,10-dihydro-N-[1-methyl-1-[3-(methylsulfonyl)phenyl]ethyl]-9-oxo-3-acridinecarboxamide

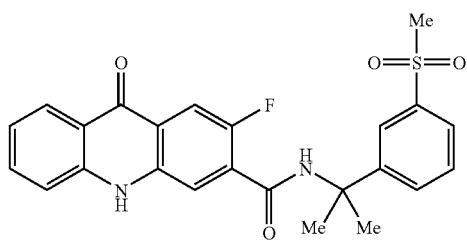

Example 299 was dissolved in a mixed solvent of CH$_2$Cl$_2$ and MeOH, excess mCPBA was added, and the reaction mixture was stirred overnight. Solvent was removed and the resulting residue was redissolved in CH$_2$Cl$_2$, then washed sequentially with aq. Na$_2$S$_2$O$_8$ and aq. NaHCO$_3$. The organic layer was dried over Na$_2$SO$_4$, concentrated, and purified by silica gel column to give Example 300 as a yellow solid. HPLC retention time=2.58 min. (Condition A) and LC/MS M$^+$+1=453.

Example 301

2-Fluoro-9,10-dihydro-N-[1-methyl-1-[3-(methylsulfinyl)phenyl]ethyl]-9-oxo-3-acridinecarboxamide

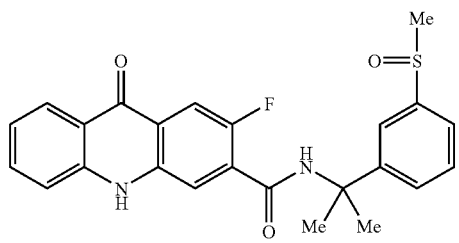

Example 301 was prepared from Example 299 following the same or similar method as described for Example 300, except one equivalent of mCPBA was used. HPLC retention time=2.62 min. (Condition A) and LC/MS M$^+$+1=437.

Examples 302-308

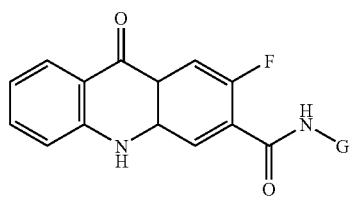

Examples 302-308 having the above formula wherein G has the values set forth in Table 25, were prepared from acid 174E by a route analogous to that used for the preparation of Example 299, 300, and 301 replacing the amine 299B with the required H$_2$N-G. The corresponding amines were prepared by a route analogous to that used for the preparation of 299B. If the products carry basic moities, they were purified by preparative HPLC.

TABLE 25

| Ex. No | —G | Compound name | HPLC time (min) Condition | M$^+$ |
|---|---|---|---|---|
| 302 | (4-SMe phenyl, C(Me)$_2$) | 2-Fluoro-9,10-dihydro-N-[1-methyl-1-[4-(methylthio)phenyl]ethyl]-9-oxo-3-acridinecarboxamide | 3.34 (A) | 421$^+$ |
| 303 | (4-S(O)Me phenyl, C(Me)$_2$) | 2-Fluoro-9,10-dihydro-N-[1-methyl-1-[4-(methylsulfinyl)phenyl]ethyl]-9-oxo-3-acridinecarboxamide | 2.62 (A) | 437$^+$ |
| 304 | (4-SO$_2$Me phenyl, C(Me)$_2$) | 2-Fluoro-9,10-dihydro-N-[1-methyl-1-[4-(methylsulfonyl)phenyl]ethyl]-9-oxo-3-acridinecarboxamide | 2.60 (A) | 453$^+$ |

TABLE 25-continued

| Ex. No | —G | Compound name | HPLC time (min) Condition | M+ |
|---|---|---|---|---|
| 305 | (2,6-dimethyl-phenyl with SMe at ortho position) | 2-Fluoro-9,10-dihydro-N-[1-methyl-1-[2-(methylthio)phenyl]ethyl]-9-oxo-3-acridinecarboxamide | 3.30 (A) | 421+ |
| 306 | (2,6-dimethyl-phenyl with S(=O)Me at ortho position) | 2-Fluoro-9,10-dihydro-N-[1-methyl-1-[2-(methylsulfinyl)phenyl]ethyl]-9-oxo-3-acridinecarboxamide | 2.60 (A) | 437+ |
| 307 | (2,6-dimethyl-phenyl with S(=O)2Me at ortho position) | 2-Fluoro-9,10-dihydro-N-[1-methyl-1-[2-(methylsulfonyl)phenyl]ethyl]-9-oxo-3-acridinecarboxamide | 2.92 (A) | 453+ |
| 308 | (3-ethylsulfonyl-phenyl with gem-dimethyl) | N-[1-[3-(Ethylsulfonyl)phenyl]-1-methylethyl]-2-fluoro-9,10-dihydro-9-oxo-3-acridinecarboxamide | 2.66 (A) | 467+ |

Example 309

2-Fluoro-9,10-dihydro-N-[1-methyl-1-[4-(4-morpholinylsulfonyl)phenyl]ethyl]-9-oxo-3-acridinecarboxamide

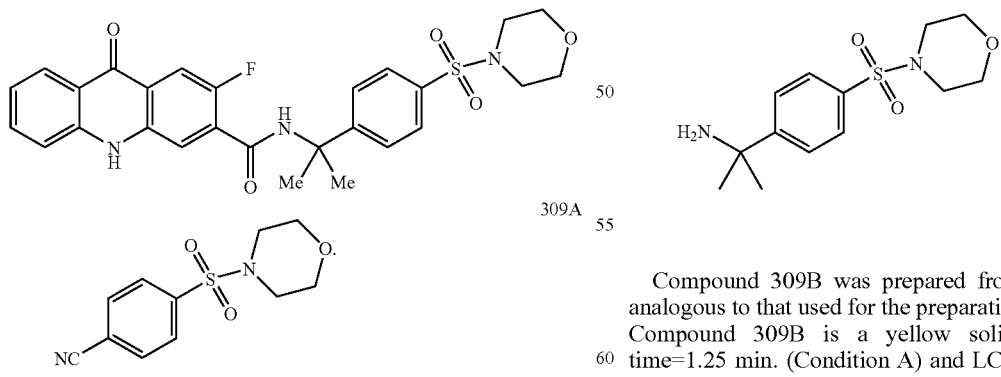

To a suspension of 4-cyanobenzenesulphonyl chloride (460 mg, 2.29 mmol) in CH₂Cl₂ (10 ml) was added morpholine (1.0 ml). The reaction mixture was stirred for 30 min., then water was added, and the combined organic layer was extracted with CH₂Cl₂, dried over Na₂SO₄, and concentrated to give 500 mg (87%) of 309A as a colorless solid. HPLC retention time 1.73 min. (Condition A) $^1$H-NMR (500 MHz, CDCl3) δ 7.85 (s, 4H), 3.73 (t, J=4.95 Hz, 4H), 3.02 (t, J=4.95 Hz, 4H).

309B.

Compound 309B was prepared from 309A by a route analogous to that used for the preparation of Compound 1D. Compound 309B is a yellow solid. HPLC retention time=1.25 min. (Condition A) and LC/MS M⁺+1=285.

309C. Example 309

Example 309 was prepared from 309B and compound 174E by a route analogous to that used for the preparation of Example 1. Compound 309C is a yellow solid. HPLC retention time=2.83 min. (Condition A) and LC/MS M⁺+1=524.

Examples 310-332

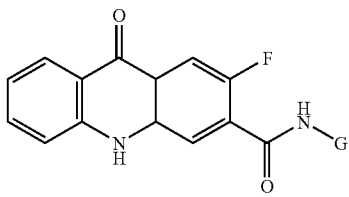

Examples 302-332 having the above formula wherein G has the values set forth in Table 26, were prepared from acid 174E by a route analogous to that used for the preparation of Example 309 replacing the amine 309B with the required $H_2N$-G. The corresponding amines were prepared by a route analogous to that used for the preparation of 309B. If the products carry basic moieties, they were purified by preparative HPLC.

TABLE 26

| Ex. No | —G | Compound name | HPLC time (min) | M+ |
|---|---|---|---|---|
| 310 | | N-[1-[4-(Aminosulfonyl)-phenyl]-1-methylethyl]-2-fluoro-9,10-dihydro-9-oxo-3-acridinecarboxamide | 2.45 (A) | 454 |
| 311 | | N-[1-[4-[(Dimethylamino)sulfonyl]phenyl]-1-methylethyl]-2-fluoro-9,10-dihydro-9-oxo-3-acridinecarboxamide | 2.81 (A) | 482 |
| 312 | | N-[1-[4-[(Ethylamino)-sulfonyl]phenyl]-1-methylethyl]-2-fluoro-9,10-dihydro-9-oxo-3-acridinecarboxamide | 2.79 (A) | 482 |
| 313 | | N-[1-[4-[(Diethylamino)-sulfonyl]phenyl]-1-methylethyl]-2-fluoro-9,10-dihydro-9-oxo-3-acridinecarboxamide | 3.08 (A) | 510 |
| 314 | | 2-Fluoro-9,10-dihydro-N-[1-methyl-1-[4-(1-pyrrolidinylsulfonyl)phenyl]-ethyl]-9-oxo-3-acridinecarboxamide | 2.94 (A) | 508 |

TABLE 26-continued

| Ex. No | —G | Compound name | HPLC time (min) | M+ |
|---|---|---|---|---|
| 315 | (4-((1-methylethyl)aminosulfonyl)phenyl)-C(Me)(Me)- | 2-Fluoro-9,10-dihydro-N-[1-methyl-1-[4-[[(1-methylethyl)amino]sulfonyl]-phenyl]ethyl]-9-oxo-3-acridinecarboxamide | 2.91 (A) | 496 |
| 316 | (4-((2-methoxyethyl)aminosulfonyl)phenyl)-C(Me)(Me)- | 2-Fluoro-9,10-dihydro-N-[1-[4-[[(2-methoxyethyl)-amino]sulfonyl]phenyl]-1-methylethyl]-9-oxo-3-acridinecarboxamide | 2.75 (A) | 512 |
| 317 | (3-(morpholinylsulfonyl)phenyl)-C(Me)(Me)- | 2-Fluoro-9,10-dihydro-N-[1-methyl-1-[3-(4-morpholinylsulfonyl)phenyl]ethyl]-9-oxo-3-acridinecarboxamide | 2.80 (A) | 524 |
| 318 | (3-(aminosulfonyl)phenyl)-C(Me)(Me)- | N-[1-[3-(Aminosulfonyl)-phenyl]-1-methylethyl]-2-fluoro-9,10-dihydro-9-oxo-3-acridinecarboxamide | 2.51 (A) | 454 |
| 319 | (3-(dimethylaminosulfonyl)phenyl)-C(Me)(Me)- | N-[1-[3-[(Dimethylamino)-sulfonyl]phenyl]-1-methyl-ethyl]-2-fluoro-9,10-dihydro-9-oxo-3-acridinecarboxamide | 2.78 (A) | 482 |
| 320 | (3-((methylamino)sulfonyl)phenyl)-C(Me)(Me)- | 2-Fluoro-9,10-dihydro-N-[1-methyl-1-[3-[(methylamino)sulfonyl]phenyl]-ethyl]-9-oxo-3-acridinecarboxamide | 2.61 (A) | 468 |

TABLE 26-continued

| Ex. No | —G | Compound name | HPLC time (min) | M+ |
|---|---|---|---|---|
| 321 | (3-[(Ethylamino)sulfonyl]phenyl with C(Me)(Me) linker) | N-[1-[3-[(Ethylamino)-sulfonyl]phenyl]-1-methyl-ethyl]-2-fluoro-9,10-dihydro-9-oxo-3-acridinecarboxamide | 2.73 (A) | 482 |
| 322 | (3-[[(1-methylethyl)amino]sulfonyl]phenyl with C(Me)(Me) linker) | 2-Fluoro-9,10-dihydro-N-[1-methyl-1-[3-[[(1-methylethyl)amino]sulfonyl]-phenyl]ethyl]-9-oxo-3-acridinecarboxamide | 2.87 (A) | 496 |
| 323 | (3-(1-pyrrolidinylsulfonyl)phenyl with C(Me)(Me) linker) | 2-Fluoro-9,10-dihydro-N-[1-methyl-1-[3-(1-pyrrolidin-ylsulfonyl)phenyl]ethyl]-9-oxo-3-acridinecarboxamide | 2.90 (A) | 508 |
| 324 | (3-[(4-methyl-1-piperazinyl)sulfonyl]phenyl with C(Me)(Me) linker) | 2-Fluoro-9,10-dihydro-N-[1-methyl-1-[3-[(4-methyl-1-piperazinyl)sulfonyl]phenyl]-ethyl]-9-oxo-3-acridinecarboxamide | 2.33 (A) | 537 |
| 325 | (3-[(Cyclopropylamino)sulfonyl]phenyl with C(Me)(Me) linker) | N-[1-[3-[(Cyclopropyl-amino)sulfonyl]phenyl]-1-methylethyl]-2-fluoro-9,10-dihydro-9-oxo-3-acridinecarboxamide | 2.78 (A) | 494 |

TABLE 26-continued

| Ex. No | —G | Compound name | HPLC time (min) | M+ |
|---|---|---|---|---|
| 326 | | N-[1-[3-[[[2-(Dimethyl-amino)ethyl]methylamino]-sulfonyl]phenyl]-1-methyl-ethyl]-2-fluoro-9,10-dihydro-9-oxo-3-acridinecarboxamide | 2.41 (A) | 539 |
| 327 | | N-[1-[3-[[[2-(Dimethyl-amino)ethyl]amino]sulfonyl]-phenyl]-1-methylethyl]-2-fluoro-9,10-dihydro-9-oxo-3-acridinecarboxamide | 2.34 (A) | 525 |
| 328 | | N-[1-[3-[(Diethylamino)-sulfonyl]phenyl]-1-methyl-ethyl]-2-fluoro-9,10-dihydro-9-oxo-3-acridinecarboxamide | 3.03 (A) | 510 |
| 329 | | N-[1-[3-(1-Azetidinyl-sulfonyl)phenyl]-1-methyl-ethyl]-2-fluoro-9,10-dihydro-9-oxo-3-acridinecarboxamide | 2.78 (A) | 494 |
| 330 | | N-[1-[3-[(Cyclobutyl-amino)sulfonyl]phenyl]-1-methylethyl]-2-fluoro-9,10-dihydro-9-oxo-3-acridinecarboxamide | 2.95 (A) | 508 |

TABLE 26-continued

| Ex. No | —G | Compound name | HPLC time (min) | M+ |
|---|---|---|---|---|
| 331 | 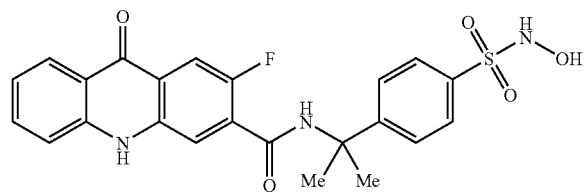 | N-[1-[3-[[(Cyclopropyl-methyl)amino]sulfonyl]-phenyl]-1-methylethyl]-2-fluoro-9,10-dihydro-9-oxo-3-acridinecarboxamide | 2.93 (A) | 508 |
| 332 | 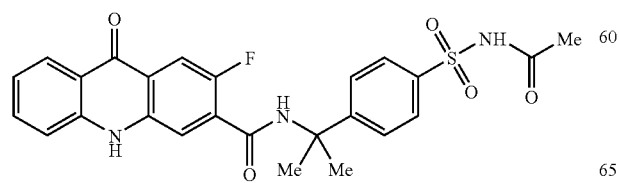 | N-[1-[4-[[[[(1,1-Dimethyl-ethyl)dimethylsilyl]oxy]-amino]sulfonyl]phenyl]-1-methylethyl]-2-fluoro-9,10-dihydro-9-oxo-3-acridinecarboxamide | 3.64 (A) | 584 |

Example 333

2-Fluoro-9,10-dihydro-N-[1-[4-[(hydroxyamino)sulfonyl]phenyl]-1-methylethyl]-9-oxo-3-acridinecarboxamide A solution of Example 332 in 95% TFA (5 ml) was stirred at room temperature for 2 hrs. TFA was removed on rotavapor and the residue was purified by silica gel column to afford 18 mg (74.6%) of Example 333 as a yellow solid. HPLC retention time=2.52 min. (Condition A) and LC/MS M++1=470.

Example 334

N-[1-[4-[(Acetylamino)sulfonyl]phenyl]-1-methylethyl]-2-fluoro-9,10-dihydro-9-oxo-3-acridinecarboxamide Example 310 (5.0 mg) was dissolved in acetone (1 ml) and a small amount of $K_2CO_3$ was added, followed by 2 drops of acetyl chloride. The reaction mixture was stirred overnight. Acetone was removed and the resulting residue was dissolved in a small amount of water and acidified with 1N HCl. Solid precipitated which was filtered and dried to give 2 mg of Example 334 as a yellow solid. HPLC retention time=2.57 min. (Condition A) and LC/MS M++1=496.

Example 335

N-[1-[3-[(Acetylamino)sulfonyl]phenyl]-1-methylethyl]-2-fluoro-9,10-dihydro-9-oxo-3-acridinecarboxamide

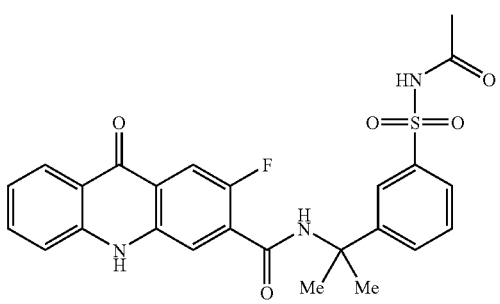

Example 335 was prepared from Example 318 in the same or similar way as Example 334. It is a yellow solid. HPLC retention time=2.55 min. (Condition A) and LC/MS M++1=496.

Example 336

2-Fluoro-9,10-dihydro-N-[1-methyl-1-[3-[(methyl-sulfonyl)amino]phenyl]ethyl]-9-oxo-3-acridinecarboxamide

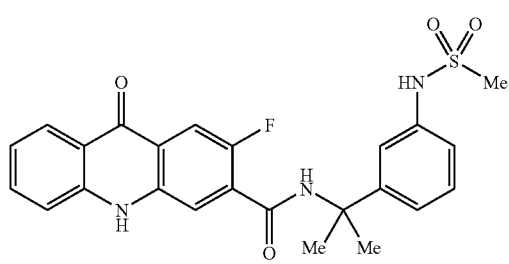

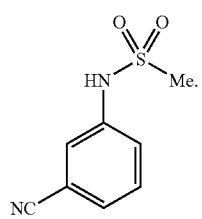

336A

To a solution of 3-aminobenzonitrile (591 mg, 5 mmol) in $CH_2Cl_2$ (10 ml) and pyridine (1.21 ml, 15 mmol) was added methanesulfonyl chloride dropwise. The reaction mixture was stirred overnight. $CH_2Cl_2$ was added and the solution was washed with 1N HCl, dried, and concentrated to give crude product which was washed with $CH_2Cl_2$ to afford 843 mg (86%) of compound 336A as a white solid. HPLC retention time=1.03 min. (Condition A). 1H-NMR (400 MHz, DMSO-d6) δ 10.21 (s, 1H), 7.49-7.58 (m, 4H), 3.10 (s, 3H).

336B.

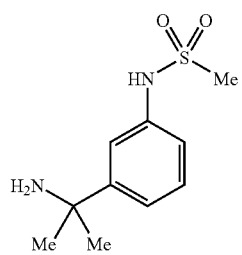

Compounds 336B were prepared from 336A by a route analogous to that used for the preparation of Compound 1D.

336C. Example 336

Example 336, a yellow solid, was prepared from acid 174E and 336B by a route analogous to that used for the preparation of Example 1. HPLC retention time=2.69 min. (Condition A) and LC/MS $M^+$+1=468.

Example 337

2-Fluoro-9,10-dihydro-N-[1-[6-(4-morpholinyl)-3-pyridinyl]cyclopropyl]-9-oxo-3-acridinecarboxamide

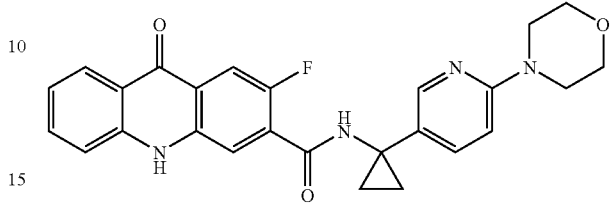

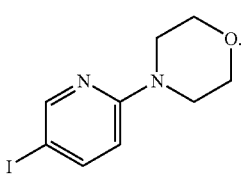

337A

2-Chloro-5-iodopyridine (2 g, 8.35 mmol) was heated in neat morpholine (6 ml) at 90° C. in a pressure tube overnight. Water was added to precipitate product, the precipiate was filtered, and the solid was washed with water and dried to give 2.29 g of 337A as a white solid. HPLC retention time=1.28 min. (Condition A) and LC/MS $M^+$+1=291.

337B. Methyl 2-tributylstannyl-2-propenoate

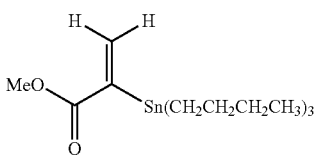

A degassed solution of $Bu_3SnH$ (8.73 g, 30 mmol) in dry THF (40 ml) was added during 40 min to a degassed solution of methyl propynoate (2.52 g, 30 mmol) and $Pd(PPh_3)_4$ (0.693 g, 0.6 mmol) in THF (40 ml). The resulting mixture was stirred for 3.5 h at room temperature under nitrogen. THF was then removed under reduced pressure and the residue was diluted with hexane (200 ml). After 12 h, the mixture was filtered on celite and the filtrate was concentrated under reduced pressure. The residue was diluted with hexane (200 ml), filtered on celite and concentrated. The residue was purified by silica gel column using hexane/EtOAc (98/2) as eluant to give 4.7 g of 337B as a colorless oil. 1H-NMR (400 MHz, CDCl3) δ 6.89 (d, J=2.64 Hz, 1H), 5.92 (d, J=2.64 Hz, 1H), 3.74 (s, 3H), 1.60-1.20 (m, 12H), 0.97 (t, J=8.34 Hz, 6H), 0.89 (t, J=7.03 Hz, 9H)

337C.

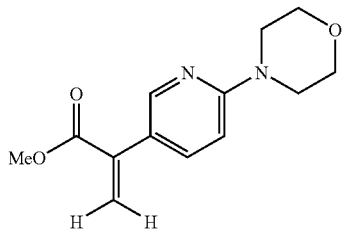

A degassed suspension of tris(dibenzylideneacetone)dipalladium(0) chloroform adduct (78 mg, 0.075 mmol) and tri-2-furylphosphine (142 mg, 0.61 mmol) in anhydrous NMP (4.3 ml) was stirred for 2 h under nitrogen to give a brown solution. A solution of 337A (290 mg 1.0 mmol) and 337B (600 mg, 1.6 mmol) in NMP (6.4 ml) was added. The resulting mixture was degassed, and then CuI (331 mg, 1.74 mmol) was added. The reaction mixture was stirred at 50° C. overnight. After it was cooled to room temperature, ether (100 ml) was added, and the mixture was filtered on celite. The filtrate was washed with water and brine, dried over MgSO$_4$, and concentrated under reduced pressure. The residue was purified by silica gel column to give 103 mg of 337C as a yellow oil. HPLC retention time=1.19 min. (Condition A) and LC/MS M$^+$+1=249.

337D.

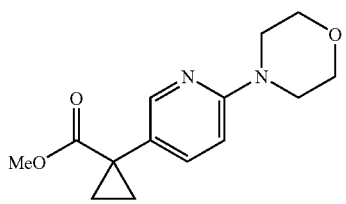

To a mixture of 40% KOH (3 ml) and Et$_2$O (20 ml) at 0° C. was added 1-methyl-3-nitro-1-nitrosoguanidine (500 mg, 3.40 mmol) portionwise. The obtained solution was swirled several times, and the ether layer solution was added to a ice-water cooled suspension of 337C (100 mg, 0.40 mmol) and Pd(OAc)$_2$ (5 mg) in Et$_2$O (6 ml). The reaction was stirred at 0° C. for 4 h, then quenched with several drops of HOAc. The reaction mixture was washed with aq. NaHCO$_3$, dried over MgSO$_4$, concentrated and purified by silica gel column to afford 58 mg of compound 337D (54.9%) as a yellow oil. HPLC retention time=1.12 min. (Condition A) and LC/MS M$^+$+1=263.

337E.

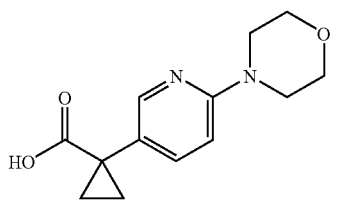

A mixture of compound 337D (180 mg, 0.69 mmol) and KOTMS (294 mg, 2.06 mmol) in THF (10 ml) was heated at 40° C. overnight. Water (2 ml) was added and the mixture was neutralized with 1N HCl. The combined organic layer was extracted with CH$_2$Cl$_2$ for 5 times, dried with Na$_2$SO$_4$, and concentrated to give 171 mg of crude 337E which was used directly in next step without purification. HPLC retention time=0.92 min. (Condition A) and LC/MS M$^+$+1=249.

337F.

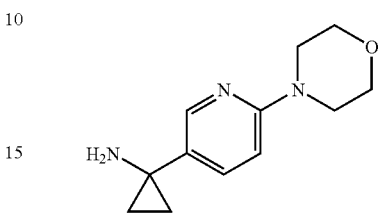

A mixture of 337E (20 mg, 0.081 mmol), diphenylphosphoryl azide (27.5 mg, 0.1 mmol) and Et$_3$N (11.1 mg, 0.11 mmol) in t-BuOH (2 ml) was stirred at 90° C. overnight. Solvent was removed under reduced pressure and the resulting residue was stirred in 95% TFA (1.5 ml) for 1 h. Purification by preparative HPLC gave 6 mg of white solid 337F as a TFA salt. HPLC retention time=0.307 min. (Condition A) and LC/MS M$^+$+1=220.

337G. Example 337

Example 337 was prepared as a yellow solid from compound 174E and 337F by a route analogous to that used for the preparation of Example 1. HPLC retention time=2.16 min. (Condition A) and LC/MS M$^+$+1=459.

Example 338

N-[1-[4-[2-(Dimethylamino)ethoxy]phenyl]-1-methylethyl]-2-fluoro-9,10-dihydro-9-oxo-3-acridinecarboxamide

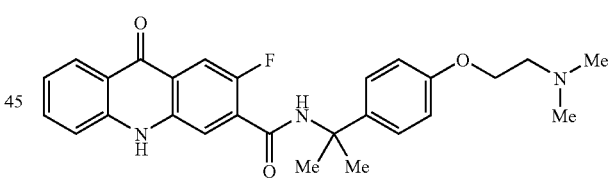

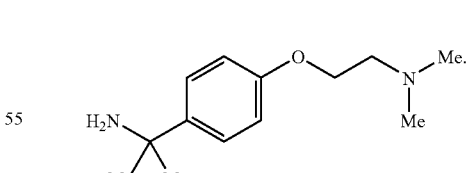

338A

A mixture of 4-cyanophenol (1.19 g, 10 mmol), 2-dimethylaminoethylchloride hydrochloride (2.16 g, 15 mmol) and K$_2$CO$_3$ (5.53 g, 40 mmol) in DMF (20 ml) was heated at 80° C. for 2 h and then filtered. The filtrate was concentrated under reduced pressure and the resulting residue was purified by silica gel column to give the 628 mg of ether intermediate. Compound 338A was then prepared by a route analogous to that used for the preparation of Compound 1D. Compound 338A was a colorless oil and had two peaks on analytical HPLC due to forming TFA salt, the peak one retention time=0.203 min, the peak two retention time=0.536 min (Condition A) and LC/MS M$^+$+1=223. 1H-NMR (400 MHz, CDCl3) δ 7.39 (d, J=8.79 Hz, 2H), 6.85 (d, J=8.79 Hz, 2H), 4.02 (t, J=5.72 Hz, 2H), 2.70 (t, J=5.72 Hz, 2H), 2.31 (s, 6H), 1.45 (s, 6H).

338B. Example 338

Example 338 was prepared as a yellow solid from 338A and 174E by a route analogous to that used for the preparation of Example 1. HPLC retention time=2.52 min. (Condition A) and LC/MS M$^+$+1=462.

Examples 339-346

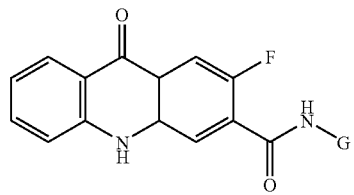

Examples 339-346 having the above formula wherein G has the values set forth in Table 27, were prepared from acid 174E by a route analogous to that used for the preparation of Example 1 replacing the amine with the required H$_2$N-G. If the products carry basic moieties, they were purified by preparative HPLC.

TABLE 27

| Ex. No | —G | Compound name | HPLC time (min) | M$^+$ |
|---|---|---|---|---|
| 339 | | 2-Fluoro-9,10-dihydro-N-[1-methyl-1-[6-(1-piperidinyl)-3-pyridinyl]-ethyl]-9-oxo-3-acridinecarboxamide | 2.37 (A) | 459 |
| 340 | | 2-Fluoro-9,10-dihydro-N-[1-methyl-1-[6-(4-methyl-1-piperazinyl)-3-pyridinyl]-ethyl]-9-oxo-3-acridinecarboxamide | 1.95 (A) | 474 |
| 341 | | N-[1-[6-(4-Ethyl-1-piperazinyl)-3-pyridinyl]-1-methylethyl]-2-fluoro-9,10-dihydro-9-oxo-3-acridinecarboxamide | 1.95 (A) | 488 |
| 342 | | 2-Fluoro-9,10-dihydro-N-[1-[6-(4-hydroxy-1-piperidinyl)-3-pyridinyl]-1-methylethyl]-9-oxo-3-acridinecarboxamide | 2.10 (A) | 475 |
| 343 | | 2-Fluoro-9,10-dihydro-N-[1-[6-(3-hydroxy-1-azetidinyl)-3-pyridinyl]-1-methylethyl]-9-oxo-3-acridinecarboxamide | 2.06 (A) | 447 |

TABLE 27-continued

| Ex. No | —G | Compound name | HPLC time (min) | M+ |
|---|---|---|---|---|
| 344 | | 2-Fluoro-9,10-dihydro-N-[1-[6-(3-hydroxy-1-pyrrolidinyl)-3-pyridinyl]-1-methylethyl]-9-oxo-3-acridinecarboxamide. | 2.11 (A) | 461 |
| 345 | | 2-Fluoro-9,10-dihydro-N-[1-[2-(3-hydroxy-1-pyrrolidinyl)-4-pyridinyl]-1-methylethyl]-9-oxo-3-acridinecarboxamide | 2.12 (A) | 461 |
| 346 | | | 2.08 (A) | 475 |

Examples 347-356

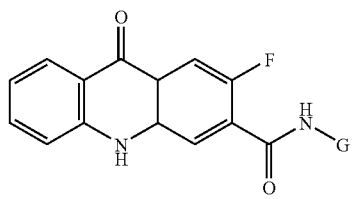

Examples 347-356 having the above formula wherein G has the values set forth in Table 28, were prepared by a route analogous to that described above for Examples 229-230, using the required H₂N-G. If the products carry basic moieties, they were purified by preparative HPLC.

TABLE 28

| Ex. No | —G | Compound name | HPLC time (min) Condition | M+ |
|---|---|---|---|---|
| 347 | | 2-Fluoro-9,10-dihydro-N-[1-[6-[(2R)-2-(methoxymethyl)-1-pyrrolidinyl]-3-pyridinyl]-1-methylethyl]-9-oxo-3-acridinecarboxamide | 2.33 (A) | 489 |

TABLE 28-continued

| Ex. No | —G | Compound name | HPLC time (min) Condition | M+ |
|---|---|---|---|---|
| 348 | | N-[1-[6-[(3S)-3-(Dimethyl-amino)-1-pyrrolidinyl]-3-pyridinyl]-1-methylethyl]-2-fluoro-9,10-dihydro-9-oxo-3-acridinecarboxamide. | 1.91 (A) | 488 |
| 349 | | N-[1-[6-[(3R)-3-(Acetylamino)-1-pyrrolidinyl]-3-pyridinyl]-1-methylethyl]-2-fluoro-9,10-dihydro-9-oxo-3-acridinecarboxamide | 2.12 (A) | 502 |
| 350 | | 2-Fluoro-9,10-dihydro-N-[1-[6-[(2R)-2-(hydroxymethyl)-1-pyrrolidinyl]-3-pyridinyl]-1-methylethyl]-9-oxo-3-acridinecarboxamide | 2.16 (A) | 475 |
| 351 | | 2-Fluoro-9,10-dihydro-N-[1-methyl-1-[6-(3-oxo-1-piperazin-yl)-3-pyridinyl]ethyl]-9-oxo-3-acridinecarboxamide | 2.01 (A) | 474 |
| 352 | | 2-Fluoro-N-[1-[6-(hexahydro-4-4-methyl-1H-1,4-diazepin-1-yl)-3-pyridinyl]-1-methylethyl]-9,10-dihydro-9-oxo-3-acridinecarboxamide | 1.91 (A) | 488 |
| 353 | | 2-Fluoro-9,10-dihydro-N-[1-[6-[(2-hydroxyethyl)amino]-3-pyridinyl]-1-methylethyl]-9-oxo-3-acridinecarboxamide | 1.98 (A) | 435 |
| 354 | | 2-Fluoro-9,10-dihydro-N-[1-[6-[(2-hydroxyethyl)methylamino]-3-pyridinyl]-1-methylethyl]-9-oxo-3-acridinecarboxamide | 2.06 (A) | 449 |

TABLE 28-continued

| Ex. No | —G | Compound name | HPLC time (min) Condition | M⁺ |
|---|---|---|---|---|
| 355 | | 2-Fluoro-9,10-dihydro-N-[1-methyl-1-[6-[((3R)-tetrahydro-3-furanyl)amino]-3-pyridinyl]-ethyl]-9-oxo-3-acridinecarboxamide | 2.13 (A) | 461 |
| 356 | | 2-Fluoro-9,10-dihydro-N-[1-methyl-1-[6-[methyl(1-methyl-3-pyrrolidinyl)amino]-3-pyridinyl]ethyl]-9-oxo-3-acridinecarboxamide | 1.93 (A) | 488 |

Example 357

2-Fluoro-9,10-dihydro-N-(1-methyl-1-phenylethyl)-9-oxo-3-acridinecarboxamide

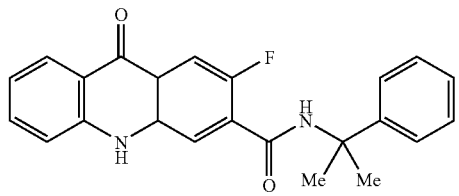

To compound 174E (30 mg, 0.117 mmol) was sequentially added Et₃N (24 mg, 0.234 mmol), 1-Methyl-1-phenyl-ethylamine (19 mg, 0.140 mmol), anhydrous DMF (0.3 mL), and BOP-CL (33 mg, 0.129 mmol). The reaction mixture was stirred for 18 hours at 50° C., then cooled to room temperature, and concentrated under reduced pressure. The crude residue was triturated with 1 mL of water, filtered, and the filtrate was collected and washed with water three times. The solid was dried in vacuo to give Example 357 as a yellow solid. HPLC retention time=3.08 min.; MS (M+H)⁺= 375.12.

Examples 358-382

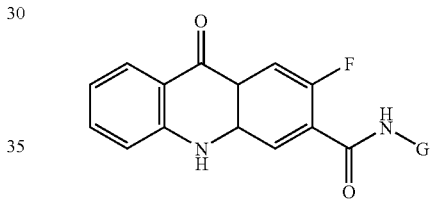

Compounds having the above formula wherein G has the values set forth in Table 29 were prepared from 174E by a route analogous to that used for the preparation of Example 357, replacing the amine with the required H₂N-G. The amines are either commercially available and/or were prepared according to previous schemes or Examples set forth herein. The final compounds may be further purified by preparative HPLC.

TABLE 29

| Ex. No | —G | Compound name | HPLC time (min)/condition | M⁺ |
|---|---|---|---|---|
| 358 | | 2-Fluoro-N-[2-(4-fluorophenyl)-1,1-dimethylethyl]-9,10-dihydro-9-oxo-3-acridinecarboxamide. | 3.36/A | 407 |
| 359 | | N-(1-Ethynylcyclohexyl)-2-fluoro-9,10-dihydro-9-oxo-3-acridinecarboxamide | 3.09/A | 363 |

TABLE 29-continued

| Ex. No | —G | Compound name | HPLC time (min)/condition | M+ |
|---|---|---|---|---|
| 360 | C(Me)₃ | N-(1,1-Dimethylethyl)-2-fluoro-9,10-dihydro-9-oxo-3-acridinecarboxamide. | 2.80/A | 313 |
| 361 | -C(Me)₂-C₆H₄-OMe (4-) | 2-Fluoro-9,10-dihydro-N-[1-(4-methoxyphenyl)-1-methylethyl]-9-oxo-3-acridinecarboxamide. | 3.09/A | 405 |
| 362 | -C(Me)₂-C₆H₃(OMe)₂ (3,4-) | N-[1-(3,4-Dimethoxyphenyl)-1-methylethyl]-2-fluoro-9,10-dihydro-9-oxo-3-acridinecarboxamide. | 2.87/A | 435 |
| 363 | -C(Me)₂-(1,3-benzodioxol-5-yl) | N-[1-(1,3-Benzodioxol-5-yl)-1-methylethyl]-2-fluoro-9,10-dihydro-9-oxo-3-acridinecarboxamide. | 3.05/A | 419 |
| 364 | -C(Me)(CN)-Ph | N-(1-Cyano-1-phenylethyl)-2-fluoro-9,10-dihydro-9-oxo-3-acridinecarboxamide. | 2.74/A | 386 |
| 365 | -C(Me)(CN)-CH₂-C₆H₄-F (4-) | N-[1-Cyano-2-(4-fluorophenyl)-1-methylethyl]-2-fluoro-9,10-dihydro-9-oxo-3-acridinecarboxamide. | 2.99/A | 418 |
| 366 | -C(Me)₂-CH(OH)-Ph | 2-Fluoro-9,10-dihydro-N-(2-hydroxy-1,1-dimethyl-2-phenyl-ethyl)-9-oxo-3-acridinecarboxamide. | 3.04/A | 405 |
| 367 | -C(Me)(Ph)-C(Me)₂-OH | 2-Fluoro-9,10-dihydro-N-(2-hydroxy-1,2-dimethyl-1-phenyl-propyl)-9-oxo-3-acridinecarboxamide. | 3.15/A | 419 |
| 368 | -C(Me)₂-Et | N-(1,1-Dimethylpropyl)-2-fluoro-9,10-dihydro-9-oxo-3-acridinecarboxamide. | 2.99/A | 327 |
| 369 | -C(Me)₂-CH₂-Ph | N-(1,1-Dimethyl-2-phenylethyl)-2-fluoro-9,10-dihydro-9-oxo-3-acridinecarboxamide. | 3.35/A | 389 |

TABLE 29-continued

| Ex. No | —G | Compound name | HPLC time (min)/condition | M+ |
|---|---|---|---|---|
| 370 | (2,3-dihydro-1,4-benzodioxin-6-yl)-C(Me)(Me)- | N-[1-(2,3-Dihydro-1,4-benzodioxin-6-yl)-1-methylethyl]-2-fluoro-9,10-dihydro-9-oxo-3-acridinecarboxamide. | 3.02/A | 433 |
| 371 | -C(Me)(Me)CH(OH)CH2Me | 2-Fluoro-9,10-dihydro-N-(2-hydroxy-1,1-dimethylpentyl)-9-oxo-3-acridinecarboxamide. | 2.96/A | 371 |
| 372 | (3-pyridinyl)-C(Me)(Me)- | 2-Fluoro-9,10-dihydro-N-[1-methyl-1-(3-pyridinyl)ethyl]-9-oxo-3-acridinecarboxamide. | 1.96/A | 376 |
| 373 | (6-methyl-3-pyridinyl)-C(Me)(Me)- | 2-Fluoro-9,10-dihydro-N-[1-methyl-1-(6-methyl-3-pyridinyl)ethyl]-9-oxo-3-acridinecarboxamide. | 2.01/A | 390 |
| 374 | (6-methoxy-3-pyridinyl)-C(Me)(Me)- | 2-Fluoro-9,10-dihydro-N-[1-(6-methoxy-3-pyridinyl)-1-methylethyl]-9-oxo-3-acridinecarboxamide. | 2.45/A | 406 |
| 375 | [6-(1-methylethyl)-3-pyridinyl]-C(Me)(Me)- | 2-Fluoro-9,10-dihydro-N-[1-methyl-1-[6-(1-methylethyl)-3-pyridinyl]ethyl]-9-oxo-3-acridinecarboxamide. | 2.22/A | 418 |
| 376 | [6-(4-thiomorpholinyl)-3-pyridinyl]-C(Me)(Me)- | 2-Fluoro-9,10-dihydro-N-[1-methyl-1-[6-(4-thiomorpholinyl)-3-pyridinyl]ethyl]-9-oxo-3-acridinecarboxamide. | 2.26/A | 477 |
| 377 | [6-[3-(methylsulfonyl)-1-pyrrolidinyl]-3-pyridinyl]-C(Me)(Me)- | 2-Fluoro-9,10-dihydro-N-[1-methyl-1-[6-[3-(methylsulfonyl)-1-pyrrolidinyl]-3-pyridinyl]ethyl]-9-oxo-3-acridinecarboxamide. | 2.26/A | 523 |

TABLE 29-continued

| Ex. No | —G | Compound name | HPLC time (min)/condition | M+ |
|---|---|---|---|---|
| 378 | | 2-Fluoro-9,10-dihydro-N-[1-methyl-1-[6-(2-methyl-1-pyrrolidinyl)-3-pyridinyl]ethyl]-9-oxo-3-acridinecarboxamide. | 2.49/A | 549 |
| 379 | | 2-Fluoro-9,10-dihydro-N-[1-methyl-1-[6-((1S,4S)-2-oxa-5-azabicyclo[2.2.1]hept-5-yl)-3-pyridinyl]ethyl]-9-oxo-3-acridinecarboxamide. | 2.30/A | 472 |
| 380 | | 2-Fluoro-9,10-dihydro-N-[1-[6-[(2S)-2-(methoxymethyl)-1-pyrrolidinyl]-3-pyridinyl]-1-methylethyl]-9-oxo-3-acridinecarboxamide | 1.43/C | 489 |
| 381 | | N-[1-[6-[(3R)-3-(Dimethylamino)-1-pyrrolidinyl]-3-pyridinyl]-1-methylethyl]-2-fluoro-9,10-dihydro-9-oxo-3-acridinecarboxamide. | 2.08/A | 488 |
| 382 | | 2-Fluoro-9,10-dihydro-N-[1-[6-[(2S)-2-(hydroxy methyl)-1-pyrrolidinyl]-3-pyridinyl]-1-methylethyl]-9-oxo-3-acridinecarboxamide. | 2.31/A | 475 |

Example 383

N-(1-Ethylcyclohexyl)-2-fluoro-9,10-dihydro-9-oxo-3-acridine carboxamide

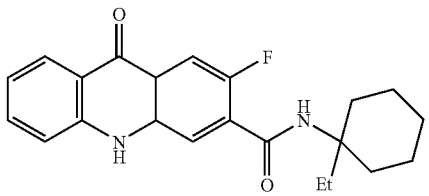

Example 383 was prepared from Example 359 using a route analogous to that described for the preparation of compound 174B. HPLC retention time=3.66 min.; MS (M+H)$^+$=367.

Example 384

N-[1-(6-Ethyl-3-pyridinyl)-1-methylethyl]-2-fluoro-9,10-dihydro-9-oxo-3-acridinecarboxamide

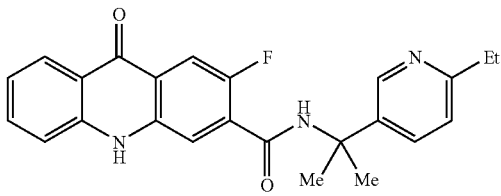

384A. 6-Vinyl-nicotinonitrile

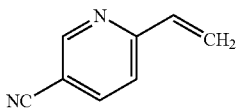

A 100 mL round bottom flask equipped with a condenser was charged with 6-Chloro-nicotinonitrile (500 mg, 3.61 mmol), Pd(PPh$_3$)$_4$ (42 mg, 0.036 mmol), PPh$_3$ (28.4 mg, 0.11 mmol), toluene (20 mL) and tributyl-vinyl-stannane (1.37 g, 4.33 mmol) under argon. The mixture was heated to reflux for three hours, then cooled to RT, quenched with water (12 mL), and extracted with EtOAc (30 mL) three times. The organic layer was combined and dried over MgSO$_4$, filtered, and concentrated in vacuo. The residue was purified by silica gel chromatography (5% EtOAc/Hexane) to afford compound 384A as a light yellow oil (535 mg). HPLC retention time=1.43 min. (condition A), M+=131.

384B. 6-Ethyl-nicotinonitrile

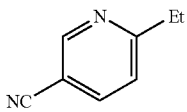

Compound 384B was prepared from 384A by a route analogous to that described for the preparation of compound 174B. HPLC retention time=1.24 min. (Condition A), M+=133.

384C. 1-(6-Ethyl-pyridin-3-yl)-1-methyl-ethylamine

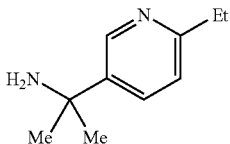

Compound 384C was prepared from 384B by a route analogous to that used for the preparation of compound 1D. HPLC retention time=0.26 min. (Condition A), M+=165.

384D. Example 384

Example 384 was prepared using compound 174E and a route analogous to that used for the preparation of Example 357, replacing the amine with 384C. HPLC retention time=2.36 min. (Condition A), M+=404.

Example 385

N-[1-(2,6-Dimethyl-3-pyridinyl)-1-methylethyl]-2-fluoro-9,10-dihydro-9-oxo-3-acridinecarboxamide

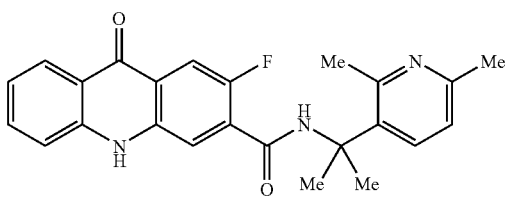

385A. 2,6-Dimethyl-nicotinonitrile

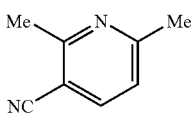

A 100 mL round bottom flask equipped with a condenser was charged with 2-Chloro-6-methyl-nicotinonitrile (1 g, 6.55 mmol), MeB(OH)$_2$ (216 mg, 7.22 mmol), K$_2$CO$_3$ (1.36 g, 19.67 mmol), and dioxane (33 mL), followed by Pd(PPh$_3$)$_4$ (758 mg, 0.66 mmol) under argon. The mixture was heated to reflux for 48 hours, and then cooled down to RT. The resulting mixture was concentrated in vacuo, treated with 1N HCl (150 mL), and extracted with EtOAc (100 mL), Et$_2$O (50 mL). The aqueous layer was basified with 50% NaOH until PH=10, and then extracted with EtOAC (100 mL) three times. The combined organic layer was dried over MgSO$_4$, filtered, and concentrated in vacuo. The crude residue was purified by silica gel chromatography (5-10% EtOAC/Hexane) to give F2A as a light yellow solid (440 mg). HPLC retention time=0.766 min./condition A, M+=133.

385B. 1-(2,6-Dimethyl-pyridin-3-yl)-1-methyl-ethylamine

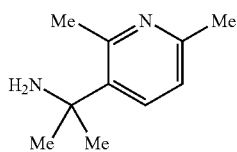

Compound 385B was prepared from 385A by a route analogous to that used for the preparation of compound 1D. HPLC retention time=0.23 min. (Condition A), M+=165.

385C. Example 385

Example 385 was prepared using compound 174E and a route analogous to that used for the preparation of Example 357, replacing the amine with 385B. HPLC retention time=2.05 min. (Condition A), M+=404.

Example 386

N-[1-(2-Ethyl-6-methyl-3-pyridinyl)-1-methylethyl]-2-fluoro-9,10-dihydro-9-oxo-3-acridinecarboxamide

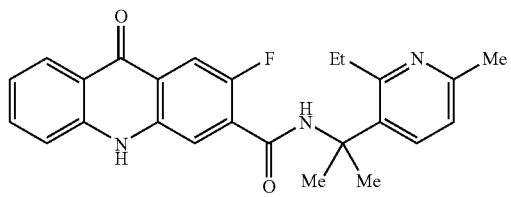

386A. 6-Methyl-2-vinyl-nicotinonitrile

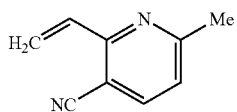

Compound 386A was prepared from 2-chloro-6-methyl-nicotinonitrile by a route analogous to that used for the preparation of compound 384A. HPLC retention time=1.81 min. (Condition A), M+=145.

386B. 2-Ethyl-6-methyl-nicotinonitrile

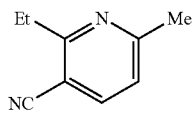

Compound 386B was prepared from 386A by a route analogous to that used for the preparation of 384B. HPLC retention time=1.18 min. (Condition A), M+=147.

386C. 1-(2-Ethyl-6-methyl-pyridin-3-yl)-1-methyl-ethylamine

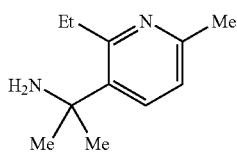

Compound 386C was prepared from 386B by a route analogous to that used for the preparation of compound 1D. HPLC retention time=0.26 min. (Condition A), M+=179.

386D. Example 386

Example 386 was prepared using compound 174E and a route analogous to that used for the preparation of Example 357, replacing the amine with 386C. HPLC retention time=2.17 min. (Condition A), M+=418.

Example 387

2-Fluoro-9,10-dihydro-N-[1-methyl-1-[3-(4-thiomorpholinyl)phenyl]ethyl]-9-oxo-3-acridinecarboxamide

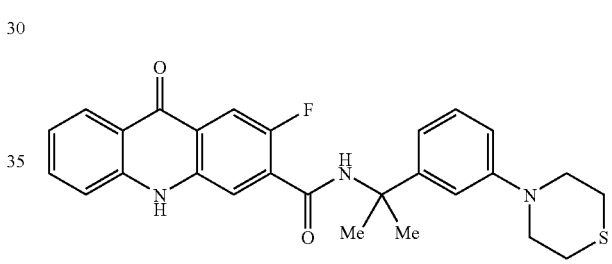

387A. 3-Thiomorpholin-4-yl-benzonitrile

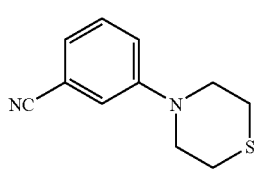

A 10 dram vial was charged with 3-bromo-benzonitrile (280 mg, 1.54 mmol), thiomorpholine (190 mg, 1.85 mmol), NaOtBu (207 mg, 2.15 mmol), BINAP (14.4 mg, 0.023 mmol), toluene (3 mL), $Pd_2(dba)_3$ (7 mg, 0.0077 mmol), and flushed with argon. The reaction mixture was heated to 85° C. for 48 h, and then cooled to RT. The resulting mixture was diluted with $Et_2O$ (10 mL), filtered through celite, and washed with $Et_2O$ (7 mL) two times. The filtrate was concentrated in vacuo and purified by silica gel chromatography (20% EtOAC/Hexane) to give compound 387A as a yellow oil (256 mg). HPLC retention time=2.48 min. (Condition A), M+=205.

387B. 1-Methyl-1-(3-thiomorpholin-4-yl-phenyl)-ethylamine

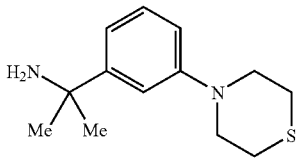

Compound 387B was prepared from 387A by a route analogous to that used for the preparation of compound 1D. HPLC retention time=1.54 min. (Condition A), M+=237.

387C. Example 387

Example 387 was prepared using compound 174E and a route analogous to that used for the preparation of Example 357, replacing the amine with 387B. HPLC retention time=3.13 min. (Condition A), M+=476.

Example 388

2-Fluoro-9,10-dihydro-N-[1-methyl-1-[3-(1,1,4-trioxido-4-thiomorpholinyl)phenyl]ethyl]-9-oxo-3-acridinecarboxamide

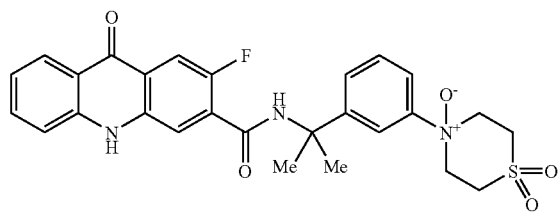

A one dram vial was charged with Example 387 (32 mg, 0.068 mmol), Na$_2$SO$_4$.2H$_2$O (81 mg, 0.25 mmol), AcOH (1 mL), and H$_2$O$_2$ (30%, 23 μL). The mixture was stirred at RT for 48 h and concentrated in vacuo. The resulting mixture was triturated with sat. NaHCO$_3$ (1 mL) and then filtered, washed with water (1 mL) two times, and dried in vacuo to give Example 388 as a yellow solid (18 mg). HPLC retention time=2.36 min. (Condition A), M+=524.

Example 389

2-Fluoro-9,10-dihydro-N-[1-methyl-1-[3-(1-oxido-4-thiomorpholinyl)phenyl]ethyl]-9-oxo-3-acridinecarboxamide

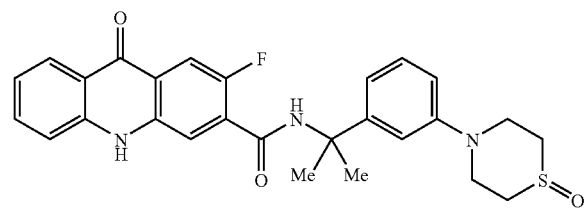

A one dram vial was charged with Example 387 (15 mg, 0.032 mmol), Na$_2$SO$_4$.2H$_2$O (2 mg, 0.0061 mmol), TFA (0.5 mL), and H$_2$O$_2$ (30%, 6 μL) at 0° C. The mixture was stirred at 0° C. for 30 min. and concentrated in vacuo. The resulting mixture was triturated with sat. NaHCO$_3$ (0.5 mL) at 0° C. and then filtered, washed with water (1 mL) two times, and dried in vacuo to give Example 389 as a yellow solid (14 mg). HPLC retention time=2.99 min. (Condition A), M+=492.

Example 390

2-Fluoro-9,10-dihydro-N-[1-methyl-1-(1-oxido-3-pyridinyl)ethyl]-9-oxo-3-acridinecarboxamide

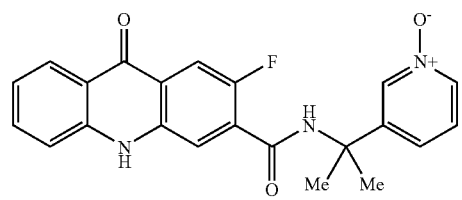

Compound 372 (14 mg, 0.029 mmol) was dissolved in CH$_2$Cl$_2$ (1 ml), excess mCPBA was added, and the reaction was stirred overnight. The mixture was diluted with CH$_2$Cl$_2$ and then it was washed with aq. Na$_2$S$_2$O$_8$, followed by aq. NaHCO$_3$, then concentrated to dryness. The resulting residue was purified by preparative HPLC and the desired fraction was concentrated, then treated with ether and DCM to give 3 mg of Example 390 as a yellow solid. HPLC retention time=2.27 min. (Condition A) and LC/MS M$^+$+1=392.

Example 391

2-Fluoro-9,10-dihydro-N-[1-methyl-1-(1-oxido-2-pyridinyl)ethyl]-9-oxo-3-acridinecarboxamide

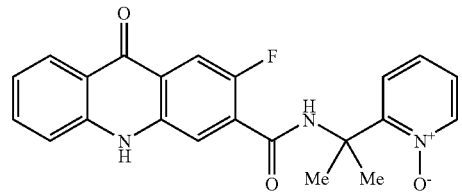

Example 391 was prepared as a yellow solid from Example 209 by a route analogous to that used for the preparation of Example 390. HPLC retention time=2.44 min. (Condition A) and LC/MS M$^+$+1=392.

Example 392

2-Fluoro-9,10-dihydro-N-[1-methyl-1-(6-methyl-1-oxido-3-pyridinyl)ethyl]-9-oxo-3-acridinecarboxamide

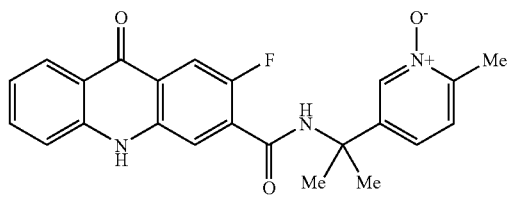

Example 392 was prepared as a yellow solid from Example 373 by a route analogous to that used for the preparation of Example 390. HPLC retention time=2.38 min. (Condition A) and LC/MS M$^{+}$+1=406.

Example 393

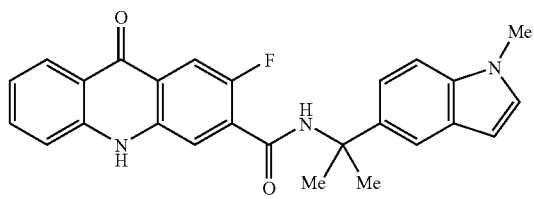

Example 393 was prepared using a reaction sequence analogous to the procedure described for the preparation of Example 105, using compound 174E in place of 1C. HPLC retention time=3.42 min. (Condition B) and LC/MS M$^{+1}$=428.

Example 394

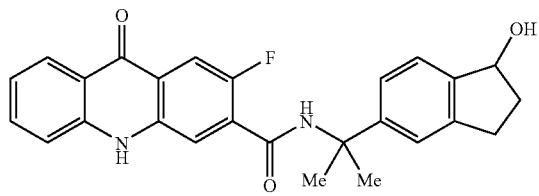

Example 394 was prepared using a reaction sequence analogous to the procedure described for the preparation of Example 108 (The hydroxy group was protected as a t-butyldimethylsilyl ether). HPLC retention time=2.82 min. (Condition B) and LC/MS M$^{+1}$=431.

Example 395

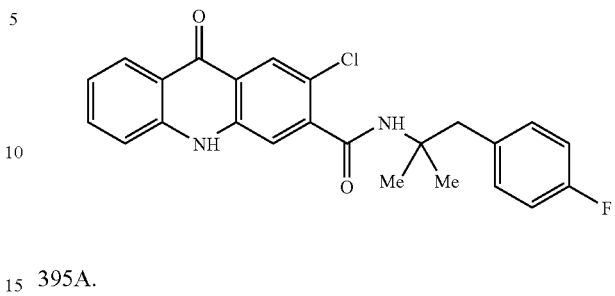

395A.

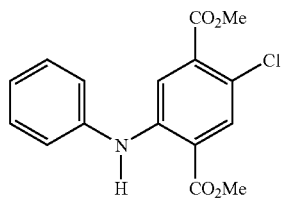

To a solution of 2,5-dichloroterephthalate (0.3 g, 1.14 mmol) in dimethoxyethane (2 mL) was sequentially added aniline (0.1 mL, 1.14 mmol) potassium phosphate (0.338 g, 1.6 mmol), Pd$_2$(dba)$_3$ (0.005 g, 0.006 mmol) and (Ph)$_2$P(Cy)$_2$ (0.008 g, 0.023 mmol). The reaction mixture was purged with nitrogen gas for ten minutes and heated at 100° C. in a sealed tube for eighteen hours. The reaction mixture was cooled to room temperature and filtered over a thin pad of celite, and the celite pad was washed with EtOAc. The filtrate was concentrated under reduced pressure and purified by silica gel flash chromatography employing hexane and EtOAc to yield compound 395A (0.265 g, 73%). $^1$H NMR (DMSO-d6): 9.2 (1H, s), 8.0 (s, 1H), 7.9 (1H, s), 7.45 (1H, s), 7.35 (1H, t), 7.25 (1H, d), 7.1 (1H, t), 3.9 (3H, s), 3.8 (3H, s).

395B.

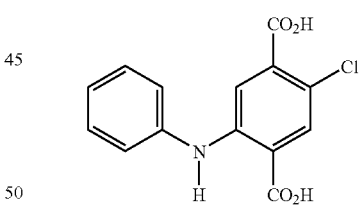

Compound 395B was prepared in a fashion analogous to compounds 1B or 175D starting from compound 395A (0.26 g, 0.815 mmol). Yield: 0.21 g (89%).

395C.

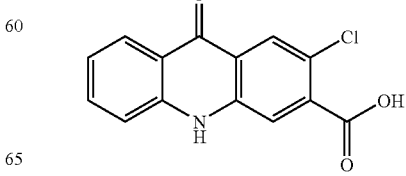

This compound was prepared in a fashion analogous to compounds 1C or 175E starting from compound 395B (0.19 g, 0.815 mmol). Yield: 0.21 g (87%). Retention time=2.64 min. (Condition A).

395D. Example 395

Example 395 was prepared following the same or similar procedure as described for 1E or 175F, using acridone acid 395C and 1-(4-fluorophenyl)-2-methyl-2-propylamine. Retention time=3.31 min. (Condition A). M+ 423.36

Examples 396-401

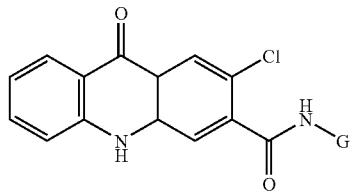

Compounds having the above formula wherein G has the values set forth in Table 30 were prepared from 395C by a route analogous to that used for the preparation of Example 395, replacing the amine with the required $H_2N$-G. The amines are either commercially available and/or were prepared according to previous schemes or Examples set forth herein. The final compounds may be further purified by preparative HPLC.

TABLE 30

| Ex. No. | G | HPLC Ret. time min) (Condition) | MS M+ |
|---|---|---|---|
| 396 | | 2.66 (A) | 329.33 |
| 397 | | 1.22 (A) | 406.12. |
| 398 | | 2.24 (A) | 461+ |
| 399 | | 2.16 (A) | 447+ |

TABLE 30-continued

| Ex. No. | G | HPLC Ret. time min) (Condition) | MS M+ |
|---|---|---|---|
| 400 | | 2.11 (A) | 447+ |
| 401 | | 2.06 (A) | 477+ |

Examples 402-403

Compounds having the above formula wherein G has the values set forth in Table 31 were prepared by a route analogous to that used for the preparation of Examples 103 and 104, respectively, using compound 395C in place of 1C for the acridone acid.

TABLE 31

| Ex. No. | —G | HPLC Ret. time (min.) (Condition) | MS M+ |
|---|---|---|---|
| 402 | | 3.10 (B) | 462 |
| 403 | | 3.08 (B) | 462 |

Example 404

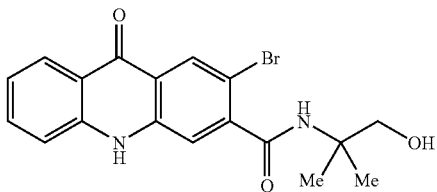

404A. 2-Bromo-9-oxo-9,10-dihydro-acridine-3-carboxylic acid

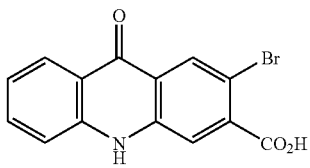

Using a route analogous to that used for the preparation of Compound 1C and dimethyl 2,5-dibromoterephthalate, Compound 404A was prepared as a yellow solid. HPLC retention time=2.603 min. (Condition A) and LC/MS $M^{+}+1=318^{+}$. $^1$H-NMR (400 MHz, DMSO-$d_6$) δ 12.05 (s, 1H), 8.37 (s, 1H), 8.22 (d, J=8.02 Hz, 1H), 7.88 (s, 1H), 7.78 (t, J=7.59 Hz, 1H), 7.55 (d, J=8.19 Hz, 1H), 7.31 (t, J=7.47 Hz, 1H.

404B. Example 404

To a mixture of acridone acid 404A (0.120 g, 0.377 mmol) and 2-amino-2-propanol (0.036 mL, 0.377 mmol) in 6 mL of anhydrous DMF was added triethylamine (0.11 mL, 0.754 mmol) followed by BOP-Cl (0.096 g, 0.377 mmol). The reaction mixture was stirred overnight at room temperature. The mixture was diluted with DCM, washed with water, and dried over anhydrous sodium sulfate. Concentration under reduced pressure followed by purification by silica gel chromatography afforded 62 mg of Example 404 as a pale yellow solid. HPLC retention time=2.53 min. (Condition B) and a LC/MS $M^{+1}$=389/391.

Examples 405-415

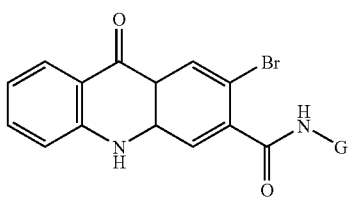

Compounds having the above formula, wherein G has the values listed in Table 32, were prepared in the same or similar manner as described for Example 404, using an appropriate amine in place of 2-amino-2-propanol. The amines are commercially available and/or can be prepared as set forth in the literature (see, e.g., *Tetrahedron*, Vol. 54, 5-6 [1998] at pp. 1013-1020), and/or as described in previous Examples herein (see, e.g., Ex. 43, 136, 137, etc.).

TABLE 32

| Ex. No. | G | HPLC ret. time (min) (Condition) | $M^+$ |
|---|---|---|---|
| 405 | ![benzodioxane with C(CH3)2] | 2.95 | 493 |
| 406 | ![CH2-phenyl-OMe with C(Me)2] | 1.83 (D) | 401.46. |
| 407 | ![CH2-pyridyl with C(Me)2] | 1.83 (D) | 401.46. |
| 408 | ![CH2-pyridyl with C(Me)2] | 1.83 (D) | 401.4 |
| 409 | ![CH(OH)-phenyl with C(Me)2] | 2.66 (D) | 329.33 |
| 410 | ![C(O)-phenyl with C(Me)2] | 1.58 (D) | 464.08. |
| 411 | ![cyclopentyl-CH2OH] | 1.51 (D) | 415.06. |
| 412 | ![Me-piperidinyl-N-CH2-phenyl] | 2.42 (D) | 504.14. |
| 413 | ![cyclopentyl with Me and CO2Me] | 2.97 (A) | 457.24. |
| 414 | ![CH2-pyridyl with C(Me)2] | 2.40 (B) | 436 |

TABLE 32-continued

| Ex. No. | G | HPLC ret. time (min) (Condition) | M+ |
|---|---|---|---|
| 415 | 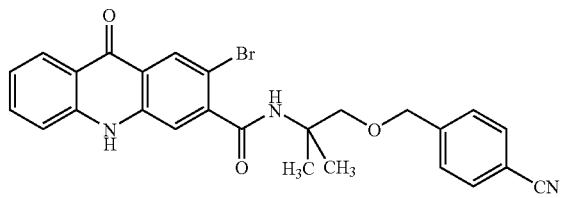 | 2.67 (A) | 374 |

Example 416

[structure: acridone with Br and amide linked to C(CH3)2-CH2-O-CH2-C6H4-CN]

Example 416 was prepared using a method analogous to that described for Example 82 using 4-cyanobenzylbromide and Example 404. The compound was either purified by silica gel chromatography or preparative HPLC. HPLC retention time=2.94 min. (Condition B) and a LC/MS $M^{+1}$=506.

Example 417

[structure: acridone with Br and amide linked to C(CH3)2-CH2-O-C(O)-NH-phenyl]

Example 417 was prepared using the procedure described for Example 88 using Example 404. HPLC retention time=3.17 min. (Condition B), and LC/MS $M^{+1}$=510.

Examples 418-419

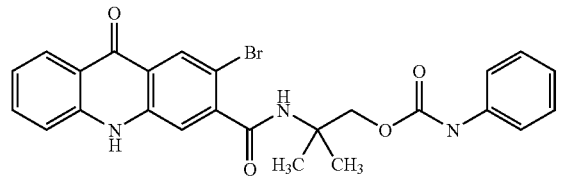

Compounds having the above formula wherein G has the values set forth in Table 33 were prepared by a route analogous to that used for the preparation of Examples 103 and 104, respectively, using compound 404A in place of 1C for the acridone acid.

TABLE 33

| Ex. No. | -G | HPLC Ret. time (min.) (Condition) | MS M+ |
|---|---|---|---|
| 418 | [benzoxazine with C(Me)2 linker, N-Me] | 3.15 (B) | 508 |
| 419 | [benzoxazine with C(Me)2 linker, N-Me, other regioisomer] | 3.08 (B) | 462 |

Example 420

[structure: acridone with CN and amide linked to C(Me)3 (t-butyl)]

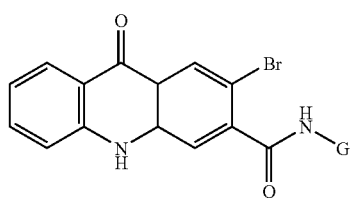

420A

In a sealed tube under argon was combined the bromoacridone 404A (0.510 g, 1.60 mM), CuCN (0.72 g, 8.0 mM), Hunig's base (0.41 g, 3.2 mM), and 5.0 mL of DME. The sealed tube was heated in an oil bath at 140° C. for 70 min. Upon cooling to room temperature, 20 mL of 1.0 N HCl was added. The suspension was filtered, washed with water (10 mL) and dried in vacuo to provide 420A (0.41 g, 97%) as a light yellow solid.

420B. Example 420

Example 420 was prepared from 420A and t-butyl amine by a route by a route analogous to that used for the preparation of Example 404. HPLC retention time=2.49 min. (Condition A), M+=322.

Example 421

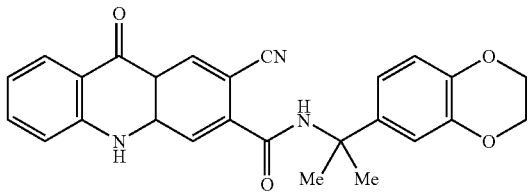

Example 421 was prepared from 420A and the amine used in the preparation of example 370 (see also, Ex. 103-104, 179-83), by a route analogous to that used for the preparation of Example 404. HPLC retention time=2.98 min. (Condition B), M+=371.

Example 422

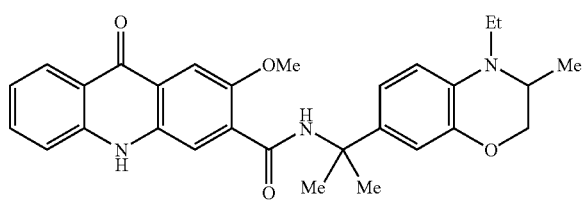

422A.

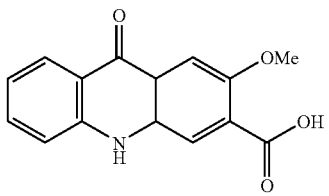

To 60% sodium hydride (0.053 g, 1.32 mmol) at 0° C. was added 12 mL of MeOH slowly. The ice-bath was removed, and the suspension was warmed to room temperature. Bromo acridone acid 404A (0.120 g, 0.377 mmol) was added, and the mixture was stirred until it became homogeneous. Copper powder (4.0 mg, 0.057 mmol) was added, and the reaction mixture was heated at reflux overnight. Analytical HPLC indicated that the reaction was only partially complete. An additional one equivalent of copper powder was added, and the reaction mixture was stirred for 2 days. Analytical HPLC indicated that the reaction was ~75% complete. The reaction mixture was cooled, filtered through Celite, concentrated, diluted with EtOAc and water, and acidified with hydrochloric acid. The organic layer was collected (the residual starting material crashed out during work up and was not soluble in EtOAc), dried over anhydrous sodium sulfate, and concentrated under reduced pressure to give 67 mg (67%) of 422A as a bright yellow solid. HPLC retention time=2.46 min. (Condition B) and LC/MS $M^{+1}$=270.

422B. Example 422

To a mixture of 422A (0.020 g, 0.074 mmol), compound 182D (0.019 g, 0.082 mmol), and triethylamine (0.03 mL, 0.223 mmol) was added BOP-Cl (0.023 g, 0.089 mmol) in 4 mL of anhydrous DMF at room temperature. The reaction mixture was stirred at room temperature overnight. The mixture was diluted with DCM, washed with water, washed with 1N aqueous sodium hydroxide (3x), and dried over anhydrous sodium sulfate. Concentration under reduced pressure followed by purification by preparative HPLC afforded Example 422 (0.012 g) as a bright yellow solid. HPLC retention time=2.84 min. (Condition B) and LC/MS $M^{+1}$=486.

Examples 423-425

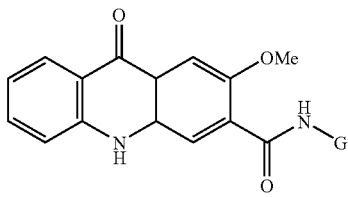

Compounds having the above formula wherein G has the values set forth in Table 34 were prepared by a route analogous to that used for the preparation of Example 422, using the appropriate amine as previously described in place of compound 182D (i.e., compound 329 for Ex. 423, t-butyl amine for Ex. 424, and 217B for Ex. 425).

TABLE 34

| Ex. No. | -G | HPLC Ret. time (min.) (Condition) | MS M+ |
|---|---|---|---|
| 423 | ![structure with sulfonyl azetidine] | 3.30 (B) | 506 |
| 424 | ![t-butyl dimethyl] | 3.22 (B) | 325 |
| 425 | ![pyridyl morpholine] | 2.33 (B) | 473 |

Example 426

9,10-Dihydro-N-[1-methyl-1-(3-pyridinyl)ethyl]-2-(methylthio)-9-oxo-3-acridinecarboxamide

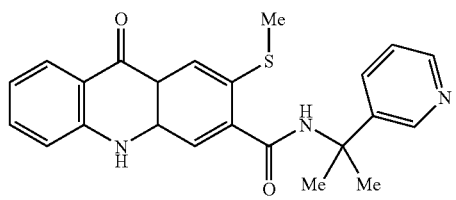

426A. 9,10-Dihydro-2-(methylthio)-9-oxo-3-acridinecarboxylic acid

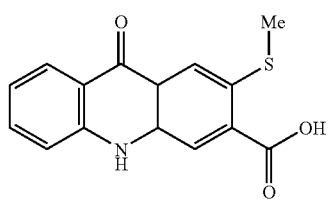

A 15 mL sealed tube was charged with compound 174E (200 mg, 0.78 mmol), NaSMe (545 mg, 7.78 mmol), and DMA (2 mL) under argon. The resulting mixture was heated to 175° C. for 7 h and then allowed to cool to RT, and further cooled to 0° C. when 1N HCl was added to adjust PH value of the solution to be ~4. The resulting red precipitate was collected by filtration, washed with water (10 mL) three times, and dried in vacuo to give 426A as a rust-red solid (163 mg). HPLC retention time=2.53 min. (Condition A). Compound 426A was used in the next step without further purification.

426B. Example 426

Example 426 was prepared from 426A by a route analogous to that used for the preparation of Example 357, replacing the amine with 1-Methyl-1-pyridin-3-yl-ethylamine. HPLC retention time=2.18, condition A; M+=404.

Examples 427-429

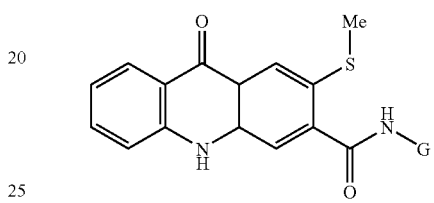

Examples 427-429 having the above formula wherein G has the values set forth in Table 35 were prepared from 426A by a route analogous to that used for the preparation of Example 426, replacing the amine with the required H₂N-G. The desired compounds may be further purified by preparative HPLC.

TABLE 35

| Ex. No | —G | Compound Name | HPLC time (min)/ Condition | M+ |
|---|---|---|---|---|
| 427 | (1-ethynyl-cyclohexyl) | 9,10-Dihydro-N-(1-ethynyl-cyclohexyl)-2-(methylthio)-9-oxo-3-acridine-carboxamide. | 2.95/B | 391 |
| 428 | (2-(4-fluoro-phenyl)-1,1-dimethyl-ethyl) | 9,10-Dihydro-N-[2-(4-fluoro-phenyl)-1,1-dimethyl-ethyl]-2-(methylthio)-9-oxo-3-acridinecarboxamide. | 3.25/A | 435 |
| 429 | (1-methyl-1-[(3-methylthio)1-phenyl]ethyl) | 9,10-Dihydro-N-{1-methyl-1-[(3-methylthio)1-phenyl)ethyl}-2-(methylthio)-9-oxo-3-acridinecarboxamide. | 3.12/A | 449 |

Examples 430 and 431

N-[2-(4-Fluorophenyl)-1,1-dimethylethyl]-9,10-dihydro-2-(methylsulfinyl)-9-oxo-3-acridinecarboxamide; and N-[2-(4-Fluorophenyl)-1,1-dimethylethyl]-9,10-dihydro-2-(methylsulfonyl)-9-oxo-3-acridinecarboxamide A vial was charged with Example 428 (22 mg) and CH$_2$Cl$_2$ (1 mL), MeOH (1 mL), followed by mCPBA (28 mg, 57-86% by weight). The mixture was stirred at RT for 30 min., and then concentrated in vacuo. Preparative HPLC of the crude mixture gave Ex. 430 as a yellow solid (2.1 mg, HPLC retention time=3.10 min./condition A, M+=451), and Ex. 431 also as a yellow solid (2.9 mg, HPLC retention time=3.102 min./condition A, M+=467).

Examples 432-437

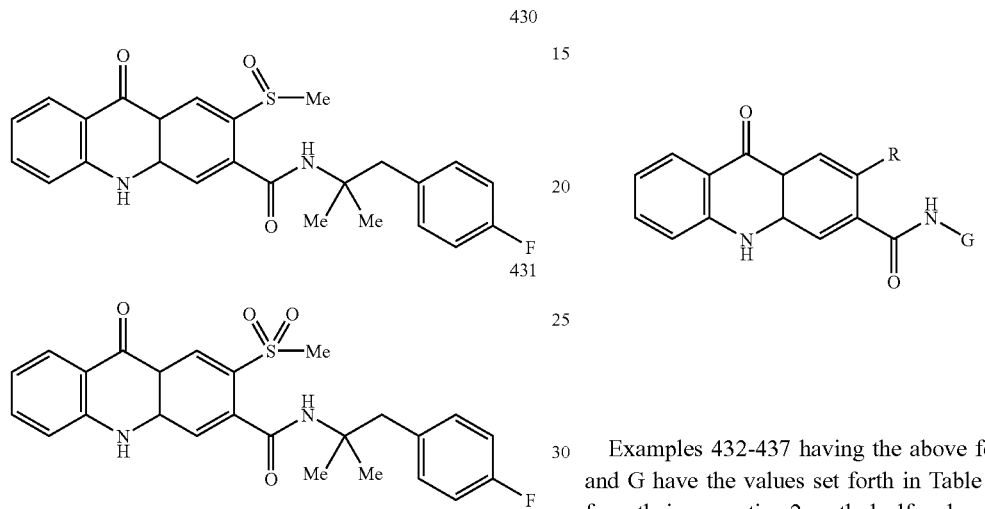

Examples 432-437 having the above formula wherein R and G have the values set forth in Table 36 were prepared from their respective 2-methylsulfanyl precursors by a route analogous to that used for the preparation of 430 and 431.

TABLE 36

| Ex. No | —R | —G | Compound name | HPLC time (min)/ Condition | M+ |
|---|---|---|---|---|---|
| 432 | S(=O)—Me | C(Me)(Me)-phenyl | 9,10-Dihydro-N-(1-methyl-1-phenylethyl)-2-(methylsulfinyl)-9-oxo-3-acridinecarboxamide. | 2.60/A | 419 |
| 433 | S(=O)$_2$—Me | C(Me)(Me)-phenyl | 9,10-Dihydro-N-(1-methyl-1-phenylethyl)-2-(methylsulfonyl)-9-oxo-3-acridinecarboxamide. | 2.70/A | 435 |
| 434 | S(=O)$_2$—Me | 1-ethynylcyclohexyl | N-(1-Ethynylcyclohexyl)-9,10-dihydro-2-(methylsulfonyl)-9-oxo-3-acridinecarboxamide. | 2.74/A | 423 |

TABLE 36-continued

| Ex. No | —R | —G | Compound name | HPLC time (min)/ Condition | M+ |
|---|---|---|---|---|---|
| 435 | methylsulfinyl (S(=O)Me) | 1-oxido-3-pyridinyl-C(Me)₂- | 9,10-Dihydro-N-[1-methyl-1-(1-oxido-3-pyridinyl)ethyl]-2-(methylsulfinyl)-9-oxo-3-acridinecarboxamide. | 1.88/A | 436 |
| 436 | methylsulfonyl (SO₂Me) | 1-oxido-3-pyridinyl-C(Me)₂- | 9,10-Dihydro-N-[1-methyl-1-(1-oxido-3-pyridinyl)ethyl]-2-(methylsulfonyl)-9-oxo-3-acridinecarboxamide. | 1.96/A | 452 |
| 437 | methylsulfonyl (SO₂Me) | 3-(methylsulfonyl)phenyl-C(Me)₂- | 9,10-Dihydro-N-[1-methyl-1-[3-(methylsulfonyl)phenyl]ethyl]-2-(methylsulfonyl)-9-oxo-3-acridinecarboxamide. | 2.29/A | 513 |

Example 438

9,10-Dihydro-N-[1-(6-methoxy-3-pyridinyl)-1-methylethyl]-2-(methylsulfonyl)-9-oxo-3-acridinecarboxamide

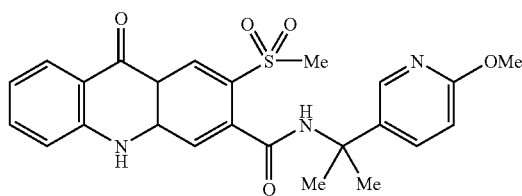

438A. 9,10-Dihydro-2-(methylsulfonyl)-9-oxo-3-acridinecarboxylic acid

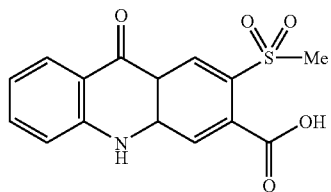

A 25 mL round bottom flask was charged with compound 426A (2-methylsulfanyl acridone acid) (350 mg, 1.23 mmol), Na₂SO₄·2H₂O (81 mg, 0.25 mmol), and TFA (6 mL). The mixture was cooled to 0° C., H₂O₂ (30%, 0.42 mL, 3.68 mmol) was added, and then the mixture was allowed to warm to RT. The reaction mixture was stirred at RT for 2.5 h and concentrated in vacuo. The resulting mixture was triturated with water (5 mL) and then filtered, washed with water (5 mL) two times, and dried in vacuo to give 438A as a rust-red solid (300 mg). HPLC retention time=2.21 min./condition A, M+=318. The compound was carried over to the next step without further purification.

438B. Example 438

Example 438 was prepared from 438A by a route analogous to that used for the preparation of Example 357. HPLC retention time=2.25 min./condition A, M+=466.

Examples 439-446

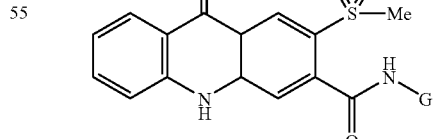

Examples 439-446 having the above formula wherein G has the values set forth in Table 37 were prepared from compound 438A following the same or similar procedure as described for Example 438. The desired compounds may be further purified by preparative HPLC.

TABLE 37

| Ex. No | —G | Compound name | HPLC time (min)/ Condition | M+ |
|---|---|---|---|---|
| 439 | (3-pyridinyl)-C(Me)(Me)- | 9,10-Dihydro-N-[1-methyl-1-(3-pyridinyl)ethyl]-2-(methylsulfonyl)-9-oxo-3-acridinecarboxamide. | 1.86/A | 436 |
| 440 | (6-methyl-3-pyridinyl)-C(Me)(Me)- | 9,10-Dihydro-N-[1-methyl-1-(6-methyl-3-pyridinyl)ethyl]-2-(methylsulfonyl)-9-oxo-3-acridinecarboxamide. | 1.92/A | 450 |
| 441 | [6-(4-morpholinyl)-3-pyridinyl]-C(Me)(Me)- | 9,10-Dihydro-N-[1-methyl-1-[6-(4-morpholinyl)-3-pyridinyl]ethyl]-2-(methylsulfonyl)-9-oxo-3-acridinecarboxamide. | 2.16/A | 521 |
| 442 | (4-ethyl-3,4-dihydro-3-methyl-2H-1,4-benzoxazin-7-yl)-C(Me)(Me)- | N-[1-(4-Ethyl-3,4-dihydro-3-methyl-2H-1,4-benzoxazin-7-yl)-1-methylethyl]-9,10-dihydro-2-(methylsulfonyl)-9-oxo-3-acridinecarboxamide. | 2.78/A | 534 |
| 443 | [6-(4-thiomorpholinyl)-3-pyridinyl]-C(Me)(Me)- | 9,10-Dihydro-2-(methylsulfonyl)-N-[1-methyl-1-[6-(4-thiomorpholinyl)-3-pyridinyl]ethyl]-9-oxo-3-acridinecarboxamide. | 2.34/A | 537 |
| 444 | [3-(1-oxido-4-thiomorpholinyl)phenyl]-C(Me)(Me)- | 9,10-Dihydro-N-[1-methyl-1-[3-(1-oxido-4-thiomorpholinyl)phenyl]ethyl]-2-(methylsulfonyl)-9-oxo-3-acridinecarboxamide. | 2.37/A | 552 |
| 445 | [3-(1-azetidinylsulfonyl)phenyl]-C(Me)(Me)- | N-[1-[3-(1-Azetidinylsulfonyl)phenyl]-1-methylethyl]-9,10-dihydro-2-(methylsulfonyl)-9-oxo-3-acridinecarboxamide. | 2.71/A | 554 |
| 446 | [2-(4-morpholinyl)-4-pyridinyl]-C(Me)(Me)- | 9,10-Dihydro-N-[1-methyl-1-[2-(4-morpholinyl)-4-pyridinyl]ethyl]-2-(methylsulfonyl)-9-oxo-3-acridinecarboxamide. | 2.20/A | 521 |

We claim:

1. A compound of formula (I),

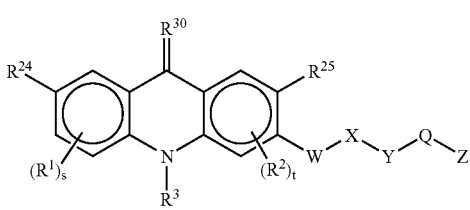

or an enantiomer, diastereomer, tautomer, or pharmaceutically-acceptable salt, thereof, wherein:

$R^1$ and $R^2$ are the same or different and at each occurrence are independently selected from halogen, cyano, alkyl, substituted alkyl, alkenyl, substituted alkenyl, alkynyl, substituted alkynyl, —O—$R^7$, —(C=O)$R^7$, —(C=O)—O—$R^7$, —NR$^8$R$^9$, —(C=O)NR$^8$R$^9$, —SR$^{20}$, —S(=O)R$^{20}$, —SO$_2$R$^{20}$ and —C≡C—Si(C$_{1-4}$alkyl)$_3$;

$R^{24}$, at each occurrence, is selected from hydrogen, halogen, nitro, cyano, alkyl, substituted alkyl, alkenyl, substituted alkenyl, alkynyl, substituted alkynyl, —O—$R^7$, —(C=O)$R^7$, —NR$^8$R$^9$, —(C=O)NR$^8$R$^9$, —SR$^{20}$, —S(=O)R$^{20}$, —SO$_2$R$^{20}$, —SO$_3$H, —SO$_3$R$^{20}$, —SO$_2$NR$^8$R$^9$, and —C≡C—Si(C$_{1-4}$alkyl)$_3$;

$R^{25}$, at each occurrence, is selected from hydrogen, halogen, nitro, cyano, alkyl, substituted alkyl, alkenyl, substituted alkenyl, alkynyl, substituted alkynyl, —O—$R^7$, —(C=O)$R^7$, —(C=O)—O—$R^7$, —NH$_2$, —NHC$_{1-4}$alkyl, —N(C$_{1-4}$alkyl)$_2$, —(C=O)NR$^8$R$^9$, —SR$^{20}$, —S(=O)R$^{20}$, —SO$_2$R$^{20}$, —SO$_3$H, —SO$_3$R$^{20}$, —SO$_2$NR$^8$R$^9$, and —C≡C—Si(C$_{1-4}$alkyl)$_3$;

$R^3$ selected from H, OH and NH$_2$;

$R^{30}$ selected from =O and =S;

W is selected from —CH$_2$—, —C(=O)—, —S(=O)—, or —S(O)$_2$—;

X is selected from —CH$_2$—, —N(R$^4$)—, and —O—, except that when W is —CH$_2$—, X is —C(=O)—;

Y is a bond or —C(R$^{40}$)(R$^{45}$)—;

Q is selected from a bond, —C(R$^{26}$)(R$^{46}$)—, —C(=O)—, —CH$_2$—O—, —CH$_2$—O—CH$_2$—, —CH$_2$—CO$_2$—NR$^4$—, —CH$_2$—CO$_2$—, —C(=O)NR$^4$—, and —CH=C(R$^{26}$)—;

Z is selected from CO$_2$H, CO$_2$alkyl, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclyl and substituted heterocyclyl;

$R^4$ is selected from H, OH and C$_{1-4}$ alkyl;

$R^7$ selected from hydrogen, alkyl, substituted alkyl, alkenyl, alkynyl, C(=O)alkyl, C(=O)substituted alkyl, C(=O)cycloalkyl, C(=O)substituted cycloalkyl, C(=O)aryl, C(=O)substituted aryl, C(=O)heterocyclo, C(=O)substituted heterocyclo, C(=O)heteroaryl, C(=O)substituted heteroaryl, C(=O)O-alkyl, C(=O)O-substituted alkyl, —C(=O)—NR$^8$R$^9$, aryl, substituted aryl, cycloalkyl, substituted cycloalkyl, heterocyclo, substituted heterocyclo, heteroaryl, and substituted heteroaryl;

$R^8$ and $R^9$ are independently selected from hydrogen, hydroxy, O(alkyl), O(substituted alkyl), alkyl, substituted alkyl, C(=O)alkyl, C(=O)substituted alkyl, C(=O)cycloalkyl, $R^8$ and $R^9$ are independently selected from hydrogen, hydroxy, O(alkyl), O(substituted alkyl), alkyl, substituted alkyl, C(=O)alkyl, C(=O)substituted alkyl, C(=O)cycloalkyl, C(=O)substituted cycloalkyl, C(=O)aryl, C(=O)substituted aryl, C(=O)O-alkyl, C(=O)O-substituted alkyl, C(=O)heterocyclo, C(=O)heteroaryl, cycloalkyl, substituted cycloalkyl, aryl, substituted aryl, heterocyclo, substituted heterocyclo, heteroaryl and substituted heteroaryl, or $R^8$ and $R^9$ are taken together with the nitrogen atom to which they are attached to form a substituted or unsubstituted heterocyclo ring of 3 to 8 atoms or substituted or unsubstituted heteroaryl ring;

$R^{20}$ is selected from alkyl and substituted alkyl;

$R^{26}$ and $R^{46}$ are independently selected from hydrogen, C$_{1-4}$alkyl, hydroxy, halogen, hydroxyC$_{1-4}$alkyl, haloC$_{1-4}$alkyl, and heterocycloC$_{1-4}$alkyl, or taken together form a C$_{3-7}$cycloalkyl ring;

$R^{40}$ and $R^{45}$ are independently selected from hydrogen, cyano, alkyl, substituted alkyl, alkenyl, substituted alkenyl, alkynyl, substituted alkynyl, cycloalkyl, substituted cycloalkyl, aryl, substituted aryl, heterocyclo, substituted heterocyclo, heteroaryl and substituted heteroaryl, or $R^{40}$ and $R^{45}$ are taken together to form a substituted or unsubstituted cycloalkyl ring of 3 to 8 atoms or a substituted or unsubstituted heterocyclo ring of 3 to 8 atoms;

s is 0, 1, 2 or 3; and t is 0, 1, or 2;

excluding a compound of the following structure:

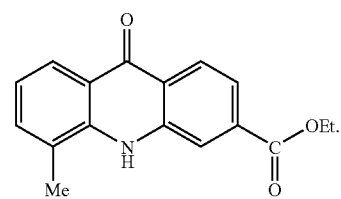

2. A compound according to claim 1, having the formula,

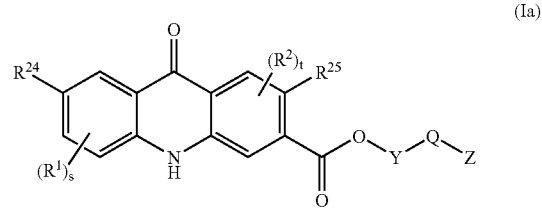

or an enantiomer, diastereomer, tautomer, or pharmaceutically-acceptable salt thereof, wherein Z is selected from cycloalkyl, substituted cycloalkyl, aryl, substituted aryl, heteroaryl, substituted heteroaryl, heterocyclyl and substituted heterocyclyl.

3. A compound according to claim 1, having the formula,

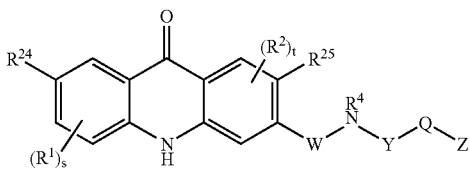

(Ib)

or an enantiomer, diastereomer, tautomer, or pharmaceutically-acceptable salt thereof, wherein W is —C(=O)—, —S(=O)—, or —S(O)$_2$—.

4. A compound according to claim 3, or an enantiomer, diastereomer, tautomer, or pharmaceutically-acceptable salt thereof, wherein W is —C(=O)—.

5. A compound according to claim 3, or an enantiomer, diastereomer, tautomer, or pharmaceutically-acceptable salt thereof, wherein:
$R^1$ and $R^2$ are the same or different and at each occurrence are independently selected from halogen, cyano, $C_{1-4}$alkyl, $C_{2-4}$alkenyl, hydroxy, —O—$C_{1-4}$alkyl, $CF_3$, —O—$CF_3$, C(=O)H, C(=O)$C_{1-4}$alkyl, —(C=O)—OH, —C(=O)O—$C_{1-4}$alkyl, —$NH_2$, —$NHC_{1-4}$alkyl, N($C_{1-4}$alkyl)$_2$, —SH, —S($C_{1-4}$alkyl), —S(=O)($C_{1-4}$alkyl), —$SO_2NH_2$, —$SO_2NHC_{1-4}$alkyl, —$SO_2N(C_{1-4}$alkyl)$_2$, and —$SO_2(C_{1-4}$alkyl);
$R^{24}$ is hydrogen, halogen, cyano, —$C_{1-4}$alkyl, —O—$C_{1-4}$alkyl, $CF_3$, —O—$CF_3$, $NHC_{1-4}$alkyl, N($C_{1-4}$alkyl)$_2$, —S($C_{1-4}$alkyl), —S(=O)($C_{1-4}$alkyl), and —$SO_2(C_{1-4}$alkyl);
$R^{25}$ is selected from hydrogen, halogen, cyano, $C_{1-4}$alkyl, $C_{2-4}$alkenyl, hydroxy, —O—$C_{1-4}$alkyl, $CF_3$, —O—$CF_3$, $NHC_{1-4}$alkyl, N($C_{1-4}$alkyl)$_2$, —S($C_{1-4}$alkyl), —S(=O)($C_{1-4}$alkyl), and —$SO_2(C_{1-4}$alkyl);
$R^4$ is H or $C_{1-4}$alkyl; and
s and t are independently 0 or 1.

6. A compound of formula (I),

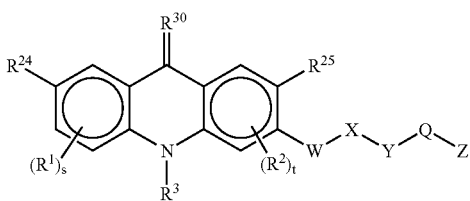

(I)

or an enantiomer, diastereomer, tautomer, or pharmaceutically-acceptable salt thereof, wherein:
$R^1$ and $R^2$ are independently selected from halogen, cyano, $C_{1-4}$alkyl, $C_{2-4}$alkenyl, hydroxy, —O—$C_{1-4}$alkyl, $CF_3$, —O—$CF_3$, C(=O)H, C(=O)$C_{1-4}$alkyl, —(C=O)—OH, —C(=O)O—$C_{1-4}$alkyl, —$NH_2$, —$NHC_{1-4}$alkyl, N($C_{1-4}$alkyl)$_2$, —SH, —S($C_{1-4}$alkyl), —S(=O)($C_{1-4}$alkyl), and —$SO_2CH_3$;
$R^{24}$ is hydrogen or halogen;
$R^{25}$ is selected from hydrogen, halogen, nitro, cyano, $C_{1-4}$alkyl, $C_{2-4}$alkenyl, hydroxy, —O—$C_{1-4}$alkyl, $CF_3$, —O—$CF_3$, C(=O)H, C(=O)$C_{1-4}$alkyl, —(C=O)—OH, —C(=O)O—$C_{1-4}$alkyl, —$NH_2$, —$NHC_{1-4}$alkyl, N($C_{1-4}$alkyl)$_2$, —SH, —S($C_{1-4}$alkyl), —S(=O)($C_{1-4}$alkyl), and —$SO_2CH_3$;
$R^3$ is H;

$R^{30}$ is =—;
W and X taken together are —C(=O)N($R^4$)—;
Y is a bond or —C($R^{40}$)($R^{45}$)—;
Q is selected from a bond, —C($R^{26}$)($R^{45}$)—, —C(=O)—, —$CH_2$—O—, —$CH_2$—O—$CH_2$—, —$CH_2$—$CO_2$—$NR^4$—, —$CH_2$—$CO_2$—, —C(=O)$NR^4$—, and —CH=C($R^{26}$)—;
Z is selected from $Z^1$ or $Z^2$, wherein when Y and Q are both a bond, Z is $Z^1$; and when Y is —C($R^{40}$)($R^{45}$) and Q is selected from a bond, —C($R^{26}$)($R^{46}$)—, —C(=O)—, —$CH_2$—O—, —$CH_2$—O—$CH_2$—, —$CH_2$—$CO_2$—$NR^4$—, —$CH_2$—$CO_2$—, —C(=O)$NR^4$—, and —CH=C($R^{26}$)—, Z is $Z^2$;
$Z^1$ is

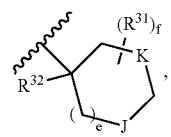

wherein J and K are each independently a bond, O, $NR^{31}$, or —$CHR^{31}$—;
$Z^2$ is selected from
a) $C_{1-6}$alkyl optionally substituted with one to two $R^{31}$;
b) piperidyl, piperazinyl, morpholinyl, or $C_{3-7}$cycloalkyl optionally substituted with one to three $R^{41}$; and
c) phenyl, napthyl, benzocyclopentyl, indolyl, tetrahydroquinolyl, oxazolyl, imidazolyl, thiazolyl, pyridyl, pyridinyl, pyrimidinyl, and pyrazinyl, optionally substituted with one to three $R^{42}$;
$R^4$ is selected from H and $C_{1-4}$alkyl;
$R^{26}$ and $R^{46}$ are independently selected from hydrogen, $C_{1-4}$alkyl, hydroxy, halogen, hydroxy$C_{1-4}$alkyl, halo$C_{1-4}$alkyl, and heterocyclo$C_{1-4}$alkyl, or taken together form a $C_{3-7}$cycloalkyl ring;
$R^{40}$ and $R^{45}$ are independently selected from hydrogen, cyano, $C_{1-6}$alkyl, and $C_{1-6}$alkyl substituted with hydroxy, or $R^{40}$ and $R^{45}$ are taken together to form a substituted or unsubstituted cycloalkyl ring of 3 to 7 atoms;
$R^{32}$ is selected from cyano, $OR^{34}$, alkyl, substituted alkyl, alkenyl, substituted alkenyl, alkynyl, and substituted alkynyl;
$R^{34}$ is selected from hydrogen, alkyl, and trifluoromethyl;
$R^{31}$ and $R^{41}$ are independently selected from =O, =$CH_2$, halogen, trifluoromethyl, $C_{2-4}$alkenyl, $C_{2-4}$alkynyl, $SR^{60}$, cyano, S(=O)alkyl, $SO_2$(alkyl), $CO_2$(alkyl), $SO_2NR^{50}R^{51}$, $NR^{50}R^{51}$, $OR^{60}$; or a group $R^{62}$; or a $C_{1-6}$alkyl optionally substituted with up to two groups selected from $R^{62}$, $NR^{50}R^{51}$, $OR^{60}$, and $SO_2$(alkyl);
$R^{42}$ is at each occurrence independently selected from halogen, trifluoromethyl, $C_{2-4}$alkenyl, $C_{2-4}$alkynyl, S(alkyl), cyano, S(=O)alkyl, $SO_2$(alkyl), $CO_2$(alkyl), $SO_2NR^{50}R^{51}$, $NR^{50}R^{51}$, $OR^{60}$; or a group $R^{62}$; or a $C_{1-6}$alkyl optionally substituted with up to two groups selected from $R^{62}$, $NH_2$, $NH(C_{1-4}$alkyl), $N(C_{1-4}$alkyl)$_2$, $OR^{60}$, and $SO_2$(alkyl);
$R^{50}$ and $R^{51}$ are independently selected from hydrogen, hydroxy, alkyl, —($CH_2$)$_d$-cycloalkyl, —($CH_2$)d-heterocyclo, O(alkyl), O(Si)($C_{1-4}$alkyl)$_3$, or $C_{1-6}$alkyl substituted with O(alkyl), $NH_2$, $NH(C_{1-4}$alkyl), or $N(C_{1-4}$alkyl)$_2$, or $R^{50}$ and $R^{51}$ together form a four to six membered heterocyclo ring, wherein when $R^{50}$ or $R^{51}$ is a heterocyclo, said heterocyclo in turn is optionally substituted with up to two groups selected from lower alkyl, $NH_2$, $NH(C_{1-4}alkyl)$, and/or $N(C_{1-4}alkyl)_2$;

$R_{60}$ is selected from hydrogen, alkyl, pyridyl, pyrimidinyl, and $C_{1-6}alkyl$ substituted with O(alkyl), $NH_2$, $NH(C_{1-4}alkyl)$, $N(C_{1-4}alkyl)_2$, or five or six membered heterocyclo, wherein each $R^{60}$ in turn is optionally substituted with up to two groups selected from $C_{1-4}alkyl$, S(alkyl), $NH_2$, $NH(C_{1-4}alkyl)$, and/or $N(C_{1-4}alkyl)_2$;

$R^{62}$ is selected from phenyl, five to seven membered heterocyclo, or five to six membered heteroaryl, wherein each $R^{62}$ in turn is optionally substituted with one to two groups selected from OH, $SO_2(alkyl)$, $CH_2$—OH, $CH_2$—$OCH_3$, $NHC(=O)CH_3$, $NH_2$, $NH(C_{1-4}alkyl)$, and/or $N(C_{1-4}alkyl)_2$;

d is 0, 1, 2, 3 or 4;
e is 1, 2, or 3;
f is 0, 1, 2, or 3;
s is 0, 1, or 2; and
t is 0 or 1.

7. A compound according to claim 1, having the formula,

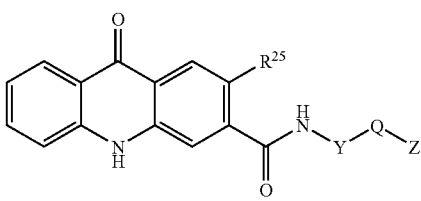

or an enantiomer, diastereomer, tautomer, or pharmaceutically-acceptable salt thereof.

8. A compound according to claim 7, or an enantiomer, diastereomer, tautomer, or pharmaceutically-acceptable salt thereof, wherein:
$R^{25}$ is selected from hydrogen, cyano, —$CH_3$, —$CH_2CH_3$, —$OCH_3$, —$SCH_3$, —S(—O)$CH_3$, —S(O)$_2CH_3$, and halogen.

9. A compound according to claim 7, or an enantiomer, diastereomer, tautomer, or pharmaceutically-acceptable salt thereof, wherein:
Y is —C($R^{40}$)($R^{45}$), wherein $R^{40}$ and $R^{45}$ are both methyl, or one of $R^{40}$ and $R^{45}$ is methyl and the other of $R^{40}$ and $R^{45}$ is cyano, or $R^{40}$ and $R^{45}$ together form cyclopropyl, cyclobutyl, or cyclopentyl.

10. A compound having the formula

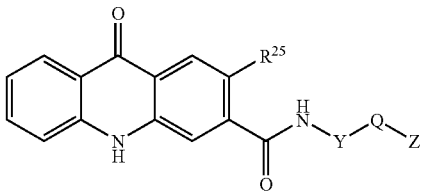

or an enantiomer, diastereomer, tautomer, or pharmaceutically-acceptable salt thereof, wherein:
$R^{25}$ is selected from hydrogen, halogen, nitro, cyano, alkyl, substituted alkyl, alkenyl, substituted alkenyl, alkynyl, substituted alkynyl, —O—$R^7$, —(C=O)$R^7$, —(C=O)—O—$R^7$, —$NH_2$, —$NHC_{1-4}alkyl$, —$N(C_{1-4}alkyl)_2$, —(C=O)$NR^8R^9$, —$SR^{20}$, —S(=O) $R^{20}$, —$SO_2R^{20}$, —$SO_3H$, —$SO_3R^{20}$, —$SO_2NR^8R^9$, and —C≡C—Si($C_{1-4}alkyl$)$_3$;

Y is a bond or C($R^{40}$)($R^{45}$)—;

Q is selected from a bond, —C($R^{26}$)($R^{46}$)—, —C(=O)—, —$CH_2$—O—, —$CH_2$—O—$CH_2$—, —$CH_2$—$CO_2$—$NR^4$—, —$CH_2$—$CO_2$—, —C(=O)$NR^4$—, and —CH=C($R^{26}$)—;

Z is pyridyl optionally substituted with up to two groups selected from alkyl, substituted alkyl, haloalkyl, halogen, $OR^{27}$, $NR^{28}R^{29}$, and four to nine membered monocyclic or bicyclic heterocyclo or substituted heterocyclo, wherein $R^{27}R^{28}$, and $R^{29}$ are each independently selected from hydrogen, alkyl, and substituted alkyl;

$R^4$ is selected from H, OH and $C_{1-4}alkyl$;

$R^7$ selected from hydrogen, alkyl, substituted alkyl, alkenyl, alkynyl, C(=O)alkyl, C(=O)substituted alkyl, C(=O)cycloalkyl, C(=O)substituted cycloalkyl, C(=O)aryl, C(=O)substituted aryl, C(=O)heterocyclo, C(=O)substituted heterocyclo, C(=O)heteroaryl, C(=O)substituted heteroaryl, C(=O)O-alkyl, C(=O)O-substituted alkyl, —C(=O)—$NR^8R^9$, aryl, substituted aryl, cycloalkyl, substituted cycloalkyl, heterocyclo, substituted heterocyclo, heteroaryl, and substituted heteroaryl;

$R^8$ and $R^9$ are independently selected from hydrogen, hydroxy, O(alkyl), O(substituted alkyl), alkyl, substituted alkyl, C(=O)alkyl, C(=O)substituted alkyl, C(=O)cycloalkyl, C(=O)substituted cycloalkyl, C(=O)aryl, C(=O)substituted aryl, C(=O)O-alkyl, C(=O)O-substituted alkyl, C(=O)heterocyclo, C(=O)heteroaryl, cycloalkyl, substituted cycloalkyl, aryl, substituted aryl, heterocyclo, substituted heterocyclo, heteroaryl and substituted heteroaryl, or $R^8$ and $R^9$ are taken together with the nitrogen atom to which they are attached to form a substituted or unsubstituted heterocyclo ring of 3 to 8 atoms or substituted or unsubstituted heteroaryl ring;

$R^{20}$ is selected from alkyl and substituted alkyl;

$R^{26}$ and $R^{46}$ are independently selected from hydrogen, $C_{1-4}alkyl$, hydroxy, halogen, hydroxy$C_{1-4}alkyl$, halo$C_{1-4}alkyl$, and heterocyclo$C_{1-4}alkyl$, or taken together form a $C_{3-7}cycloalkyl$ ring; and $R^{40}$ and $R^{45}$ are independently selected from hydrogen, cyano, alkyl, substituted alkyl, alkenyl, substituted alkenyl, alkynyl, substituted alkynyl, cycloalkyl, substituted cycloalkyl, aryl, substituted aryl, heterocyclo, substituted heterocyclo, heteroaryl and substituted heteroaryl, or $R^{40}$ and $R^{45}$ are taken together to form a substituted or unsubstituted cycloalkyl ring of 3 to 8 atoms or a substituted or unsubstituted heterocyclo ring of 3 to 8 atoms.

11. A compound having the formula

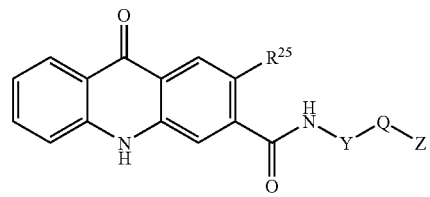

or an enantiomer, diastereomer, tautomer, or pharmaceutically-acceptable salt thereof, wherein:

R²⁵ is selected from hydrogen, halogen, nitro, cyano, alkyl, substituted alkyl, alkenyl, substituted alkenyl, alkynyl, substituted alkynyl, —O—R⁷, —(C=O)R⁷, —(C=O)—O—R⁷, —NH₂, —NHC₁₋₄alkyl, —N(C₁₋₄alkyl)₂, —(C=O)NR⁸R⁹, —SR²⁰, —S(=O)R²⁰, —SO₂R²⁰, —SO₃H, —SO₃R²⁰, —SO₂NR⁸R⁹, and —C≡C—Si(C₁₋₄alkyl)₃;

Y is a bond or —C(R⁴⁰)(R⁴⁵)—;

R⁷ selected from hydrogen, alkyl, substituted alkyl, alkenyl, alkynyl, C(=O)alkyl, C(=O)substituted alkyl, C(=O)cycloalkyl, C(=O)substituted cycloalkyl, C(=O)aryl, C(=O)substituted aryl, C(=O)heterocyclo, C(=O)substituted heterocyclo, C(=O)heteroaryl, C(=O)substituted heteroaryl, C(=O)O-alkyl, C(=O) O-substituted alkyl, —C(=O)—NR⁸R⁹, aryl, substituted aryl, cycloalkyl, substituted cycloalkyl, heterocyclo, substituted heterocyclo, heteroaryl, and substituted heteroaryl;

R⁸ and R⁹ are independently selected from hydrogen, hydroxy, O(alkyl), O(substituted alkyl), alkyl, substituted alkyl, C(=O)alkyl, C(=O)substituted alkyl, C(=O)cycloalkyl, C(=O)substituted cycloalkyl, C(=O)aryl, C(=O)substituted aryl, C(=O)O-alkyl, C(=O)O-substituted alkyl, C(=O)heterocyclo, C(=O)heteroaryl, cycloalkyl, substituted cycloalkyl, aryl, substituted aryl, heterocyclo, substituted heterocyclo, heteroaryl and substituted heteroaryl, or R⁸ and R⁹ are taken together with the nitrogen atom to which they are attached to form a substituted or unsubstituted heterocyclo ring of 3 to 8 atoms or substituted or unsubstituted heteroaryl ring;

R²⁰ is selected from alkyl and substituted alkyl;

R²⁰ and R⁴⁵ are independently selected from hydrogen, cyano, alkyl, substituted alkyl, alkenyl, substituted alkenyl, alkynyl, substituted alkynyl, cycloalkyl, substituted cycloalkyl, aryl, substituted aryl, heterocyclo, substituted heterocyclo, heteroaryl and substituted heteroaryl, or R40 and R⁴⁵ are taken together to form a substituted or unsubstituted cycloalkyl ring of 3 to 8 atoms or a substituted or unsubstituted heterocyclo ring of 3 to 8 atoms;

Q-Z taken together comprise a group selected from:

C₁₋₄alkyl optionally substituted with up to two R³¹;

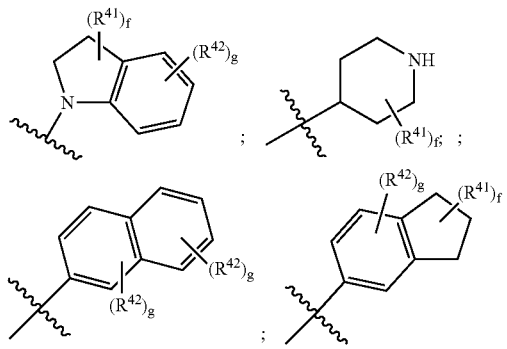

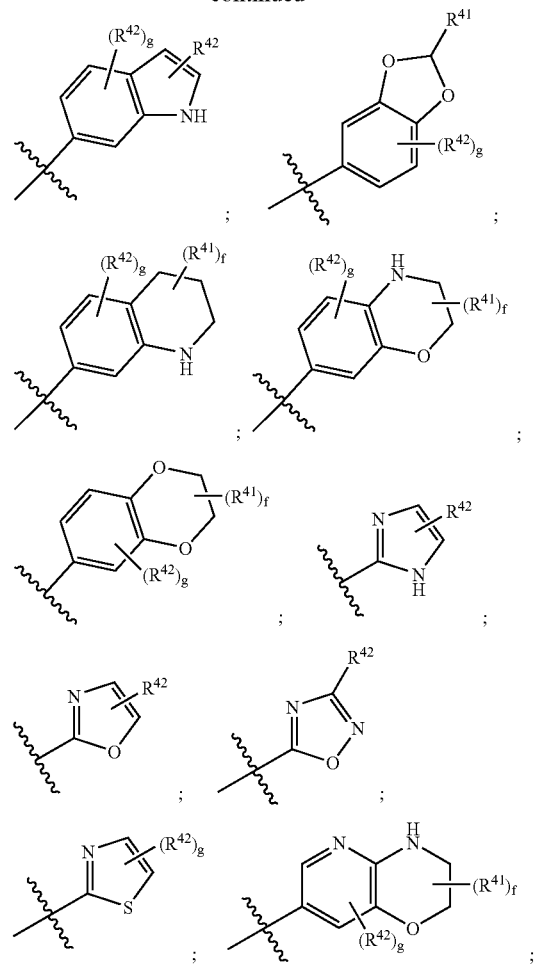

or, Q is selected from a bond, —CH(R²⁶)—, —CH₂—O—, —CH₂—O—CH₂—, and —CH₂—CO₂—NH—, and Z is selected from

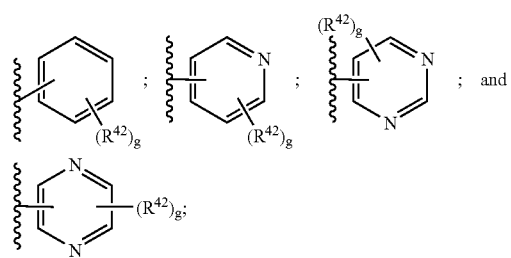

R²⁶ is selected from hydrogen, hydroxy, halogen, hydroxyC₁₋₄alkyl, and haloC₁₋₄alkyl;

R³¹ and R⁴¹ are at each occurrence independently selected from =O, =CH₂, halogen, trifluoromethyl, C₂₋₄alkenyl, C₂₋₄alkynyl, S(alkyl), cyano, S(=O)alkyl, SO₂(alkyl), CO₂(alkyl), SO₂NR⁵⁰R⁵¹, NR⁵⁰R⁵¹, OR⁵¹; or a group R⁶²; or a C₁₋₆alkyl optionally substituted with up to two groups selected from R⁶², NH₂, NH(C₁₋₄alkyl), N(C₁₋₄alkyl)₂, OR⁶⁰, and SO₂(alkyl);

R⁴² is at each occurrence independently selected from halogen, trifluoromethyl, C₂₋₄alkenyl, C₂₋₄alkynyl, S(alkyl), cyano, S(=O)alkyl, SO₂(alkyl), CO₂(alkyl), SO₂NR⁵⁰R⁵¹, NR⁵⁰R⁵¹, OR⁶⁰ or a group R⁶²; or a $C_{1-6}$alkyl optionally substituted with up to two groups selected from R⁶², NH₂, NH($C_{1-4}$alkyl), N($C_{1-4}$alkyl)₂, OR⁶⁰, and SO₂(alkyl);

R⁵⁰ and R⁵¹ are independently selected from hydrogen, hydroxy, alkyl, —(CH₂)d-cycloalkyl, —(CH₂)d-heterocyclo, O(alkyl), O(Si)($C_{1-4}$alkyl)₃, or $C_{1-6}$alkyl substituted with O(alkyl), NH₂, NH($C_{1-4}$alkyl), or N($C_{1-4}$alkyl)₂, or R⁵⁰ and R⁵¹ together form a four to six membered heterocyclo ring, wherein when R⁵⁰ or R⁵¹ is a heterocyclo, said heterocyclo in turn is optionally substituted with lower alkyl, NH₂, NH($C_{1-4}$alkyl), or N($C_{1-4}$alkyl)₂;

R⁶⁰ is hydrogen, alkyl, pyridyl or pyrimidinyl in turn optionally substituted with $C_{1-4}$alkyl, S(alkyl), NH₂, NH($C_{1-4}$alkyl), N($C_{1-4}$alkyl)₂, or $C_{1-6}$alkyl substituted with O(alkyl), NH₂, NH($C_{1-4}$alkyl), N($C_{1-4}$alkyl)₂, or five or six membered heterocyclo;

R⁶² is selected from phenyl, tetrahydrofuryl, azetidinyl, morpholinyl, thiamorpholinyl, piperazinyl, pyrrolidinyl, diazapinyl, seven membered bicyclic heterocyclo having at least one nitrogen atom and zero or one oxygen atom, wherein each R⁶² in turn is optionally substituted with one to two of OH, SO₂(alkyl), CH₂—OH, CH₂—OCH₃, NHC(=O)CH₃, NH₂, NH($C_{1-4}$alkyl), and/or N($C_{1-4}$alkyl)₂;

d is 0, 1, or 2;

f is 0, 1, 2 or 3; and g is 0, 1 or 2.

12. A compound of formula (I),

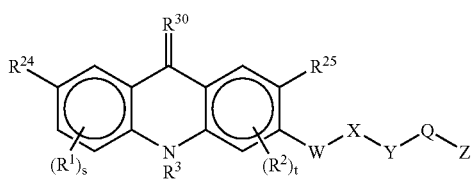

(I)

or an enantiomer, diastereomer, tautomer, or pharmaceutically-acceptable salt thereof, wherein:

R¹ and R² are the same or different and at each occurrence are independently selected from halogen, cyano, alkyl, substituted alkyl, alkenyl, substituted alkenyl, alkynyl, substituted alkynyl, —O—R⁷, —(C=O)R⁷, —(C=O)—O—R⁷, —NR⁸R⁹, —(C=O)NR⁸R⁹, —SR²⁰, —S(=O)R²⁰, —SO₂R²⁰ and R²⁴ is selected from hydrogen, halogen, nitro, cyano, alkyl, substituted alkyl, alkenyl, substituted alkenyl, alkynyl, substituted alkynyl, —O—R⁷, —(C=O)R⁷, —NR⁸R⁹, —(C=O)NR⁸R⁹, —SR²⁰, —S(=O)R²⁰, —SO₂R²⁰, —SO₃H, —SO₃R²⁰, —SO₂NR⁸R⁹, and —C≡C—Si($C_{1-4}$alkyl)₃;

R²⁵ is selected from hydrogen, halogen, nitro, cyano, alkyl, substituted alkyl, alkenyl, substituted alkenyl, alkynyl, substituted alkynyl, —O—R⁷, —(C=O)R⁷, —(C=O)—O—R⁷, —NH₂, —NHC_{1-4}alkyl, —N($C_{1-4}$alkyl)₂, —(C=O)NR⁸R⁹, —SR²⁰, —S(=O)R²⁰, —SO₂R²⁰, —SO₃H, —SO₃R²⁰, —SO₂NR⁸R⁹, and —C≡C—Si($C_{1-4}$alkyl)₃;

R³ selected from H, OH and NH₂;

R³⁰ selected from =O and =S;

W is selected from —CH₂—, —C(=O)—, —S(=O)—, or —S(O)₂—;

X is selected from —CH₂—, —N(R⁴)—, and —O—, except that when W is —CH₂—, X is —C(=O)—;

Y is a bond or —C(R⁴⁰)(R⁴⁵)—;

Q is selected from a bond, —C(R²⁶)(R⁴⁶)—, —C(=O)—, —CH₂—O—, —CH₂—O—CH₂—, —CH₂—CO₂—NR⁴—, —CH₂—CO₂—, —C(=O)NR⁴—, and —CH=C(R²⁶)—;

R⁴ is selected from H, OH and $C_{1-4}$alkyl;

R⁷ selected from hydrogen, alkyl, substituted alkyl, alkenyl, alkynyl, C(=O)alkyl, C(=O)substituted alkyl, C(=O)cycloalkyl, C(=O)substituted cycloalkyl, C(=O)aryl, C(=O)substituted aryl, C(=O)heterocyclo, C(=O)substituted heterocyclo, C(=O)heteroaryl, C(=O)substituted heteroaryl, C(=O)O-alkyl, C(=O)O-substituted alkyl, —C(=O)—NR⁸R⁹, aryl, substituted aryl, cycloalkyl, substituted cycloalkyl, heterocyclo, substituted heterocyclo, heteroaryl, and substituted heteroaryl;

R⁸ and R⁹ are independently selected from hydrogen, hydroxy, O(alkyl), O(substituted alkyl), alkyl, substituted alkyl, C(=O)alkyl, C(=O)substituted alkyl, C(=O)cycloalkyl, C(=O)substituted cycloalkyl, C(=O)aryl, C(=O)substituted aryl, C(=O)O-alkyl, C(=O)O-substituted alkyl, C(=O)heterocyclo, C(=O)heteroaryl, cycloalkyl, substituted cycloalkyl, aryl, substituted aryl, heterocyclo, substituted heterocyclo, heteroaryl and substituted heteroaryl, or R⁸ and R² are taken together with the nitrogen atom to which they are attached to form a substituted or unsubstituted heterocyclo ring of 3 to 8 atoms or substituted or unsubstituted heteroaryl ring;

R²⁰ is selected from alkyl and substituted alkyl;

R²⁶ and R⁴⁶ are independently selected from hydrogen, $C_{1-4}$alkyl, hydroxy, halogen, hydroxy$C_{1-4}$alkyl, halo$C_{1-4}$alkyl, and heterocyclo$C_{1-4}$alkyl, or taken together form a $C_{3-7}$cycloalkyl ring;

R⁴⁰ and R⁴⁵ are independently selected from hydrogen, cyano, alkyl, substituted alkyl, alkenyl, substituted alkenyl, alkynyl, substituted alkynyl, cycloalkyl, substituted cycloalkyl, aryl, substituted aryl, heterocyclo, substituted heterocyclo, heteroaryl and substituted heteroaryl, or R⁴⁰ and R⁴⁵ are taken together to form a substituted or unsubstituted cycloalkyl ring of 3 to 8 atoms or a substituted or unsubstituted heterocyclo ring of 3 to 8 atoms;

s is 0, 1, 2 or 3;

t is 0, 1, or 2; and

Z is selected from:

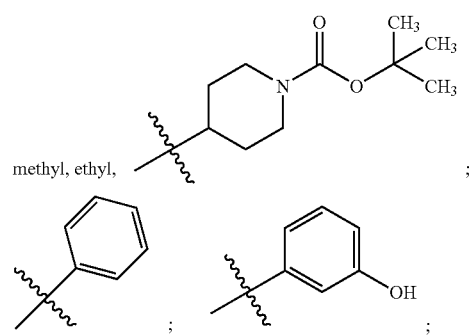

methyl, ethyl,

-continued
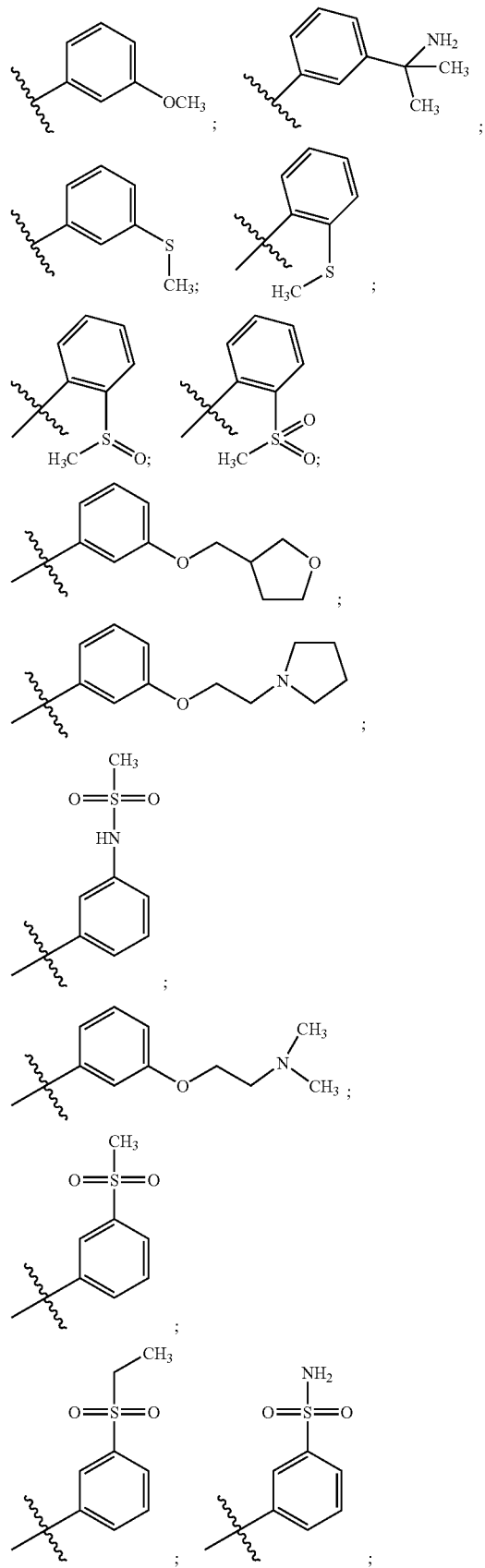
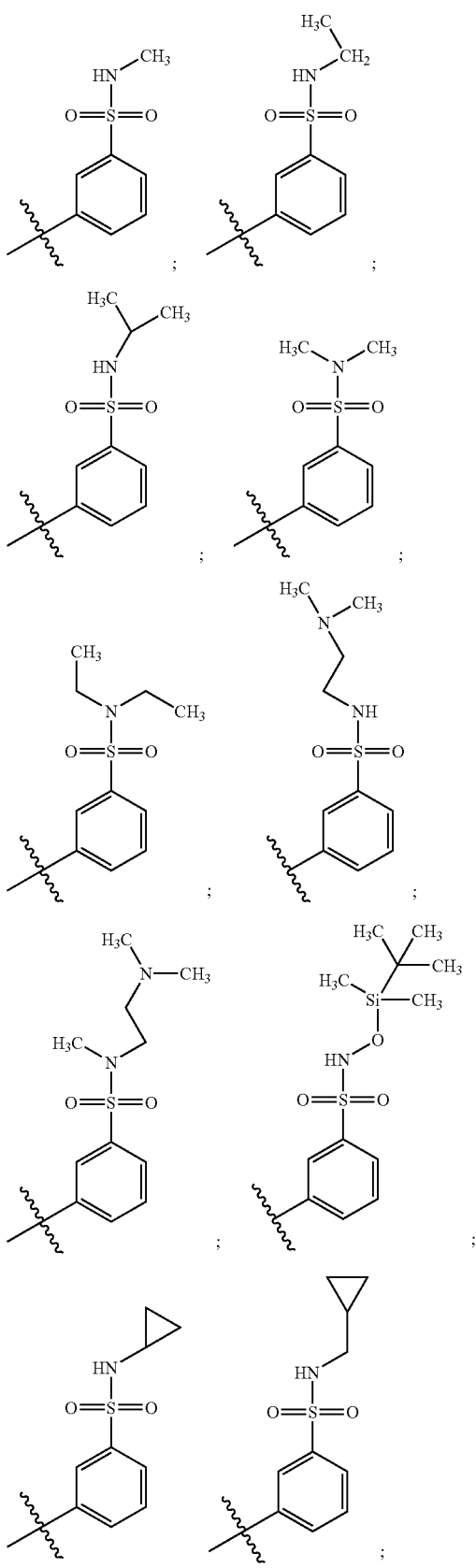

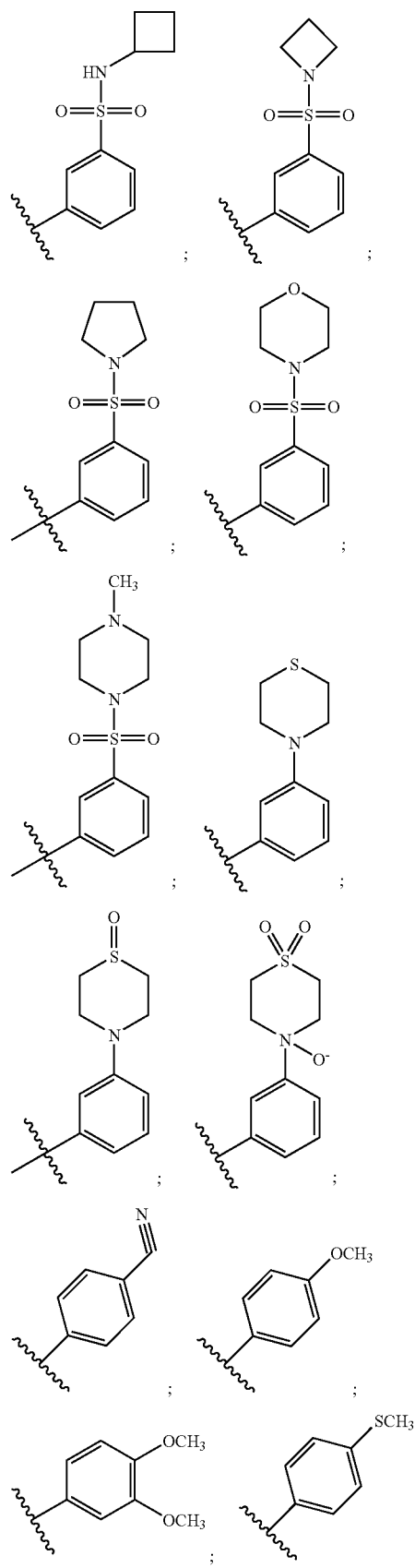
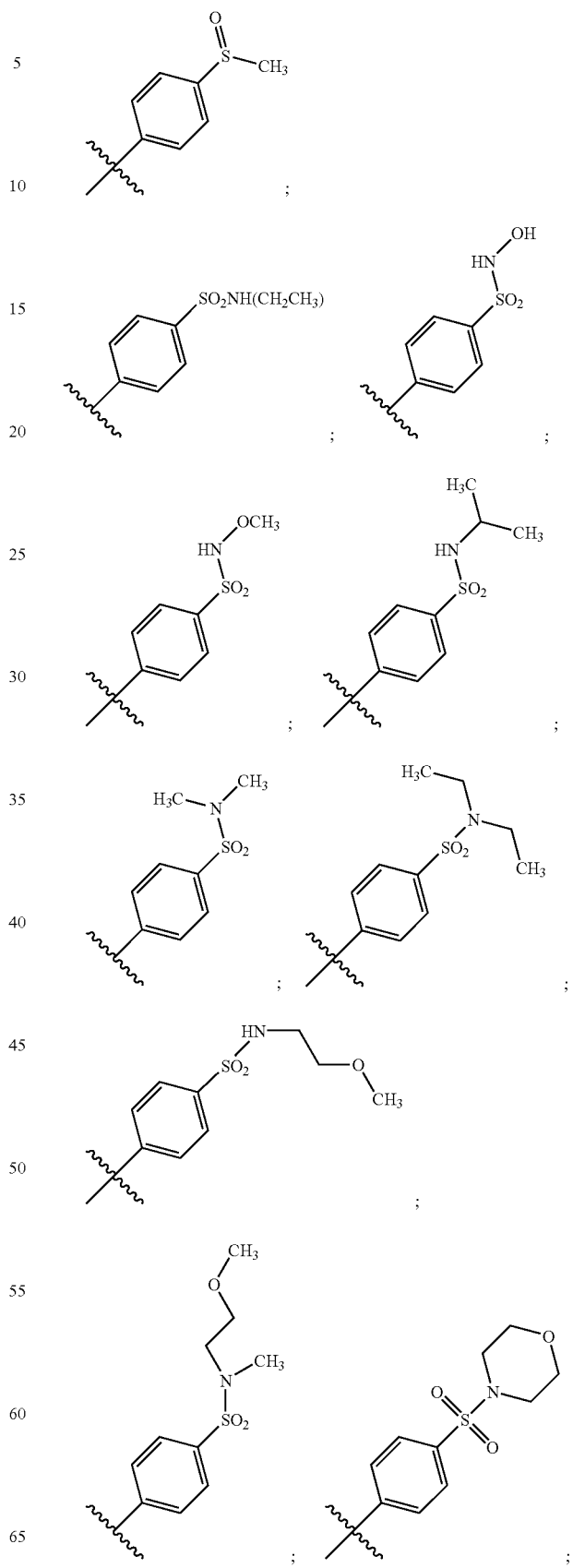

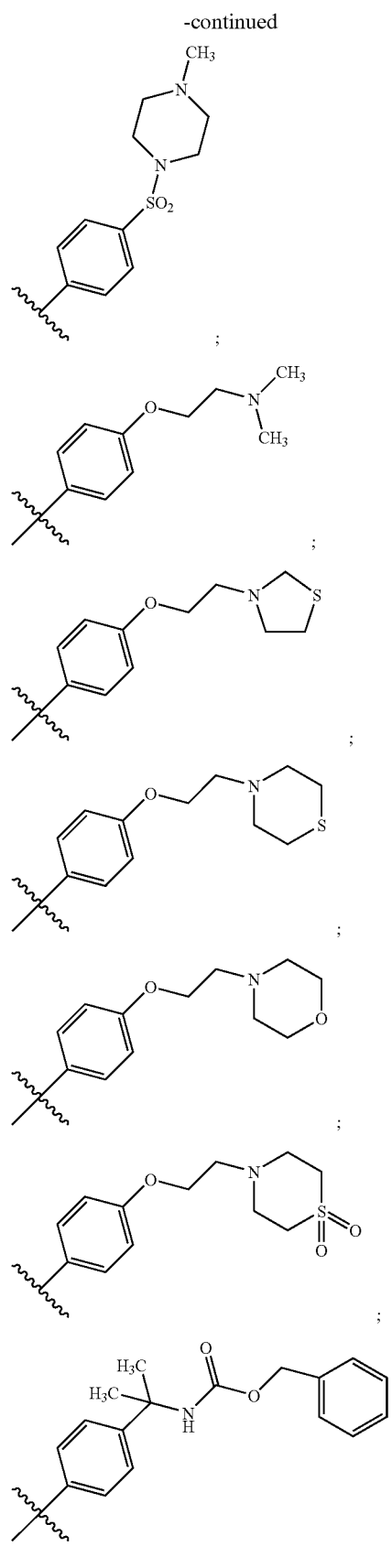
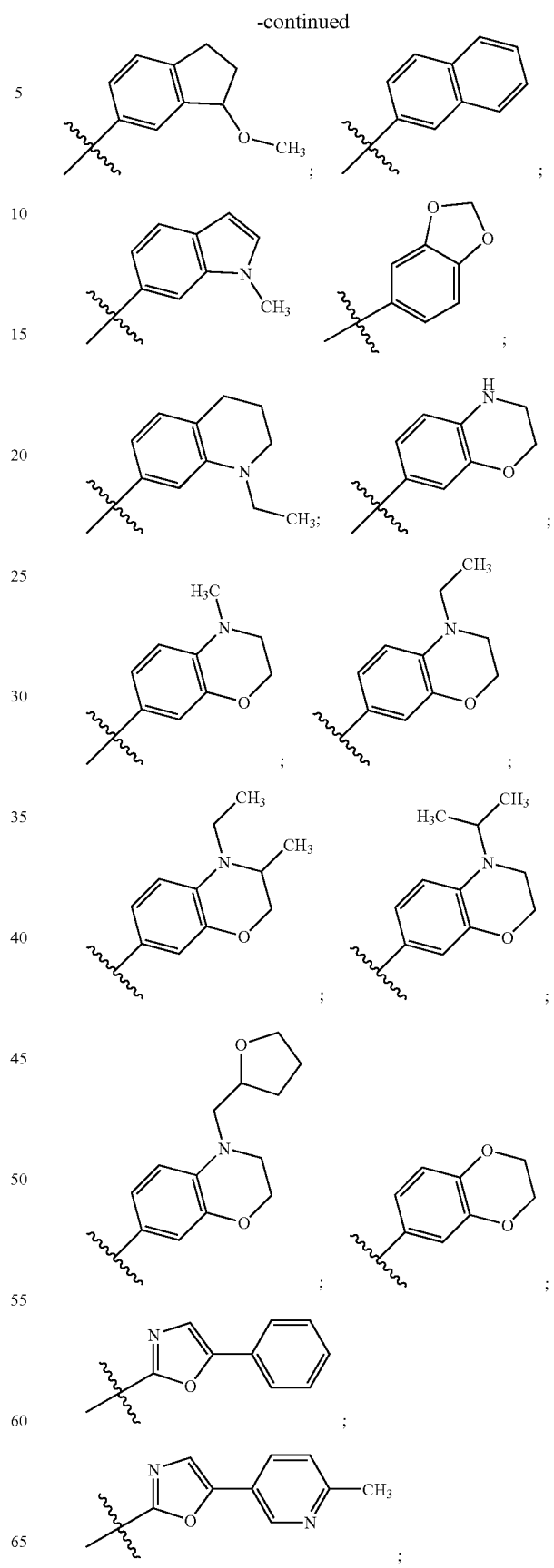

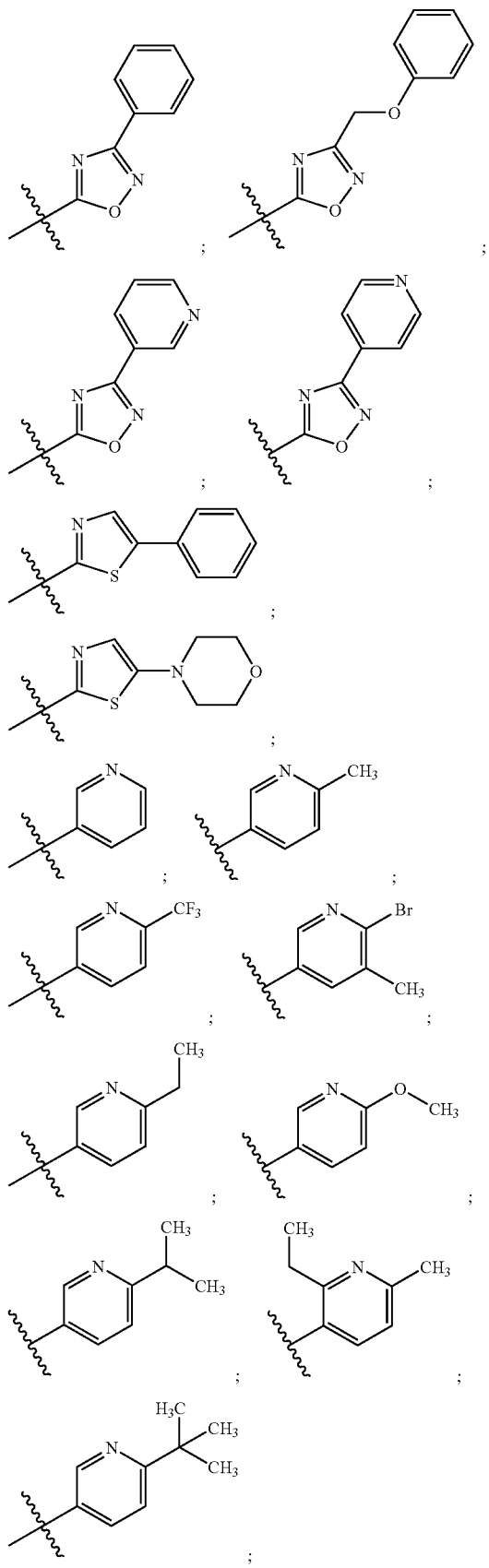
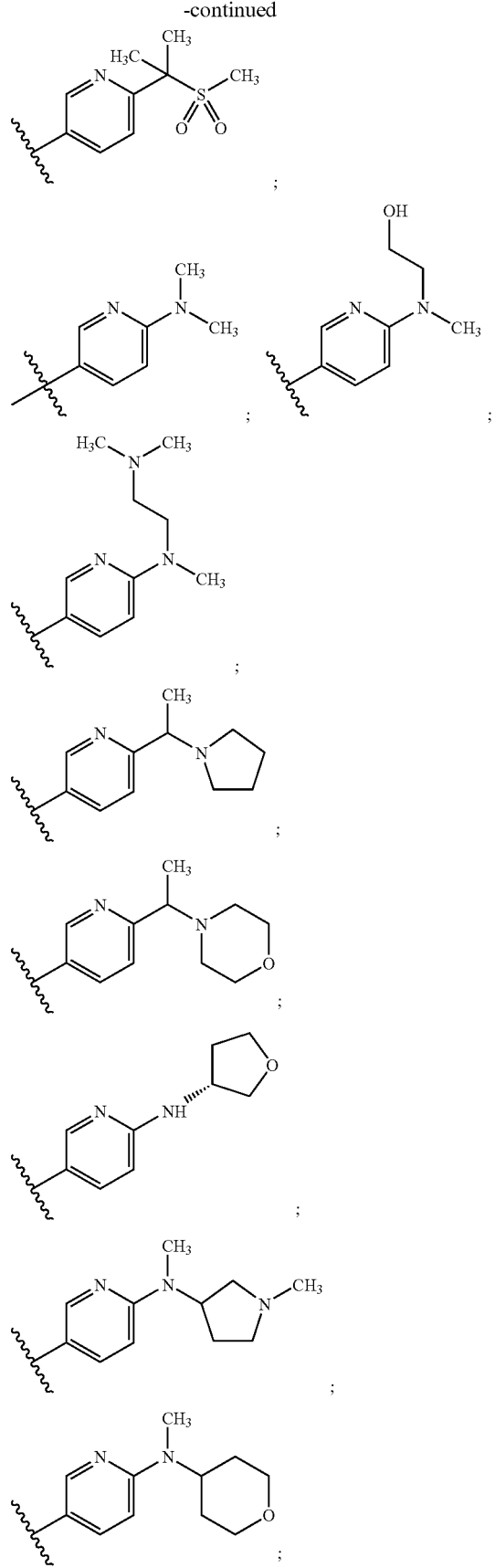

-continued
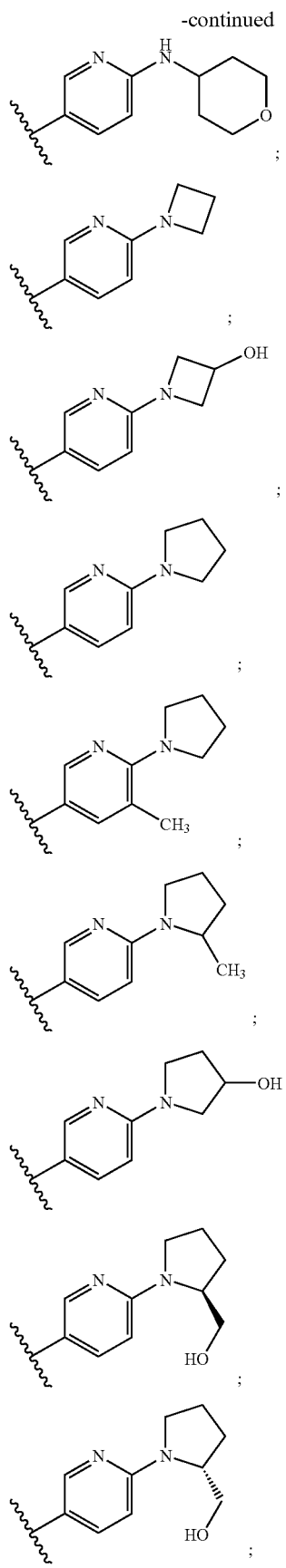
-continued
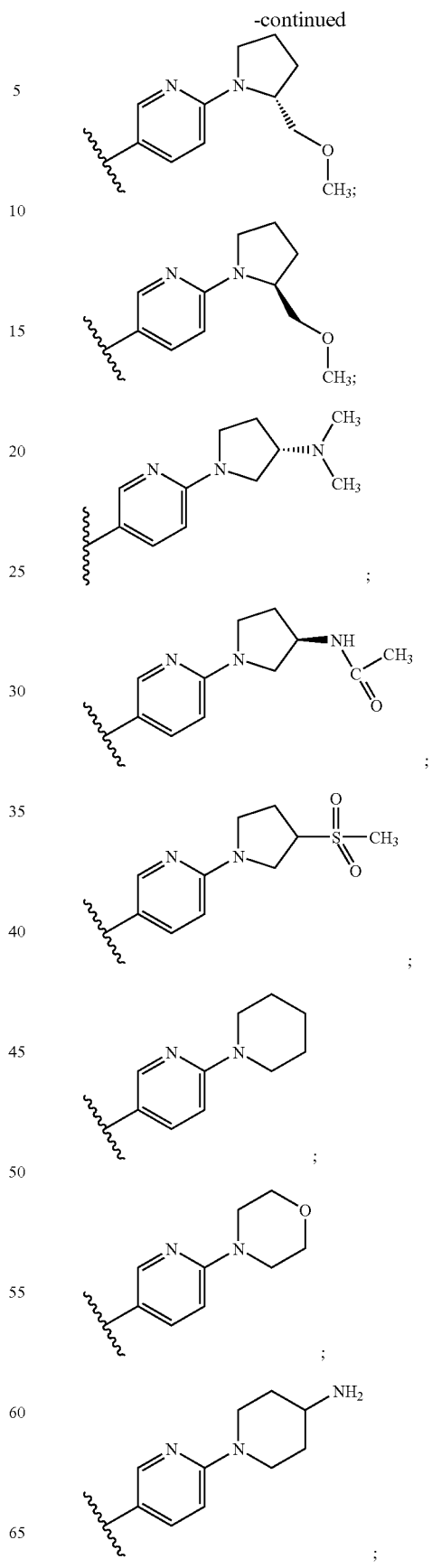

-continued
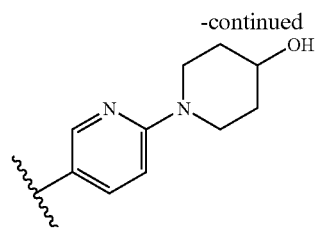
;
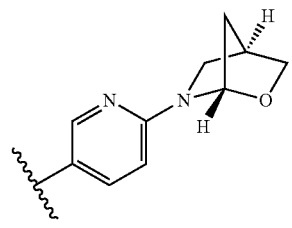
;
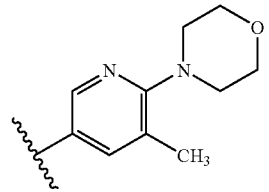
;
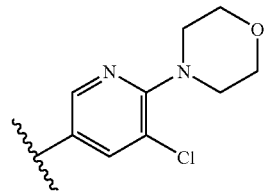
;
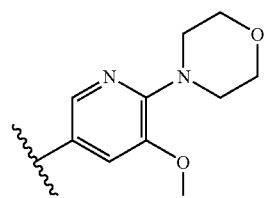
;
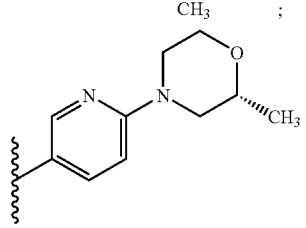
;
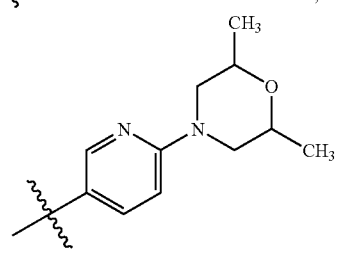
;
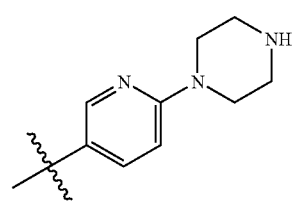
;
-continued
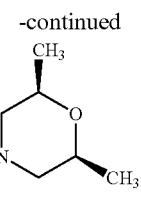
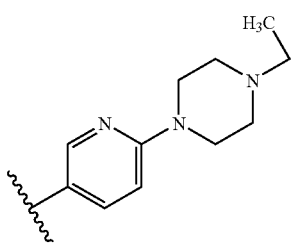
;
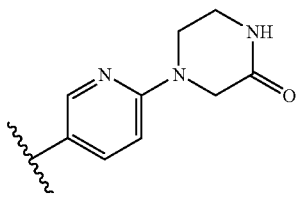
;
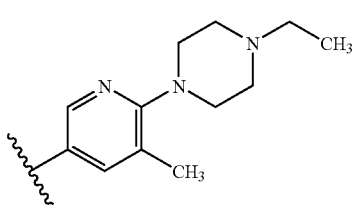
;
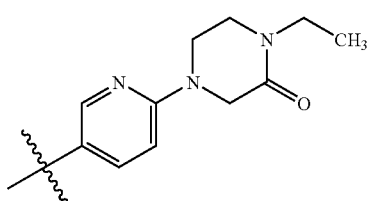
;
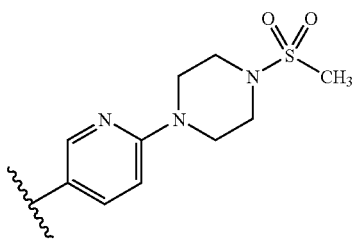
;
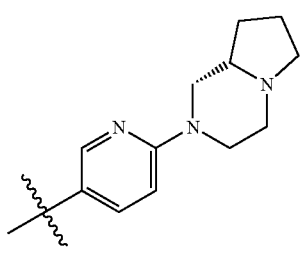
;

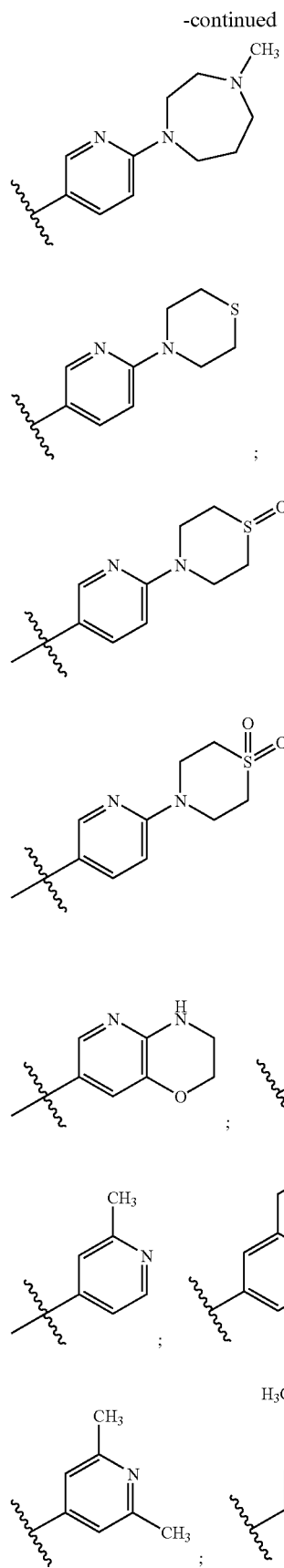
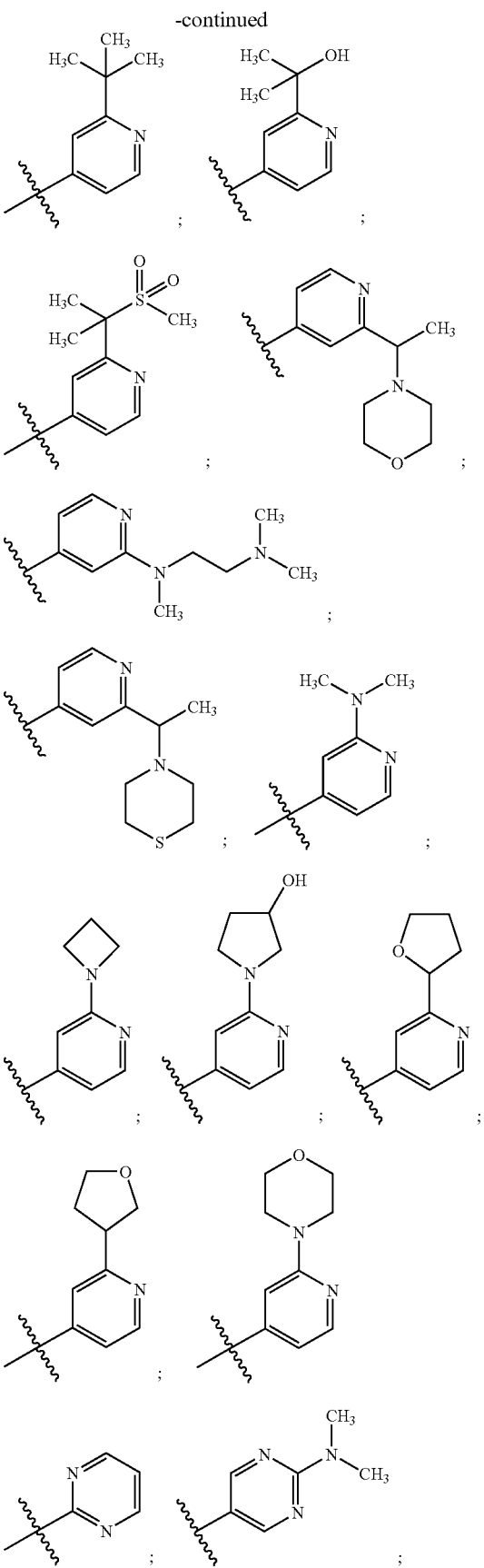

-continued

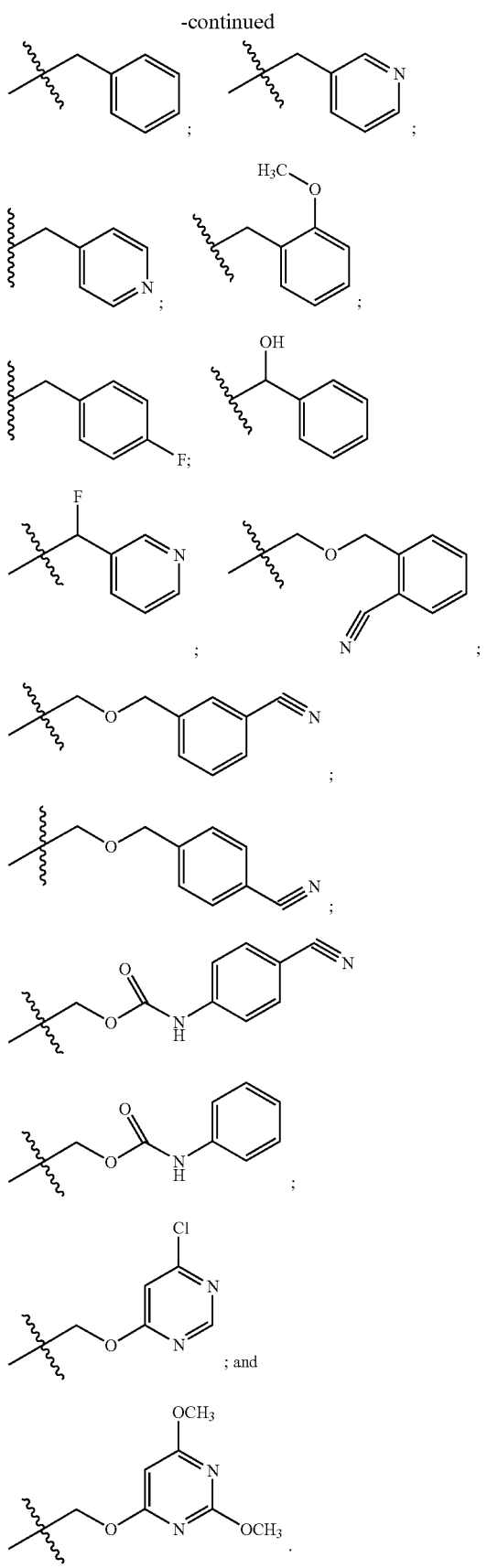

13. A compound of formula (I),

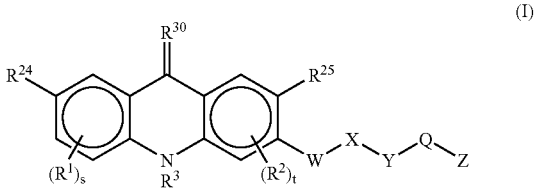

or an enantiomer, diastereomer, tautomer, or pharmaceutically-acceptable salt thereof, wherein:

$R^1$ and $R^2$ are the same or different and at each occurrence are independently selected from halogen, cyano, alkyl, substituted alkyl, alkenyl, substituted alkenyl, alkynyl, substituted alkynyl, —O—$R^7$, —(C=O)$R^7$, —(C=O)—O—$R^7$, —$NR^8R^9$, —(C=O)$NR^8R^9$, —$SR^{20}$, —S(=O)$R^{20}$, —$SO_2R^{20}$ and —C≡C—Si($C_{1-4}$alkyl)$_3$;

$R^{24}$ is selected from hydrogen, halogen, nitro, cyano, alkyl, substituted alkyl, alkenyl, substituted alkenyl, alkynyl, substituted alkynyl, —O—$R^7$, —(C=O)$R^7$, —$NR^8R^9$, —(C=O)$NR^8R^9$, —$SR^{20}$, —S(=O)$R^{20}$, —$SO_2R^{20}$, —$SO_3H$, —$SO_3R^{20}$, —$SO_2NR^8R^9$, and —C≡C—Si($C_{1-4}$alkyl)$_3$;

$R^{25}$ is selected from hydrogen, halogen, nitro, cyano, alkyl, substituted alkyl, alkenyl, substituted alkenyl, alkynyl, substituted alkynyl, —O—$R^7$, —(C=O)$R^7$, —(C=O)—O—$R^7$, —$NH_2$, —$NHC_{1-4}$alkyl, —N($C_{1-4}$alkyl)$_2$, —(C=O)$NR^8R^9$, —$SR^{20}$, —S(=O)$R^{20}$, —$SO_2R^{20}$, —$SO_3H$, —$SO_3R^{20}$, —$SO_2NR^8R^9$, and —C≡C—Si($C_{1-4}$alkyl)$_3$;

$R^3$ selected from H, OH and $NH_2$;

$R^{30}$ is selected from =O and =S;

W is selected from —$CH_2$—, —C(=O)—, —S(=O)—, or —S(O)$_2$—;

X is selected from —$CH_2$—, N($R^4$)—, and —O—, except that when W is —$CH_2$—, X is C(=O)—;

Q is selected from a bond, —C($R^{26}$)($R^{46}$)—, —C(=O)—, —$CH_2$—O—, —$CH_2$—O—$CH_2$—, —$CH_2$—$CO_2$—$NR^4$—, —$CH_2$—$CO_2$—, —C(=O)$NR^4$—, and —CH=C($R^{26}$)—;

$R^4$ is selected from H, OH and $C_{1-4}$alkyl;

$R^7$ selected from hydrogen, alkyl, substituted alkyl, alkenyl, alkynyl, C(=O)alkyl, C(=O)substituted alkyl, C(=O)cycloalkyl, C(=O)substituted cycloalkyl, C(=O)aryl, C(=O)substituted aryl, C(=O)heterocyclo, C(=O)substituted heterocyclo, C(=O)heteroaryl, C(=O)substituted heteroaryl, C(=O)O-alkyl, C(=O)O-substituted alkyl, —C(=O)—$NR^8R^9$, aryl, substituted aryl, cycloalkyl, substituted cycloalkyl, heterocyclo, substituted heterocyclo, heteroaryl, and substituted heteroaryl;

$R^8$ and $R^9$ are independently selected from hydrogen, hydroxy, O(alkyl), O(substituted alkyl), alkyl, substituted alkyl, C(=O)alkyl, C(=O)substituted alkyl, C(=O)cycloalkyl, C(=O)substituted cycloalkyl, C(=O)aryl, C(=O)substituted aryl, C(=O)O-alkyl, C(=O)O-substituted alkyl, C(=O)heterocyclo, C(=O)heteroaryl, cycloalkyl, substituted cycloalkyl, aryl, substituted aryl, heterocyclo, substituted heterocyclo, heteroaryl and substituted heteroaryl, or $R^8$ and $R^9$ are taken together with the nitrogen atom to which they are attached to form a substituted or unsubstituted heterocyclo ring of 3 to 8 atoms or substituted or unsubstituted heteroaryl ring;

$R^{20}$ is selected from alkyl and substituted alkyl;

$R^{26}$ and $R^{46}$ are independently selected from hydrogen, $C_{1-4}$alkyl, hydroxy, halogen, hydroxy$C_{1-4}$alkyl, halo$C_{1-4}$alkyl, and heterocyclo$C_{1-4}$alkyl, or taken together form a $C_{3-7}$cycloalkyl ring;

$R^{40}$ and $R^{45}$ are independently selected from hydrogen, cyano, alkyl, substituted alkyl, alkenyl, substituted alkenyl, alkynyl, substituted alkynyl, cycloalkyl, substituted cycloalkyl, aryl, substituted aryl, heterocyclo, substituted heterocyclo, heteroaryl and substituted heteroaryl, or $R^{40}$ and $R^{45}$ are taken together to form a substituted or unsubstituted cycloalkyl ring of 3 to 8 atoms or a substituted or unsubstituted heterocyclo ring of 3 to 8 atoms;

s is 0, 1, 2 or 3;

t is 0, 1, or 2;

Y is a bond and Z is selected from

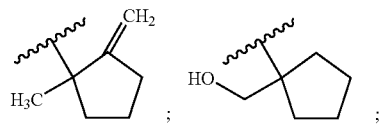

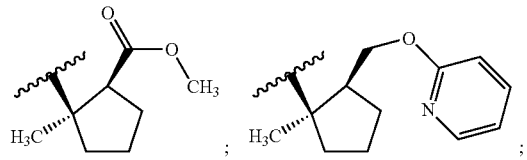

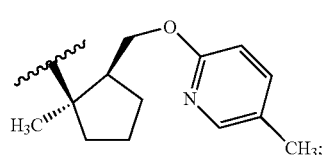

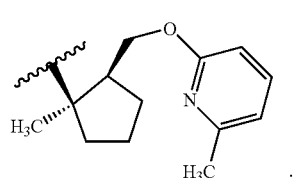

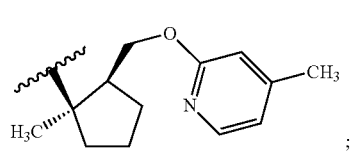

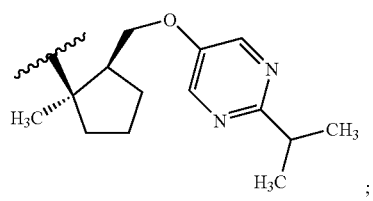

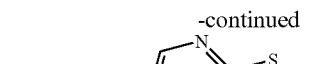

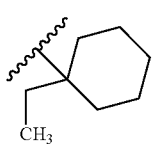

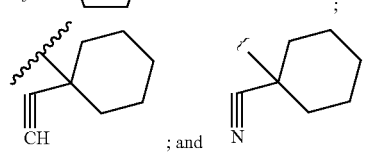

; and

.

14. A compound according to claim 1, having the formula:

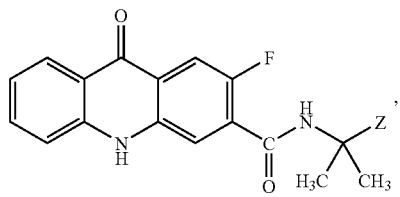

or an enantiomer, diastereomer, tautomer, or pharmaceutically-acceptable salt thereof.

15. A compound having the formula:

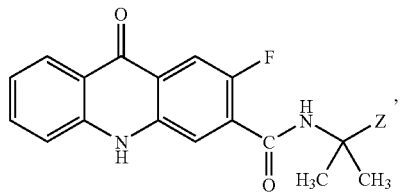

or an enantiomer, diastereomer, tautomer, or pharmaceutically-acceptable salt thereof, wherein Z is selected from one of:

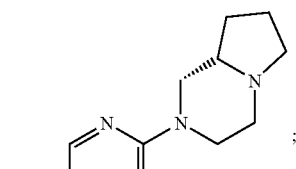

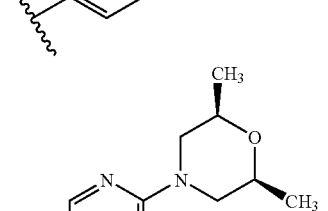

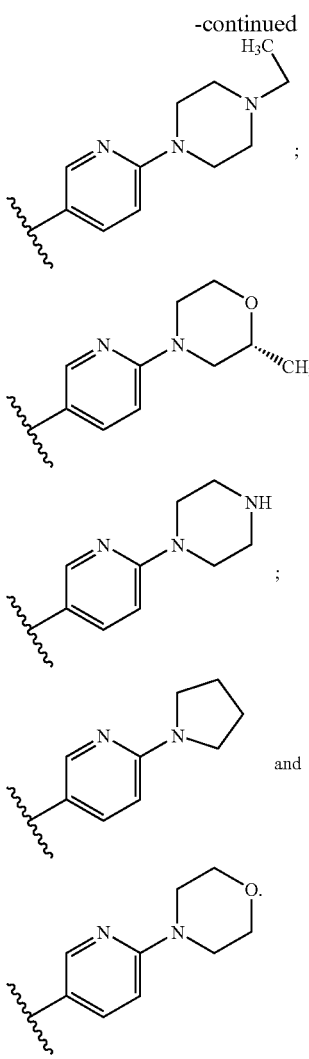

16. A pharmaceutical composition comprising a compound according to claim 1 and a pharmaceutically acceptable carrier.

17. A method of treating psoriasis, transplant rejection, and rheumatoid arthritis comprising administering to a subject in need of treatment thereof an effective amount of at least one compound of formula (I),

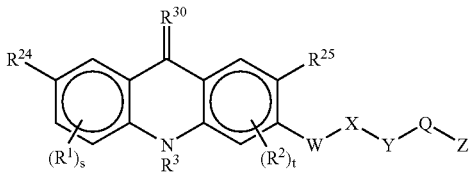

or a enantiomer, diastereomer, tautomer, or pharmaceutically-acceptable salt thereof, wherein:

$R^1$ and $R^2$ are then or different and at each occurrence are independently selected from halogen, cyano, alkyl, substituted alkyl, alkenyl, substituted alkenyl, alkynyl, substituted alkynyl, —O—$R^7$, —(C=O)$R^7$, —(C=O)—O—$R^7$, —$NR^8R^9$, —(C=O)$NR^8R^9$, —$SR^{20}$, —S(=O)$R^{20}$, —$SO_2R^{20}$ and —C≡C—Si($C_{1-4}$alkyl)$_3$;

$R^{24}$ is selected from hydrogen, halogen, nitro, cyano, alkyl, substituted alkyl, alkenyl, substituted alkenyl, alkynyl, substituted alkynyl, —O—$R^7$, —(C=O)$R^7$, —$NR^8R^9$, —(C=O)$NR^8R^9$, —$SR^{20}$, —S(=O)$R^{20}$, —$SO_2R^{20}$, —$SO_3H$, —$SO_3R^{20}$, —$SO_2NR^8R^9$, and —C≡C—Si($C_{1-4}$alkyl)$_3$;

$R^{25}$ is selected from hydrogen, halogen, nitro, cyano, alkyl, substituted alkyl, alkenyl, substituted alkenyl, alkynyl, substituted alkynyl, —O—$R^7$, —(CO)$R^7$, —(C=O)—O—$R^7$, —$NH_2$, —$NHC_{1-4}$alkyl, —N($C_{1-4}$alkyl)$_2$, —(C=O)$NR^8R^9$, —$SR^{20}$, —S(=O)$R^{20}$, —$SO_2R^{20}$, —$SO_3H$, —$SO_3R^{20}$, —$SO_2NR^8R^9$, and —C≡C—Si($C_{1-4}$alkyl)$_3$;

$R^3$ is selected from H, OH and $NH_2$;

$R^{30}$ is selected from =O and =S;

W is selected from —$CH_2$—, —C(=O)—, —S(=O)—, or —S(O)$_2$—;

X is selected from —$CH_2$—, —N($R^4$)—, and —O—, except that when W is —$CH_2$—, X is —C(=O)—;

Y is a bond or —C($R^{40}$)($R^{45}$)—;

Q is selected from a bond, —C($R^{26}$)($R^{46}$)—, —C(=O)—, —$CH_2$—O—, —$CH_2$—O—$CH_2$—, $CH_2$—$CO_2$—$NR^4$—, —$CH_2$—$CO_2$—, —C(=O)$NR^4$—, and —CH=C($R^{26}$)—;

Z is selected from $CO_2H$, $CO_2$alkyl, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclyl and substituted heterocyclyl $R^4$ is selected from H, OH and $C_{1-4}$ alkyl;

$R^7$ selected from hydrogen, alkyl, substituted alkyl, alkenyl, alkynyl, C(=O)alkyl, C(=O)substituted alkyl, C(=O)cycloalkyl, C(=O)substituted cycloalkyl, C(=O)aryl, C(=O)substituted aryl, C(=O)heterocyclo, C(=O)substituted heterocyclo, C(=O)heteroaryl, C(=O)substituted heteroaryl, C(=O)O-alkyl, C(=O)O-substituted alkyl, —C(=O)—$NR^8R^9$, aryl, substituted aryl, cycloalkyl, substituted cycloalkyl, heterocyclo, substituted heterocyclo, heteroaryl, and substituted heteroaryl;

$R^8$ and $R^9$ are independently selected from hydrogen, hydroxy, O(alkyl), O(substituted alkyl), alkyl, substituted alkyl, C(=O)alkyl, C(=O)substituted alkyl, C(=O)cycloalkyl, C(=O)substituted cycloalkyl, C(=O)aryl, C(=O)substituted aryl, C(=O)O-alkyl, C(=O)O-substituted alkyl, C(=O)heterocyclo, C(=O)heteroaryl, cycloalkyl, substituted cycloalkyl, aryl, substituted aryl, heterocyclo, substituted heterocyclo, heteroaryl and substituted heteroaryl, or $R^8$ and $R^9$ are taken together with the nitrogen atom to which they are attached to form a substituted or unsubstituted heterocyclo ring of 3 to 8 atoms or substituted or unsubstituted heteroaryl ring;

$R^{20}$ is selected from alkyl and substituted alkyl;

$R^{26}$ and $R^{46}$ are independently selected from hydrogen, $C_{1-4}$alkyl, hydroxy, halogen, hydroxy$C_{1-4}$alkyl, halo$C_{1-4}$alkyl, and heterocyclo$C_{1-4}$alkyl, or taken together form a $C_{3-7}$cycloalkyl ring;

$R^{40}$ and $R^{45}$ are independently selected from hydrogen, cyano, alkyl, substituted alkyl, alkenyl, substituted alkenyl, alkynyl, substituted alkynyl, cycloalkyl, substituted cycloalkyl, aryl, substituted aryl, heterocyclo, substituted heterocyclo, heteroaryl and substituted heteroaryl, or $R^{40}$ and $R^{45}$ are taken together to form a substituted or unsubstituted cycloalkyl ring of 3 to 8 atoms or a substituted or unsubstituted heterocyclo ring of 3 to 8 atoms;

s is 0, 1, 2 or 3; and t is 0, 1, or 2.

18. A pharmaceutical composition comprising a compound according to claim 6 and a pharmaceutically acceptable carrier.

19. A method of treating psoriasis, transplant rejection, and rheumatoid arthritis comprising administering to a subject in need of treatment thereof an effective amount of at least one compound according to claim 6.

20. A pharmaceutical composition comprising a compound according to claim 10 and a pharmaceutically acceptable carrier.

21. A method of treating psoriasis, transplant rejection, and rheumatoid arthritis comprising administering to a subject in need of treatment thereof an effective amount of at least one compound according to claim 10.

22. A pharmaceutical composition comprising a compound according to claim 11 and a pharmaceutically acceptable carrier.

23. A method of treating psoriasis, transplant rejection, and rheumatoid arthritis comprising administering to a subject in need of treatment thereof an effective amount of at least one compound according to claim 11.

24. A pharmaceutical composition comprising a compound according to claim 12 and a pharmaceutically acceptable carrier.

25. A method of treating psoriasis, transplant rejection, and rheumatoid arthritis comprising administering to a subject in need of treatment thereof an effective amount of at least one compound according to claim 12.

26. A pharmaceutical composition comprising a compound according to claim 13 and a pharmaceutically acceptable carrier.

27. A method of treating psoriasis, transplant rejection, and rheumatoid arthritis comprising administering to a subject in need of treatment thereof an effective amount of at least one compound according to claim 13.

28. A pharmaceutical composition comprising a compound according to claim 15 and a pharmaceutically acceptable carrier.

29. A method of treating psoriasis, transplant rejection, and rheumatoid arthritis comprising administering to a subject in need of treatment thereof an effective amount of at least one compound according to claim 15.

* * * * *

UNITED STATES PATENT AND TRADEMARK OFFICE
CERTIFICATE OF CORRECTION

PATENT NO.         : 7,312,209 B2
APPLICATION NO. : 10/324306
DATED                  : April 27, 2004
INVENTOR(S)       : Edwin J. Iwanowicz et al.

It is certified that error appears in the above-identified patent and that said Letters Patent is hereby corrected as shown below:

In the Claims:

Column 226, lines 1 to 4, Claim 1, delete "$R^8$ and $R^9$ are independently selected from hydrogen, hydroxy, O(alkyl), O(substituted alkyl), alkyl, substituted alkyl, C(=O)alkyl, C(=O)substituted alkyl, C(O=)cycloalkyl,".

Column 228, line 1, Claim 6, change "$R^{30}$ is ==—" to -- $R^{30}$ is =O --.

Column 228, line 4, Claim 6, change "-C($R^{26}$)($R^{45}$)-" to -- -C($R^{26}$)($R^{46}$)- --.

Column 230, line 12, Claim 10, change "$R^{27}R^{28}$" to -- $R^{27}$, $R^{28}$ --.

Column 231, line 39, Claim 11, change "$R^{20}$" to -- $R^{40}$ --.

Column 231, line 45, Claim 11, change "R40" to -- $R^{40}$ --.

Column 232, line 62, Claim 11, change "$OR^{51}$" to -- $OR^{60}$ --.

Column 233, line 7, Claim 11, change "-($CH_2$)d-cycloalkyl" to -- -($CH_2$)$_d$-cycloalkyl --.

Column 233, lines 7 to 8, Claim 11, change "-($CH_2$)d-heterocyclo" to -- -($CH_2$)$_d$-heterocyclo --.

Column 233, lines 34 to 40, Claim 12, change

"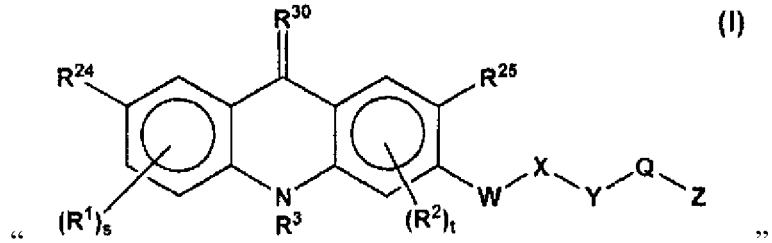"

to

UNITED STATES PATENT AND TRADEMARK OFFICE
CERTIFICATE OF CORRECTION

PATENT NO. : 7,312,209 B2
APPLICATION NO. : 10/324306
DATED : April 27, 2004
INVENTOR(S) : Edwin J. Iwanowicz et al.

It is certified that error appears in the above-identified patent and that said Letters Patent is hereby corrected as shown below:

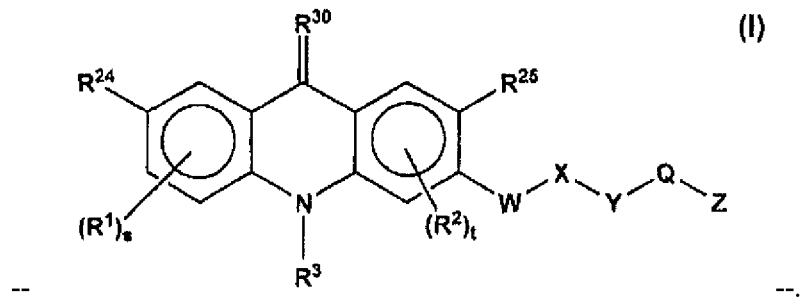

Column 233, line 50, Claim 12, after "and", insert -- -C≡C-Si($C_{1-4}$alkyl)$_3$; --.

Column 234, line 30, Claim 12, change "$R^2$" to -- $R^9$ --.

Column 250, lines 4 to 10, Claim 13, change

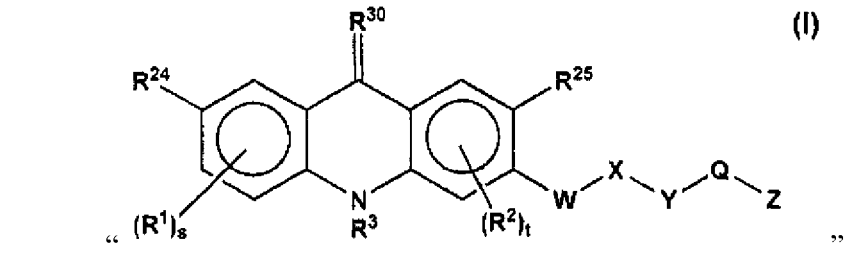

to

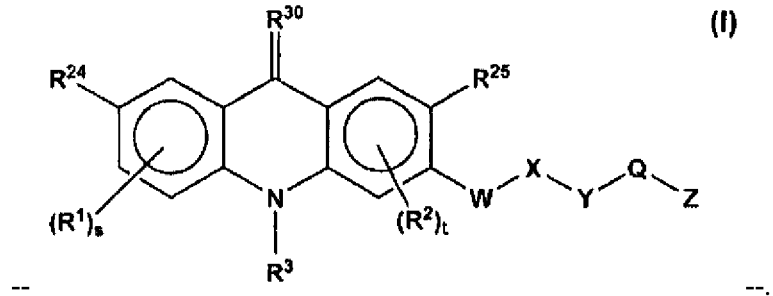

Column 250, line 40, Claim 13, change "C(=O)-" to -- -C(=O)- --.

UNITED STATES PATENT AND TRADEMARK OFFICE
CERTIFICATE OF CORRECTION

PATENT NO. : 7,312,209 B2
APPLICATION NO. : 10/324306
DATED : April 27, 2004
INVENTOR(S) : Edwin J. Iwanowicz et al.

It is certified that error appears in the above-identified patent and that said Letters Patent is hereby corrected as shown below:

Column 252, lines 22 to 28, Claim 14, change

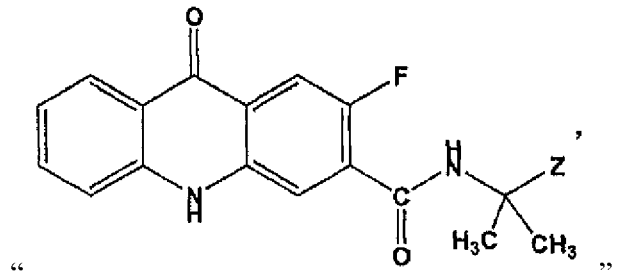

" to

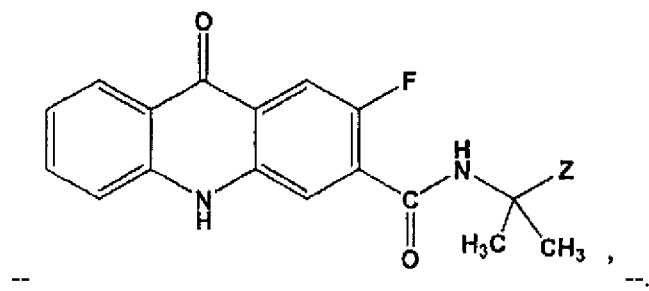

-- --.

Column 252, lines 36 to 42, Claim 15, change

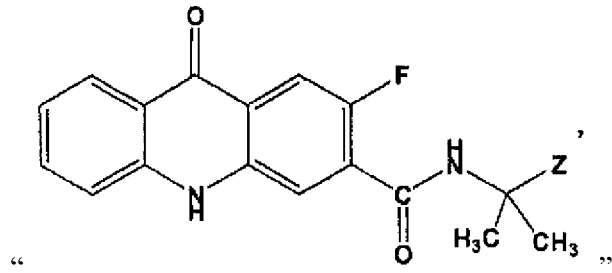

" to

UNITED STATES PATENT AND TRADEMARK OFFICE
CERTIFICATE OF CORRECTION

PATENT NO. : 7,312,209 B2  
APPLICATION NO. : 10/324306  
DATED : April 27, 2004  
INVENTOR(S) : Edwin J. Iwanowicz et al.

It is certified that error appears in the above-identified patent and that said Letters Patent is hereby corrected as shown below:

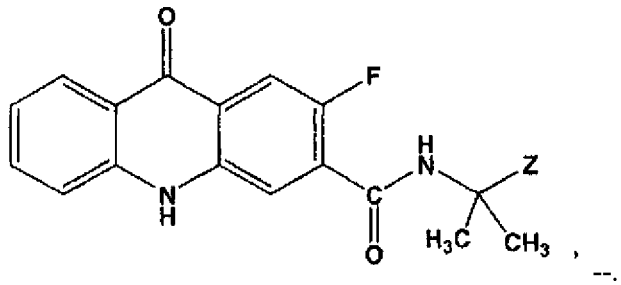

--                                                                              --.

Column 253, lines 53 to 59, Claim 17, change

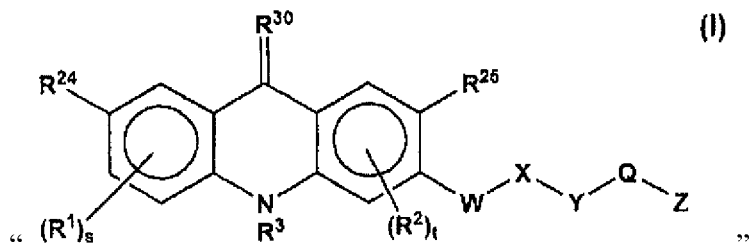

to

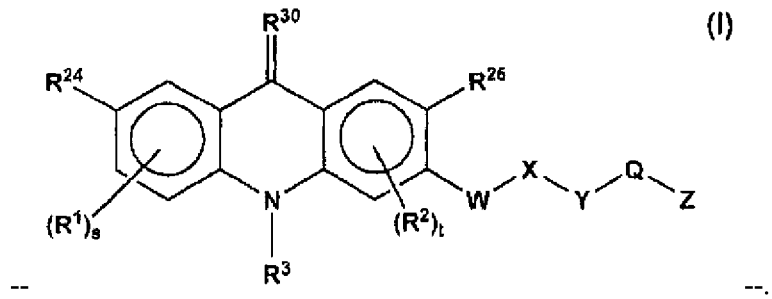

--                                                                              --.

Column 253, line 62, Claim 17, change "a" to -- an --.

UNITED STATES PATENT AND TRADEMARK OFFICE
CERTIFICATE OF CORRECTION

| | |
|---|---|
| PATENT NO. | : 7,312,209 B2 |
| APPLICATION NO. | : 10/324306 |
| DATED | : April 27, 2004 |
| INVENTOR(S) | : Edwin J. Iwanowicz et al. |

It is certified that error appears in the above-identified patent and that said Letters Patent is hereby corrected as shown below:

Column 253, line 64, Claim 17, change "then" to -- the same --.

Column 254, line 12, Claim 17, change "-(CO)R$^7$" to -- -(C=O)R$^7$ --.

Signed and Sealed this

First Day of December, 2009

David J. Kappos
*Director of the United States Patent and Trademark Office*